(12) United States Patent
Wang et al.

(10) Patent No.: US 9,994,581 B2
(45) Date of Patent: Jun. 12, 2018

(54) BROMODOMAIN INHIBITORS

(71) Applicant: AbbVie Inc., North Chicago, IL (US)

(72) Inventors: Le Wang, Vernon Hills, IL (US); Robin R. Frey, Libertyville, IL (US); Todd M. Hansen, Grayslake, IL (US); Dachun Liu, Vernon Hills, IL (US); William J. McClellan, Waukegan, IL (US); Keith F. McDaniel, Wauconda, IL (US); John K. Pratt, Kenosha, WI (US); Carol K. Wada, Evanston, IL (US)

(73) Assignee: AbbVie Inc., North Chicago, IL (US)

( * ) Notice: Subject to any disclaimer, the term of this patent is extended or adjusted under 35 U.S.C. 154(b) by 0 days. days.

(21) Appl. No.: 15/103,215

(22) PCT Filed: Dec. 10, 2014

(86) PCT No.: PCT/CN2014/093466
§ 371 (c)(1),
(2) Date: Jun. 9, 2016

(87) PCT Pub. No.: WO2015/085925
PCT Pub. Date: Jun. 18, 2015

(65) Prior Publication Data
US 2017/0015673 A1      Jan. 19, 2017

Related U.S. Application Data

(63) Continuation-in-part of application No. PCT/CN2013/088948, filed on Dec. 10, 2013.

(51) Int. Cl.
*C07D 491/22*     (2006.01)
*C07D 491/056*    (2006.01)
*A61K 45/06*      (2006.01)
*A61K 31/4353*    (2006.01)
*C07D 491/153*    (2006.01)

(52) U.S. Cl.
CPC ...... *C07D 491/056* (2013.01); *A61K 31/4353* (2013.01); *A61K 45/06* (2013.01); *C07D 491/153* (2013.01); *C07D 491/22* (2013.01)

(58) Field of Classification Search
CPC .................................................. C07D 491/22
See application file for complete search history.

(56) References Cited

U.S. PATENT DOCUMENTS

2004/0006082 A1   1/2004   Harada et al.
2010/0286127 A1   11/2010  Miyoshi et al.

FOREIGN PATENT DOCUMENTS

| WO | WO-2011054841 | A1 | 5/2011 |
|----|---------------|----|----|
| WO | WO-2011054843 | A1 | 5/2011 |
| WO | WO-2012075383 | A2 | 6/2012 |
| WO | WO-2012075456 | A1 | 6/2012 |
| WO | WO-2013097052 | A1 | 7/2013 |
| WO | WO-2013097601 | A1 | 7/2013 |

OTHER PUBLICATIONS

PCT/CN2013/088948 International Search Report (2013).
PCT/CN2014/093466 International Search Report (2014).

*Primary Examiner* — Bruck Kifle
(74) *Attorney, Agent, or Firm* — Michael S. Montgomery

(57) ABSTRACT

The present invention provides for compounds of formula (I) wherein $R^x$, X, Y, $Y^1$, $L^1$, $A^1$, $A^2$, $A^3$, $A^4$, $A^5$, $A^6$, $A^7$, and $A^8$, have any of the values defined in the specification, and pharmaceutically acceptable salts thereof, that are useful as agents in the treatment of diseases and conditions, including inflammatory diseases, cancer, and AIDS. Also provided are pharmaceutical compositions comprised of one or more compounds of formula (I).

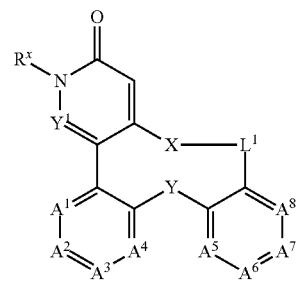

(I)

22 Claims, No Drawings

BROMODOMAIN INHIBITORS

BACKGROUND

Bromodomains refer to conserved protein structural folds which bind to N-acetylated lysine residues that are found in some proteins. The BET family of bromodomain containing proteins is comprised of four members (BRD2, BRD3, BRD4 and BRDt). Each member of the BET family employs two bromodomains to recognize N-acetylated lysine residues found primarily, but not exclusively, on the amino-terminal tails of histone proteins. These interactions modulate gene expression by recruiting transcription factors to specific genome locations within chromatin. For example, histone-bound BRD4 recruits the transcription factor P-TEFb to promoters, resulting in the expression of a subset of genes involved in cell cycle progression (Yang et al., Mol. Cell. Biol. 28: 967-976 (2008)). BRD2 and BRD3 also function as transcriptional regulators of growth promoting genes (LeRoy et al., Mol. Cell 30: 51-60 (2008)). BET family members were recently established as being important for the maintenance of several cancer types (Zuber et al., Nature 478: 524-528 (2011); Mertz et al; Proc. Nat'l. Acad. Sci. 108: 16669-16674 (2011); Delmore et al., Cell 146: 1-14, (2011); Dawson et al., Nature 478: 529-533 (2011)). BET family members have also been implicated in mediating acute inflammatory responses through the canonical NF-KB pathway (Huang et al., Mol. Cell. Biol. 29: 1375-1387 (2009)) resulting in the upregulation of genes associated with the production of cytokines (Nicodeme et al., Nature 468: 1119-1123, (2010)). Suppression of cytokine induction by BET bromodomain inhibitors has been shown to be an effective approach to treat inflammation-mediated kidney disease in an animal model (Zhang, et al., J. Biol. Chem. 287: 28840-28851 (2012)). BRD2 function has been linked to predisposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). BET bromodomain inhibitors have also been shown to reactivate HIV transcription in models of latent T cell infection and latent monocyte infection (Banerjee, et al, J. Leukocyte Biol. doi:10.1189/jlb.0312165). BRDt has an important role in spermatogenesis that is blocked by BET bromodomain inhibitors (Matzuk, et al., Cell 150: 673-684 (2012)). Thus, compounds that inhibit the binding of BET family bromodomains to their cognate acetylated lysine proteins are being pursued for the treatment of cancer, inflammatory diseases, kidney diseases, diseases involving metabolism or fat accumulation, and some viral infections, as well as for providing a method for male contraception. Accordingly, there is an ongoing medical need to develop new drugs to treat these indications.

SUMMARY

In one aspect the present invention provides for compounds of formula (I) or pharmaceutically acceptable salts thereof,

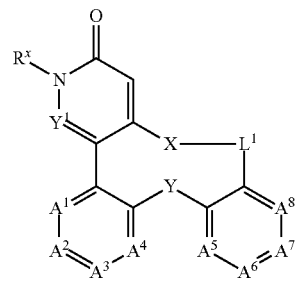

(I)

wherein
$R^x$ is $C_1$-$C_3$ alkyl;
$Y^1$ is N or $CR^y$, wherein $R^y$ is H, halogen, $C_1$-$C_3$ alkyl, or $C_1$-$C_3$ haloalkyl;
$A^1$ is N or $CR^1$, $A^2$ is N or $CR^2$, $A^3$ is N or $CR^3$; and $A^4$ is N or $CR^4$; wherein zero, one, or two of $A^1$, $A^2$, $A^3$, and $A^4$ are N;
$A^5$ is N or $CR^5$, $A^6$ is N or $CR^6$, $A^7$ is N or $CR^7$; and $A^8$ is N or $CR^8$; wherein zero, one, or two of $A^5$, $A^6$, $A^7$, and $A^8$ are N;
$R^1$, $R^2$, $R^3$, $R^4$, $R^5$, $R^6$, $R^7$, and $R^8$, are each independently hydrogen, halogen, $NO_2$, $G^a$, $C_1$-$C_6$ haloalkyl, —CN, —$OR^a$, —$S(O)_2R^c$, —$C(O)R^a$, —$C(O)OR^a$, —$S(O)_2NR^aR^b$, —$C(O)NR^aR^b$, $NR^aR^b$, —$N(R^b)S(O)_2R^c$, —$N(R^b)C(O)OR^c$, —$N(R^b)C(O)NR^aR^b$, —$N(R^b)C(O)R^c$, $C_2$-$C_6$ alkenyl, $C_2$-$C_6$ alkynyl, or $C_1$-$C_6$ alkyl; wherein the $C_2$-$C_6$ alkenyl, $C_2$-$C_6$ alkynyl, and $C_1$-$C_6$ alkyl are optionally substituted with one substituent selected from the group consisting of—
CN, —$OR^a$, —$S(O)_2R^c$, —$S(O)_2NR^aR^b$, —$C(O)R^a$, —$C(O)OR^a$, —$C(O)NR^aR^b$, $NR^aR^b$, —$N(R^b)S(O)_2R^c$, —$N(R^b)C(O)OR^c$, —$N(R^b)C(O)NR^aR^b$, —$N(R^b)C(O)R^c$, and $G^a$;
X is $CR^9R^{10}$, O, or $N(R^{11})$;
Y is O or $N(R^{12})$;
$R^9$ and $R^{10}$ are each independently hydrogen, halogen, —CN, $C_1$-$C_6$ haloalkyl, $G^b$, $C_1$-$C_6$ alkyl, —$OR^d$, —$NR^dR^e$, or —$C(O)NR^dR^e$;
$R^{11}$ and $R^{12}$ are each independently hydrogen or $C_1$-$C_3$ alkyl;
$L^1$ is —$(CR^{13}R^{14})_m$—W—$(CR^{15}R^{16})_n$—; wherein —$(CR^{15}R^{16})_n$— is attached to the ring containing $A^5$, $A^6$, $A^7$, and $A^8$; wherein
m is 1, 2, or 3;
n is 0, 1, 2, or 3;
W is a bond, O, $N(R^{17})$, —CH=CH—, —C(O)—N($R^{18}$)—, —$S(O)_2$—$N(R^{18})$—, —$N(R^{18})$—C(O)—, or —$N(R^{18})$—$S(O)_2$—; wherein
$R^{17}$ is hydrogen, $C_1$-$C_6$ haloalkyl, $G^c$, —$S(O)_2R^f$, —$S(O)_2N(R^g)_2$, —$S(O)_2N(R^g)C(O)R^f$, —$S(O)_2N(R^g)C(O)OR^f$, —$C(O)R^f$, —$C(O)OR^f$, —$C(O)N(R^g)_2$, $C_2$-$C_6$ alkenyl, $C_2$-$C_6$ alkynyl, or $C_1$-$C_6$ alkyl; wherein the $C_2$-$C_6$ alkenyl, $C_2$-$C_6$ alkynyl, and $C_1$-$C_6$ alkyl are optionally substituted with one substituent selected from the group consisting of—
CN, —$OR^a$, —$S(O)_2R^a$, —$S(O)_2NR^aR^b$, —$C(O)R^a$, —$C(O)OR^a$, —$C(O)NR^aR^b$, $NR^aR^b$, —$N(R^b)S(O)_2R^c$, —$N(R^b)C(O)OR^c$, —$N(R^b)C(O)NR^aR^b$, —$N(R^b)C(O)R^c$, and $G^c$;
and $R^{18}$, at each occurrence, is independently hydrogen, $C_1$-$C_6$ haloalkyl, $G^c$, $C_2$-$C_6$ alkenyl, $C_2$-$C_6$ alkynyl, or $C_1$-$C_6$ alkyl; wherein the $C_2$-$C_6$ alkenyl, $C_2$-$C_6$ alkynyl, and $C_1$-$C_6$ alkyl are optionally substituted with one substituent selected from the group consisting of—
CN, —OR$^a$, —S(O)$_2$R$^a$, —S(O)$_2$NR$^a$R$^b$, —C(O)R$^a$, —C(O)OR$^a$, —C(O)NR$^a$R$^b$, NR$^a$R$^b$, —N(R$^b$)S(O)$_2$R$^c$, —N(R$^b$)C(O)OR$^c$, —N(R$^b$)C(O)NR$^a$R$^b$, —N(R$^b$)C(O)R$^c$, and G$^c$;

$R^{13}$ and $R^{14}$, at each occurrence, are each independently hydrogen, halogen, —CN, $C_1$-$C_6$ haloalkyl, G$^b$, $C_1$-$C_6$ alkyl, —OR$^d$, —NR$^d$R$^e$, or —C(O)NR$^d$R$^e$; $R^{13}$ and $R^{14}$ together may be an oxo group;

$R^{15}$ and $R^{16}$, at each occurrence, are each independently hydrogen, halogen, —CN, $C_1$-$C_6$ haloalkyl, G$^b$, $C_1$-$C_6$ alkyl, —OR$^d$, —NR$^d$R$^e$, or —C(O)NR$^d$R$^e$; $R^{15}$ and $R^{16}$ together may be an oxo group;

R$^a$ and R$^b$, at each occurrence, are each independently hydrogen, $C_1$-$C_6$ alkyl, $C_1$-$C_6$ haloalkyl, G$^a$, or —($C_1$-$C_6$ alkylenyl)-G$^a$;

R$^c$, at each occurrence, is independently $C_1$-$C_6$ alkyl, $C_1$-$C_6$ haloalkyl, G$^a$, or —($C_1$-$C_6$ alkylenyl)-G$^a$;

R$^d$, at each occurrence, is independently hydrogen, $C_1$-$C_6$ haloalkyl, G$^b$, or $C_1$-$C_6$ alkyl; wherein the $C_1$-$C_6$ alkyl is optionally substituted with one substituent selected from the group consisting of—
CN, —OR$^a$, —S(O)$_2$R$^a$, —S(O)$_2$NR$^a$R$^b$, —C(O)R$^a$, —C(O)OR$^a$, —C(O)NR$^a$R$^b$, NR$^a$R$^b$, —N(R$^b$)S(O)$_2$R$^c$, —N(R$^b$)C(O)OR$^c$, —N(R$^b$)C(O)NR$^a$R$^b$, —N(R$^b$)C(O)R$^c$, and G$^b$;

R$^e$, at each occurrence, is independently hydrogen, $C_1$-$C_6$ alkyl, $C_1$-$C_6$ haloalkyl, G$^b$, or —($C_1$-$C_6$ alkylenyl)-G$^b$;

R$^f$, at each occurrence, is independently $C_1$-$C_6$ alkyl, $C_1$-$C_6$ haloalkyl, G$^c$, or —($C_1$-$C_6$ alkylenyl)-G$^c$;

R$^g$, at each occurrence, is independently hydrogen, $C_1$-$C_6$ alkyl, $C_1$-$C_6$ haloalkyl, or —($C_1$-$C_6$ alkylenyl)-G$^c$;

G$^a$, G$^b$, and G$^c$, at each occurrence, are each independently phenyl, $C_3$-$C_6$ cycloalkyl, $C_4$-$C_6$ heterocycle, or $C_5$-$C_6$ heteroaryl, each of which is optionally substituted with 1, 2, 3, 4, or 5 R$^u$ groups;

R$^u$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, NO$_2$, —OR$^h$, —OC(O)R$^i$, —OC(O)NR$^j$R$^k$, —SR$^h$, —S(O)$_2$R$^h$, —S(O)$_2$NR$^j$R$^k$, —C(O)R$^h$, —C(O)OR$^h$, —C(O)NR$^j$R$^k$, —NR$^j$R$^k$, —N(R$^h$)C(O)R$^i$, —N(R$^h$)S(O)$_2$R$^i$, —N(R$^h$)C(O)O(R$^i$), —N(R$^h$)C(O)NR$^j$R$^k$, —($C_1$-$C_6$ alkylenyl)-OR$^h$, —($C_1$-$C_6$ alkylenyl)-OC(O)R$^i$, —($C_1$-$C_6$ alkylenyl)-OC(O)NR$^j$R$^k$, —($C_1$-$C_6$ alkylenyl)-SR$^h$, —($C_1$-$C_6$ alkylenyl)-S(O)$_2$R$^h$, —($C_1$-$C_6$ alkylenyl)-S(O)$_2$NR$^j$R$^k$, —($C_1$-$C_6$ alkylenyl)-C(O)R$^h$, —($C_1$-$C_6$ alkylenyl)-C(O)OR$^h$, —($C_1$-$C_6$ alkylenyl)-C(O)NR$^j$R$^k$, —($C_1$-$C_6$ alkylenyl)-NR$^j$R$^k$, —($C_1$-$C_6$ alkylenyl)-N(R$^h$)C(O)R$^i$, —($C_1$-$C_6$ alkylenyl)-N(R$^h$)S(O)$_2$R$^i$, —($C_1$-$C_6$ alkylenyl)-N(R$^h$)C(O)O(R$^i$), —($C_1$-$C_6$ alkylenyl)-N(R$^h$)C(O)NR$^j$R$^k$, or —($C_1$-$C_6$ alkylenyl)-CN;

R$^h$, R$^j$, R$^k$, at each occurrence, are each independently hydrogen, $C_1$-$C_6$ alkyl, or $C_1$-$C_6$ haloalkyl; and R$^i$, at each occurrence, is independently $C_1$-$C_6$ alkyl or $C_1$-$C_6$ haloalkyl.

In another aspect, the present invention provides for methods for treating or preventing disorders that are ameliorated by inhibition of BET. Such methods comprise of administering to the subject a therapeutically effective amount of a compound of formula (I), (I-a), or (I-b), or a pharmaceutically acceptable salt thereof, alone, or in combination with a pharmaceutically acceptable carrier.

Some of the methods are directed to treating or preventing an inflammatory disease or cancer or AIDS.

In another aspect, the present invention relates to methods of treating cancer in a subject comprising administering a therapeutically effective amount of a compound of formula (I), (I-a), or (I-b) or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor. In certain embodiments, the methods further comprise administering a therapeutically effective amount of at least one additional therapeutic agent. In certain embodiments, the additional therapeutic agent is selected from the group consisting of cytarabine, bortezomib, and 5-azacitidine.

In another aspect, the present invention relates to methods of treating a disease or condition in a subject comprising administering a therapeutically effective amount of a compound of formula (I), (I-a), or (I-b) or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, cardiac myopathy, chronic obstructive pulmonary disease (COPD), Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent.

In another aspect, the present invention relates to methods of treating a chronic kidney disease or condition in a subject comprising administering a therapeutically effective amount of a compound of formula (I), (I-a), or (I-b) or a pharmaceutically acceptable salt thereof, to a subject in need thereof, wherein said chronic kidney disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent.

In another aspect, the present invention relates to methods of treating an acute kidney injury or disease or condition in a subject comprising administering a therapeutically effective amount of a compound of formula (I), (I-a), or (I-b) or a pharmaceutically acceptable salt thereof, to a subject in need thereof, wherein said acute kidney injury or disease or condition is selected from the group consisting of: ischemia-reperfusion induced, cardiac and major surgery induced, percutaneous coronary intervention induced, radio-contrast agent induced, sepsis induced, pneumonia induced, and drug toxicity induced. In certain embodiments, the methods further comprise administering a therapeutically effective amount of at least one additional therapeutic agent.

In another aspect, the present invention relates to methods of treating AIDS in a subject comprising administering a therapeutically effective amount of a compound of formula (I), (I-a), or (I-b) or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity, dyslipidemia, hypercholesterolemia, Alzheimer's disease, metabolic syndrome, hepatic steatosis, type II diabetes, insulin resistance, diabetic retinopathy or diabetic neuropathy in a subject comprising administering a therapeutically effective amount of a compound of formula (I), (I-a), or (I-b) or a pharmaceutically acceptable salt thereof, to a subject in need thereof. In certain embodiments, the methods further comprise administering a therapeutically effective amount of at least one additional therapeutic agent.

In another aspect, the present invention relates to methods of preventing conception by inhibiting spermatogenesis in a subject comprising administering a therapeutically effective amount of a compound of formula (I), (I-a), or (I-b) or a pharmaceutically acceptable salt thereof, to a subject in need thereof. In certain embodiments, the methods further comprise administering a therapeutically effective amount of at least one additional therapeutic agent.

A further aspect of the invention provides the use of a compound of formula (I), (I-a), or (I-b), alone or in combination with at least one additional therapeutic agent, in the manufacture of a medicament for treating or preventing conditions and disorders disclosed herein, and with or without a pharmaceutically acceptable carrier.

Pharmaceutical compositions comprising a compound of formula (I), (I-a), or (I-b), or a pharmaceutically acceptable salt, alone or in combination with at least one additional therapeutic agent, are also provided.

DETAILED DESCRIPTION

Disclosed herein are compounds of formula (I)

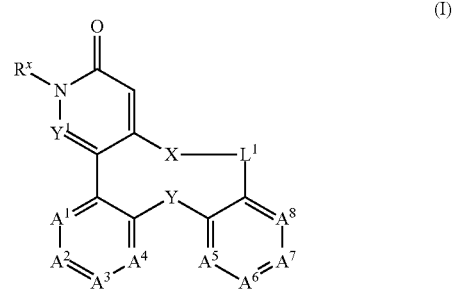

(I)

wherein $R^x$, X, Y, $Y^1$, $L^1$, $A^1$, $A^2$, $A^3$, $A^4$, $A^5$, $A^6$, $A^7$, and $A^8$ are defined above in the Summary of the Invention and below in the Detailed Description. Further, compositions comprising such compounds and methods for treating conditions and disorders using such compounds and compositions are also disclosed.

Compounds disclosed herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds that can be isolated from a reaction mixture.

Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_6$ alkenyl" means an alkenyl group containing 2-6 carbon atoms. Non-limiting examples of alkenyl include buta-1,3-dienyl, ethenyl, 2-propenyl, 2-methyl-2-propenyl, 3-butenyl, 4-pentenyl, and 5-hexenyl.

The term "alkenylene" means a divalent group derived from a straight or branched chain hydrocarbon of 2 to 6 carbon atoms and contains at least one carbon-carbon double bond. Representative examples of alkenylene include, but are not limited to, —CH=CH— and —CH₂CH=CH—.

The term "alkyl" as used herein, means a saturated, straight or branched hydrocarbon chain radical. In some instances, the number of carbon atoms in an alkyl moiety is indicated by the prefix "$C_x$-$C_y$", wherein x is the minimum and y is the maximum number of carbon atoms in the substituent. Thus, for example, "$C_1$-$C_6$ alkyl" refers to an alkyl substituent containing from 1 to 6 carbon atoms and "$C_1$-$C_3$ alkyl" refers to an alkyl substituent containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent radical derived from a straight or branched, saturated hydrocarbon chain, for example, of 1 to 10 carbon atoms or of 1 to 6 carbon atoms ($C_1$-$C_6$ alkylenyl) or of 1 to 4 carbon atoms ($C_1$-$C_4$ alkylenyl) or of 1 to 3 carbon atoms ($C_1$-$C_3$ alkylenyl) or of 2 to 6 carbon atoms ($C_2$-$C_6$ alkylenyl). Examples of alkylene and alkylenyl include, but are not limited to, —CH₂—, —CH₂CH₂—, —C(CH₃)₂—, —CH₂CH₂CH₂—, —CH₂CH₂CH₂CH₂—, and —CH₂CH(CH₃)CH₂—.

The term "$C_2$-$C_6$ alkynyl" as used herein, means a straight or branched chain hydrocarbon radical containing from 2 to 6 carbon atoms and containing at least one carbon-carbon triple bond. Representative examples of $C_2$-$C_6$ alkynyl include, but are not limited, to acetylenyl, 1-propynyl, 2-propynyl, 3-butynyl, 2-pentynyl, and 1-butynyl.

The term "cycloalkyl" as used herein, refers to a radical that is a monocyclic cyclic alkyl, a bicyclic cycloalkyl, or a spiro cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. The monocyclic and the bicyclic cycloalkyl groups may contain one or two alkylene bridges, each consisting of one, two, three, or four carbon atoms in length, and each bridge links two non-adjacent carbon atoms of the ring system. Non-limiting examples of bicyclic ring systems include bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, tricyclo[3.3.1.0³,⁷]nonane (octahydro-2,5-methanopentalene or noradamantane), and tricyclo[3.3.1.1³,⁷]decane (adamantane). A spiro cycloalkyl is a monocyclic cycloalkyl wherein two substituents on the same carbon atom of the monocyclic cycloalkyl ring together with said carbon atom form a second monocyclic cycloalkyl ring. The monocyclic, the bicyclic, and the spiro cycloalkyl groups are attached to the parent molecular moiety through any substitutable atom contained within the ring system.

The term "$C_3$-$C_6$ cycloalkyl" as used herein, means cyclopropyl, cyclobutyl, cyclopentyl, and cyclohexyl.

The term "cycloalkenyl" as used herein, means a monocyclic or a bicyclic hydrocarbon ring radical. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, or three carbon atoms, and each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyls can be attached to the parent molecular moiety through any substitutable atom contained within the ring systems.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, or six hydrogen atoms are replaced by halogen. The term "$C_1$-$C_3$ haloalkyl" means a $C_1$-$C_3$ alkyl group, as defined herein, in which one, two, three, four, or five hydrogen atoms are replaced by halogen. Representative examples of haloalkyl include, but are not limited to, chloromethyl, 2-fluoroethyl, 2,2-difluoroethyl, 2,2,2-trifluoroethyl, trifluoromethyl, difluoromethyl, pentafluoroethyl, 2-chloro-3-fluoropentyl, trifluorobutyl, and 3,3,3-trifluoropropyl.

The term "heterocycle" or "heterocyclic" as used herein, means a radical of a monocyclic heterocycle, a bicyclic heterocycle, and a spiro heterocycle. A monocyclic heterocycle is a three-, four-, five-, six-, seven-, or eight-membered carbocyclic ring also containing at least one heteroatom independently selected from the group consisting of O, N, and S. A three- or four-membered ring contains zero or one double bond, and one heteroatom selected from the group consisting of O, N, and S. When two O atoms or one O atom and one S atom are present in a heterocyclic ring, then the two O atoms or one O atom and one S atom are not bonded directly to each other. A five-membered ring contains zero or one double bond and one, two, or three heteroatoms selected from the group consisting of O, N, and S. Examples of five-membered heterocyclic rings include those containing in the ring: 1 O; 1 S; 1 N; 2 N; 3 N; 1 S and 1 N; 1 S, and 2 N; 1 O and 1 N; or 1 O and 2 N. Examples of 5-membered heterocyclic groups include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl. A six-membered ring contains zero, one, or two double bonds and one, two, or three heteroatoms selected from the group consisting of O, N, and S. Examples of six-membered heterocyclic rings include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 Q and 1 N; and 1 O and 2 N. Examples of 6-membered heterocyclic groups include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, 1,1-dioxo-hexahydro-1-thiopyranyl, 1,1-dioxo-1λ⁶-thiomorpholinyl, thiomorpholinyl, thioxanyl, and trithianyl. Seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,4-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Representative examples of bicyclic heterocycles include, but are not limited to, benzopyranyl, benzothiopyranyl, 2,3-dihydrobenzofuranyl, 2,3-dihydrobenzothienyl, 2,3-dihydro-1H-indolyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1(5H)-yl. The monocyclic heterocycle and the bicyclic heterocycle may contain one or two alkylene bridges or an alkenylene bridge, or mixture thereof, each consisting of no more than four carbon atoms and each linking two non adjacent atoms of the ring system. Examples of such bridged heterocycle include, but are not limited to, azabicyclo[2.2.1]heptyl (including 2-azabicyclo[2.2.1]hept-2-yl), 8-azabicyclo[3.2.1]oct-8-yl, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). A spiro heterocycle is a monocyclic heterocycle wherein two substituents on the same carbon atom of the monocyclic heterocycle ring together with said carbon atom form a second ring system selected from a monocyclic cycloalkyl, a bicyclic cycloalkyl, a monocyclic heterocycle, or a bicyclic heterocycle. Examples of spiro heterocycle include, but not limited to, 6-azaspiro[2.5]oct-6-yl, 1'H, 4H-spiro[1,3-benzodioxine-2,4'-piperidin]-1'-yl, 1'H, 3H-spiro[2-benzofuran-1,4'-piperidin]-1'-yl, and 1,4-dioxa-8-azaspiro[4.5]dec-8-yl. The monocyclic, the bicyclic and the spiro heterocycles are connected to the parent molecular moiety through any carbon atom or any nitrogen atom contained within the ring systems. The nitrogen and sulfur heteroatoms in the heterocycle rings may optionally be oxidized (e.g. 1,1-dioxidotetrahydrothienyl, 1,1-dioxido-1,2-thiazolidinyl, 1,1-dioxidothiomorpholinyl)) and the nitrogen atoms may optionally be quarternized.

The term "$C_4$-$C_6$ heterocycle" or "$C_4$-$C_6$ heterocyclic" as used herein, means a 4, 5, or 6 membered monocyclic heterocycle as defined herein above. Non-limiting examples of $C_4$-$C_6$ heterocycle include azetidinyl, pyrrolidinyl, tetrahydrofuranyl, tetrahydropyranyl, piperazinyl, piperidinyl, and morpholinyl.

The term "heteroaryl" as used herein, means a monocyclic heteroaryl and a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups are connected to the parent molecular moiety through any substitutable carbon atom or any substitutable nitrogen atom contained within the ring systems. The nitrogen atom in the heteroaryl rings may optionally be oxidized and may optionally be quarternized.

The term "$C_5$-$C_6$ heteroaryl" as used herein, means a 5- or 6-membered monocyclic heteroaryl ring as described above. Examples of $C_5$-$C_6$ heteroaryl include, but are not limited to, furanyl, thienyl, pyrazolyl, imidazolyl, oxazolyl, 1,3-thiazolyl, 1,2,4-oxadiazolyl, 1,2,4-triazolyl, pyridinyl, pyrimidinyl, and pyrazinyl.

The term "heteroatom" as used herein, means a nitrogen, oxygen, and sulfur.

The term "oxo" as used herein, means a =O group.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing", and "prevention" also include delaying the onset of a disease and/or its attendant symptoms and reducing a subject's risk of acquiring a disease.

The phrase "therapeutically effective amount" means an amount of a compound or a pharmaceutically acceptable salt thereof, sufficient to prevent the development of or to alleviate to some extent one or more of the symptoms of the condition or disorder being treated when administered alone or in conjunction with another therapeutic agent for treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, horses, dogs, cats, rabbits, rats, mice and the like. In preferred embodiments, the subject is a human.

Compounds

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

$R^x$ is $C_1$-$C_3$ alkyl.

In certain embodiments, $R^x$ is methyl.

$Y^1$ is N or $CR^y$.

In certain embodiments, $Y^1$ is N or $CR^y$ wherein $R^y$ is H.

In certain embodiments, $Y^1$ is N.

In certain embodiments, $Y^1$ is $CR^y$. In some such embodiments, $R^y$ is H.

$A^1$ is N or $CR^1$, $A^2$ is N or $CR^2$, $A^3$ is N or $CR^3$, and $A^4$ is N or $CR^4$; wherein zero, one, or two of $A^1$, $A^2$, $A^3$, and $A^4$ are N.

In certain embodiments, $A^1$ is N or $CR^1$, $A^2$ is N or $CR^2$, $A^3$ is N or $CR^3$, and $A^4$ is N or $CR^4$; wherein zero or one of $A^1$, $A^2$, $A^3$, and $A^4$ is N.

In certain embodiments, $A^1$ is $CR^1$, $A^2$ is $CR^2$, $A^3$ is $CR^3$, and $A^4$ is $CR^4$; or $A^1$ is $CR^1$, $A^2$ is $CR^2$, $A^3$ is $CR^3$, and $A^4$ is N.

In certain embodiments, $A^1$ is $CR^1$, $A^2$ is $CR^2$, $A^3$ is $CR^3$, and $A^4$ is $CR^4$.

In certain embodiments, one of $A^1$, $A^2$, $A^3$, and $A^4$ is N.

In certain embodiments, $A^1$ is $CR^1$, $A^2$ is $CR^2$, $A^3$ is $CR^3$, and $A^4$ is N.

$A^5$ is N or $CR^5$, $A^6$ is N or $CR^6$, $A^7$ is N or $CR^7$, and $A^8$ is N or $CR^8$; wherein zero, one, or two of $A^5$, $A^6$, $A^7$, and $A^8$ are N.

In certain embodiments, $A^5$ is N or $CR^5$, $A^6$ is N or $CR^6$, $A^7$ is N or $CR^7$, and $A^8$ is N or $CR^8$; wherein zero or one of $A^5$, $A^6$, $A^7$, and $A^8$ is N.

In certain embodiments, $A^5$ is $CR^5$, $A^6$ is $CR^6$, $A^7$ is $CR^7$, and $A^8$ is $CR^8$; or $A^5$ is N, $A^6$ is $CR^6$, $A^7$ is $CR^7$, and $A^8$ is $CR^8$; or $A^5$ is $CR^5$, $A^6$ is N, $A^7$ is $CR^7$, and $A^8$ is $CR^8$.

In certain embodiments, $A^5$ is $CR^5$, $A^6$ is $CR^6$, $A^7$ is $CR^7$, and $A^8$ is $CR^8$.

In certain embodiments, one of $A^5$, $A^6$, $A^7$, and $A^8$ is N.

In certain embodiments, $A^5$ is N, $A^6$ is $CR^6$, $A^7$ is $CR^7$, and $A^8$ is $CR^8$.

In certain embodiments, $A^5$ is $CR^5$, $A^6$ is N, $A^7$ is $CR^7$, and $A^8$ is $CR^8$.

$R^1$, $R^2$, $R^3$, $R^4$, $R^5$, $R^6$, $R^7$, and $R^8$, are each independently hydrogen, halogen, $NO_2$, $G^a$, $C_1$-$C_6$ haloalkyl, —CN, —$OR^a$, —$S(O)_2R^c$, —$C(O)R^a$, —$C(O)OR^a$, —$S(O)_2NR^aR^b$, —$C(O)NR^aR^b$, $NR^aR^b$, —$N(R^b)S(O)_2R^c$, —$N(R^b)C(O)OR^c$, —$N(R^b)C(O)NR^aR^b$, —$N(R^b)C(O)R^c$, $C_2$-$C_6$ alkenyl, $C_2$-$C_6$ alkynyl, or $C_1$-$C_6$ alkyl; wherein the $C_2$-$C_6$ alkenyl, $C_2$-$C_6$ alkynyl, and $C_1$-$C_6$ alkyl are optionally substituted with one substituent selected from the group consisting of—CN, —$OR^a$, —$S(O)_2R^c$, —$S(O)_2NR^aR^b$, —$C(O)R^a$, —$C(O)OR^a$, —$C(O)NR^aR^b$, $NR^aR^b$, —$N(R^b)S(O)_2R^c$, —$N(R^b)C(O)OR^c$, —$N(R^b)C(O)NR^aR^b$, —$N(R^b)C(O)R^c$, and $G^a$.

In certain embodiments, $R^1$, $R^3$, $R^4$, and $R^8$, at each occurrence, are each independently hydrogen, halogen, $C_1$-$C_6$ haloalkyl, —$OR^a$, —CN, or unsubstituted $C_1$-$C_6$ alkyl; wherein $R^a$ is hydrogen, $C_1$-$C_6$ alkyl, or $C_1$-$C_6$ haloalkyl.

In certain embodiments, $R^1$, $R^3$, $R^4$, and $R^8$, at each occurrence, are each independently hydrogen or halogen.

In certain embodiments, $R^1$, $R^3$, $R^4$, and $R^8$ are hydrogen.

In certain embodiments, $R^1$, $R^3$, and $R^8$, at each occurrence, are each independently hydrogen, halogen, $C_1$-$C_6$ haloalkyl, —$OR^a$, —CN, or unsubstituted $C_1$-$C_6$ alkyl. In some such embodiments, $R^a$ is hydrogen, $C_1$-$C_6$ alkyl, or $C_1$-$C_6$ haloalkyl.

In certain embodiments, $R^1$, $R^3$, and $R^8$, at each occurrence, are each independently hydrogen or halogen.

In certain embodiments, $R^1$, $R^3$, and $R^8$ are hydrogen.

In certain embodiments, $R^5$ is hydrogen or halogen. In some such embodiments, the halogen is F.

In certain embodiments, $R^5$ is hydrogen.

In certain embodiments, $R^5$ is halogen. In some such embodiments, the halogen is F.

In certain embodiments, $R^6$ is hydrogen or halogen. In some such embodiments, the halogen is F or Cl.

In certain embodiments, $R^6$ is hydrogen.

In certain embodiments, $R^6$ is halogen. In some such embodiments, the halogen is F or Cl.

In certain embodiments, $R^7$ is hydrogen, halogen, $C_1$-$C_6$ haloalkyl, —$OR^a$, —CN, or unsubstituted $C_1$-$C_6$ alkyl. In some such embodiments, $R^a$ is hydrogen, $C_1$-$C_6$ alkyl, or $C_1$-$C_6$ haloalkyl.

In certain embodiments, $R^7$ is hydrogen, halogen, $C_1$-$C_6$ haloalkyl, —CN, or —$OR^a$. In some such embodiments, $R^a$ is hydrogen, $C_1$-$C_6$ alkyl, or $C_1$-$C_6$ haloalkyl. In some such embodiments, $R^a$ is $C_1$-$C_6$ haloalkyl. In some such embodiments, $R^a$ is $C_1$-$C_3$ haloalkyl. In some such embodiments, $R^a$ is —$CF_3$.

In certain embodiments, $R^7$ is hydrogen, halogen, or —CN.

In certain embodiments, $R^7$ is halogen. In some such embodiments, the halogen is F or Cl. In some such embodiments, the halogen is F. In some such embodiments, the halogen is Cl.

In certain embodiments, $R^2$ is hydrogen, —$S(O)_2R^c$, —$C(O)OR^a$, —$S(O)_2NR^aR^b$, $NR^aR^b$, —$N(R^b)S(O)_2R^c$, —$N(R^b)C(O)NR^aR^b$, —$N(R^b)C(O)R^c$, or $C_1$-$C_6$ alkyl wherein the $C_1$-$C_6$ alkyl is substituted with one substituent selected from the group consisting of—$OR^a$ and —$S(O)_2R^c$.

In certain embodiments, $R^2$ is hydrogen, —$S(O)_2R^c$, —$C(O)OR^a$, —$S(O)_2NR^aR^b$, $NR^aR^b$, —$N(R^b)S(O)_2R^c$, —$N(R^b)C(O)NR^aR^b$, —$N(R^b)C(O)R^c$, —$CH_2$—$OR^a$, or —CH$_2$—S(O)$_2$R$^c$. In some such embodiments, R$^a$ is hydrogen, C$_1$-C$_6$ alkyl, or C$_1$-C$_6$ haloalkyl, R$^b$ is hydrogen or C$_1$-C$_6$ alkyl; and R$^c$ is C$_1$-C$_6$ alkyl, C$_1$-C$_6$ haloalkyl, or optionally substituted C$_3$-C$_6$ cycloalkyl.

In certain embodiments, R$^2$ is —S(O)$_2$R$^c$, —N(R$^b$)S(O)$_2$R$^c$, or —CH$_2$—S(O)$_2$R$^c$. In some such embodiments, R$^b$ is hydrogen or C$_1$-C$_3$ alkyl, and R$^c$ is C$_1$-C$_3$ alkyl or unsubstituted cyclopropyl. In some such embodiments, R$^b$ is hydrogen, and R$^c$ is C$_1$-C$_3$ alkyl. In some such embodiments, R$^b$ is hydrogen, and R$^c$ is methyl or ethyl.

In certain embodiments, R$^2$ is —S(O)$_2$R$^c$ or —N(R$^b$)S(O)$_2$R$^c$. In some such embodiments, R$^b$ is hydrogen, and R$^c$ is C$_1$-C$_3$ alkyl. In some such embodiments, R$^b$ is hydrogen, and R$^c$ is methyl or ethyl.

X is CR$^9$R$^{10}$, O, or N(R$^{11}$).
In certain embodiments, X is CR$^9$R$^{10}$.
In certain embodiments, X is O.
In certain embodiments, X is N(R$^{11}$).
Y is O or N(R$^{12}$).
In certain embodiments, Y is O.
In certain embodiments, Y is N(R$^{12}$).
L$^1$ is —(CR$^{13}$R$^{14}$)$_m$—W—(CR$^{15}$R$^{16}$)$_n$—; wherein —(CR$^{15}$R$^{16}$)$_n$— is attached to the ring containing A$^5$, A$^6$, A$^7$, and A$^8$; wherein m is 1, 2, or 3; n is 0, 1, 2, or 3; and W is a bond, O, N(R$^{17}$), —CH=CH—, —C(O)—N(R$^{18}$)—, —S(O)$_2$—N(R$^{18}$)—, —N(R$^{18}$)—C(O)—, or —N(R$^{18}$)—S(O)$_2$—.

In certain embodiments, W is a bond, O, N(R$^{17}$), —CH=CH—, or —N(R$^{18}$)—C(O)—.
In certain embodiments, W is O, N(R$^{17}$), or —CH=CH—.
In certain embodiments, W is O or N(R$^{17}$).
In certain embodiments, W is O.
In certain embodiments, W is N(R$^{17}$).
In certain embodiments, W is —CH=CH— or —N(R$^{18}$)—C(O)—.
In certain embodiments, W is —CH=CH—.
In certain embodiments, W is —N(R$^{18}$)—C(O)—.
In certain embodiments of formula (I), W is a bond. Such compounds can be represented by formula (I-a),

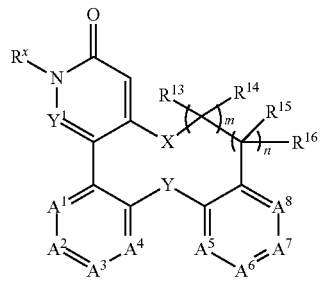

(I-a)

wherein n is 1 or 2, and R$^x$, A$^1$, A$^2$, A$^3$, A$^4$, A$^5$, A$^6$, A$^7$, A$^8$, X, Y, Y$^1$, R$^{13}$, R$^{14}$, R$^{15}$, R$^{16}$, and m, are as disclosed in the Summary and embodiments herein above and below.

In certain embodiments of formula (I) and (I-a), m is 3, and n is 2.
In certain embodiments of formula (I) and (I-a), m is 3, and n is 1.
In certain embodiments of formula (I) and (I-a), m is 2, and n is 1.
In certain embodiments of formula (I) and (I-a), m is 1, and n is 1.

In certain embodiments of formula (I) m is 1, 2, or 3, n is 1 or 2, and W is a bond.
In certain embodiments of formula (I), m is 3, n is 2, and W is a bond.
In certain embodiments of formula (I) m is 3, n is 1, and W is a bond.
In certain embodiments of formula (I) m is 2, n is 1, and W is a bond.
In certain embodiments of formula (I) m is 1, n is 1, and W is a bond.
In certain embodiments of formula (I), m is 2, n is 1, and W is O, N(R$^{17}$), —CH=CH—, —C(O)—N(R$^{18}$)—, —S(O)$_2$—N(R$^{18}$)—, —N(R$^{18}$)—C(O)—, or —N(R$^{18}$)—S(O)$_2$—. In some such embodiments, W is O, N(R$^{17}$), or —CH=CH—. In some such embodiments, W is O or N(R$^{17}$). In some such embodiments, W is O. In some such embodiments, W is N(R$^{17}$). In some such embodiments, W is —CH=CH—.

In certain embodiments of formula (I), n is 0. Such compounds can be represented by formula (I-b)

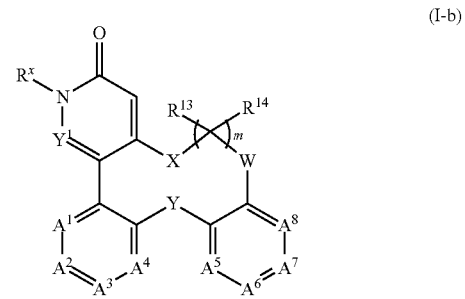

(I-b)

wherein W is O, N(R$^{17}$), —CH=CH—, —C(O)—N(R$^{18}$)—, —S(O)$_2$—N(R$^{18}$)—, —N(R$^{18}$)—C(O)—, or —N(R$^{18}$)—S(O)$_2$—; and R$^x$, A$^1$, A$^2$, A$^3$, A$^4$, A$^5$, A$^6$, A$^7$, A$^8$, X, Y, Y$^1$, W, R$^{13}$, R$^{14}$, and m have values as disclosed in the Summary and embodiments herein above and below.

In certain embodiments of formula (I-b), m is 2 or 3. In some such embodiments, W is —CH=CH— or —N(R$^{18}$)—C(O)—. In some such embodiments, W is —CH=CH—. In some such embodiments, W is —N(R$^{18}$)—C(O)—.

In certain embodiments of formula (I), m is 2 or 3, and n is 0.

In certain embodiments of formula (I), m is 2 or 3, n is 0, and W is O, N(R$^{17}$), —CH=CH—, —C(O)—N(R$^{18}$)—, —S(O)$_2$—N(R$^{18}$)—, —N(R$^{18}$)—C(O)—, or —N(R$^{18}$)—S(O)$_2$—. In some such embodiments, W is —CH=CH— or —N(R$^{18}$)—C(O)—. In some such embodiments, W is —CH=CH—. In some such embodiments, W is —N(R$^{18}$)—C(O)—.

R$^{13}$ and R$^{14}$, at each occurrence, are each independently hydrogen, halogen, —CN, C$_1$-C$_6$ haloalkyl, G$^b$, C$_1$-C$_6$ alkyl, —OR$^d$, —NR$^d$R$^e$, or —C(O)NR$^d$R$^e$; R$^{13}$ and R$^{14}$ together may be an oxo group.

In certain embodiments, R$^{13}$ and R$^{14}$, at each occurrence, are each independently hydrogen, halogen, —CN, C$_1$-C$_6$ haloalkyl, G$^b$, C$_1$-C$_6$ alkyl, —OR$^d$, —NR$^d$R$^e$, or —C(O)NR$^d$R$^e$.

In certain embodiments, R$^{13}$ and R$^{14}$, at each occurrence, are each independently hydrogen or C$_1$-C$_6$ alkyl.

In certain embodiments, R$^{13}$ and R$^{14}$ are hydrogen.
R$^{15}$ and R$^{16}$, at each occurrence, are each independently hydrogen, halogen, —CN, C$_1$-C$_6$ haloalkyl, G$^b$, C$_1$-C$_6$ alkyl, —OR$^d$, —NR$^d$R$^e$, or —C(O)NR$^d$R$^e$; R$^{15}$ and R$^{16}$ together may be an oxo group.

In certain embodiments, $R^{15}$ and $R^{16}$, at each occurrence, are each independently hydrogen, halogen, —CN, $C_1$-$C_6$ haloalkyl, $G^b$, $C_1$-$C_6$ alkyl, —$OR^d$, —$NR^dR^e$, or —C(O)$NR^dR^e$.

In certain embodiments, $R^{15}$ and $R^{16}$, at each occurrence, are each independently hydrogen or $C_1$-$C_6$ alkyl.

In certain embodiments, $R^{15}$ and $R^{16}$ are hydrogen.

$R^{17}$ is hydrogen, $C_1$-$C_6$ haloalkyl, $G^c$, —S(O)$_2R^f$, —S(O)$_2$N(R$^g$)$_2$, —S(O)$_2$N(R$^g$)C(O)R$^f$, —S(O)$_2$N(R$^g$)C(O)OR$^f$, —C(O)R$^f$, —C(O)OR$^f$, —C(O)N(R$^g$)$_2$, $C_2$-$C_6$ alkenyl, $C_2$-$C_6$ alkynyl, or $C_1$-$C_6$ alkyl; wherein the $C_2$-$C_6$ alkenyl, $C_2$-$C_6$ alkynyl, and $C_1$-$C_6$ alkyl are optionally substituted with one substituent selected from the group consisting of —CN, —OR$^a$, —S(O)$_2$R$^a$, —S(O)$_2$NR$^a$R$^b$, —C(O)R$^a$, —C(O)OR$^a$, —C(O)NR$^a$R$^b$, NR$^a$R$^b$, —N(R$^b$)S(O)$_2$R$^c$, —N(R$^b$)C(O)OR$^c$, —N(R$^b$)C(O)NR$^a$R$^b$, —N(R$^b$)C(O)R$^c$, and $G^c$.

In certain embodiments, $R^{17}$ is hydrogen, $C_1$-$C_6$ haloalkyl, $G^c$, —S(O)$_2$R$^f$, —S(O)$_2$N(R$^g$)C(O)R$^f$, —S(O)$_2$N(R$^g$)C(O)OR$^f$, —C(O)R$^f$, —C(O)OR$^f$, —C(O)N(R$^g$)$_2$, or $C_1$-$C_6$ alkyl; wherein the $C_1$-$C_6$ alkyl is optionally substituted with one $G^c$ group. In some such embodiments, $G^c$ is optionally substituted $C_3$-$C_6$ cycloalkyl. In some such embodiments, $G^c$ is unsubstituted cyclopropyl. In some such embodiments, $R^f$ and $R^g$, at each occurrence, are each independently hydrogen or $C_1$-$C_6$ alkyl.

In certain embodiments, $R^{17}$ is hydrogen or unsubstituted $C_1$-$C_6$ alkyl.

In certain embodiments, $R^{17}$ is unsubstituted $C_1$-$C_6$ alkyl.

$R^{18}$ is hydrogen, $C_1$-$C_6$ haloalkyl, $G^c$, $C_2$-$C_6$ alkenyl, $C_2$-$C_6$ alkynyl, or $C_1$-$C_6$ alkyl; wherein the $C_2$-$C_6$ alkenyl, $C_2$-$C_6$ alkynyl, and $C_1$-$C_6$ alkyl are optionally substituted with one substituent selected from the group consisting of —CN, —OR$^a$, —S(O)$_2$R$^a$, —S(O)$_2$NR$^a$R$^b$, —C(O)R$^a$, —C(O)OR$^a$, —C(O)NR$^a$R$^b$, NR$^a$R$^b$, —N(R$^b$)S(O)$_2$R$^c$, —N(R$^b$)C(O)OR$^c$, —N(R$^b$)C(O)NR$^a$R$^b$, —N(R$^b$)C(O)R$^c$, and $G^c$.

In certain embodiments, $R^{18}$ is hydrogen.

Various embodiments of substituents $R^x$, X, Y, $Y^1$, $L^1$, W, m, n, $A^1$, $A^2$, $A^3$, $A^4$, $A^5$, $A^6$, $A^7$, $A^8$, $R^1$, $R^2$, $R^3$, $R^4$, $R^5$, $R^6$, $R^7$, $R^8$, $R^{13}$, $R^{14}$, $R^{15}$, $R^{16}$, $R^{17}$, and $R^{18}$ have been discussed above. These substituents embodiments can be combined to form various embodiments of compounds of formula (I), (I-a), and (I-b). All embodiments of compounds of formula (I), (I-a), and (I-b) formed by combining the substituent embodiments discussed above are within the scope of Applicant's invention, and some illustrative embodiments of the compounds of formula (I), (I-a), and (I-b) are provided below.

In one embodiment, the invention is directed to compounds of formula (I), (I-a), and (I-b), wherein $R^x$ is methyl; $Y^1$ is N or CR$^y$ wherein R$^y$ is H; $A^1$ is N or CR$^1$, $A^2$ is N or CR$^2$, $A^3$ is N or CR$^3$, and $A^4$ is N or CR$^4$; wherein zero or one of $A^1$, $A^2$, $A^3$, and $A^4$ is N; and $A^5$ is N or CR$^5$, $A^6$ is N or CR$^6$, $A^7$ is N or CR$^7$, and $A^8$ is N or CR$^8$; wherein zero or one of $A^5$, $A^6$, $A^7$, and $A^8$ is N. In some such embodiments, $Y^1$ is N. In some such embodiments, $Y^1$ is CR$^y$ wherein R$^y$ is H.

In one embodiment, the invention is directed to compounds of formula (I), (I-a), and (I-b), wherein $R^x$ is methyl; $Y^1$ is N or CR$^y$ wherein R$^y$ is H; $R^1$, $R^3$, $R^4$, $R^5$, $R^6$, and $R^8$ are each independently hydrogen or halogen; $R^7$ is hydrogen, halogen, $C_1$-$C_6$ haloalkyl, —OR$^a$, —CN, or unsubstituted $C_1$-$C_6$ alkyl; and $R^2$ is hydrogen, —S(O)$_2$R$^c$, —C(O)OR$^a$, —S(O)$_2$NR$^a$R$^b$, NR$^a$R$^b$, —N(R$^b$)S(O)$_2$R$^c$, —N(R$^b$)C(O)NR$^a$R$^b$, —N(R$^b$)C(O)R$^c$, or $C_1$-$C_6$ alkyl wherein the $C_1$-$C_6$ alkyl is substituted with one substituent selected from the group consisting of —OR$^a$ and —S(O)$_2$R$^c$. In some such embodiments, $Y^1$ is N. In some such embodiments, $Y^1$ is CR$^y$ wherein R$^y$ is H.

In one embodiment, the invention is directed to compounds of formula (I), (I-a), and (I-b), wherein $R^x$ is methyl, $Y^1$ is N or CR$^y$ wherein R$^y$ is H; X is O, and Y is O. In some such embodiments, $Y^1$ is N. In some such embodiments, $Y^1$ is CR$^y$ wherein R$^y$ is H.

In one embodiment, the invention is directed to compounds of formula (I), (I-a), and (I-b), wherein $R^x$ is methyl; $Y^1$ is N or CR$^y$ wherein R$^y$ is H; X is O; Y is O; $A^1$ is N or CR$^1$, $A^2$ is N or CR$^2$, $A^3$ is N or CR$^3$, and $A^4$ is N or CR$^4$; wherein zero or one of $A^1$, $A^2$, $A^3$, and $A^4$ is N; and $A^5$ is N or CR$^5$, $A^6$ is N or CR$^6$, $A^7$ is N or CR$^7$, and $A^8$ is N or CR$^8$; wherein zero or one of $A^5$, $A^6$, $A^7$, and $A^8$ is N. In some such embodiments, $Y^1$ is N. In some such embodiments, $Y^1$ is CR$^y$ wherein R$^y$ is H.

In one embodiment, the invention is directed to compounds of formula (I), wherein $R^x$ is methyl, $Y^1$ is N or CR$^y$ wherein R$^y$ is H; and $L^1$ is —(CR$^{13}$R$^{14}$)$_m$—W—(CR$^{15}$R$^{16}$)$_n$—; wherein W is a bond, O, N(R$^{17}$), —CH=CH—, or —N(R$^{18}$)—C(O)—. In some such embodiments, $Y^1$ is N. In some such embodiments, $Y^1$ is CR$^y$ wherein R$^y$ is H.

In one embodiment, the invention is directed to compounds of formula (I), wherein $R^x$ is methyl, $Y^1$ is N or CR$^y$ wherein R$^y$ is H; $L^1$ is —(CR$^{13}$R$^{14}$)$_m$—W—(CR$^{15}$R$^{16}$)$_n$—; wherein m is 1, 2, or 3; n is 1 or 2; and W is a bond. In some such embodiments, $Y^1$ is N. In some such embodiments, $Y^1$ is CR$^y$ wherein R$^y$ is H.

In one embodiment, the invention is directed to compounds of formula (I), wherein $R^x$ is methyl, $Y^1$ is N or CR$^y$ wherein R$^y$ is H; $L^1$ is —(CR$^{13}$R$^{14}$)$_m$—W—(CR$^{15}$R$^{16}$)$_n$—; wherein m is 2, n is 1, and W is O, N(R$^{17}$), or —CH=CH—. In some such embodiments, $Y^1$ is N. In some such embodiments, $Y^1$ is CR$^y$ wherein R$^y$ is H.

In one embodiment, the invention is directed to compounds of formula (I), wherein $R^x$ is methyl, $Y^1$ is N or CR$^y$ wherein R$^y$ is H; $L^1$ is —(CR$^{13}$R$^{14}$)$_m$—W—(CR$^{15}$R$^{16}$)$_n$—; wherein m is 2 or 3, n is 0, and W is —CH=CH— or —N(R$^{18}$)—C(O)—. In some such embodiments, $Y^1$ is N. In some such embodiments, $Y^1$ is CR$^y$ wherein R$^y$ is H.

In one embodiment, the invention is directed to compounds of formula (I), wherein $R^x$ is methyl, $Y^1$ is N or CR$^y$ wherein R$^y$ is H; $L^1$ is —(CR$^{13}$R$^{14}$)$_m$—W—(CR$^{15}$R$^{16}$)$_n$—; wherein W is a bond, O, N(R$^{17}$), —CH=CH—, or —N(R$^{18}$)—C(O)—, X is O, and Y is 0. In some such embodiments, $A^1$ is N or CR$^1$, $A^2$ is N or CR$^2$, $A^3$ is N or CR$^3$, and $A^4$ is N or CR$^4$; wherein zero or one of $A^1$, $A^2$, $A^3$, and $A^4$ is N; and $A^5$ is N or CR$^5$, $A^6$ is N or CR$^6$, $A^7$ is N or CR$^7$, and $A^8$ is N or CR$^8$; wherein zero or one of $A^5$, $A^6$, $A^7$, and $A^8$ is N. In some such embodiments, $A^1$ is CR$^1$, $A^2$ is CR$^2$, $A^3$ is CR$^3$, and $A^4$ is CR$^4$; or $A^1$ is CR$^1$, $A^2$ is CR$^2$, $A^3$ is CR$^3$, and $A^4$ is N; and $A^5$ is CR$^5$, $A^6$ is CR$^6$, $A^7$ is CR$^7$, and $A^8$ is CR$^8$; or $A^5$ is N, $A^6$ is CR$^6$, $A^7$ is CR$^7$, and $A^8$ is CR$^8$; or $A^5$ is CR$^5$, $A^6$ is N, $A^7$ is CR$^7$, and $A^8$ is CR$^8$. In some such embodiments, $A^1$ is CR$^1$, $A^2$ is CR$^2$, $A^3$ is CR$^3$, and $A^4$ is CR$^4$; and $A^5$ is CR$^5$, $A^6$ is CR$^6$, $A^7$ is CR$^7$, and $A^8$ is CR$^8$. In some such embodiments, $A^1$ is CR$^1$, $A^2$ is CR$^2$, $A^3$ is CR$^3$, and $A^4$ is N; and $A^5$ is CR$^5$, $A^6$ is CR$^6$, $A^7$ is CR$^7$, and $A^8$ is CR$^8$.

In one embodiment, the invention is directed to compounds of formula (I), wherein $R^x$ is methyl, $Y^1$ is N or CR$^y$ wherein R$^y$ is H; $L^1$ is —(CR$^{13}$R$^{14}$)$_m$—W—(CR$^{15}$R$^{16}$)$_n$—; wherein m is 1, 2, or 3; n is 1 or 2; W is a bond, X is O, and Y is O. In some such embodiments, $A^1$ is N or CR$^1$, $A^2$ is N or CR$^2$, $A^3$ is N or CR$^3$, and $A^4$ is N or CR$^4$; wherein zero or one of $A^1$, $A^2$, $A^3$, and $A^4$ is N; and $A^5$ is N or CR$^5$, $A^6$ is N or CR$^6$, A$^7$ is N or CR$^7$, and A$^8$ is N or CR$^8$; wherein zero or one of A$^5$, A$^6$, A$^7$, and A$^8$ is N. In some such embodiments, A$^1$ is CR$^1$, A$^2$ is CR$^2$, A$^3$ is CR$^3$, and A$^4$ is CR$^4$; or A$^1$ is CR$^1$, A$^2$ is CR$^2$, A$^3$ is CR$^3$, and A$^4$ is N; and A$^5$ is CR$^5$, A$^6$ is CR$^6$, A$^7$ is CR$^7$, and A$^8$ is CR$^8$; or A$^5$ is N, A$^6$ is CR$^6$, A$^7$ is CR$^7$, and A$^8$ is CR$^8$; or A$^5$ is CR$^5$, A$^6$ is N, A$^7$ is CR$^7$, and A$^8$ is CR$^8$. In some such embodiments, A$^1$ is CR$^1$, A$^2$ is CR$^2$, A$^3$ is CR$^3$, and A$^4$ is CR$^4$; and A$^5$ is CR$^5$, A$^6$ is CR$^6$, A$^7$ is CR$^7$, and A$^8$ is CR$^8$. In some such embodiments, A$^1$ is CR$^1$, A$^2$ is CR$^2$, A$^3$ is CR$^3$, and A$^4$ is N; and A$^5$ is CR$^5$, A$^6$ is CR$^6$, A$^7$ is CR$^7$, and A$^8$ is CR$^8$.

In one embodiment, the invention is directed to compounds of formula (I), wherein R$^x$ is methyl, Y$^1$ is N or CR$^y$ wherein R$^y$ is H; L$^1$ is —(CR$^{13}$R$^{14}$)$_m$—W—(CR$^{15}$R$^{16}$)$_n$—; wherein m is 2, n is 1, W is O, N(R$^{17}$), or —CH=CH—, X is O, and Y is O. In some such embodiments, A$^1$ is N or CR$^1$, A$^2$ is N or CR$^2$, A$^3$ is N or CR$^3$, and A$^4$ is N or CR$^4$; wherein zero or one of A$^1$, A$^2$, A$^3$, and A$^4$ is N; and A$^5$ is N or CR$^5$, A$^6$ is N or CR$^6$, A$^7$ is N or CR$^7$, and A$^8$ is N or CR$^8$; wherein zero or one of A$^5$, A$^6$, A$^7$, and A$^8$ is N. In some such embodiments, A$^1$ is CR$^1$, A$^2$ is CR$^2$, A$^3$ is CR$^3$, and A$^4$ is CR$^4$; or A$^1$ is CR$^1$, A$^2$ is CR$^2$, A$^3$ is CR$^3$, and A$^4$ is N; and A$^5$ is CR$^5$, A$^6$ is CR$^6$, A$^7$ is CR$^7$, and A$^8$ is CR$^8$; or A$^5$ is N, A$^6$ is CR$^6$, A$^7$ is CR$^7$, and A$^8$ is CR$^8$; or A$^5$ is CR$^5$, A$^6$ is N, A$^7$ is CR$^7$, and A$^8$ is CR$^8$. In some such embodiments, A$^1$ is CR$^1$, A$^2$ is CR$^2$, A$^3$ is CR$^3$, and A$^4$ is CR$^4$; and A$^5$ is CR$^5$, A$^6$ is CR$^6$, A$^7$ is CR$^7$, and A$^8$ is CR$^8$. In some such embodiments, A$^1$ is CR$^1$, A$^2$ is CR$^2$, A$^3$ is CR$^3$, and A$^4$ is N; and A$^5$ is CR$^5$, A$^6$ is CR$^6$, A$^7$ is CR$^7$, and A$^8$ is CR$^8$.

In one embodiment, the invention is directed to compounds of formula (I), wherein R$^x$ is methyl, Y$^1$ is N or CR$^y$ wherein R$^y$ is H; L$^1$ is —(CR$^{13}$R$^{14}$)$_m$—W—(CR$^{15}$R$^{16}$)$_n$—; wherein m is 2 or 3, n is 0, W is —CH=CH— or —N(R$^{18}$)—C(O)—, X is O, and Y is O. In some such embodiments, A$^1$ is N or CR$^1$, A$^2$ is N or CR$^2$, A$^3$ is N or CR$^3$, and A$^4$ is N or CR$^4$; wherein zero or one of A$^1$, A$^2$, A$^3$, and A$^4$ is N; and A$^5$ is N or CR$^5$, A$^6$ is N or CR$^6$, A$^7$ is N or CR$^7$, and A$^8$ is N or CR$^8$; wherein zero or one of A$^5$, A$^6$, A$^7$, and A$^8$ is N. In some such embodiments, A$^1$ is CR$^1$, A$^2$ is CR$^2$, A$^3$ is CR$^3$, and A$^4$ is CR$^4$; or A$^1$ is CR$^1$, A$^2$ is CR$^2$, A$^3$ is CR$^3$, and A$^4$ is N; and A$^5$ is CR$^5$, A$^6$ is CR$^6$, A$^7$ is CR$^7$, and A$^8$ is CR$^8$; or A$^5$ is N, A$^6$ is CR$^6$, A$^7$ is CR$^7$, and A$^8$ is CR$^8$; or A$^5$ is CR$^5$, A$^6$ is N, A$^7$ is CR$^7$, and A$^8$ is CR$^8$. In some such embodiments, A$^1$ is CR$^1$, A$^2$ is CR$^2$, A$^3$ is CR$^3$, and A$^4$ is CR$^4$; and A$^5$ is CR$^5$, A$^6$ is CR$^6$, A$^7$ is CR$^7$, and A$^8$ is CR$^8$. In some such embodiments, A$^1$ is CR$^1$, A$^2$ is CR$^2$, A$^3$ is CR$^3$, and A$^4$ is N; and A$^5$ is CR$^5$, A$^6$ is CR$^6$, A$^7$ is CR$^7$, and A$^8$ is CR$^8$.

In one embodiment, the invention is directed to compounds of formula (I), wherein R$^x$ is methyl, Y$^1$ is N or CR$^y$ wherein R$^y$ is H; L$^1$ is —(CR$^{13}$R$^{14}$)$_m$—W—(CR$^{15}$R$^{16}$)$_n$—; wherein W is a bond, O, N(R$^{17}$), —CH=CH—, or —N(R$^{18}$)—C(O)—, X is O, Y is O; R$^1$, R$^3$, R$^4$, R$^5$, R$^6$, and R$^8$ are each independently hydrogen or halogen; R$^7$ is hydrogen, halogen, C$_1$-C$_6$ haloalkyl, —OR$^a$, —CN, or unsubstituted C$_1$-C$_6$ alkyl; and R$^2$ is hydrogen, —S(O)$_2$R$^c$, —C(O)OR$^a$, —S(O)$_2$NR$^a$R$^b$, NR$^a$R$^b$, —N(R$^b$)S(O)$_2$R$^c$, —N(R$^b$)C(O)NR$^a$R$^b$, —N(R$^b$)C(O)R$^c$, or C$_1$-C$_6$ alkyl wherein the C$_1$-C$_6$ alkyl is substituted with one substituent selected from the group consisting of —OR$^a$ and —S(O)$_2$R$^c$. In some such embodiments, Y$^1$ is N. In some such embodiments, Y$^1$ is CR$^y$ wherein R$^y$ is H.

In one embodiment, the invention is directed to compounds of formula (I), wherein R$^x$ is methyl, Y$^1$ is N or CR$^y$ wherein R$^y$ is H; L$^1$ is —(CR$^{13}$R$^{14}$)$_m$—W—(CR$^{15}$R$^{16}$)$_n$—; wherein m is 1, 2, or 3; n is 1 or 2; W is a bond, X is O, Y is O, R$^1$, R$^3$, R$^4$, R$^5$, R$^6$, and R$^8$ are each independently hydrogen or halogen; R$^7$ is hydrogen, halogen, C$_1$-C$_6$ haloalkyl, —OR$^a$, —CN, or unsubstituted C$_1$-C$_6$ alkyl; and R$^2$ is hydrogen, —S(O)$_2$R$^c$, —C(O)OR$^a$, —S(O)$_2$NR$^a$R$^b$, NR$^a$R$^b$, —N(R$^b$)S(O)$_2$R$^c$, —N(R$^b$)C(O)NR$^a$R$^b$, —N(R$^b$)C(O)R$^c$, or C$_1$-C$_6$ alkyl wherein the C$_1$-C$_6$ alkyl is substituted with one substituent selected from the group consisting of —OR$^a$ and —S(O)$_2$R$^c$. In some such embodiments, Y$^1$ is N. In some such embodiments, Y$^1$ is CR$^y$ wherein R$^y$ is H.

In one embodiment, the invention is directed to compounds of formula (I), wherein R$^x$ is methyl, Y$^1$ is N or CR$^y$ wherein R$^y$ is H; L$^1$ is —(CR$^{13}$R$^{14}$)$_m$—W—(CR$^{15}$R$^{16}$)$_n$—; wherein m is 2, n is 1, W is O, N(R$^{17}$), or —CH=CH—, X is O, Y is O, R$^1$, R$^3$, R$^4$, R$^5$, R$^6$, and R$^8$ are each independently hydrogen or halogen; R$^7$ is hydrogen, halogen, C$_1$-C$_6$ haloalkyl, —OR$^a$, —CN, or unsubstituted C$_1$-C$_6$ alkyl; and R$^2$ is hydrogen, —S(O)$_2$R$^c$, —C(O)OR$^a$, —S(O)$_2$NR$^a$R$^b$, NR$^a$R$^b$, —N(R$^b$)S(O)$_2$R$^c$, —N(R$^b$)C(O)NR$^a$R$^b$, —N(R$^b$)C(O)R$^c$, or C$_1$-C$_6$ alkyl wherein the C$_1$-C$_6$ alkyl is substituted with one substituent selected from the group consisting of —OR$^a$ and —S(O)$_2$R$^c$. In some such embodiments, Y$^1$ is N. In some such embodiments, Y$^1$ is CR$^y$ wherein R$^y$ is H.

In one embodiment, the invention is directed to compounds of formula (I), wherein R$^x$ is methyl, Y$^1$ is N or CR$^y$ wherein R$^y$ is H; L$^1$ is —(CR$^{13}$R$^{14}$)$_m$—W—(CR$^{15}$R$^{16}$)$_n$—; wherein m is 2 or 3, n is 0, W is —CH=CH— or —N(R$^{18}$)—C(O)—, X is O, Y is O, R$^1$, R$^3$, R$^4$, R$^5$, R$^6$, and R$^8$ are each independently hydrogen or halogen; R$^7$ is hydrogen, halogen, C$_1$-C$_6$ haloalkyl, —OR$^a$, —CN, or unsubstituted C$_1$-C$_6$ alkyl; and R$^2$ is hydrogen, —S(O)$_2$R$^c$, —C(O)OR$^a$, —S(O)$_2$NR$^a$R$^b$, NR$^a$R$^b$, —N(R$^b$)S(O)$_2$R$^c$, —N(R$^b$)C(O)NR$^a$R$^b$, —N(R$^b$)C(O)R$^c$, or C$_1$-C$_6$ alkyl wherein the C$_1$-C$_6$ alkyl is substituted with one substituent selected from the group consisting of —OR$^a$ and —S(O)$_2$R$^c$. In some such embodiments, Y$^1$ is N. In some such embodiments, Y$^1$ is CR$^y$ wherein R$^y$ is H.

In one embodiment, the invention is directed to compounds of formula (I-a), wherein n is 1 or 2; R$^x$ is methyl; Y$^1$ is N or CR$^y$ wherein R$^y$ is H; X is O; Y is O; and R$^2$ is hydrogen, —S(O)$_2$R$^c$, —C(O)OR$^a$, —S(O)$_2$NR$^a$R$^b$, NR$^a$R$^b$, —N(R$^b$)S(O)$_2$R$^c$, —N(R$^b$)C(O)NR$^a$R$^b$, —N(R$^b$)C(O)R$^c$, —CH$_2$—OR$^a$ or —CH$_2$—S(O)$_2$R$^c$. In some such embodiments, Y$^1$ is N. In some such embodiments, Y$^1$ is CR$^y$ wherein R$^y$ is H.

In one embodiment, the invention is directed to compounds of formula (I-a), wherein n is 1 or 2; R$^x$ is methyl; Y$^1$ is N or CR$^y$ wherein R$^y$ is H; X is O; Y is O; R$^2$ is hydrogen, —S(O)$_2$R$^c$, —C(O)OR$^a$, —S(O)$_2$NR$^a$R$^b$, NR$^a$R$^b$, —N(R$^b$)S(O)$_2$R$^c$, —N(R$^b$)C(O)NR$^a$R$^b$, —N(R$^b$)C(O)R$^c$, —CH$_2$—OR$^a$ or —CH$_2$—S(O)$_2$R$^c$; A$^1$ is CR$^1$, A$^2$ is CR$^2$, A$^3$ is CR$^3$, and A$^4$ is CR$^4$; or A$^1$ is CR$^1$, A$^2$ is CR$^2$, A$^3$ is CR$^3$, and A$^4$ is N; and A$^5$ is CR$^5$, A$^6$ is CR$^6$, A$^7$ is CR$^7$, and A$^8$ is CR$^8$; or A$^5$ is N, A$^6$ is CR$^6$, A$^7$ is CR$^7$, and A$^8$ is CR$^8$; or A$^5$ is CR$^5$, A$^6$ is N, A$^7$ is CR$^7$, and A$^8$ is CR$^8$. In some such embodiments, Y$^1$ is N. In some such embodiments, Y$^1$ is CR$^y$ wherein R$^y$ is H.

In one embodiment, the invention is directed to compounds of formula (I-a), wherein n is 1 or 2; R$^x$ is methyl; Y$^1$ is N or CR$^y$ wherein R$^y$ is H; X is O; Y is O; R$^2$ is hydrogen, —S(O)$_2$R$^c$, —C(O)OR$^a$, —S(O)$_2$NR$^a$R$^b$, NR$^a$R$^b$, —N(R$^b$)S(O)$_2$R$^c$, —N(R$^b$)C(O)NR$^a$R$^b$, —N(R$^b$)C(O)R$^c$, —CH$_2$—OR$^a$ or —CH$_2$—S(O)$_2$R$^c$; and R$^{13}$, R$^{14}$, R$^{15}$, and R$^{16}$, at each occurrence, are each independently hydrogen or C$_1$-C$_6$ alkyl. In some such embodiments, Y$^1$ is N. In some such embodiments, Y$^1$ is CR$^y$ wherein R$^y$ is H.

In one embodiment, the invention is directed to compounds of formula (I-a), wherein n is 1 or 2; R$^x$ is methyl; Y$^1$ is N or CR$^y$ wherein R$^y$ is H; X is O; Y is O; R$^1$, R$^3$, R$^4$, $R^5$, $R^6$, and $R^8$, are each independently hydrogen or halogen; $R^2$ is —S(O)$_2$R$^c$, —N(R$^b$)S(O)$_2$R$^c$, or —CH$_2$—S(O)$_2$R$^c$; and $R^7$ is hydrogen, halogen, C$_1$-C$_6$ haloalkyl, —CN, or —OR$^a$. In some such embodiments, $Y^1$ is N. In some such embodiments, $Y^1$ is CR$^y$ wherein R$^y$ is H.

In one embodiment, the invention is directed to compounds of formula (I-a), wherein m is 3; n is 2; R$^x$ is methyl; $Y^1$ is N or CR$^y$ wherein R$^y$ is H; X is O; Y is O; $R^1$, $R^3$, $R^4$, $R^5$, $R^6$, and $R^8$, are each independently hydrogen or halogen; $R^2$ is —S(O)$_2$R$^c$, —N(R$^b$)S(O)$_2$R$^c$, or —CH$_2$—S(O)$_2$R$^c$; $R^7$ is hydrogen, halogen, C$_1$-C$_6$ haloalkyl, —CN, or —OR$^a$; and $R^{13}$, $R^{14}$, $R^{15}$, and $R^{16}$, at each occurrence, are each independently hydrogen or C$_1$-C$_6$ alkyl. In some such embodiments, $Y^1$ is N. In some such embodiments, $Y^1$ is CR$^y$ wherein R$^y$ is H.

In one embodiment, the invention is directed to compounds of formula (I-a), wherein m is 3; n is 2; R$^x$ is methyl; $Y^1$ is CR$^y$ wherein R$^y$ is H; X is O; Y is O; $A^1$ is CR$^1$, $A^2$ is CR$^2$, $A^3$ is CR$^3$, and $A^4$ is CR$^4$; or $A^1$ is CR$^1$, $A^2$ is CR$^2$, $A^3$ is CR$^3$, and $A^4$ is N; $A^5$ is CR$^5$, $A^6$ is CR$^6$, $A^7$ is CR$^7$, and $A^8$ is CR$^8$; $R^1$, $R^3$, $R^4$, $R^5$, $R^6$, and $R^8$, are hydrogen; $R^7$ is halogen; $R^2$ is —S(O)$_2$R$^c$, —N(R$^b$)S(O)$_2$R$^c$, or —CH$_2$—S(O)$_2$R$^c$; $R^{13}$, $R^{14}$, $R^{15}$, and $R^{16}$ are hydrogen; R$^b$ is hydrogen; and R$^c$ is C$_1$-C$_3$ alkyl.

In one embodiment, the invention is directed to compounds of formula (I-a), wherein m is 3; n is 2; R$^x$ is methyl; $Y^1$ is N; X is O; Y is O; $A^1$ is CR$^1$, $A^2$ is CR$^2$, $A^3$ is CR$^3$, and $A^4$ is CR$^4$; $A^5$ is CR$^5$, $A^6$ is CR$^6$, $A^7$ is CR$^7$, and $A^8$ is CR$^8$; or $A^5$ is CR$^5$, $A^6$ is N, $A^7$ is CR$^7$, and $A^8$ is CR$^8$; $R^1$, $R^3$, $R^4$, $R^5$, $R^6$, and $R^8$, are each independently hydrogen or halogen; $R^7$ is hydrogen, halogen, or —CN; $R^2$ is —S(O)$_2$R$^c$, —N(R$^b$)S(O)$_2$R$^c$, or —CH$_2$—S(O)$_2$R$^c$; $R^{13}$, $R^{14}$, $R^{15}$, and $R^{16}$ are hydrogen; R$^b$ is hydrogen; and R$^c$ is C$_1$-C$_3$ alkyl.

In one embodiment, the invention is directed to compounds of formula (I-a), wherein m is 2; n is 1; R$^x$ is methyl; $Y^1$ is N or CR$^y$ wherein R$^y$ is H; X is O; Y is O; $R^1$, $R^3$, $R^4$, $R^5$, $R^6$, and $R^8$, are each independently hydrogen or halogen; $R^2$ is —S(O)$_2$R$^c$, —N(R$^b$)S(O)$_2$R$^c$, or —CH$_2$—S(O)$_2$R$^c$; $R^7$ is hydrogen, halogen, C$_1$-C$_6$ haloalkyl, —CN, or —OR$^a$; and $R^{13}$, $R^{14}$, $R^{15}$, and $R^{16}$, at each occurrence, are each independently hydrogen or C$_1$-C$_6$ alkyl. In some such embodiments, $Y^1$ is N. In some such embodiments, $Y^1$ is CR$^y$ wherein R$^y$ is H.

In one embodiment, the invention is directed to compounds of formula (I-a), wherein m is 2; n is 1; R$^x$ is methyl; $Y^1$ is CR$^y$ wherein R$^y$ is H; X is O; Y is O; $A^1$ is CR$^1$, $A^2$ is CR$^2$, $A^3$ is CR$^3$, and $A^4$ is CR$^4$; or $A^1$ is CR$^1$, $A^2$ is CR$^2$, $A^3$ is CR$^3$, and $A^4$ is N; $A^5$ is CR$^5$, $A^6$ is CR$^6$, $A^7$ is CR$^7$, and $A^8$ is CR$^8$; $R^1$, $R^3$, $R^4$, $R^5$, $R^6$, and $R^8$, are hydrogen; $R^7$ is halogen; $R^2$ is —S(O)$_2$R$^c$, —N(R$^b$)S(O)$_2$R$^c$, or —CH$_2$—S(O)$_2$R$^c$; $R^{13}$, $R^{14}$, $R^{15}$, and $R^{16}$ are hydrogen; R$^b$ is hydrogen; and R$^c$ is C$_1$-C$_3$ alkyl.

In one embodiment, the invention is directed to compounds of formula (I-a), wherein m is 2; n is 1; R$^x$ is methyl; $Y^1$ is N; X is O; Y is O; $A^1$ is CR$^1$, $A^2$ is CR$^2$, $A^3$ is CR$^3$, and $A^4$ is CR$^4$; $A^5$ is CR$^5$, $A^6$ is CR$^6$, $A^7$ is CR$^7$, and $A^8$ is CR$^8$; or $A^5$ is CR$^5$, $A^6$ is N, $A^7$ is CR$^7$, and $A^8$ is CR$^8$; $R^1$, $R^3$, $R^4$, $R^5$, $R^6$, and $R^8$, are each independently hydrogen or halogen; $R^7$ is hydrogen, halogen, or —CN; $R^2$ is —S(O)$_2$R$^c$, —N(R$^b$)S(O)$_2$R$^c$, or —CH$_2$—S(O)$_2$R$^c$; $R^{13}$, $R^{14}$, $R^{15}$, and $R^{16}$ are hydrogen; R$^b$ is hydrogen; and R$^c$ is C$_1$-C$_3$ alkyl.

In one embodiment, the invention is directed to compounds of formula (I-a), wherein m is 1; n is 1; R$^x$ is methyl; $Y^1$ is N or CR$^y$ wherein R$^y$ is H; X is O; Y is O; $R^1$, $R^3$, $R^4$, $R^5$, $R^6$, and $R^8$, are each independently hydrogen or halogen; $R^2$ is —S(O)$_2$R$^c$, —N(R$^b$)S(O)$_2$R$^c$, or —CH$_2$—S(O)$_2$R$^c$; $R^7$ is hydrogen, halogen, C$_1$-C$_6$ haloalkyl, —CN, or —OR$^a$; and $R^{13}$, $R^{14}$, $R^{15}$, and $R^{16}$, at each occurrence, are each independently hydrogen or C$_1$-C$_6$ alkyl. In some such embodiments, $Y^1$ is N. In some such embodiments, $Y^1$ is CR$^y$ wherein R$^y$ is H.

In one embodiment, the invention is directed to compounds of formula (I-a), wherein m is 1; n is 1; R$^x$ is methyl; $Y^1$ is CR$^y$ wherein R$^y$ is H; X is O; Y is O; $A^1$ is CR$^1$, $A^2$ is CR$^2$, $A^3$ is CR$^3$, and $A^4$ is CR$^4$; or $A^1$ is CR$^1$, $A^2$ is CR$^2$, $A^3$ is CR$^3$, and $A^4$ is N; $A^5$ is CR$^5$, $A^6$ is CR$^6$, $A^7$ is CR$^7$, and $A^8$ is CR$^8$; $R^1$, $R^3$, $R^4$, $R^5$, $R^6$, and $R^8$, are hydrogen; $R^7$ is halogen; $R^2$ is —S(O)$_2$R$^c$, —N(R$^b$)S(O)$_2$R$^c$, or —CH$_2$—S(O)$_2$R$^c$; $R^{13}$, $R^{14}$, $R^{15}$, and $R^{16}$ are hydrogen; R$^b$ is hydrogen; and R$^c$ is C$_1$-C$_3$ alkyl.

In one embodiment, the invention is directed to compounds of formula (I-a), wherein m is 1; n is 1; R$^x$ is methyl; $Y^1$ is N; X is O; Y is O; $A^1$ is CR$^1$, $A^2$ is CR$^2$, $A^3$ is CR$^3$, and $A^4$ is CR$^4$; $A^5$ is CR$^5$, $A^6$ is CR$^6$, $A^7$ is CR$^7$, and $A^8$ is CR$^8$; or $A^5$ is CR$^5$, $A^6$ is N, $A^7$ is CR$^7$, and $A^8$ is CR$^8$; $R^1$, $R^3$, $R^4$, $R^5$, $R^6$, and $R^8$, are each independently hydrogen or halogen; $R^7$ is hydrogen, halogen, or —CN; $R^2$ is —S(O)$_2$R$^c$, —N(R$^b$)S(O)$_2$R$^c$, or —CH$_2$—S(O)$_2$R$^c$; $R^{13}$, $R^{14}$, $R^{15}$, and $R^{16}$ are hydrogen; R$^b$ is hydrogen; and R$^c$ is C$_1$-C$_3$ alkyl.

In one embodiment, the invention is directed to compounds of formula (I-a), wherein m is 3; n is 1; R$^x$ is methyl; $Y^1$ is N or CR$^y$ wherein R$^y$ is H; X is O; Y is O; $R^1$, $R^3$, $R^4$, $R^5$, $R^6$, and $R^8$, are each independently hydrogen or halogen; $R^2$ is —S(O)$_2$R$^c$, —N(R$^b$)S(O)$_2$R$^c$, or —CH$_2$—S(O)$_2$R$^c$; $R^7$ is hydrogen, halogen, C$_1$-C$_6$ haloalkyl, —CN, or —OR$^a$; and $R^{13}$, $R^{14}$, $R^{15}$, and $R^{16}$, at each occurrence, are each independently hydrogen or C$_1$-C$_6$ alkyl. In some such embodiments, $Y^1$ is N. In some such embodiments, $Y^1$ is CR$^y$ wherein R$^y$ is H.

In one embodiment, the invention is directed to compounds of formula (I-a), wherein m is 3; n is 1; R$^x$ is methyl; $Y^1$ is CR$^y$ wherein R$^y$ is H; X is O; Y is O; $A^1$ is CR$^1$, $A^2$ is CR$^2$, $A^3$ is CR$^3$, and $A^4$ is CR$^4$; or $A^1$ is CR$^1$, $A^2$ is CR$^2$, $A^3$ is CR$^3$, and $A^4$ is N; $A^5$ is CR$^5$, $A^6$ is CR$^6$, $A^7$ is CR$^7$, and $A^8$ is CR$^8$; $R^1$, $R^3$, $R^4$, $R^5$, $R^6$, and $R^8$, are hydrogen; $R^7$ is halogen; $R^2$ is —S(O)$_2$R$^c$, —N(R$^b$)S(O)$_2$R$^c$, or —CH$_2$—S(O)$_2$R$^c$; $R^{13}$, $R^{14}$, $R^{15}$, and $R^{16}$ are hydrogen; R$^b$ is hydrogen; and R$^c$ is C$_1$-C$_3$ alkyl.

In one embodiment, the invention is directed to compounds of formula (I-a), wherein m is 3; n is 1; R$^x$ is methyl; $Y^1$ is N; X is O; Y is O; $A^1$ is CR$^1$, $A^2$ is CR$^2$, $A^3$ is CR$^3$, and $A^4$ is CR$^4$; $A^5$ is CR$^5$, $A^6$ is CR$^6$, $A^7$ is CR$^7$, and $A^8$ is CR$^8$; or $A^5$ is CR$^5$, $A^6$ is N, $A^7$ is CR$^7$, and $A^8$ is CR$^8$; $R^1$, $R^3$, $R^4$, $R^5$, $R^6$, and $R^8$, are each independently hydrogen or halogen; $R^7$ is hydrogen, halogen, or —CN; $R^2$ is —S(O)$_2$R$^c$, —N(R$^b$)S(O)$_2$R$^c$, or —CH$_2$—S(O)$_2$R$^c$; $R^{13}$, $R^{14}$, $R^{15}$, and $R^{16}$ are hydrogen; R$^b$ is hydrogen; and R$^c$ is C$_1$-C$_3$ alkyl.

In one embodiment, the invention is directed to compounds of formula (I-b), wherein R$^x$ is methyl; $Y^1$ is CR$^y$ wherein R$^y$ is H; m is 2 or 3; and W is —CH=CH— or —N(R$^{18}$)—C(O)—.

In one embodiment, the invention is directed to compounds of formula (I-b), wherein R$^x$ is methyl; $Y^1$ is CR$^y$ wherein R$^y$ is H; W is O, N(R$^{17}$), —CH=CH—, —C(O)—N(R$^{18}$)—, —S(O)$_2$—N(R$^{18}$)—, —N(R$^{18}$)—C(O)—, or —N(R$^{18}$)—S(O)$_2$—; X is O, and Y is O.

In one embodiment, the invention is directed to compounds of formula (I-b), wherein R$^x$ is methyl; $Y^1$ is CR$^y$ wherein R$^y$ is H; X is O, Y is O; m is 2 or 3; W is —CH=CH— or —N(R$^{18}$)—C(O)—; and $R^2$ is hydrogen, —S(O)$_2$R$^c$, —C(O)OR$^a$, —S(O)$_2$NR$^a$R$^b$, NR$^a$R$^b$, —N(R$^b$)S(O)$_2$R$^c$, —N(R$^b$)C(O)NR$^a$R$^b$, —N(R$^b$)C(O)R$^c$, —CH$_2$—OR$^a$, or —CH$_2$—S(O)$_2$R$^c$. In some such embodiments, R$^2$ is —S(O)$_2$R$^c$, —N(R$^b$)S(O)$_2$R$^c$, or —CH$_2$—S(O)$_2$R$^c$; R$^b$ is hydrogen; and R$^c$ is C$_1$-C$_3$ alkyl.

In one embodiment, the invention is directed to compounds of formula (I-b), wherein R$^x$ is methyl; Y$^1$ is CR$^y$ wherein R$^y$ is H; X is O, Y is O; m is 2 or 3; W is —CH=CH— or —N(R$^{18}$)—C(O)—; and R$^2$ is —S(O)$_2$R$^c$, —N(R$^b$)S(O)$_2$R$^c$, or —CH$_2$—S(O)$_2$R$^c$; R$^b$ is hydrogen; R$^c$ is C$_1$-C$_3$ alkyl; R$^{13}$, R$^{14}$, and R$^{18}$ are hydrogen; and R$^1$, R$^3$, R$^4$, R$^5$, R$^6$, R$^7$, and R$^8$, are each independently hydrogen or halogen.

Compounds of formula (I), (I-a), and (I-b) may contain one or more asymmetrically substituted atoms. Compounds of formula (I), (I-a), and (I-b) may also exist as individual stereoisomers (including enantiomers and diastereomers) and mixtures thereof. Individual stereoisomers of compounds of formula (I), (I-a), and (I-b) may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Compounds of formula (I), (I-a), and (I-b) may also include the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or heterocycle are designated as being of cis or trans configuration.

Within the present invention it is to be understood that compounds disclosed herein may exhibit the phenomenon of tautomerism and all tautomeric isomers are included in the scope of the invention.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Present compounds are named using ChemDraw Ultra Version 12.0.

Exemplary compounds of formula (I) include, but are not limited to:

16-(ethylsulfonyl)-2-methyl-7,8-dihydro-2H-dibenzo[4,5:7,8][1,6]dioxacycloundecino[3,2-c]pyridin-3(6H)-one;
3-(ethylsulfonyl)-6-methyl-10,11-dihydrodibenzo[4,5:7,8][1,6]dioxecino[3,2-c]pyridin-7(6H)-one;
10-chloro-16-(ethylsulfonyl)-2-methyl-7,8-dihydro-2H-dibenzo[4,5:7,8][1,6]dioxacycloundecino[3,2-c]pyridin-3(6H)-one;
17-(ethylsulfonyl)-2-methyl-6,7,8,9-tetrahydrodibenzo[4,5:7,8][1,6]dioxacyclododecino[3,2-c]pyridin-3(2H)-one;
N-(10-chloro-2-methyl-3-oxo-3,6,7,8-tetrahydro-2H-dibenzo[4,5:7,8][1,6]dioxacycloundecino[3,2-c]pyridin-16-yl)ethanesulfonamide;
N-(10,12-difluoro-2-methyl-3-oxo-3,6,7,8-tetrahydro-2H-dibenzo[4,5:7,8][1,6]dioxacycloundecino[3,2-c]pyridin-16-yl)ethanesulfonamide;
16-amino-10-chloro-2-methyl-7,8-dihydro-2H-dibenzo[4,5:7,8][1,6]dioxacycloundecino[3,2-c]pyridin-3(6H)-one;
17-amino-11-chloro-2-methyl-6,7,8,9-tetrahydrodibenzo[4,5:7,8][1,6]dioxacyclododecino[3,2-c]pyridin-3(2H)-one;
N-(11-chloro-2-methyl-3-oxo-2,3,6,7,8,9-hexahydrodibenzo[4,5:7,8][1,6]dioxacyclododecino[3,2-c]pyridin-17-yl)ethanesulfonamide;
1-(10-chloro-2-methyl-3-oxo-3,6,7,8-tetrahydro-2H-dibenzo[4,5:7,8][1,6]dioxacycloundecino[3,2-c]pyridin-16-yl)-3-ethylurea;
N-(10-chloro-2-methyl-3-oxo-3,6,7,8-tetrahydro-2H-dibenzo[4,5:7,8][1,6]dioxacycloundecino[3,2-c]pyridin-16-yl)acetamide;
N-(10-chloro-2-methyl-3-oxo-3,6,7,8-tetrahydro-2H-dibenzo[4,5:7,8][1,6]dioxacycloundecino[3,2-c]pyridin-16-yl)methanesulfonamide;
11-chloro-17-(ethylsulfonyl)-2-methyl-6,7,8,9-tetrahydrodibenzo[4,5:7,8][1,6]dioxacyclododecino[3,2-c]pyridin-3(2H)-one;
N-(11,13-difluoro-2-methyl-3-oxo-2,3,6,7,8,9-hexahydrodibenzo[4,5:7,8][1,6]dioxacyclododecino[3,2-c]pyridin-17-yl)ethanesulfonamide;
(E)-N-(12-chloro-2-methyl-3-oxo-3,6,7,10-tetrahydro-2H-dibenzo[4,5:7,8][1,6]dioxacyclotridecino[3,2-c]pyridin-18-yl)ethanesulfonamide;
(E)-N-(12-chloro-2-methyl-3-oxo-3,6,7,8-tetrahydro-2H-dibenzo[4,5:7,8][1,6]dioxacyclotridecino[3,2-c]pyridin-18-yl)ethanesulfonamide;
N-(11-chloro-2,6-dimethyl-3-oxo-2,3,6,7,8,9-hexahydrodibenzo[4,5:7,8][1,6]dioxacyclododecino[3,2-c]pyridin-17-yl)ethanesulfonamide;
(E)-N-(11-chloro-2-methyl-3-oxo-2,3,6,7-tetrahydrodibenzo[4,5:7,8][1,6]dioxacyclododecino[3,2-c]pyridin-17-yl)ethanesulfonamide;
N-(12-chloro-2-methyl-3-oxo-3,6,7,8,9,10-hexahydro-2H-dibenzo[4,5:7,8][1,6]dioxacyclotridecino[3,2-c]pyridin-18-yl)ethanesulfonamide;
17-(ethylsulfonyl)-11,13-difluoro-2-methyl-6,7,8,9-tetrahydrodibenzo[4,5:7,8][1,6]dioxacyclododecino[3,2-c]pyridin-3(2H)-one;
17-(cyclopropylsulfonyl)-11,13-difluoro-2-methyl-6,7,8,9-tetrahydrodibenzo[4,5:7,8][1,6]dioxacyclododecino[3,2-c]pyridin-3(2H)-one;
17-(ethylsulfonyl)-11-fluoro-2-methyl-6,7,8,9-tetrahydrodibenzo[4,5:7,8][1,6]dioxacyclododecino[3,2-c]pyridin-3(2H)-one;
17-(ethylsulfonyl)-12-fluoro-2-methyl-6,7,8,9-tetrahydrodibenzo[4,5:7,8][1,6]dioxacyclododecino[3,2-c]pyridin-3(2H)-one;
(E)-12-chloro-17-(ethylsulfonyl)-2-methyl-6,7-dihydrodibenzo[4,5:7,8][1,6]dioxacyclododecino[3,2-c]pyridin-3(2H)-one;
12-chloro-17-(ethylsulfonyl)-2-methyl-6,7,8,9-tetrahydrodibenzo[4,5:7,8][1,6]dioxacyclododecino[3,2-c]pyridin-3(2H)-one;
N-(2-methyl-3-oxo-2,3,6,7,8,9-hexahydrobenzo[4,5][1,6]dioxacyclododecino[3,2-c:7,8-c']dipyridin-17-yl)ethanesulfonamide;
11-chloro-2-methyl-6,7,8,9-tetrahydrobenzo[11,12][1,6]dioxacyclododecino[2,3-b:4,5-c']dipyridin-3(2H)-one;
17-amino-2-methyl-6,7,8,9-tetrahydrobenzo[4,5][1,6]dioxacyclododecino[3,2-c:7,8-c']dipyridin-3(2H)-one;
N-[2-methyl-3-oxo-11-(trifluoromethyl)-2,3,6,7,8,9-hexahydrodibenzo[4,5:7,8][1,6]dioxacyclododecino[3,2-c]pyridin-17-yl]ethanesulfonamide;
N-[2-methyl-3-oxo-11-(trifluoromethoxy)-2,3,6,7,8,9-hexahydrodibenzo[4,5:7,8][1,6]dioxacyclododecino[3,2-c]pyridin-17-yl]methanesulfonamide;
methyl 11-chloro-2-methyl-3-oxo-2,3,6,7,8,9-hexahydrobenzo[11,12][1,6]dioxacyclododecino[2,3-b:4,5-c']dipyridine-17-carboxylate;

17-amino-11-chloro-2-methyl-6,7,8,9-tetrahydrobenzo[11,12][1,6]dioxacyclododecino[2,3-b:4,5-c']dipyridin-3(2H)-one;
N-(11-chloro-2-methyl-3-oxo-2,3,6,7,8,9-hexahydrobenzo[11,12][1,6]dioxacyclododecino[2,3-b:4,5-c']dipyridin-17-yl)ethanesulfonamide;
11-chloro-17-(ethylsulfonyl)-2-methyl-6,7,8,9-tetrahydrobenzo[11,12][1,6]dioxacyclododecino[2,3-b:4,5-c']dipyridin-3(2H)-one;
N-(11,13-difluoro-2-methyl-3-oxo-2,3,6,7,8,9-hexahydrobenzo[11,12][1,6]dioxacyclododecino[2,3-b:4,5-c']dipyridin-17-yl)ethanesulfonamide;
11-chloro-2-methyl-17-[(methylsulfonyl)methyl]-6,7,8,9-tetrahydrodibenzo[4,5:7,8][1,6]dioxacyclododecino[3,2-c]pyridin-3(2H)-one;
N-[2-methyl-3-oxo-11-(trifluoromethoxy)-2,3,6,7,8,9-hexahydrodibenzo[4,5:7,8][1,6]dioxacyclododecino[3,2-c]pyridin-17-yl]ethanesulfonamide;
11-chloro-2-methyl-3-oxo-2,3,6,7,8,9-hexahydrobenzo[11,12][1,6]dioxacyclododecino[2,3-b:4,5-c']dipyridine-17-carboxylic acid;
11-chloro-17-(hydroxymethyl)-2-methyl-6,7,8,9-tetrahydrobenzo[11,12][1,6]dioxacyclododecino[2,3-b:4,5-c']dipyridin-3(2H)-one;
11-chloro-2-methyl-17-((methylsulfonyl)methyl)-6,7,8,9-tetrahydrobenzo[11,12][1,6]dioxacyclododecino[2,3-b:4,5-c']dipyridin-3(2H)-one;
N-(3-chloro-12-methyl-11-oxo-5,6,7,8,11,12-hexahydrobenzo[4,5][1,6]dioxacyclododecino[7,8-b:3,2-c']dipyridin-15-yl)ethanesulfonamide;
17-(ethylsulfonyl)-2-methyl-6,7,8,9-tetrahydrobenzo[4,5][1,6]dioxacyclododecino[3,2-c:7,8-c']dipyridin-3(2H)-one;
11,13-difluoro-2-methyl-17-((methylsulfonyl)methyl)-6,7,8,9-tetrahydrobenzo[11,12][1,6]dioxacyclododecino[2,3-b:4,5-c']dipyridin-3(2H)-one;
N-(12-chloro-2-methyl-3-oxo-2,3,6,7,8,9-hexahydrodibenzo[4,5:7,8][1,6]dioxacyclododecino[3,2-c]pyridin-17-yl)methanesulfonamide;
N-(11-cyano-2-methyl-3-oxo-2,3,6,7,8,9-hexahydrodibenzo[4,5:7,8][1,6]dioxacyclododecino[3,2-c]pyridin-17-yl)ethanesulfonamide;
N-(12-methyl-11-oxo-5,6,7,8,11,12-hexahydrobenzo[4,5][1,6]dioxacyclododecino[7,8-b:3,2-c']dipyridin-15-yl)ethanesulfonamide;
N-(11-cyano-2-methyl-3-oxo-2,3,6,7,8,9-hexahydrodibenzo[4,5:7,8][1,6]dioxacyclododecino[3,2-c]pyridin-17-yl)methanesulfonamide;
N-(11,12-difluoro-2-methyl-3-oxo-2,3,6,7,8,9-hexahydrodibenzo[4,5:7,8][1,6]dioxacyclododecino[3,2-c]pyridin-17-yl)ethanesulfonamide;
N-(11-fluoro-2-methyl-3-oxo-2,3,6,7,8,9-hexahydrodibenzo[4,5:7,8][1,6]dioxacyclododecino[3,2-c]pyridin-17-yl)ethanesulfonamide;
N-(11-fluoro-2-methyl-3-oxo-2,3,6,7,8,9-hexahydrodibenzo[4,5:7,8][1,6]dioxacyclododecino[3,2-c]pyridin-17-yl)methanesulfonamide;
N-(2-methyl-3-oxo-11-(trifluoromethyl)-2,3,6,7,8,9-hexahydrodibenzo[4,5:7,8][1,6]dioxacyclododecino[3,2-c]pyridin-17-yl)methanesulfonamide;
N-(12-chloro-2-methyl-3-oxo-2,3,6,7,8,9-hexahydrodibenzo[4,5:7,8][1,6]dioxacyclododecino[3,2-c]pyridin-17-yl)ethanesulfonamide;
11-chloro-17-(ethylsulfonyl)-2-methyl-6,7,8,9-tetrahydrodibenzo[4,5:7,8][1,6]dioxacyclododecino[3,2-c]pyridazin-3(2H)-one;
17-(ethylsulfonyl)-2-methyl-3-oxo-2,3,6,7,8,9-hexahydrodibenzo[4,5:7,8][1,6]dioxacyclododecino[3,2-c]pyridazine-11-carbonitrile;
N-(11-chloro-2-methyl-3-oxo-2,3,6,7,8,9-hexahydrodibenzo[4,5:7,8][1,6]dioxacyclododecino[3,2-c]pyridazin-17-yl)ethanesulfonamide;
N-(11-cyano-2-methyl-3-oxo-2,3,6,7,8,9-hexahydrodibenzo[4,5:7,8][1,6]dioxacyclododecino[3,2-c]pyridazin-17-yl)ethanesulfonamide;
17-(ethylsulfonyl)-11,13-difluoro-2-methyl-6,7,8,9-tetrahydrodibenzo[4,5:7,8][1,6]dioxacyclododecino[3,2-c]pyridazin-3(2H)-one;
N-(11,13-difluoro-2-methyl-3-oxo-2,3,6,7,8,9-hexahydrodibenzo[4,5:7,8][1,6]dioxacyclododecino[3,2-c]pyridazin-17-yl)ethanesulfonamide;
17-(ethylsulfonyl)-2-methyl-6,7,8,9-tetrahydrobenzo[4,5]pyrido[3',4':7,8][1,6]dioxacyclododecino[3,2-c]pyridazin-3(2H)-one;
17-(ethylsulfonyl)-2,13-dimethyl-6,7,8,9-tetrahydrodibenzo[4,5:7,8][1,6]dioxacyclododecino[3,2-c]pyridin-3(2H)-one;
N-(11-chloro-8-ethyl-2-methyl-3-oxo-2,3,6,7,8,9-hexahydrodibenzo[f,i]pyrido[3,4-k][1,8,4]dioxazacyclododecin-17-yl)ethanesulfonamide;
N-(8-acetyl-11-chloro-2-methyl-3-oxo-2,3,6,7,8,9-hexahydrodibenzo[f,i]pyrido[3,4-k][1,8,4]dioxazacyclododecin-17-yl)acetamide;
17-amino-11-chloro-2-methyl-7,8-dihydrodibenzo[f,i]pyrido[3,4-k][1,8,4]dioxazacyclododecine-3,9(2H,6H)-dione;
N-(11-chloro-2-methyl-3,9-dioxo-2,3,6,7,8,9-hexahydrodibenzo[f,i]pyrido[3,4-k][1,8,4]dioxazacyclododecin-17-yl)ethanesulfonamide;
N-(11-chloro-2-methyl-3-oxo-2,3,6,7-tetrahydro-9H-dibenzo[6,7:9,10][1,4,8]trioxacyclododecino[11,12-c]pyridin-17-yl)ethanesulfonamide;
N-[11-chloro-2-methyl-8-(methylsulfonyl)-3-oxo-2,3,6,7,8,9-hexahydrodibenzo[f,i]pyrido[3,4-k][1,8,4]dioxazacyclododecin-17-yl]ethanesulfonamide;
N-(8-acetyl-11-chloro-2-methyl-3-oxo-2,3,6,7,8,9-hexahydrodibenzo[f,i]pyrido[3,4-k][1,8,4]dioxazacyclododecin-17-yl)ethanesulfonamide;
ethyl 11-chloro-17-[(ethylsulfonyl)amino]-2-methyl-3-oxo-2,3,6,7-tetrahydrodibenzo[f,i]pyrido[3,4-k][1,8,4]dioxazacyclododecine-8(9H)-carboxylate;
11-chloro-N-ethyl-17-[(ethylsulfonyl)amino]-2-methyl-3-oxo-2,3,6,7-tetrahydrodibenzo[f,i]pyrido[3,4-k][1,8,4]dioxazacyclododecine-8(9H)-carboxamide;
tert-butyl 11-chloro-17-[(ethylsulfonyl)amino]-2-methyl-3-oxo-2,3,6,7-tetrahydrodibenzo[f,i]pyrido[3,4-k][1,8,4]dioxazacyclododecine-8(9H)-carboxylate;
N-(11-chloro-2-methyl-3-oxo-2,3,6,7,8,9-hexahydrodibenzo[f,i]pyrido[3,4-k][1,8,4]dioxazacyclododecin-17-yl)ethanesulfonamide;
N-[11-chloro-8-(cyclopropylmethyl)-2-methyl-3-oxo-2,3,6,7,8,9-hexahydrodibenzo[f,i]pyrido[3,4-k][1,8,4]dioxazacyclododecin-17-yl]ethanesulfonamide;
N-[11-chloro-2-methyl-3-oxo-8-(3,3,3-trifluoropropyl)-2,3,6,7,8,9-hexahydrodibenzo[f,i]pyrido[3,4-k][1,8,4]dioxazacyclododecin-17-yl]ethanesulfonamide;
N-(11-chloro-8-cyclobutyl-2-methyl-3-oxo-2,3,6,7,8,9-hexahydrodibenzo[f,i]pyrido[3,4-k][1,8,4]dioxazacyclododecin-17-yl)ethanesulfonamide;
ethyl ({11-chloro-17-[(ethylsulfonyl)amino]-2-methyl-3-oxo-2,3,6,7-tetrahydrodibenzo[f,i]pyrido[3,4-k][1,8,4]dioxazacyclododecin-8(9H)-yl}sulfonyl)carbamate;
N-({11-chloro-17-[(ethylsulfonyl)amino]-2-methyl-3-oxo-2,3,6,7-tetrahydrodibenzo[f,i]pyrido[3,4-k][1,8,4]dioxazacyclododecin-8(9H)-yl}sulfonyl)acetamide;
ethyl 11-chloro-2-methyl-3-oxo-2,3,6,7-tetrahydro-9H-dibenzo[6,7:9,10][1,4,8]trioxacyclododecino[11,12-c]pyridine-17-carboxylate; and
11-chloro-2-methyl-17-((methylsulfonyl)methyl)-6,7-dihydro-2H-dibenzo[6,7:9,10][1,4,8]trioxacyclododecino[11,12-c]pyridin-3(9H)-one.

Compounds of formula (I), (I-a), and (I-b) may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I), (I-a), and (I-b) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I), (I-a), and (I-b) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds described herein, including compounds of general formula (I), (I-a), or (I-b), and specific examples, may be prepared, for example, through the reaction routes depicted in schemes 1-6. The variables $A^1$, $A^2$, $A^3$, $A^4$, $A^5$, $A^6$, $A^7$, $A^8$, $Y^1$, $R^x$, and $R^{17}$, used in the following schemes have the meanings as set forth in the summary and detailed description sections unless otherwise noted.

Abbreviations used in the descriptions of the schemes and the specific examples have the following meanings: DMSO for dimethyl sulfoxide, $Pd(PPh_3)_4$ for tetrakis(triphenylphosphine)palladium(0), THF for tetrahydrofuran, TFA for trifluoroacetic acid, and HPLC for high performance liquid chromatography.

Compounds of general formula (I-a) wherein X and Y are O, $R^{13}$, $R^{14}$, $R^{15}$ and $R^{16}$ are hydrogen, n is 1 or 2, and m is 1, 2, or 3, may be prepared using general procedure as described in Scheme 1.

Scheme 1

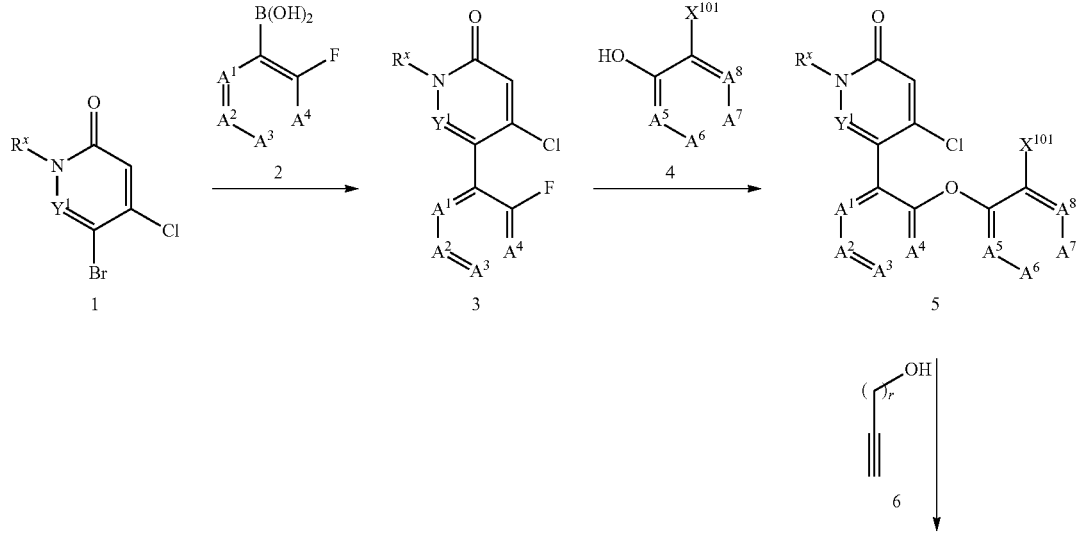

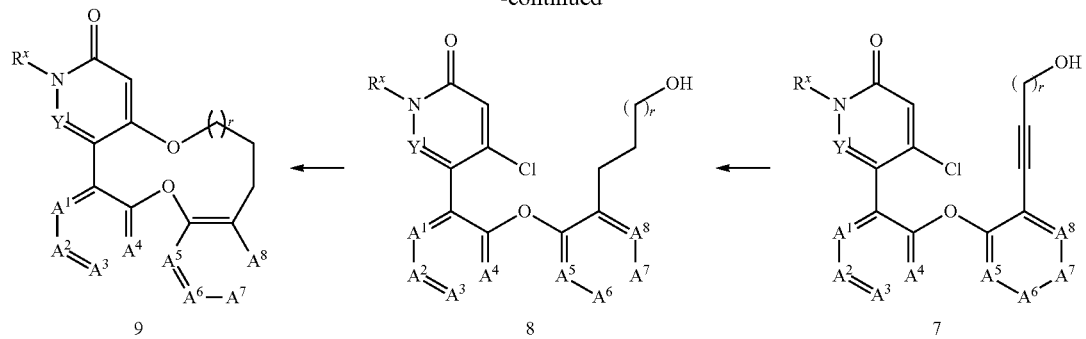

Compounds of formula (3) may be prepared by treating compounds of formula (1) with a boronic acid or derivatives thereof (e.g. boronic esters) of formula (2), under Suzuki coupling conditions (N. Miyama and A. Suzuki, Chem. Rev. 1995, 95:2457-2483, J. Organomet. Chem. 1999, 576:147-148). In general, the conversion may be facilitated by a palladium catalyst such as, but not limited to, tetrakis(triphenylphosphine)palladium(0), tris(dibenzylideneacetone)dipalladium(0), or palladium(II)acetate, an optional ligand such as, but not limited to, 2-dicyclohexylphosphino-2',4',6'-triisopropylbiphenyl, 2-dicyclohexylphosphino-2',4',6'-triisopropylbiphenyl (X-phos), or 1,1'-bis(diphenylphosphanyl) ferrocene, and a base such as, but not limited to, carbonates, acetates, or phosphates of sodium, potassium, or cesium; or cesium fluoride. The reaction is generally conducted in a suitable solvent and at temperatures ranging from about 50° C. to about 120° C. Non-limiting examples of suitable solvents include methanol, dimethoxyethane, N,N-dimethylformamide, dimethylsulfoxide, dioxane, tetrahydrofuran, and water, or a mixture thereof. Compounds of formula (5) may be prepared by treating compounds of formula (3) with compounds of formula (4) wherein $X^{101}$ is I, Br, or Cl, under basic conditions. Displacement of the fluorine atom of formula (3) with alcohols of formula (4) may be accomplished in a solvent such as, but not limited to, dimethylsulfoxide, dimethylformamide, dioxane, or tetrahydrofuran and in the presence of a base such as, but not limited to, carbonate of cesium, potassium, or sodium, and at a temperature from about 40° C. to about 120° C. Compounds of formula (7) may be prepared by treating compounds of formula (5) with alkynes of formula (6) wherein r is 1, 2, or 3, under Sonagashira Coupling conditions (R. Chincilla and C. Najera, Chem. Soc. Reviews, 2011, 40, 5084-5121). In general, the conversion may be facilitated by a palladium catalyst such as, but not limited to, bis(triphenylphosphine)palladium(II) chloride, tetrakis(triphenylphosphine)palladium(0), tris(dibenzylideneacetone)dipalladium(0), or palladium(II)acetate, along with a copper catalyst such as but not limited to copper(I) iodide or copper(I) chloride, and a base such as, but not limited to, triethylamine, carbonates, acetates, or phosphates of sodium, potassium, and cesium; or cesium fluoride. The reaction is generally conducted in a suitable solvent and at temperatures ranging from about 50° C. to about 120° C. Non-limiting examples of suitable solvents include methanol, ethanol, acetonitrile, dimethoxyethane, N,N-dimethylformamide, dimethylsulfoxide, dioxane, tetrahydrofuran, and water, or a mixture thereof. Compounds of formula (8) may be prepared by treating compounds of formula (7) with a catalyst such as, but not limited to, platinum on carbon, under hydrogen pressure, in a solvent such as, but not limited to, tetrahydrofuran. Compounds of formula (9) may be prepared by treating compounds of formula (8) with a base, such as but not limited to, sodium hydride, in a solvent such as, but not limited to, dioxane or tetrahydrofuran, at temperatures between about 25° C. and about 100° C.

Compounds of formula (I-a) wherein X and Y are O, $R^{13}$, $R^{14}$, $R^{15}$ and $R^{16}$ are hydrogen, n is 1 or 2, and m is 1, 2, or 3, may be prepared as illustrated in Scheme 2.

Scheme 2

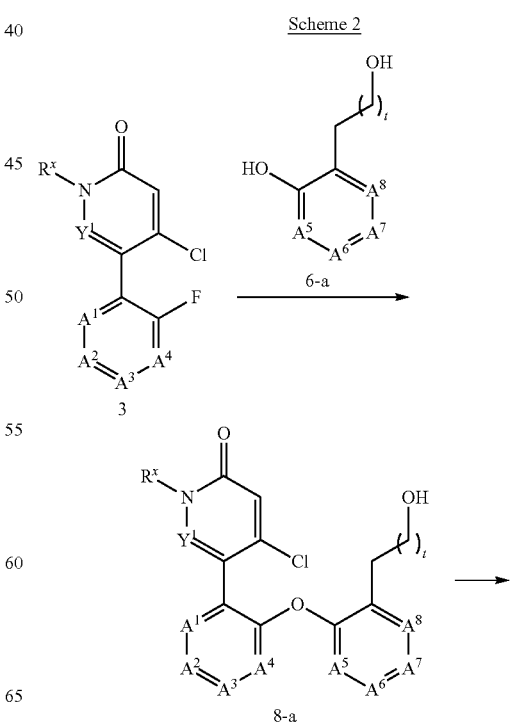

29
-continued

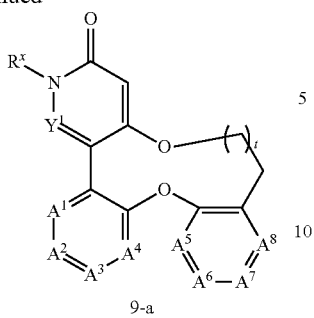
9-a

Compounds of formula (3) may be treated with alcohols of formula (6-a) wherein t is 1, 2, 3, or 4, using the conditions outlined for the transformation of (3) to (5) in Scheme 1, to provide compounds of formula (8-a). Conversion of compounds (8-a) to (9-a) may be achieved by using reaction conditions outlined in Scheme 1 for the transformation of (8) to (9).

Alternatively, compounds of formula (9) may be prepared as shown in Scheme 3.

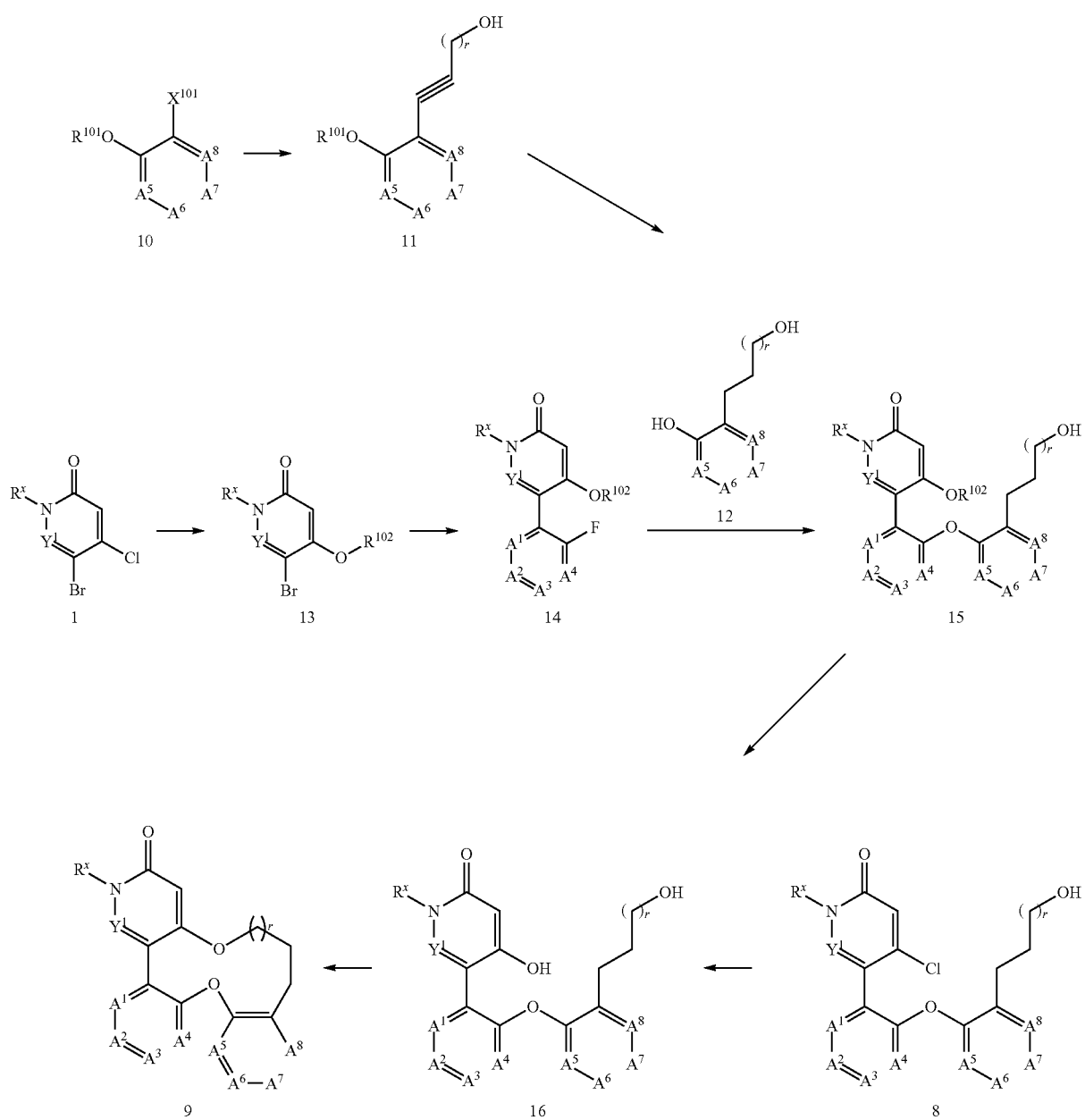

Compounds of formula (11) wherein $R^{101}$ is hydrogen, methyl, or a suitable protecting group (for example, benzyl or 2,4-dimethoxybenzyl) may be prepared by treating compounds of formula (10) wherein $X^{101}$ is I, Br, or Cl with alkynes of formula (6) under Sonagashira Coupling conditions (R. Chincilla and C. Najera, Chem. Soc. Reviews, 2011, 40, 5084-5121) as outlined in Scheme 1. Compounds (12) may be synthesized, for example, by reduction of (11) in the presence of hydrogen and a catalyst, as described in Scheme 1, followed by removal of the protecting group or the methyl group.

Removal of the benzyl protecting group may be achieved by catalytic hydrogenolysis under palladium catalysis in the presence of hydrogen. Removal of the 2,4-dimethoxy benzyl protecting group may be accomplished by reaction with an acid, such as, but not limited to, trifluoroacetic acid in a solvent such as, but not limited to, dichloromethane at temperatures such as but not limited to about 0° C. to ambient temperature.

Removal of the methyl group may be accomplished by treatment with boron tribromoborane in a solvent such as, but not limited to, dichloromethane, and at temperatures ranging from about −78° C. to ambient temperature.

Displacement of chloropyridone (1) with a suitable alcohol ($R^{102}OH$) in the presence of a base such as, but not limited to, sodium hydride or potassium t-butoxoide, in a solvent such as, but not limited to, dioxane, tetrahydrofuran, or 2-methyltetrahydrofuran, at temperatures ranging from about 0° C. to about 150° C. provides compounds of formula (13) wherein $R^{102}$ is a suitable protecting group such as, but not limited to, benzyl or 2,4-dimethoxybenzyl. Suzuki coupling of compounds (13) with a boronic acid or derivatives thereof (e.g. boronic esters) of formula (2) provides compounds of general formula (14). Displacement of the fluorine atom of general formula (14) with alcohols of formula (12) provides compounds of general formula (15). Removal of the protecting group, $R^{102}$, provides compounds (16). Compounds of formula (16) may also be prepared by hydrolysis of compounds of formula (8) in the presence of a base such as, but not limited to, aqueous sodium hydroxide or aqueous lithium hydroxide. Formation of compounds of formula (9) may be accomplished by Mitsunobu Reaction (Swamy, K. C.; Kumar, N. N.; Balaraman, E.; Kumar, K. V. (2009). "Mitsunobu and Related Reactions: Advances and Applications". *Chemical Reviews* 109 (6): 2551-2651) of compounds (16). The reaction is generally conducted in the presence of a reagent such as, but not limited to, cyanomethylenetributylphosphorane, in a solvent such as, but not limited to, dioxane, and at temperatures ranging from about 50° C. to about 100° C.

Scheme 4 outlined an alternative route for the synthesis of compounds of general formula (9).

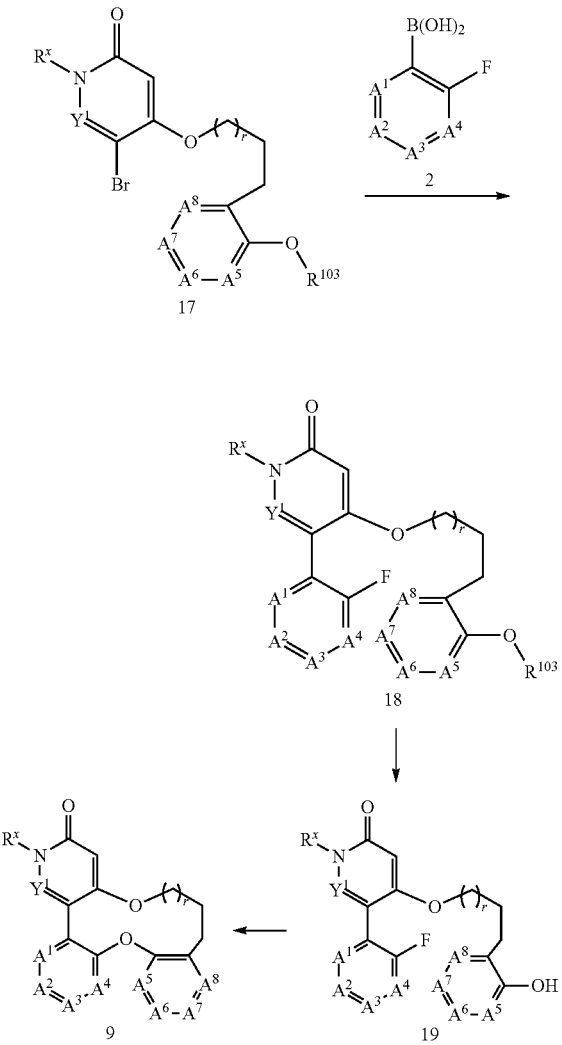

Compounds of formula (9) may also be prepared according to Scheme 4. Displacement of chloropyridone (1) with a suitable alcohol of formula (12-a) wherein $R^{103}$ is is a suitable protecting group such as, but not limited to, methyl, benzyl or 2,4-dimethoxy benzyl, provides compounds of formula (17). Suzuki coupling of compounds (17) with a boronic acid or derivatives thereof (e.g. boronic esters) of formula (2) provides compounds of formula (18). Deprotection of compounds of formula (18) provides compounds (19). Intramolecular displacement of the fluorine atom of compound (19) by reaction with a base, such as, but not limited to, cesium carbonate or potassium carbonate, in a solvent such as, but not limited to, acetonitrile or dimethylsulfoxide, or mixtures thereof, at temperatures ranging from about 50° C. to about 150° C., provides compounds of formula (9).

Compounds of general formula (I-b) wherein X and Y are O, W is —CH═CH—, $R^{13}$ and $R^{14}$ are hydrogen, and m is 2 or 3, may be prepared according to general procedure as shown in Scheme 5.

Scheme 5

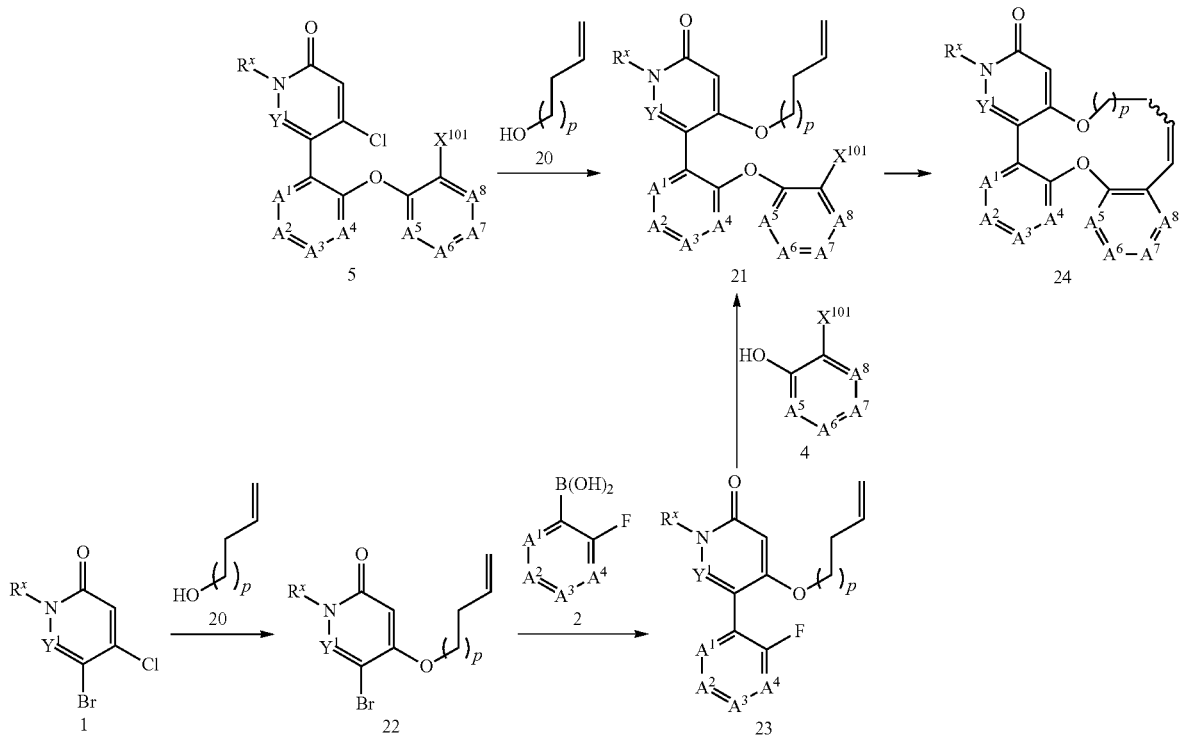

Displacement of chloropyridone (5) with a suitable alcohol of formula (20) wherein p is 1 or 2, provides compounds of formula (21). Generation of compounds of formula (21) can also be accomplished by (a) displacement of chloropyridone (1) with a suitable alcohol of formula (20) wherein p is 1 or 2, (b) Suzuki coupling reaction of compounds (22) with a boronic acid or derivatives thereof (e.g. boronic esters) of formula (2), and (c) displacement of fluorine from compounds (23) with alcohols of formula (4). Intramolecular Heck reaction of compounds (21) in the presence of a catalyst such as, but not limited to, tetrakis(triphenylphosphine) or diacetoxypalladium, and with or without a base, such as, but not limited to, triethylamine, provides compounds of formula (24). The reaction is generally conducted in a solvent such as, but not limited to, dimethylformamide or acetonitrile, and at temperatures ranging from about 50° C. to about 150° C. Reduction of compounds of formula (24) in the presence a catalyst such as, but not limited to, platinum on carbon or palladium on carbon, in a hydrogen atmosphere at pressures of 25 to 100 psi in a solvent such as but not limited to tetrahydrofuran, provides compounds of general formula (I-a) wherein X and Y are O, n is 1 or 2, m is 3, and $R^{13}$, $R^{14}$, $R^{15}$, and $R^{16}$ are hydrogen.

Compounds of general formula (I) wherein X and Y are O, $L^1$ is —$(CR^{13}R^{14})_m$—W—$(CR^{15}R^{16})_n$—, m is 2 or 3, n is 1, $R^{13}$, $R^{14}$, $R^{15}$, and $R^{16}$ are hydrogen, and W is $N(R^{17})$, may be prepared according to general procedure as shown in Scheme 6.

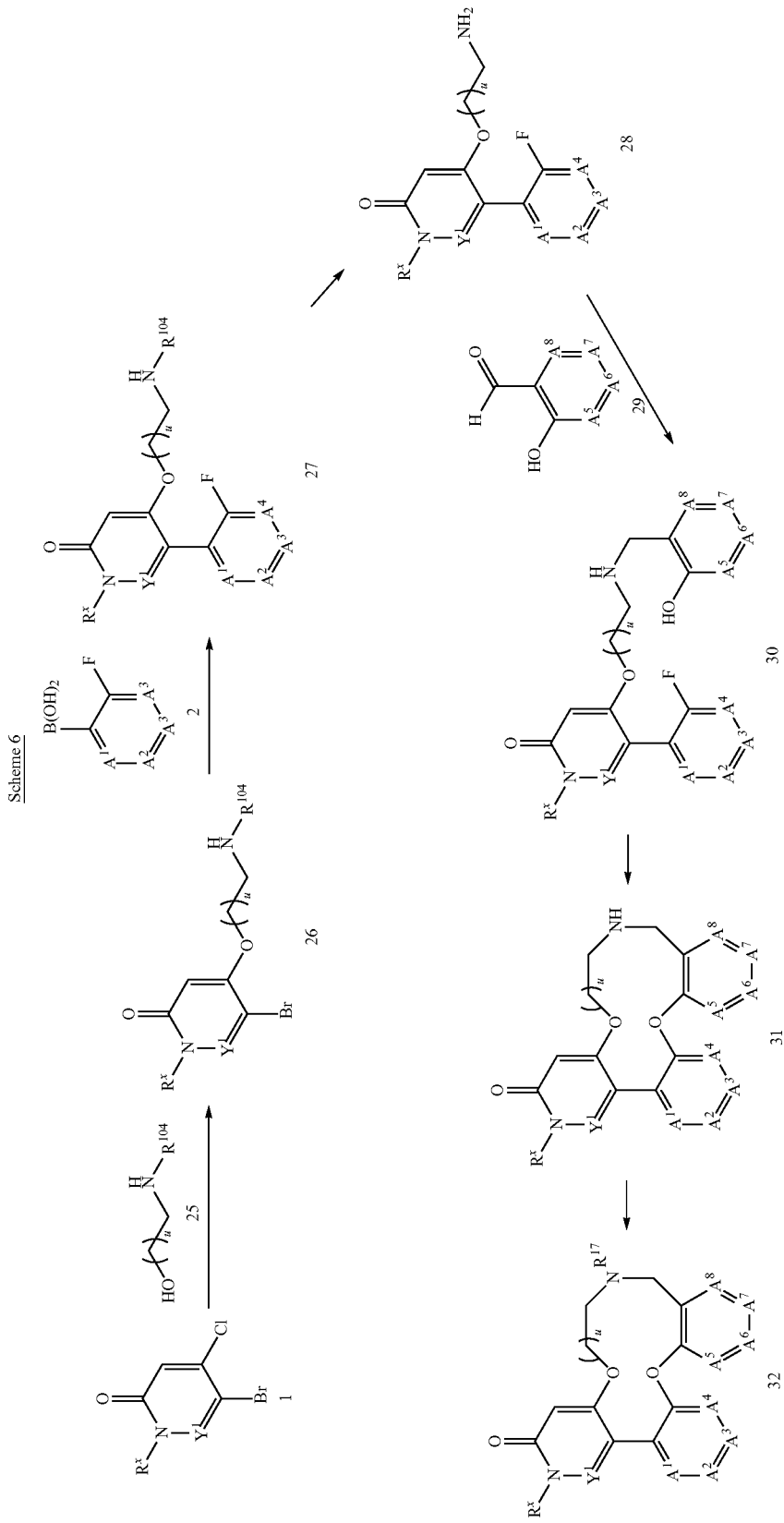

Displacement of chloropyridone (5) with a suitable alcohol of formula (25) wherein u is 1 or 2, and $R^{104}$ is a suitable nitrogen protecting group such as, but not limited to, tert-butoxycarbonyl (Boc), provides compounds of formula (26). Suzuki coupling of compounds (26) with a boronic acid or derivatives thereof (e.g. boronic esters) of formula (2) provides compounds of formula (27). Deprotection of compounds of formula (27) provides compounds of formula (28). Thus, a suitable nitrogen protecting group such as tert-butoxycarbonyl may be removed by reaction with an acid, such as but not limited to, hydrochloric acid or trifluoroacetic acid, in a solvent such as, but not limited to, dioxane at temperatures ranging from about 0° C. to ambient temperature. Compounds of formula (30) may be prepared by the reaction of amines (28) with aldehydes of formula (29) in the presence of an acid, such as but not limited to acetic acid, in a solvent such as but not limited to tetrahydrofuran, at temperatures ranging from ambient temperature to about 50° C., followed by reaction with a reducing agent, such as, but not limited to, sodium triacetoxyborohydride, or sodium cyanoborohydride, in a solvent such as, but not limited to, tetrahydrofuran at temperatures ranging from ambient temperature to about 50° C. Intramolecular displacement of fluorine of compounds (30) provides compounds of formula (31). Reaction of compounds of formula (31) with reagents such as alkyl halides, sulfonyl chlorides, acyl chlorides, alkyl chloroformates, or isocyanates, in the presence of a base such as but not limited to, triethylamine, in a solvent such as, but not limited to, tetrahydrofuran, at temperatures ranging from about 0° C. to about 50° C. provides compounds of general formula (32).

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be further processed in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Pharmaceutical Compositions

This invention also provides for pharmaceutical compositions comprising a therapeutically effective amount of a compound of formula (I), (I-a), or (I-b), or a pharmaceutically acceptable salt thereof together with a pharmaceutically acceptable carrier, diluent, or excipient therefore. The phrase "pharmaceutical composition" refers to a composition suitable for administration in medical or veterinary use.

The pharmaceutical compositions that comprise a compound of formula (I), (I-a), or (I-b), alone or or in combination with a second therapeutic agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula (I), (I-a), or (I-b). In certain embodiments, the compound of formula (I), (I-a), or (I-b) may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 μg/kg to 100 mg/kg for a typical subject.

For administration, compounds of the formula (I), (I-a), or (I-b) may be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula (I), (I-a), or (I-b) may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), (I-a), or (I-b), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds of formula (I), (I-a), or (I-b), or pharmaceutically acceptable salts thereof, and pharmaceutical compositions comprising a compound of formula (I), (I-a), or (I-b), or a pharmaceutically acceptable salt thereof, can be administered to a subject suffering from a bromodomain-mediated disorder or condition. The term "administering" refers to the method of contacting a compound with a subject. Thus, the compounds of formula (I), (I-a), or (I-b) may be administered by injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of formula (I), (I-a), or (I-b) may be administered transdermally, topically, via implantation, transdermally, topically, and via implantation. In certain embodiments, the compounds of the formula (I), (I-a), or (I-b) may be delivered orally. The compounds can also be delivered rectally, bucally, intravaginally, ocularly, andially, or by insufflation. Bromodomain-mediated disorders and conditions can be treated prophylactically, acutely, and chronically using compounds of formula (I), (I-a), or (I-b), depending on the nature of the disorder or condition. Typically, the host or subject in each of these methods is human, although other mammals can also benefit from the administration of a compound of formula (I), (I-a), or (I-b).

A "bromodomain-mediated disorder or condition" is characterized by the participation of one or more bromodomains (e.g., BRD4) in the inception, manifestation of one or more symptoms or disease markers, severity, or progression of a disorder or condition. Accordingly, compounds of formula (I), (I-a), or (I-b) may be used to treat cancer, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

Further, present compounds may be used to treat inflammatory diseases, inflammatory conditions, and autoimmune diseases, including, but not limited to: Addison's disease, acute gout, ankylosing spondylitis, asthma, atherosclerosis, Behcet's disease, bullous skin diseases, cardiac myopathy, chronic obstructive pulmonary disease (COPD), Crohn's disease, dermatitis, eczema, giant cell arteritis, glomerulonephritis, heart failure, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

Compounds of formula (I), (I-a), or (I-b), or pharmaceutically acceptable salts thereof, may be used to treat AIDS.

The compounds of formula (I), (I-a), or (I-b) may be co-administered to a subject. The term "co-administered" means the administration of two or more different therapeutic agents or treatments (e.g., radiation treatment) that are administered to a subject by combination in the same pharmaceutical composition or separate pharmaceutical compositions. Thus co-administration involves administration at the same time of a single pharmaceutical composition comprising two or more therapeutic agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, J. of Immunology 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include ABT-199, AT-101 ((−) gossypol), GENASENSE® (G3139 or oblimersen (Bcl-2-targeting antisense oligonucleotide)), IPI-194, IPI-565, N-(4-(4-(((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicate), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF 1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, present compounds may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

The compounds of the invention can also be co-administered with a therapeutically effective amount of one or more agents to treat an inflammatory disease or condition, or autoimmune disease, where examples of the agents include, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g., NIK, IKK, p38 or MAP kinase inhibitors), IL-1β converting enzyme inhibitors, T-cell signaling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (etanercept) and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. In certain embodiments, combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of the invention may be co-administered include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of formula (I), (I-a), or (I-b) may be combined include the following: TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™) inhibitors and PDE4 inhibitors. A compound of formula (I), (I-a), or (I-b) may be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrosewater; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of formula (I), (I-a), or (I-b) may be co-administered include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of formula (I), (I-a), or (I-b) may be combined with antibodies to cell surface molecules such as CD2, CD3, CD4, CD8, CD19, CD20, CD25, CD28, CD30, CD40, CD45, CD69, CD80, CD86, CD90 or their ligands. A compound of formula (I), (I-a), or (I-b) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

A compound of formula (I), (I-a), or (I-b) may also be co-administered with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of formula (I), (I-a), or (I-b) may be co-administered include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (HUMIRA®), CA2 (infliximab), CDP 571, TNFR-Ig constructs, (p75TNFRIgG (ENBREL®) and p55TNFRIgG (LENERCEPT®).

Non-limiting examples of therapeutic agents for asthma with which a compound of formula (I), (I-a), or (I-b) may be co-administered include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/dmethorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of formula (I), (I-a), or (I-b) may be co-administered include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for psoriasis with which a compound of formula (I), (I-a), or (I-b) may be co-administered include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of formula (I), (I-a), or (I-b) may be co-administered include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), and efalizumab.

Preferred examples of therapeutic agents for SLE (Lupus) with which a compound of formula (I), (I-a), or (I-b) may be co-administered include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of formula (I), (I-a), or (I-b) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of formula (I), (I-a), or (I-b) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of formula (I), (I-a), or (I-b) may be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of formula (I), (I-a), or (I-b) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (adalimumab), CA2 (infliximab), CDP 571, TNFR-Ig constructs, (p75TNFRIgG (etanercept) and p55TNFRIgG (LENERCEPT™).

The compounds of the invention can also be co-administered with a therapeutically effective amount of one or more agents used in the prevention or treatment of AIDS, where examples of the agents include, HIV reverse transcriptase inhibitors, HIV protease inhibitors, immunomodulators, and other retroviral drugs. Examples of reverse transcriptase inhibitors include, but are not limited to, abacavir, adefovir, didanosine, dipivoxil delavirdine, efavirenz, lamivudine, nevirapine, stavudine zalcitabine, and zidovudine. Examples of protease inhibitors include, but are not limited to, amprenavir, indinavir, lopinavir, nelfinavir, ritonavir, and saquinavir.

The following Examples may be used for illustrative purposes and should not be deemed to narrow the scope of the invention.

EXAMPLES

Example A-1

16-(ethylsulfonyl)-2-methyl-7,8-dihydro-2H-dibenzo[4,5:7,8][1,6]dioxacycloundecino[3,2-c]pyridin-3(6H)-one Example A-1a 5-bromo-4-chloropyridin-2-ol 5-Bromo-4-chloropyridin-2-amine (2.01 g, 9.69 mmol) was dissolved in 75% (v/v) sulfuric acid (40.2 mL, 566 mmol) and then chilled in an ice bath. A solution of sodium nitrite (2.21 g, 32.0 mmol) in water (20.1 mL) was added dropwise. The reaction mixture was stirred for 3 hours at ice/water bath temperature. The mixture was concentrated under reduced pressure and aqueous ammonia (15 mL) was added dropwise. The resulting white precipitate was collected via vacuum filtration and the filter cake washed with cold water (100 mL) and then dried in a vacuum oven for 24 hours to give 1.94 g (95%) of the title compound.

Example A-1b 5-bromo-4-chloro-1-methylpyridin-2(1H)-one

A 1 L round bottom flask with stirbar was charged with Example A-1a (27.45 g, 132 mmol), cesium carbonate (51.53 g, 158 mmol) and dimethylformamide (325 mL). Methyl iodide (10 mL, 160 mmol) was added dropwise to the suspension and the mixture stirred at ambient temperature for 1 hour. The mixture was poured into a separatory funnel containing 1:1 saturated aqueous sodium chloride:water (1000 mL) and extracted with ethyl acetate (1000 mL). The organics were washed with saturated aqueous sodium chloride, dried (anhydrous magnesium sulfate), filtered, concentrated, then triturated with 100 mL of 10% ethyl acetate/heptanes. The solids were collected and vacuum dried to provide 20.76 g of product. The filtrate was evaporated and the residue purified by flash chromatography (silica gel, 0-100% ethyl acetate/heptanes) to provide a further 1.06 g of product. Total: 21.82 g (74.5%).

Example A-1c (3-bromo-4-fluorophenyl)(ethyl)sulfane

A mixture of 3-bromo-4-fluorobenzenethiol (3.89 g, 18.8 mmol) and 5.0 M sodium hydroxide (3.95 mL, 19.7 mmol) in methanol (50 mL) was stirred at 0° C. for 10 minutes. To this solution was added iodoethane (1.80 mL, 22.5 mmol). The reaction mixture was stirred at ambient temperature for 6 hours. The solvent was evaporated under reduced pressure, and the residue was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated to provide the title compound (4.35 g, 98% yield).

Example A-1d 2-bromo-4-(ethylsulfonyl)-1-fluorobenzene

Example A-1c (4.4 g, 18.7 mmol) in dichloromethane (300 mL) was treated with 3-chloroperbenzoic acid (10.2 g, 41.2 mmol). The reaction mixture was stirred at ambient temperature for 6 hours. The solvent was evaporated under reduced pressure, and the residue was taken up into ethyl acetate and was washed with saturated aqueous $NaHCO_3$ solution (150 mL). The aqueous layer was extracted with additional ethyl acetate three times. The combined organic layers were washed with saturated aqueous sodium chloride, dried over anhydrous magnesium sulfate, filtered, and concentrated. The residue was purified by flash chromatography (silica gel, 15% ethyl acetate in hexane) to afford the title compound (4.4 g, 88% yield).

Example A-1e 2-(5-(ethylsulfonyl)-2-fluorophenyl)-4,4,5,5-tetramethyl-1,3,2-dioxaborolane 4,4,4',4',5,5,5',5'-Octamethyl-2,2'-bi(1,3,2-dioxaborolane) (13.31 g, 52.4 mmol), Example A-1d (10 g, 37.4 mmol), potassium acetate (7.35 g, 74.9 mmol), and $PdCl_2$(dppf) (0.822 g, 1.12 mmol) were combined in dioxane (100 mL) and DMSO (3 mL), sparged with nitrogen gas for 30 minutes, and heated at 90° C. under nitrogen for 16 hours. The reaction mixture was partitioned between ethyl acetate and water and filtered through a plug of Celite to remove elemental palladium. The aqueous layer was extracted with additional ethyl acetate twice. The combined organic layers were washed with saturated aqueous sodium chloride, dried over anhydrous sodium sulfate, treated with mercaptopropyl silica gel for 15 minutes, filtered and concentrated. The crude product was recrystallized from heptane/ethyl acetate (4:1) to afford the title compound (8.0 g, 63% yield).

Example A-1f 4-chloro-5-(5-(ethylsulfonyl)-2-fluorophenyl)-1-methylpyridin-2(1H)-one A mixture of Example A-1b (1.112 g, 5 mmol), Example A-1e (1.571 g, 5 mmol), 1,3,5,7-tetramethyl-6-phenyl-2,4,8-trioxa-6-phosphaadamantane (0.171 g, 0.585 mmol), tris(dibenzylideneacetone)dipalladium (0) (0.137 g, 0.150 mmol), and potassium phosphate (2.65 g, 12.50 mmol) in dioxane (16 mL) and water (4 mL) was degassed and back-filled with nitrogen several times. The reaction mixture was heated at 60° C. for 16 hours. The reaction mixture was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The residue was purified by flash column chromatography on silica gel, eluting with 60% ethyl acetate in hexanes to give the title compound (0.72 g, 44% yield).

Example A-1g 4-chloro-5-(5-(ethylsulfonyl)-2-(2-iodophenoxy)phenyl)-1-methylpyridin-2(1H)-one A mixture of Example A-1f (0.46 g, 1.395 mmol), 2-iodophenol (0.307 g, 1.395 mmol), and cesium carbonate (0.454 g, 1.395 mmol) in dimethyl sulfoxide (10 mL) was heated at 100° C. overnight. After cooling to ambient temperature the reaction mixture was partitioned between water and ethyl acetate. The aqueous layer was separated and extracted with additional ethyl acetate twice. The combined organic layers were washed with saturated aqueous sodium chloride, dried over anhydrous magnesium sulfate, filtered, and concentrated. The residue was purified by flash chromatography on silica gel, eluting 1:1 ethyl acetate/hexanes to give the title compound (0.46 g, 62% yield).

Example A-1h 4-chloro-5-{5-(ethylsulfonyl)-2-[2-(3-hydroxyprop-1-yn-1-yl)phenoxy]phenyl}-1-methylpyridin-2(1H)-one A mixture of Example A-1g (0.1 g, 0.189 mmol), prop-2-yn-1-ol (0.021 g, 0.378 mmol), copper(I) iodide (7.19 mg, 0.038 mmol), triethylamine (0.540 mL, 3.78 mmol), and bis(triphenylphosphine)palladium(II) chloride (0.013 g, 0.019 mmol) in dimethylformamide (2 mL) was heated at 80° C. for 2 hours. After cooling to ambient temperature the reaction mixture was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by flash chromatography on silica gel, eluting 2:1 ethyl acetate/hexanes to give the title compound (0.055 g, 0.120 mmol, 63.6% yield).

Example A-1i 4-chloro-5-(5-(ethylsulfonyl)-2-(2-(3-hydroxypropyl)phenoxy)phenyl)-1-methylpyridin-2(1H)-one Example A-1h (0.03 g, 0.066 mmol) and tetrahydrofuran (10 mL) were added to 5% Pt/C (wet, 18 mg, 0.039 mmol) in a 50 mL pressure bottle and stirred at 50 psi in a $H_2$ atmosphere until all of the starting material was consumed. The mixture was filtered through a nylon membrane and concentrated. The residue was purified by reverse phase Preparative HPLC (C18, 10-70% acetonitrile in water (0.1% TFA)) to give the title compound (0.018 g, 0.039 mmol, 60% yield).

Example A-1j 16-(ethylsulfonyl)-2-methyl-7,8-dihydro-2H-dibenzo[4,5:7,8][1,6]dioxacycloundecino[3,2-c]pyridin-3(6H)-one A mixture of Example A-1i (0.018 g, 0.039 mmol) and 60% sodium hydride (4.7 mg, 0.107 mmol) in dioxane (3 mL) was heated at 85° C. overnight. After cooling to ambient temperature the reaction mixture was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by reverse phase Preparative HPLC (C18, 10-70% acetonitrile/water (0.1% TFA)) to give the title compound (0.008 g, 0.019 mmol, 48% yield). $^1$H NMR (500 MHz, DMSO-$d_6$) δ 7.84-7.85 (m, 2H), 7.76 (dd, J=8.7, 1.98 Hz, 1H), 7.43 (d, J=7.02 Hz, 1H), 7.27-7.37 (m, 2H), 7.11 (d, J=7.63 Hz, 1H), 6.63 (d, J=8.54 Hz, 1H), 6.14 (s, 1H), 4.38-4.40 (m, 1H), 3.56-3.61 (m, 2H), 3.44 (s, 3H), 3.30 (q, J=7.32 Hz, 2H), 2.57-2.63 (m, 1H), 2.10-2.14 (m, 1H), 1.61-1.66 (M, 1H), 1.14 (t, J=7.32 Hz, 3H). MS (ESI+) m/z 426.1 (M+H)$^-$.

Example A-2

3-(ethylsulfonyl)-6-methyl-10,11-dihydrodibenzo[4,5:7,8][1,6]dioxecino[3,2-c]pyridin-7(6H)-one Example A-2a 4-chloro-5-(5-(ethylsulfonyl)-2-(2-(2-hydroxyethyl)phenoxy)phenyl)-1-methylpyridin-2(1H)-one Example A-2a was prepared according to the procedure used for the preparation of Example A-1g, substituting 2-(2-hydroxyethyl)phenol for 2-iodophenol, to provide the title compound.

Example A-2b 3-(ethylsulfonyl)-6-methyl-10,11-dihydrodibenzo[4,5:7,8][1,6]dioxecino[3,2-c]pyridin-7(6H)-one Example A-2b was prepared according to the procedure used for the preparation of Example A-1j, substituting Example A-2b for Example A-1i, to provide the title compound. $^1$H NMR (500 MHz, DMSO-$d_6$) δ 7.84-7.85 (m, 2H), 7.76 (dd, J=8.7, 1.98 Hz, 1H), 7.43 (d, J=7.02 Hz, 1H), 7.27-7.37 (m, 2H), 7.11 (d, J=7.63 Hz, 1H), 6.63 (d, J=8.54 Hz, 1H), 6.14 (s, 1H), 4.38-4.40 (m, 1H), 3.56-3.61 (m, 2H), 3.44 (s, 3H), 3.30 (q, J=7.32 Hz, 2H), 2.57-2.63 (m, 1H), 2.10-2.14 (m, 1H), 1.61-1.66 (M, 1H), 1.14 (t, J=7.32 Hz, 3H). MS (ESI+) m/z 426.1 (M+H)+.

Example A-3

10-chloro-16-(ethylsulfonyl)-2-methyl-7,8-dihydro-2H-dibenzo[4,5:7,8][1,6]dioxacycloundecino[3,2-c]pyridin-3(6H)-one

Example A-3a 4-chloro-5-(2-(4-chloro-2-iodophenoxy)-5-(ethylsulfonyl)phenyl)-1-methylpyridin-2(1H)-one A mixture of A-1f (0.5 g, 1.516 mmol), 4-chloro-2-iodophenol (0.386 g, 1.516 mmol), and cesium carbonate (0.494 g, 1.516 mmol) in DMSO (10 mL) was heated at 100° C. overnight. After cooling to ambient temperature the reaction mixture was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The residue was purified by Preparative HPLC (C18, 10-70% acetonitrile/water (0.1% TFA)) to afford title compound (0.055 g, 0.097 mmol, 6.43% yield).

Example A-3b 4-chloro-5-(2-(4-chloro-2-(3-hydroxyprop-1-yn-1-yl)phenoxy)-5-(ethylsulfonyl)phenyl)-1-methylpyridin-2(1H)-one Example A-3b was prepared according to the procedure used for the preparation of Example A-1h, substituting Example A-3a for Example A-1g, to provide the title compound.

Example A-3c 4-chloro-5-(2-(4-chloro-2-(3-hydroxypropyl)phenoxy)-5-(ethylsulfonyl)phenyl)-1-methylpyridin-2(1H)-one Example A-3c was prepared according to the procedure used for the preparation of Example A-1i, substituting Example A-3b for Example A-1h, to provide the title compound.

Example A-3d 10-chloro-16-(ethylsulfonyl)-2-methyl-7,8-dihydro-2H-dibenzo[4,5:7,8][1,6]dioxacycloundecino[3,2-c]pyridin-3(6H)-one Example A-3d was prepared according to the procedure used for the preparation of Example A-1j, substituting Example A-3c for Example A-1i, to provide the title compound. $^1$H NMR (500 MHz, DMSO-$d_6$) δ 7.48 (s, 2H), 7.75 (d, J=7.93 Hz, 1H), 7.54 (s, 1H), 7.39 (d, J=8.54 Hz, 1H), 7.15 (d, J=8.54 Hz, 1H), 6.68 (d, J=8.55 Hz, 1H), 6.12 (s, 1H), 4.37 (m, 1H), 3.44 (s, 3H), 3.30 (q, J=7.32 Hz, 2H), 2.07-2.13 (m, 1H), 2.10-2.141.61-1.66 (m, 1H), 1.13 (t, J=6.87 Hz, 3H). MS (DCI+) m/z 460.0 (M+H)+.

Example A-4

17-(ethylsulfonyl)-2-methyl-6,7,8,9-tetrahydrodibenzo[4,5:7,8][1,6]dioxacyclododecino[3,2-c]pyridin-3(2H)-one

Example A-4a 4-chloro-5-(5-(ethylsulfonyl)-2-(2-(4-hydroxybut-1-yn-1-yl)phenoxy)phenyl)-1-methylpyridin-2(1H)-one Example A-4a was prepared according to the procedure used for the preparation of Example A-1h, substituting but-3-yn-1-ol for prop-2-yn-1-ol, to provide the title compound.

Example A-4b 4-chloro-5-(5-(ethylsulfonyl)-2-(2-(4-hydroxybutyl)phenoxy)phenyl)-1-methylpyridin-2(1H)-one Example A-4b was prepared according to the procedure used for the preparation of Example A-1i, substituting Example A-4a for Example A-1h, to provide the title compound.

Example A-4c 17-(ethylsulfonyl)-2-methyl-6,7,8,9-tetrahydrodibenzo[4,5:7,8][1,6]dioxacyclododecino[3,2-c]pyridin-3(2H)-one Example A-4c was prepared according to the procedure used for the preparation of Example A-1j, substituting Example A-4b for Example A-1i, to provide the title compound. $^1$H NMR (500 MHz, DMSO-$d_6$) δ 7.74-7.48 (m, 3H), 7.40 (dd, J=7.32, 1.53 Hz, 1H), 7.31-7.35 (m, 1H), 7.23-7.26 (m, 1H), 7.11 (d, J=7.02 Hz, 1H), 6.70 (d, J=8.55 Hz, 1H), 5.91 (s, 1H), 4.09-4.16 (m, 2H), 3.43 (s, 3H), 3.28 (q, J=7.32 Hz, 2H), 2.40-2.55 (m, 2H), 1.7 (m, 3H), 1.38-1.48 (m, 1H), 1.14 (t, J=7.32 Hz, 3H). MS (ESI+) m/z 440.2 (M+H)+.

Example A-5

N-(10-chloro-2-methyl-3-oxo-3,6,7,8-tetrahydro-2H-dibenzo[4,5:7,8][1,6]dioxacycloundecino[3,2-c]pyridin-16-yl)ethanesulfonamide

Example A-5a 4-chloro-5-(2-fluoro-5-nitrophenyl)-1-methylpyridin-2(1H)-one

A mixture of A-1b (2.23 g, 10 mmol), (2-fluoro-5-nitrophenyl)boronic acid (2.40 g, 13.0 mmol), tris(dibenzylideneacetone)dipalladium(0) (0.458 g, 0.50 mmol), tri-tert-butylphosphonium tetrafluoroborate (0.290 g, 1.00 mmol), and cesium fluoride (4.56 g, 30 mmol) in tetrahydrofuran (40 mL) was subjected to vacuum and nitrogen gas cycle several times. The reaction mixture was heated at 45° C. overnight. After cooling to ambient temperature, the reaction mixture was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated under reduced pressure. The residue was purified by flash chromatography (silica gel, 4:6 acetone/heptanes) to give the title compound (2.2 g, 79% yield)

Example A-5b 4-chloro-5-(2-(4-chloro-2-iodophenoxy)-5-nitrophenyl)-1-methylpyridin-2(1H)-one A mixture of Example A-5a (2.83 g, 10 mmol), 4-chloro-2-iodophenol (3.46 g, 13.60 mmol), and cesium carbonate (4.43 g, 13.60 mmol) in DMSO (40 mL) was heated at 70° C. for 2 hours. After cooling to ambient temperature the reaction mixture was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by flash column chromatography on silica gel, eluting with 1:1 ethyl acetate/heptanes to afford the title compound (3.85 g, 7.45 mmol, 74.5% yield).

Example A-5c 4-chloro-5-(2-(4-chloro-2-(3-hydroxyprop-1-yn-1-yl)phenoxy)-5-nitrophenyl)-1-methylpyridin-2(1H)-one Example A-5c was prepared according to the procedure used for the preparation of Example A-1h, substituting Example A-5b for Example A-1g, to provide the title compound.

Example A-5d 5-(5-amino-2-(4-chloro-2-(3-hydroxypropyl)phenoxy)phenyl)-4-chloro-1-methylpyridin-2(1H)-one Example A-5d was prepared according to the procedure used for the preparation of Example A-1i, substituting Example A-5c for Example A-1h, to provide the title compound.

Example A-5e 16-amino-10-chloro-2-methyl-7,8-dihydro-2H-dibenzo[4,5:7,8][1,6]dioxacycloundecino[3,2-c]pyridin-3(6H)-one Example A-5d (0.21 g, 0.501 mmol) in dimethylformamide (15 mL) was treated with 60% sodium hydride (0.120 g, 3.01 mmol). The reaction mixture was heated at 85° C. for 4 hours. After cooling to ambient temperature, the reaction mixture was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The residue was purified by flash column chromatography on silica gel, eluting with 8:1 ethyl acetate/heptanes to afford the title compound (0.080 g, 0.209 mmol, 41.7% yield).

Example A-5f

N-(10-chloro-2-methyl-3-oxo-3,6,7,8-tetrahydro-2H-dibenzo[4,5:7,8][1,6]dioxacycloundecino[3,2-c]pyridin-16-yl)ethanesulfonamide A mixture of Example A-5e (0.080 g, 0.209 mmol), ethanesulfonyl chloride (0.067 g, 0.522 mmol), and triethylamine (0.106 g, 1.045 mmol) in dichloromethane (5 mL) was stirred at ambient temperature for 2 hours. The solvent was evaporated under reduced pressure, and the residue was treated with dioxane (3 mL) and aqueous sodium hydroxide (2.0 N, 2 mL). The reaction mixture was heated at 90° C. for 2 hours. After cooling to ambient temperature, the reaction mixture was partitioned between 0.5 N HCl and ethyl acetate. The aqueous layer was extracted with additional ethyl acetate three times. The combined organic layers were washed with saturated aqueous sodium chloride, dried over anhydrous magnesium sulfate, filtered, and concentrated. The residue was purified by Preparative HPLC (C18, 10-70% acetonitrile/0.1% TFA in water) to afford the title compound (0.069 g, 0.145 mmol, 69.5% yield). $^1$H NMR (500 MHz, DMSO-$d_6$) δ 9.62 (s, 1H), 7.67 (s, 1H), 7.46 (d, J=2.75 Hz, 1H), 7.31 (dd, J=8.54, 2.75 Hz, 1H), 7.17 (d, J=2.75 Hz, 1H), 7.08 (dd, J=8.7, 2.59 Hz, 1H), 7.04 (d, J=8.54 Hz, 1H), 6.45 (d, J=8.85 Hz, 1H), 6.07 (s, 1H), 4.29-4.35 (m, 1H), 3.41 (s, 3H), 3.05-3.11 (m, 2H), 2.66 (m, 1H), 2.46 (m, 1H), 2.07 (m, 1H), 1.67 (m, 1H), 1.2 (t, J=7.32 Hz, 3H). MS (ESI+) m/z 475.1 (M+H)$^+$.

Example A-6

N-(10,12-difluoro-2-methyl-3-oxo-3,6,7,8-tetrahydro-2H-dibenzo[4,5:7,8][1,6]dioxacycloundecino[3,2-c]pyridin-16-yl)ethanesulfonamide Example A-6a 4-chloro-5-(2-(2,4-difluoro-6-iodophenoxy)-5-nitrophenyl)-1-methylpyridin-2(1H)-one Example A-6a was prepared according to the procedure used for the preparation of Example A-5b, substituting 2,4-difluoro-6-iodophenol for 4-chloro-2-iodophenol, to provide the title compound.

Example A-6b 4-chloro-5-(2-(2,4-difluoro-6-(3-hydroxyprop-1-yn-1-yl)phenoxy)-5-nitrophenyl)-1-methylpyridin-2(1H)-one Example A-6b was prepared according to the procedure used for the preparation of Example A-1h, substituting Example A-6a for Example A-1g, to provide the title compound.

Example A-6c 5-(5-amino-2-(2,4-difluoro-6-(3-hydroxypropyl)phenoxy)phenyl)-4-chloro-1-methylpyridin-2(1H)-one Example A-6c was prepared according to the procedure used for the preparation of Example A-1i, substituting Example A-6b for Example A-1h, to provide the title compound.

Example A-6d 16-amino-10,12-difluoro-2-methyl-7,8-dihydro-2H-dibenzo[4,5:7,8][1,6]dioxacycloundecino[3,2-c]pyridin-3(6H)-one Example A-6d was prepared according to the procedure used for the preparation of Example A-5e, substituting Example A-6c for Example A-5d, to provide the title compound.

Example A-6e

N-(10,12-difluoro-2-methyl-3-oxo-3,6,7,8-tetrahydro-2H-dibenzo[4,5:7,8][1,6]dioxacycloundecino[3,2-c]pyridin-16-yl)ethanesulfonamide Example A-6e was prepared according to the procedure used for the preparation of Example A-5f, substituting Example A-6d for Example A-5e, to provide the title compound. $^1$H NMR (500 MHz, DMSO-$d_6$) δ 9.66 (s, 1H), 7.74 (s, 1H), 7.30-7.35 (m, 1H), 7.15-7.18 (m, 2H), 7.09 (dd, J=8.85, 2.75 Hz, 1H), 6.48 (d, J=8.85 Hz, 1H), 6.13 (s, 1H), 4.34-4.37 (m, 1H), 3.62-3.68 (m, 1H), 3.43 (s, 3H), 3.06-3.13 (m, 2H), 2.63-2.70 (m, 1H), 2.47-2.53 (m, 1H), 2.08-2.12 (m, 1H), 1.65-1.67 (m, 1H), 1.22 (t, J=7.32 Hz, 3H). MS (ESI+) m/z 477.1 (M+H)$^+$.

Example A-7

16-amino-10-chloro-2-methyl-7,8-dihydro-2H-dibenzo[4,5:7,8][1,6]dioxacycloundecino[3,2-c]pyridin-3(6H)-one The title compound was prepared as described in Example A-5e. The crude product was further purified by reverse phase Preparative HPLC (C18, 10-70% acetonitrile/water (0.1% TFA)) to provide the analytically pure title compound in TFA salt. $^1$H NMR (500 MHz, DMSO-$d_6$) δ 7.64 (s, 1H), 7.48 (d, J=2.75 Hz, 1H), 7.33 (dd, J=8.54, 2.44 Hz, 1H), 7.08 (d, J=2.14 Hz, 1H), 7.04 (d, J=8.54 Hz, 1H), 7.00 (dd, J=8.54, 2.44 Hz, 1H), 6.48 (d, J=8.85 Hz, 1H), 6.08 (s, 1H), 4.32 (m, 1H), 3.41 (s, 3H), 2.67 (m, 1H), 2.47 (m, 1H), 2.07 (m, 1H), 1.67 (m, 1H). MS (ESI+) m/z 383.2 (M+H)$^+$.

Example A-8

17-amino-11-chloro-2-methyl-6,7,8,9-tetrahydrodibenzo[4,5:7,8][1,6]dioxacyclododecino[3,2-c]pyridin-3(2H)-one

Example A-8a 4-chloro-5-(2-(4-chloro-2-(4-hydroxybut-1-yn-1-yl)phenoxy)-5-nitrophenyl)-1-methylpyridin-2(1H)-one Example A-8a was prepared according to the procedure used for the preparation of Example A-1h, substituting but-3-yn-1-ol for prop-2-yn-1-ol, and Example A-5b for Example A-1g, respectively, to provide the title compound.

Example A-8b 5-(5-amino-2-(4-chloro-2-(4-hydroxybutyl)phenoxy)phenyl)-4-chloro-1-methylpyridin-2(1H)-one Example A-8b was prepared according to the procedure used for the preparation of Example A-1i, substituting Example A-8a for Example A-1h, to provide the title compound.

Example A-8c 17-amino-11-chloro-2-methyl-6,7,8,9-tetrahydrodibenzo[4,5:7,8][1,6]dioxacyclododecino[3,2-c]pyridin-3(2H)-one Example A-8c was prepared according to the procedure used for the preparation of Example A-5e, substituting Example A-8b for Example A-5d, to provide the crude product. The crude product was further purified by reverse phase Preparative HPLC (C18, 10-70% acetonitrile/water (0.1% TFA)) to provide the title compound as a TFA salt. $^1$H NMR (500 MHz, DMSO-$d_6$) δ 7.65 (s, 1H), 7.47 (d, J=2.44 Hz, 1H), 7.34 (dd, J=8.54, 2.75 Hz, 1H), 7.10 (d, J=8.54 Hz, 1H), 7.04-7.06 (m, 2H), 6.52 (d, J=8.85 Hz, 1H), 5.89 (s, 1H), 4.09-4.13 (m, 2H), 3.41 (s, 3H), 2.41-2.54 (m, 2H), 1.68 (br s, 3H), 1.35-1.37 (m, 1H). MS (ESI+) m/z 397.2 (M+H)$^+$.

Example A-9

N-(11-chloro-2-methyl-3-oxo-2,3,6,7,8,9-hexahydrodibenzo[4,5:7,8][1,6]dioxacyclododecino[3,2-c]pyridin-17-yl)ethanesulfonamide Example A-9 was prepared according to the procedure used for the preparation of Example A-5f, substituting Example A-8c for Example A-5e, to provide the title compound. $^1$H NMR (500 MHz, DMSO-$d_6$) δ 9.60 (s, 1H), 7.67 (s, 1H), 7.45 (d, J=2.75 Hz, 1H), 7.32 (dd, J=8.54, 2.75 Hz, 1H), 7.06-7.10 (m, 3H), 6.47 (d, J=8.85 Hz, 1H), 5.87 (s, 1H), 4.10 (t, J=4.43 Hz, 2H), 3.41 (s, 3H), 3.04-3.11 (m, 2H), 2.42-2.50 (m, 2H), 1.67-1.70 (m, 3H), 1.34-1.36 (m, 1H), 1.22 (t, J=7.32 Hz, 3H). MS (ESI+) m/z 489.1 (M+H)$^+$.

Example A-10

1-(10-chloro-2-methyl-3-oxo-3,6,7,8-tetrahydro-2H-dibenzo[4,5:7,8][1,6]dioxacycloundecino[3,2-c]pyridin-16-yl)-3-ethylurea A mixture of Example A-7 (0.015 g, 0.039 mmol), isocyanatoethane (8.35 mg, 0.118 mmol), and triethylamine (0.024 g, 0.235 mmol) in dichloromethane (2 mL) was stirred at 45° C. overnight. The solvent was evaporated under reduced pressure, and the residue was purified by reverse phase Preparative HPLC (C18, 10-70% acetonitrile/water (0.1% TFA)) to give the title compound (0.012 g, 0.026 mmol, 67.5% yield). $^1$H NMR (500 MHz, DMSO-$d_6$) δ 8.33 (s, 1H), 7.64 (s, 1H), 7.44 (d, J=2.75 Hz, 1H), 7.42 (d, J=2.75 Hz, 1H), 7.29 (dd, J=8.54, 2.75 Hz, 1H), 7.15 (dd, J=8.85, 2.75 Hz, 1H), 7.00 (d, J=8.54 Hz, 1H), 6.36 (d, J=8.85 Hz, 1H), 6.14 (br s, 2H), 4.32 (br s, 1H), 3.62 (m, 1H), 3.40 (s, 3H), 3.08-3.11 (m, 2H), 2.72 (m, 1H), 2.45 (m, 1H), 2.07 (m, 1H), 1.68 (m, 1H), 1.04 (t, J=7.17 Hz, 3H). MS (ESI+) m/z 454.2 (M+H)$^+$.

Example A-11

N-(10-chloro-2-methyl-3-oxo-3,6,7,8-tetrahydro-2H-dibenzo[4,5:7,8][1,6]dioxacycloundecino[3,2-c]pyridin-16-yl)acetamide A mixture of Example A-7 (0.015 g, 0.039 mmol), acetyl chloride (6.15 mg, 0.078 mmol), and triethylamine (0.024 g, 0.235 mmol) in dichloromethane (2 mL) was stirred at ambient temperature for 2 hours. The solvent was evaporated under reduced pressure, and the residue was purified by reverse phase Preparative HPLC (C18, 10-70% acetonitrile/water (0.1% TFA)) to give the title compound (0.013 g, 0.031 mmol, 78% yield). $^1$H NMR (500 MHz, DMSO-d$_6$) δ 9.90 (s, 1H), 7.66 (s, 1H), 7.60 (d, J=2.75 Hz, 1H), 7.45 (d, J=2.75 Hz, 1H), 7.35 (dd, J=8.85, 2.75 Hz, 1H), 7.30 (dd, J=8.54, 2.75 Hz, 1H), 7.03 (d, J=8.54 Hz, 1H), 6.42 (d, J=8.55 Hz, 1H), 6.06 (br s, 2H), 4.32 (br s, 1H), 3.62 (m, 1H), 3.40 (s, 3H), 2.69 (m, 1H), 2.45 (m, 1H), 2.02-2.07 (m, 4H), 1.67 (m, 1H). MS (ESI+) m/z 425.2 (M+H)$^+$.

Example A-12

N-(10-chloro-2-methyl-3-oxo-3,6,7,8-tetrahydro-2H-dibenzo[4,5:7,8][1,6]dioxacycloundecino[3,2-c]pyridin-16-yl)methanesulfonamide Example A-12 was prepared according to the procedure used for the preparation of Example A-5f, substituting Example A-7 for Example A-5e, and methanesulfonyl chloride for ethanesulfonyl chloride, respectively, to provide the title compound. $^1$H NMR (500 MHz, DMSO-d$_6$) δ 9.56 (s, 1H), 7.69 (s, 1H), 7.60 (d, J=2.75 Hz, 1H), 7.32 (dd, J=8.54, 2.75 Hz, 1H), 7.17 (d, J=2.75 Hz, 1H), 7.09 (dd, J=8.54, 2.75 Hz, 1H), 7.04 (d, J=8.54 Hz, 1H), 6.47 (d, J=8.55 Hz, 1H), 6.07 (s, 1H), 4.31-4.35 (m, 1H), 3.41 (s, 3H), 2.98 (s, 3H), 2.64-2.69 (m, 1H), 2.43-2.48 (m, 1H), 2.03-2.07 (m, 1H), 1.64-1.70 (m, 1H). MS (ESI+) m/z 461.1 (M+H)$^+$.

Example A-13

11-chloro-17-(ethylsulfonyl)-2-methyl-6,7,8,9-tetrahydrodibenzo[4,5:7,8][1,6]dioxacyclododecino[3,2-c]pyridin-3(2H)-one

Example A-13a 4-chloro-5-(2-(4-chloro-2-(4-hydroxybut-1-yn-1-yl)phenoxy)-5-(ethylsulfonyl)phenyl)-1-methylpyridin-2(1H)-one Example A-13a was prepared according to the procedure used for the preparation of Example A-1h, substituting but-3-yn-1-ol for prop-2-yn-1-ol, and Example A-3a for Example A-1g, respectively, to provide the title compound.

Example A-13b 4-chloro-5-(2-(4-chloro-2-(4-hydroxybutyl)phenoxy)-5-(ethylsulfonyl)phenyl)-1-methylpyridin-2(1H)-one Example A-13b was prepared according to the procedure used for the preparation of Example A-1i, substituting Example A-13a for Example A-1h, to provide the title compound.

Example A-13c 11-chloro-17-(ethylsulfonyl)-2-methyl-6,7,8,9-tetrahydrodibenzo[4,5:7,8][1,6]dioxacyclododecino[3,2-c]pyridin-3(2H)-one Example A-13c was prepared according to the procedure used for the preparation of Example A-1j, substituting Example A-13b for Example A-1i, to provide the title compound. $^1$H NMR (500 MHz, DMSO-d$_6$) δ 7.75-7.79 (m, 3H), 7.51 (d, J=2.75 Hz, 1H), 7.38 (dd, J=8.54, 2.75 Hz, 1H), 7.17 (d, J=8.54 Hz, 1H), 6.74 (d, J=8.54 Hz, 1H), 5.91 (s, 1H), 4.07-4.16 (m, 1H), 3.43 (s, 3H), 3.30 (q, J=7.32 Hz, 2H), 2.42-2.54 (m, 2H), 2.43-2.48 (m, 1H), 1.69 (m, 3H), 1.36-1.38 (m, 1H), 1.14 (t, J=7.32 Hz, 3H). MS (ESI+) m/z 474.1 (M+H)$^+$.

Example A-14

N-(11,13-difluoro-2-methyl-3-oxo-2,3,6,7,8,9-hexahydrodibenzo[4,5:7,8][1,6]dioxacyclododecino[3,2-c]pyridin-17-yl)ethanesulfonamide

Example A-14a 4-chloro-5-(2-(2,4-difluoro-6-(4-hydroxybut-1-yn-1-yl)phenoxy)-5-nitrophenyl)-1-methylpyridin-2(1H)-one Example A-14a was prepared according to the procedure used for the preparation of Example A-1h, substituting but-3-yn-1-ol for prop-2-yn-1-ol, and Example A-6a for Example A-1g, respectively, to provide the title compound.

Example A-14b 5-(5-amino-2-(2,4-difluoro-6-(4-hydroxybutyl)phenoxy)phenyl)-4-chloro-1-methylpyridin-2(1H)-one Example A-14b was prepared according to the procedure used for the preparation of Example A-1i, substituting Example A-14a for Example A-1h, to provide the title compound.

Example A-14c 17-amino-11,13-difluoro-2-methyl-6,7,8,9-tetrahydrodibenzo[4,5:7,8][1,6]dioxacyclododecino[3,2-c]pyridin-3(2H)-one Example A-14c was prepared according to the procedure used for the preparation of Example A-5e, substituting Example A-14b for Example A-5d, to provide the title compound.

Example A-14d

N-(11,13-difluoro-2-methyl-3-oxo-2,3,6,7,8,9-hexahydrodibenzo[4,5:7,8][1,6]dioxacyclododecino[3,2-c]pyridin-17-yl)ethanesulfonamide Example A-14d was prepared according to the procedure used for the preparation of Example A-5f, substituting Example A-14c for Example A-5e, to provide the title compound. $^1$H NMR (500 MHz, DMSO-d$_6$) δ 9.64 (s, 1H), 7.74 (s, 1H), 7.28-7.32 (m, 1H), 7.14 (d, J=8.85 Hz, 1H), 7.10 (dd, J=8.85, 2.75 Hz, 1H), 7.06 (d, J=2.75 Hz, 1H), 6.43

(dd, J=8.85, 2.75 Hz, 1H), 5.89 (s, 1H), 4.11 (m, 2H), 3.41 (s, 3H), 3.05-3.13 (m, 2H), 2.45-2.56 (m, 2H), (m, 1H), 1.65-1.70 (m, 3H), 1.35-1.39 (m, 1H), 1.22 (t, J=7.32 Hz, 3H). MS (ESI+) m/z 491.1 (M+H)$^+$.

Example A-15

(E)-N-(12-chloro-2-methyl-3-oxo-3,6,7,10-tetra-hydro-2H-dibenzo[4,5:7,8][1,6]dioxacyclotridecino[3,2-c]pyridin-18-yl)ethanesulfonamide

Example A-15a 5-(5-amino-2-(4-chloro-2-iodophenoxy)phenyl)-4-chloro-1-methylpyridin-2(1H)-one A mixture of Example A-5b (0.8 g, 1.547 mmol), iron powder (0.432 g, 7.74 mmol), and ammonium hydrochloride (0.166 g, 3.09 mmol) in tetrahydrofuran (5 mL), water (1 mL) and ethanol (5 mL) was heated at 90° C. for 2 hours. The reaction mixture was cooled to ambient temperature and filtered through Celite. The filter cake was rinsed with ethyl acetate several times. The resulting combined filtrate was then poured into water. The organic layer was separated, and the aqueous layer was extracted with ethyl acetate several times. The combined organic layers were washed with saturated aqueous sodium chloride, dried over anhydrous magnesium sulfate, filtered, and concentrated. The residue was purified by flash chromatography on silica gel, eluting with 9:1 ethyl acetate/heptanes to give the title compound (0.74 g, 1.519 mmol, 98% yield).

Example A-15b 5-(5-amino-2-(4-chloro-2-iodophenoxy)phenyl)-1-methyl-4-(pent-4-en-1-yloxy)pyridin-2(1H)-one A mixture of Example A-15a (0.11 g, 0.190 mmol), pent-4-en-1-ol (0.049 g, 0.570 mmol), and 60% sodium hydride (0.046 g, 1.139 mmol) in dioxane (3 mL) was heated at 95° C. overnight. After cooling to ambient temperature the reaction mixture was partitioned between water and ethyl acetate. The aqueous layer was extracted with additional ethyl acetate several times. The combined organic layers were washed with saturated aqueous sodium chloride, dried over anhydrous magnesium sulfate, filtered, and concentrated. The residue was purified by flash chromatography on silica gel, eluting with 2% methanol in ethyl acetate to afford the title compound (0.09 g, 0.143 mmol, 75% yield).

Example A-15c

N-(4-(4-chloro-2-iodophenoxy)-3-(1-methyl-6-oxo-4-(pent-4-en-1-yloxy)-1,6-dihydropyridin-3-yl)phenyl)ethanesulfonamide Example A-15c was prepared according to the procedure used for the preparation of Example A-5f, substituting Example A-15b for Example A-5e, to provide the title compound.

Example A-15d (E)-N-(12-chloro-2-methyl-3-oxo-3,6,7,10-tetra-hydro-2H-dibenzo[4,5:7,8][1,6]dioxacyclotridecino[3,2-c]pyridin-18-yl)ethanesulfonamide A mixture of Example A-15c (0.062 g, 0.099 mmol), triethylamine (0.050 g, 0.493 mmol), and tetrakis(triphenylphosphine)palladium(0) (0.046 g, 0.039 mmol) in dimethylformamide (9 mL) was degassed and back-filled with nitrogen several times. The reaction mixture was heated at 100° C. overnight. After cooling to ambient temperature the reaction mixture was partitioned between water and ethyl acetate. The aqueous layer was extracted with additional ethyl acetate several times. The combined organic layers were washed with saturated aqueous sodium chloride, dried over anhydrous magnesium sulfate, filtered, and concentrated. The residue was purified by flash column chromatography on silica gel, eluting with 2% methanol in ethyl acetate to afford the crude product. This material was further purified by reverse phase Prep HPLC (C18, 10-70% acetonitrile/water (0.1% TFA)) to give the title compound (0.013 g, 0.026 mmol, 26.3% yield). $^1$H NMR (500 MHz, DMSO-d$_6$) δ 9.86 (s, 1H), 7.49 (s, 1H), 7.24-7.26 (m, 2H), 7.03-7.06 (m, 2H), 6.98 (d, J=8.76 Hz, 1H), 6.20 (d, J=8.76 Hz, 1H), 5.80 (s, 1H), 5.50 (m, 1H), 5.09 (m, 1H), 4.27 (m, 1H), 4.10 (m, 1H), 3.24 (s, 3H), 3.10-3.16 (m, 2H), 2.63 (m, 1H), 2.20 (m, 1H), 1.22-1.26 (m, 3H). MS (APCI+) m/z 501.1 (M+H)$^+$.

Example A-16

(E)-N-(12-chloro-2-methyl-3-oxo-3,6,7,8-tetra-hydro-2H-dibenzo[4,5:7,8][1,6]dioxacyclotridecino[3,2-c]pyridin-18-yl)ethanesulfonamide The title compound was isolated as a second product in the preparation of Example A-15d, and eluted as the fraction in the reverse phase preparative HPLC purification (C18, 10-70% acetonitrile/water (0.1% TFA)). $^1$H NMR (500 MHz, DMSO-d$_6$) δ 9.60 (s, 1H), 7.62 (s, 1H), 7.40 (d, J=2.75 Hz, 1H), 7.28 (dd, J=8.54, 2.75 Hz, 1H), 7.12 (dd, J=8.7, 2.9 Hz, 1H), 7.04 (d, J=2.75 Hz, 1H), 7.00 (d, J=8.85 Hz, 1H), 6.52 (d, J=8.85 Hz, 1H), 6.23-6.27 (m, 1H), 6.06-6.16 (m, 1H), 5.82 (s, 1H), 4.07-4.07 (m, 1H), 3.91-3.96 (m, 1H), 3.36 (s, 3H), 3.05-3.11 (m, 2H), 2.36-2.40 (m, 1H), 2.25-2.27 (m, 1H), 1.91-1.95 (m, 1H), 1.67-1.69 (m, 1H), 1.20-1.23 (m, 3H). MS (ESI$^+$) m/z 501.2 (M+H)$^+$.

Example A-17

N-(11-chloro-2,6-dimethyl-3-oxo-2,3,6,7,8,9-hexa-hydrodibenzo[4,5:7,8][1,6]dioxacyclododecino[3,2-c]pyridin-17-yl)ethanesulfonamide

Example A-17a

N-(3-(4-chloro-1-methyl-6-oxo-1,6-dihydropyridin-3-yl)-4-(4-chloro-2-iodophenoxy)phenyl)ethanesulfonamide Example A-17a was prepared according to the procedure used for the preparation of Example A-5f, substituting Example A-15a for Example A-5e, to provide the title compound.

Example A-17b

N-(3-(4-chloro-1-methyl-6-oxo-1,6-dihydropyridin-3-yl)-4-(4-chloro-2-(4-hydroxypent-1-yn-1-yl)phenoxy)phenyl)ethanesulfonamide Example A-17b was prepared according to the procedure used for the preparation of Example A-1h, substituting pent-4-yn-2-ol for prop-2-yn-1-ol, and Example A-17a for Example A-1g, respectively, to provide the title compound.

Example A-17c

N-(3-(4-chloro-1-methyl-6-oxo-1,6-dihydropyridin-3-yl)-4-(4-chloro-2-(4-hydroxypentyl)phenoxy)phenyl)ethanesulfonamide Example A-17c was prepared according to the procedure used for the preparation of Example A-1i, substituting Example A-17b for Example A-1h, to provide the title compound.

Example A-17d

N-(11-chloro-2,6-dimethyl-3-oxo-2,3,6,7,8,9-hexahydrodibenzo[4,5:7,8][1,6]dioxacyclododecino[3,2-c]pyridin-17-yl)ethanesulfonamide Example A-17d was prepared according to the procedure used for the preparation of Example A-5e, substituting Example A-17c for Example A-5d, to provide the title compound. $^1$H NMR (500 MHz, DMSO-$d_6$) δ 9.60 (s, 1H), 7.63 (s, 1H), 7.43 (d, J=2.75 Hz, 1H), 7.32 (dd, J=8.54, 2.44 Hz, 1H), 7.07-7.10 (m, 3H), 6.43 (d, J=8.85 Hz, 1H), 5.88 (s, 1H), 4.51-4.54 (m, 1H), 3.40 (s, 3H), 3.07-3.13 (m, 2H), 2.33-2.45 (m, 2H), 1.73-1.78 (m, 1H), 1.62-1.67 (m, 1H), 1.40-1.46 (m, 1H), 1.21-1.27 (m, 7H). MS (ESI+) m/z 503.1 (M+H)$^+$.

Example A-18

(E)-N-(11-chloro-2-methyl-3-oxo-2,3,6,7-tetrahydrodibenzo[4,5:7,8][1,6]dioxacyclododecino[3,2-c]pyridin-17-yl)ethanesulfonamide Example A-18a N-(3-(4-(but-3-en-1-yloxy)-1-methyl-6-oxo-1,6-dihydropyridin-3-yl)-4-(4-chloro-2-iodophenoxy)phenyl)ethanesulfonamide Example A-18a was prepared according to the procedure used for the preparation of Example A-15b, substituting Example A-17a for Example A-15a, and but-3-en-1-ol for pent-4-en-1-ol, respectively, to provide the title compound.

Example A-18b (E)-N-(11-chloro-2-methyl-3-oxo-2,3,6,7-tetrahydrodibenzo[4,5:7,8][1,6]dioxacyclododecino[3,2-c]pyridin-17-yl)ethanesulfonamide Example A-18b was prepared according to the procedure used for the preparation of Example A-15d, substituting Example A-18a for Example A-15c, to provide the title compound. $^1$H NMR (500 MHz, DMSO-$d_6$) δ 9.62 (s, 1H), 7.63 (s, 1H), 7.38-7.41 (m, 1H), 7.10 (dd, J=8.85, 2.75 Hz, 1H), 7.01 (d, J=2.75, Hz, 1H), 6.50 (d, J=8.85 Hz, 1H), 6.03 (d, J=16.48 Hz, 1H), 5.88 (s, 1H), 5.66-5.73 (m, 1H), 4.16-4.20 (m, 1H), 3.89-3.95 (m, 1H), 3.41 (s, 3H), 3.05 (q, J=7.32 Hz, 2H), 2.31-2.48 (m, 2H), 1.19 (t, J=7.32 Hz, 3H). MS (ESI+) m/z 487.1 (M+H)$^+$.

Example A-19

N-(12-chloro-2-methyl-3-oxo-3,6,7,8,9,10-hexahydro-2H-dibenzo[4,5:7,8][1,6]dioxacyclotridecino[3,2-c]pyridin-18-yl)ethanesulfonamide Example A-19 was prepared according to the procedure used for the preparation of Example A-1i, substituting Example A-16 for Example A-1h, to provide the title compound. $^1$H NMR (500 MHz, DMSO-$d_6$) δ 9.59 (s, 1H), 7.64 (s, 1H), 7.45 (d, J=2.75 Hz, 1H), 7.28 (dd, J=8.54, 2.75 Hz, 1H), 7.07 (dd, J=8.7, 2.75, Hz, 1H), 7.03 (d, J=2.44 hz, 1H), 6.91 (d, J=8.54 Hz, 1H), 6.29 (d, J=8.85 Hz, 1H), 5.88 (s, 1H), 4.05 (t, J=9.46 Hz, 1H), 3.92-3.95 (m, 1H), 3.40 (s, 3H), 3.07 (q, J=7.32 Hz, 2H), 2.62-2.67 (m, 1H), 2.17-2.22 (m, 1H), 1.77-1.80 (m, 1H), 1.65-1.67 (m, 1H), 1.44-1.53 (m, 4H), 1.21 (t, J=7.48 Hz, 3H). MS (ESI+) m/z 503.1 (M+H)$^+$.

Example A-20

17-(ethylsulfonyl)-11,13-difluoro-2-methyl-6,7,8,9-tetrahydrodibenzo[4,5:7,8][1,6]dioxacyclododecino[3,2-c]pyridin-3(2H)-one Example A-20a 4-(2-(benzyloxy)-3,5-difluorophenyl)but-3-yn-1-ol 2-(Benzyloxy)-1-bromo-3,5-difluorobenzene (1.8 g, 6.02 mmol), but-3-yn-1-ol (0.844 g, 12.0 mmol) and triethylamine (8.39 mL, 60.2 mmol) were combined in dimethylformamide (15.04 mL) and degassed for 10 minutes and left under nitrogen. Copper (I) iodide (0.115 g, 0.602 mmol) and tetrakis(triphenylphosphine)palladium(0) (0.348 g, 0.301 mmol) were added together and degassed for another 5 minutes. The reaction mixture was heated at 80° C. for three hours. The reaction mixture was cooled to ambient temperature and poured into water and dichloromethane. The layers were separated and the aqueous layer was extracted twice with dichloromethane. The combined organics were dried (anhydrous magnesium sulfate), filtered and concentrated by rotary evaporation. The residue was purified by flash column chromatography (silica gel, 10-75% ethyl acetate/heptane) to provide the title compound (1.67 g, 5.79 mmol, 96% yield).

Example A-20b 2,4-difluoro-6-(4-hydroxybutyl)phenol

Example A-20a (7.54 g, 26.2 mmol) was dissolved in tetrahydrofuran (131 mL) and the solution was added to 20% PdOH$_2$ (1.836 g, 2.62 mmol) in a 500 mL pressure bottle and stirred at ambient temperature for 16 hours at 30 psi (H$_2$). The mixture was filtered through a nylon membrane and the filtrate was concentrated by rotary evaporation to provide the title compound (5.18 g, 25.6 mmol, 98% yield).

Example A-20c 4-(2-(2-bromo-4-(ethylsulfonyl)phenoxy)-3,5-difluorophenyl)butan-1-ol Example A-20b (1.00 g, 4.95 mmol) and Example A-1d (1.453 g, 5.44 mmol) were combined in DMSO (20 mL).

Cesium carbonate (2.417 g, 7.42 mmol) was added and the reaction mixture was stirred at 80° C. for 20 minutes. The reaction mixture was poured into ethyl acetate and water and the layers were separated. The aqueous phase was extracted with ethyl acetate and the combined organics were dried (anhydrous magnesium sulfate), filtered, and concentrated by rotary evaporation. The residue was purified by flash column chromatography (silica gel, 0-100% ethyl acetate/heptane) to provide the title compound (1.89 g, 4.21 mmol, 85% yield).

Example A-20d 4-(benzyloxy)-5-bromo-1-methylpyridin-2(1H)-one

Benzyl alcohol (93 µl, 0.899 mmol) was dissolved in 2-methyltetrahydrofuran (2248 µl) under nitrogen and the solution was cooled to 0° C. Potassium tert-butoxide (1 M in tetrahydrofuran, 899 µL, 0.899 mmol) was added dropwise and the mixture was stirred at 0° C. for 30 minutes. A suspension of Example A-1b (100 mg, 0.450 mmol) in 2-methyltetrahydrofuran (1 mL) was added dropwise. The solution was stirred at 0° C. for an additional 20 minutes and then warmed to ambient temperature. Saturated ammonium chloride was added and the mixture was diluted with dichloromethane and water. The resulting aqueous layer was extracted with dichloromethane. The combined organic phases were dried (anhydrous magnesium sulfate), filtered, and concentrated by rotary evaporation. The residue was recrystallized from methanol to provide the title compound (55 mg). The filtrate from the recrystallization was evaporated and the residue purified by flash chromatography (silica gel, 0-100% hexane/ethyl acetate) to provide the title compound (38 mg). Total yield: 70%.

Example A-20e 4-(benzyloxy)-1-methyl-5-(4,4,5,5-tetramethyl-1,3,2-dioxaborolan-2-yl)pyridin-2(1H)-one Example A-20d (9.3 g, 31.6 mmol), oven dried potassium acetate (7.14 g, 72.7 mmol), and 4,4,4',4',5,5,5',5'-octamethyl-2,2'-bi(1,3,2-dioxaborolane) (12.04 g, 47.4 mmol) were combined in a flask and purged with nitrogen for 10 minutes. Dicyclohexyl(2',4',6'-triisopropyl-[1,1'-biphenyl]-2-yl)phosphine (1.507 g, 3.16 mmol) and tris(dibenzylideneacetone)dipalladium (0.724 g, 0.790 mmol) were added and the mixture was sparged with nitrogen. Dioxane (101 mL) was degassed for 10 minutes and then added to the reaction mixture. The reaction mixture was stirred for 7 hours at 80° C., cooled to ambient temperature and silica gel was added. The mixture was concentrated by rotary evaporation. The dried silica loaded with the reaction mixture was placed over a bed of silica gel and ethyl acetate was passed over until all color came off. The filtrate was concentrated by rotary evaporation and the residue was purified by trituration from cold diethyl ether to provide the title compound (7 g, 20.52 mmol, 64.9% yield).

Example A-20f 4-(benzyloxy)-5-(2-(2,4-difluoro-6-(4-hydroxybutyl)phenoxy)-5-(ethylsulfonyl)phenyl)-1-methylpyridin-2(1H)-one Example A-20e (252 mg, 0.738 mmol), Example A-20c (221 mg, 0.492 mmol), potassium phosphate tribasic (261 mg, 1.230 mmol), 1,3,5,7-tetramethyl-6-phenyl-2,4,8-trioxa-6-phosphaadamantane (20.13 mg, 0.069 mmol) and tris(dibenzylideneacetone)dipalladium (19.37 mg, 0.021 mmol) were combined in a microwave vial and purged with nitrogen for 30 minutes. Dioxane (2 mL) and water (0.5 mL) were degassed with nitrogen for 20 minutes. The solvent mixture was added via syringe and the reaction mixture was heated in a microwave reactor for 1 hour at 100° C. The reaction mixture was cooled to ambient temperature and filtered through Celite. Ethyl acetate and water were added and layers were separated. The aqueous layer was extracted with ethyl acetate and the combined organics were dried (anhydrous magnesium sulfate), filtered and concentrated by rotary evaporation. The residue was purified by flash chromatography (silica gel, 0-100% ethyl acetate/heptane) to give the title compound (242 mg, 0.415 mmol, 84% yield).

Example A-20g 5-(2-(2,4-difluoro-6-(4-hydroxybutyl)phenoxy)-5-(ethylsulfonyl)phenyl)-4-hydroxy-1-methylpyridin-2(1H)-one Example A-20f (360 mg, 0.617 mmol) and 10% Pd—C (65.6 mg, 0.062 mmol) were combined in a round bottom flask under nitrogen. Ethanol (6.17 mL) was added and a hydrogen balloon was attached via needle/septum. The reaction mixture was stirred overnight at ambient temperature. The reaction mixture was filtered through Celite and the filtrate was concentrated by rotary evaporation to provide the title compound.

Example A-20h 17-(ethylsulfonyl)-11,13-difluoro-2-methyl-6,7,8,9-tetrahydrodibenzo[4,5:7,8][1,6]dioxacyclododecino[3,2-c]pyridin-3(2H)-one Example A-20g (289 mg, 0.586 mmol) was taken up in toluene (53 mL) at ambient temperature. A solution of 2-(trimethylphosphoranylidene)acetonitrile (0.5 M in tetrahydrofuran, 2.93 mL, 1.464 mmol) was added dropwise. The reaction mixture was heated to 75° C. and stirred for 2 hours and then cooled to ambient temperature. The reaction mixture was concentrated and the residue was taken up in a minimum amount of dichloromethane which was loaded directly onto silica gel and purified by flash column chromatography (silica gel, 0.5-5% methanol/dichloromethane) to give the title compound (152 mg, 0.320 mmol, 54.6% yield over two steps). $^1$H NMR (400 MHz, DMSO-d$_6$) δ 7.85 (s, 1H), 7.83-7.75 (m, 2H), 7.42-7.31 (m, 1H), 7.20 (d, J=8.8 Hz, 1H), 6.75 (dd, J=8.7, 2.5 Hz, 1H), 5.91 (s, 1H), 4.13 (d, J=4.6 Hz, 2H), 3.42 (s, 3H), 3.36-3.27 (m, 2H), 2.65-2.53 (m, 1H), 2.53-2.41 (m, 1H), 1.71 (d, J=4.0 Hz, 3H), 1.40 (d, J=9.1 Hz, 1H), 1.14 (t, J=7.3 Hz, 3H). MS (ESI+) m/z 476.2 (M+H)$^-$.

Example A-21

17-(cyclopropylsulfonyl)-11,13-difluoro-2-methyl-6,7,8,9-tetrahydrodibenzo[4,5:7,8][1,6]dioxacyclododecino[3,2-c]pyridin-3(2H)-one

Example A-21a (3-bromo-4-fluorophenyl)(cyclopropyl)sulfane

Example A-21a was prepared according to the procedure used for the preparation of Example A-1c, substituting iodocyclopropane for iodoethane, to provide the title compound.

Example A-21b 2-bromo-4-(cyclopropylsulfonyl)-1-fluorobenzene

Example A-21b was prepared according to the procedure used for the preparation of Example A-1d, substituting Example A-21a for Example A-1c, to provide the title compound.

Example A-21c 4-(2-(2-bromo-4-(cyclopropylsulfonyl)phenoxy)-3,5-difluorophenyl)butan-1-ol Example A-21c was prepared according to the procedure used for the preparation of Example A-20c, substituting Example A-21b for Example A-1d, to provide the title compound.

Example A-21d 4-(benzyloxy)-5-(5-(cyclopropylsulfonyl)-2-(2,4-difluoro-6-(4-hydroxybutyl)phenoxy)phenyl)-1-methylpyridin-2(1H)-one Example A-21d was prepared according to the procedure used for the preparation of Example A-20f, substituting Example A-21c for Example A-20c, to provide the title compound.

Example A-21e 5-(5-(cyclopropylsulfonyl)-2-(2,4-difluoro-6-(4-hydroxybutyl)phenoxy)phenyl)-4-hydroxy-1-methylpyridin-2(1H)-one Example A-21e was prepared according to the procedure used for the preparation of Example A-20g, substituting Example A-21d for Example A-20f, to provide the title compound.

Example A-21f 17-(cyclopropylsulfonyl)-11,13-difluoro-2-methyl-6,7,8,9-tetrahydrodibenzo[4,5:7,8][1,6]dioxacyclododecino[3,2-c]pyridin-3(2H)-one Example A-21f was prepared according to the procedure used for the preparation of Example A-20h, substituting Example A-21e for Example A-20g, to provide the title compound. $^1$H NMR (400 MHz, DMSO-d$_6$) δ 7.88-7.73 (m, 3H), 7.43-7.29 (m, 1H), 7.20 (d, J=8.8 Hz, 1H), 6.74 (dd, J=8.6, 2.5 Hz, 1H), 5.92 (s, 1H), 4.14 (d, J=3.5 Hz, 2H), 3.43 (s, 3H), 3.03-2.80 (m, 1H), 2.59 (dd, J=11.8, 7.6 Hz, 1H), 2.49-2.42 (m, 1H), 1.68 (m, 3H), 1.44 (d, J=11.0 Hz, 1H), 1.10 (dd, J=31.0, 6.0 Hz, 4H). MS (ESI+) m/z 488.2 (M+H)$^+$.

Example A-22

17-(ethylsulfonyl)-11-fluoro-2-methyl-6,7,8,9-tetrahydrodibenzo[4,5:7,8][1,6]dioxacyclododecino[3,2-c]pyridin-3(2H)-one

Example A-22a 5-bromo-4-(but-3-en-1-yloxy)-1-methylpyridin-2(1H)-one

A mixture of A-1b (1.009 g, 14.00 mmol) and but-3-en-1-ol (1.009 g, 14.00 mmol) in tetrahydrofuran (20 mL) was cooled to 0° C. To this solution was added potassium tert-butoxide (1.683 g, 15.00 mmol). The cold bath was removed, and the reaction mixture was stirred at ambient temperature for 2 hours. The resulting solid was filtered off, and the filtrate was concentrated. The residue was purified by flash column chromatography on silica gel, eluting with 1:4 heptanes/ethyl acetate to give the title compound. (1.8 g, 6.97 mmol, 69.7% yield).

Example A-22b 4-(but-3-en-1-yloxy)-5-(5-(ethylsulfonyl)-2-fluorophenyl)-1-methylpyridin-2(1H)-one Example A22b was prepared according to the procedure used for the preparation of Example A-1f, substituting Example A-22a for Example A-1b, to provide the title compound.

Example A-22c 4-(but-3-en-1-yloxy)-5-(5-(ethylsulfonyl)-2-(4-fluoro-2-iodophenoxy)phenyl)-1-methylpyridin-2(1H)-one Example A-22c was prepared according to the procedure used for the preparation of Example A-1g, substituting Example A-22b for Example A-1f, and 4-fluoro-2-iodophenol for 2-iodophenol, respectively, to provide the title compound.

Example A-22d (E)-17-(ethylsulfonyl)-11-fluoro-2-methyl-6,7-dihydrodibenzo[4,5:7,8][1,6]dioxacyclododecino[3,2-c]pyridin-3(2H)-one Example A-22d was prepared according to the procedure used for the preparation of Example A-15d, substituting Example A-22c for Example A-15c, to provide the title compound.

Example A-22e 17-(ethylsulfonyl)-11-fluoro-2-methyl-6,7,8,9-tetrahydrodibenzo[4,5:7,8][1,6]dioxacyclododecino[3,2-c]pyridin-3(2H)-one Example A-22e was prepared according to the procedure used for the preparation of Example A-1i, substituting Example A-22d for Example A-1h, to provide the title compound. ¹H NMR (500 MHz, DMSO-d₆) δ 7.74-7.79 (m, 3H), 7.28 (dd, J=8.54, 2.75 Hz, 1H), 7.14-7.17 (m, 1H), 6.70 (d, J=8.54 Hz, 1H), 5.90 (s, 1H), 4.09-4.14 (m, 2H), 3.43 (s, 3H), 3.30 (q, J=7.32 Hz, 2H), 2.41-2.54 (m, 2H), 1.70 (m, 3H), 1.37 (m, 1H), 1.14 (t, J=7.32 Hz, 3H). MS (ESI+) m/z 503.1 (M+H)⁺.

Example A-23

17-(ethylsulfonyl)-12-fluoro-2-methyl-6,7,8,9-tetrahydrodibenzo[4,5:7,8][1,6]dioxacyclododecino[3,2-c]pyridin-3(2H)-one Example A-23a 4-(but-3-en-1-yloxy)-5-(5-(ethylsulfonyl)-2-(5-fluoro-2-iodophenoxy)phenyl)-1-methylpyridin-2(1H)-one Example A-23a was prepared according to the procedure used for the preparation of Example A-1g, substituting Example A-22b for Example A-1f, and 5-fluoro-2-iodophenol for 2-iodophenol, respectively, to provide the title compound.

Example A-23b (E)-17-(ethylsulfonyl)-12-fluoro-2-methyl-6,7-dihydrodibenzo[4,5:7,8][1,6]dioxacyclododecino[3,2-c]pyridin-3(2H)-one Example A-23b was prepared according to the procedure used for the preparation of Example A-15d, substituting Example A-23a for Example A-15c, to provide the title compound.

Example A-23c 17-(ethylsulfonyl)-12-fluoro-2-methyl-6,7,8,9-tetrahydrodibenzo[4,5:7,8][1,6]dioxacyclododecino[3,2-c]pyridin-3(2H)-one Example A-23c was prepared according to the procedure used for the preparation of Example A-1i, substituting Example A-23b for Example A-1h, to provide the title compound. ¹H NMR (500 MHz, DMSO-d₆) δ 7.75-7.80 (m, 3H), 7.44 (d, J=7.48 Hz, 1H), 7.09-7.14 (m, 2H), 6.78 (d, J=8.85 Hz, 1H), 5.91 (s, 1H), 4.09-4.14 (m, 2H), 3.43 (s, 3H), 3.30 (q, J=7.32 Hz, 2H), 2.38-2.54 (m, 2H), 1.69 (m, 3H), 1.34-1.39 (m, 1H), 1.14 (t, J=7.32 Hz, 3H). MS (ESI+) m/z 458.2 (M+H)⁺.

Example A-24

(E)-12-chloro-17-(ethylsulfonyl)-2-methyl-6,7-dihydrodibenzo[4,5:7,8][1,6]dioxacyclododecino[3,2-c]pyridin-3(2H)-one Example A-24a 4-(but-3-en-1-yloxy)-5-(2-(5-chloro-2-iodophenoxy)-5-(ethylsulfonyl)phenyl)-1-methylpyridin-2(1H)-one Example A-24a was prepared according to the procedure used for the preparation of Example A-1g, substituting Example A-22b for Example A-1f, and 5-chloro-2-iodophenol for 2-iodophenol, respectively, to provide the title compound.

Example A-24b (E)-12-chloro-17-(ethylsulfonyl)-2-methyl-6,7-dihydrodibenzo[4,5:7,8][1,6]dioxacyclododecino[3,2-c]pyridin-3(2H)-one Example A-24b was prepared according to the procedure used for the preparation of Example A-5f, substituting Example A-24a for Example A-1h, to provide the title compound. ¹H NMR (500 MHz, DMSO-d₆) δ 7.79 (dd, J=8.54, 2.44 Hz, 1H), 7.69-7.70 (m, 2H), 7.38-7.41 (m, 3H), 6.75 (d, J=8.85 Hz, 1H), 6.00 (d, J=16.17 Hz, 1H), 5.88 (s, 1H), 5.60-5.68 (m, 1H), 4.14-4.18 (m, 2H), 3.88-3.94 (m, 1H), 3.41 (s, 3H), 3.29 (q, J=7.32 Hz, 2H), 2.33-2.39 (m, 2H), 1.10 (t, J=7.32 Hz, 3H). MS (ESI+) m/z 472.1 (M+H)⁺.

Example A-25

12-chloro-17-(ethylsulfonyl)-2-methyl-6,7,8,9-tetrahydrodibenzo[4,5:7,8][1,6]dioxacyclododecino[3,2-c]pyridin-3(2H)-one Example A-25 was prepared according to the procedure used for the preparation of Example A-1i, substituting Example A-24b for Example A-1h, to provide the title compound. ¹H NMR (500 MHz, DMSO-d₆) δ 7.75-7.80 (m, 3H), 7.43 (d, J=8.24 Hz, 1H), 7.33 (dd, J=8.24, 2.14 Hz, 1H), 7.28 (d, J=2.14 Hz, 1H), 6.75 (d, J=8.85 Hz, 1H), 5.90 (s, 1H), 4.08-4.14 (m, 2H), 3.43 (s, 3H), 3.30 (q, J=7.32 Hz, 2H), 2.42-2.54 (m, 2H), 1.69 (m, 3H), 1.35 (m, 1H), 1.14 (t, J=7.48 Hz, 3H). MS (ESI+) m/z 474.2 (M+H)⁻.

Example A-26

N-(2-methyl-3-oxo-2,3,6,7,8,9-hexahydrobenzo[4,5][1,6]dioxacyclododecino[3,2-c:7,8-c']dipyridin-17-yl)ethanesulfonamide Example A-26a 4-(3-methoxypyridin-4-yl)but-3-yn-1-ol Example A-26a was prepared according to the procedure used for the preparation of Example A-1h, substituting but-3-yn-1-ol for prop-2-yn-1-ol, and 4-bromo-3-methoxypyridine for Example A-1g, respectively, to provide the title compound.

Example A-26b 4-(3-methoxypyridin-4-yl)butan-1-ol

Example A-26b was prepared according to the procedure used for the preparation of Example A-1i, substituting Example A-26a for Example A-1h, to provide the title compound.

Example A-26c 5-bromo-4-(4-(3-methoxypyridin-4-yl)butoxy)-1-methylpyridin-2(1H)-one Example A-26c was prepared according to the procedure used for the preparation of Example A-22a, substituting Example A-26b for but-3-en-1-ol, to provide the title compound.

Example A-26d 5-(2-fluoro-5-nitrophenyl)-4-(4-(3-methoxypyridin-4-yl)butoxy)-1-methylpyridin-2(1H)-one Example A-26d was prepared according to the procedure used for the preparation of Example A-1f, substituting Example A-26b for Example A-1b, and 2-(2-fluoro-5-nitrophenyl)-4,4,5,5-tetramethyl-1,3,2-dioxaborolane for Example A-1e, respectively, to provide the title compound.

Example A-26e 5-(2-fluoro-5-nitrophenyl)-4-(4-(3-hydroxypyridin-4-yl)butoxy)-1-methylpyridin-2(1H)-one A mixture of Example A-26d (0.25 g, 0.585 mmol) in dichloromethane (10 mL) was cooled to −78° C. To this solution was added 1.0 N tribromoborane in dichloromethane (2.92 mL, 2.92 mmol). The cold bath was removed, and reaction mixture was stirred at ambient temperature for 4 hours. Saturated aqueous sodium bicarbonate (10 mL) was added to this reaction mixture slowly and stirred for 20 minutes. The organic phase was separated, and the aqueous layer was extracted with additional dichloromethane three times. The combined organic layers were washed with saturated aqueous sodium chloride, dried over anhydrous magnesium sulfate, filtered, and concentrated. The residue was purified by flash column chromatography on silica gel, eluting with 10% methanol in ethyl acetate to give the title compound (0.22 g, 0.532 mmol, 91% yield).

Example A-26f 2-methyl-17-nitro-6,7,8,9-tetrahydrobenzo[4,5][1,6]dioxacyclododecino[3,2-c:7,8-c']dipyridin-3(2H)-one A mixture of Example A-26e (0.22 g, 0.532 mmol) and cesium carbonate (0.208 g, 0.639 mmol) in acetonitrile (40 mL) was heated at 80° C. overnight. The solvent was evaporated under reduced pressure, and the residue was purified by flash chromatography, eluting with 10% methanol/ethyl acetate, to give the title compound (0.10 g, 0.254 mmol, 47.8% yield).

Example A-26g 17-amino-2-methyl-6,7,8,9-tetrahydrobenzo[4,5][1,6]dioxacyclododecino[3,2-c:7,8-c']dipyridin-3(2H)-one Example A-26d was prepared according to the procedure used for the preparation of Example A-15a, substituting Example A-26f for Example A-5b, to provide the title compound.

Example A-26h

N-(2-methyl-3-oxo-2,3,6,7,8,9-hexahydrobenzo[4,5][1,6]dioxacyclododecino[3,2-c:7,8-c']dipyridin-17-yl)ethanesulfonamide The TFA salt of the title compound was prepared according to the procedure used for the preparation of Example A-5f, substituting Example A-26g for Example A-5e. $^1$H NMR (500 MHz, DMSO-$d_6$) δ 9.68 (s, 1H), 8.49-8.50 (m, 2H), 7.69 (s, 1H), 7.63 (d, J=4.88 Hz, 1H), 7.06-7.12 (m, 2H), 6.53-6.55 (m, 1H), 5.89 (s, 1H), 4.10-4.16 (m, 2H), 3.42 (s, 3H), 3.07-3.13 (m, 2H), 2.58 (t, J=7.78 Hz, 2H), 1.70-1.82 (m, 3H), 1.37-1.40 (m, 1H), 1.23 (t, J=7.32 Hz, 3H). MS (ESI+) m/z 456.2 (M+H)$^-$.

Example A-27

11-chloro-2-methyl-6,7,8,9-tetrahydrobenzo[11,12][1,6]dioxacyclododecino[2,3-b:4,5-c']dipyridin-3(2H)-one

Example A-27a 4-(5-chloro-2-methoxyphenyl)but-3-yn-1-ol

A solution of 2-bromo-4-chloro-1-methoxybenzene (15 g, 67.7 mmol), copper(I) iodide (1.290 g, 6.77 mmol) and Pd(PPh$_3$)$_4$ (3.91 g, 3.39 mmol) in pyrrolidine (35 mL) was degassed with nitrogen. But-3-yn-1-ol (9.49 g, 135 mmol) was added via cannula and the reaction mixture was heated at 80° C. for 18 hours. The reaction mixture was cooled to room temperature and partitioned between saturated aqueous ammonium chloride and ethyl acetate (3×300 mL). The organic layers were combined, washed with water, saturated aqueous sodium chloride, dried (anhydrous sodium sulfate), filtered, and concentrated. Purification by flash chromatography (silica gel, 0-40% ethyl acetate in heptanes) afforded the title compound (12.5 g, 88%).

Example A-27b 4-(5-chloro-2-methoxyphenyl)butan-1-ol

The product from Example A-27a (8.38 g, 39.8 mmol) in tetrahydrofuran (100 mL) was added to 5% Pt/C (8.0 g, Johnson-Matthey #B103032-5, 58.9% water content) in a 250 mL stainless steel pressure bottle and shaken for 24 hours under 30 psi of hydrogen at ambient temperature. The mixture was filtered through a nylon membrane and concentrated to afford the title compound (8.52 g, 99%).

Example A-27c 5-bromo-4-(4-(5-chloro-2-methoxyphenyl)butoxy)-1-methylpyridin-2(1H)-one The product from Example A-27b (10 g, 46.6 mmol) (azeotroped 2× with toluene to remove adventitious water) and Example A-1b (12.43 g, 55.9 mmol) were combined in anhydrous dioxane (200 mL) and treated carefully with potassium t-butoxide (1N in tetrahydrofuran, 60.6 mL, 60.6 mmol). The reaction mixture was stirred for 18 hours at ambient temperature, diluted with water (700 mL) and stirred for 1 hour. The resulting solid was collected by filtration and triturated in diethyl ether (200 mL) to afford the title compound 14.1 g, 75% yield).

Example A-27d

2'-chloro-4-(4-(5-chloro-2-methoxyphenyl)butoxy)-1-methyl-[3,3'-bipyridin]-6(1H)-one (2-chloropyridin-3-yl)boronic acid (0.196 g, 1.248 mmol), Example A-27c (0.25 g, 0.624 mmol), bis(triphenylphosphine)palladium(II) dichloride (0.031 g, 0.044 mmol) and 2.0 M aqueous sodium carbonate (0.624 mL, 1.248 mmol) were combined in anhydrous 1,2-dimethoxyethane (3.12 mL), sparged with argon for 10 minutes and heated in a microwave reactor at 120° C. for 1 hour. The reaction mixture was cooled and partitioned between ethyl acetate and water. The organic layer was washed with saturated aqueous sodium chloride, dried (anhydrous sodium sulfate), treated with 3-mercaptopropyl functionalized silica gel for twenty minutes, filtered, and concentrated. Purification by flash chromatography (silica gel, 1-4% methanol in dichloromethane) afforded the title compound (0.155 g, 57%).

Example A-27e

2'-chloro-4-(4-(5-chloro-2-hydroxyphenyl)butoxy)-1-methyl-[3,3'-bipyridin]-6(1H)-one To a solution of Example A-27d (0.15 g, 0.346 mmol) in dichloromethane (3.46 mL) at −78° C. under nitrogen was added drop-wise 1.0 M boron tribromide in dichloromethane (1.731 mL, 1.731 mmol). The mixture was allowed to warm to 0° C., stirred for 15 minutes and carefully neutralized with saturated aqueous sodium bicarbonate to pH 10. The mixture was then diluted with ethyl acetate and water. The organic layer was washed with saturated aqueous sodium chloride, dried (anhydrous sodium sulfate), filtered and concentrated to afford the title compound (0.141 g, 97%).

Example A-27f 11-chloro-2-methyl-6,7,8,9-tetrahydrobenzo[11,12][1,6]dioxacyclododecino[2,3-b:4,5-c']dipyridin-3(2H)-one Example A-27e (0.05 g, 0.119 mmol) and cesium carbonate (0.097 g, 0.298 mmol) were combined in a mixture of acetonitrile (8.0 mL) and DMSO (2.0 mL) under nitrogen in a sealed tube and heated in a microwave reactor at 150° C. for 1 hour. The mixture was cooled to ambient temperature and partitioned between ethyl acetate and water. The organic layer was washed with saturated aqueous sodium chloride, dried (anhydrous sodium sulfate), filtered, and concentrated. Purification by reverse phase HPLC (C18, 0-100% acetonitrile/water (0.1% TFA)) afforded the title compound as a TFA salt (0.0015 g, 3%). $^1$H NMR (400 MHz, DMSO-$d_6$) δ 8.02 (dd, J=4.88, 1.83 Hz, 1H), 7.73 (s, 1H), 7.71 (dd, J=7.32, 1.83 Hz, 1H), 7.37 (d, J=2.44 Hz, 1H), 7.27 (dd, J=8.54, 2.75 Hz, 1H), 7.14 (dd, J=7.32, 4.88 Hz, 1H), 7.07 (d, J=8.54 Hz, 1H), 5.90 (s, 1H), 4.10 (d, J=6.10 Hz, 2H), 3.41 (s, 3H), 2.52-2.58 (m, 1H), 2.26-2.37 (m, 1H), 1.59-1.76 (m, 3H), 1.33-1.44 (m, 1H). MS (APCI+) m/z 383 (M+H)$^+$.

Example A-28

17-amino-2-methyl-6,7,8,9-tetrahydrobenzo[4,5][1,6]dioxacyclododecino[3,2-c:7,8-c']dipyridin-3(2H)-one The preparation of the title compound was described in the synthesis of Example A-26g to give the crude product. The crude product was further purified by reverse phase Preparative HPLC (C18, 10-70% acetonitrile/water (0.1% TFA)) to provide the title compound as TFA salt. $^1$H NMR (500 MHz, DMSO-$d_6$) δ 8.45 (d, J=5.19 Hz, 1H), 8.42 (s, 1H), 7.68 (s, 1H), 7.54 (d, J=4.88 Hz, 1H), 7.14-7.15 (m, 2H), 6.58-6.60 (m, 1H), 5.91 (s, 1H), 4.10-4.13 (m, 2H), 3.42 (s, 3H), 2.58 (t, J=7.78 Hz, 2H), 1.38-1.70 (m, 3H), 1.37-1.40 (m, 1H). MS (ESI+) m/z 364.2 (M+H)$^+$.

Example A-29

N-[2-methyl-3-oxo-11-(trifluoromethyl)-2,3,6,7,8,9-hexahydrodibenzo[4,5:7,8][1,6]dioxacyclododecino[3,2-c]pyridin-17-yl]ethanesulfonamide

Example A-29a 4-chloro-5-(2-(2-iodo-4-(trifluoromethyl)phenoxy)-5-nitrophenyl)-1-methylpyridin-2(1H)-one Example A-29a was prepared according to the procedure used for the preparation of Example A-5b, substituting 4-trifluoromethyl-2-iodophenol for 4-chloro-2-iodophenol, to provide the title compound.

Example A-29b 5-(5-amino-2-(2-iodo-4-(trifluoromethyl)phenoxy)phenyl)-4-chloro-1-methylpyridin-2(1H)-one Example A-29b was prepared according to the procedure used for the preparation of Example A-15a, substituting Example A-26f for Example A-5b, to provide the title compound.

Example A-29c 5-(5-amino-2-(2-iodo-4-(trifluoromethyl)phenoxy)phenyl)-4-(but-3-en-1-yloxy)-1-methylpyridin-2(1H)-one Sodium (0.088 g, 3.84 mmol) was added to but-3-en-1-ol (6.92 g, 96 mmol). After all the sodium was dissolved, Example A-29b (1 g, 1.921 mmol) was added. The reaction mixture was stirred at 75° C. overnight. After cooling to ambient temperature the reaction mixture was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The residue was purified by flash column chromatography on silica gel, eluting with ethyl acetate to afford the title compound (550 mg, 0.959 mmol, 49.9% yield).

Example A-29d (E)-17-amino-2-methyl-11-(trifluoromethyl)-6,7-dihydrodibenzo[4,5:7,8][1,6]dioxacyclododecino[3,2-c]pyridin-3(2H)-one Example A-26d was prepared according to the procedure used for the preparation of Example A-15d, substituting Example A-29c for Example A-15c, to provide the title compound.

Example A-29e 17-amino-2-methyl-11-(trifluoromethyl)-6,7,8,9-tetrahydrodibenzo[4,5:7,8][1,6]dioxacyclododecino[3,2-c]pyridin-3(2H)-one Example A-29e was prepared according to the procedure used for the preparation of Example A-1i, substituting Example A-29d for Example A-1h, to provide the title compound.

Example A-29f

N-[2-methyl-3-oxo-11-(trifluoromethyl)-2,3,6,7,8,9-hexahydrodibenzo[4,5:7,8][1,6]dioxacyclododecino[3,2-c]pyridin-17-yl]ethanesulfonamide Example A-29f was prepared according to the procedure used for the preparation of Example A-5f, substituting Example A-29e for Example A-5e, to provide the title compound. $^1$H NMR (400 MHz, CD$_3$OD) δ 7.64 (d, J=2.0 Hz, 1H), 7.61 (s, 1H), 7.57 (m, 1H), 7.20 (d, J=8.4 Hz, 1H), 7.16 (d, J=2.7 Hz, 1H), 7.12 (dd, J=8.8, 2.8 Hz, 1H), 6.52 (d, J=8.8 Hz, 1H), 6.01 (s, 1H), 4.23-4.12 (m, 2H), 3.56 (s, 3H), 3.08 (q, J=7.4 Hz, 2H), 2.64-2.58 (m, 2H), 1.85-1.82 (m, 3H), 1.51-1.45 (m, 1H), 1.32 (t, J=7.4 Hz, 3H). MS (ESI+) m/z 523.2 (M+H)$^+$.

Example A-30

N-[2-methyl-3-oxo-11-(trifluoromethoxy)-2,3,6,7,8,9-hexahydrodibenzo[4,5:7,8][1,6]dioxacyclododecino[3,2-c]pyridin-17-yl]methanesulfonamide

Example A-30a 4-chloro-5-(2-(2-iodo-4-(trifluoromethoxy)phenoxy)-5-nitrophenyl)-1-methylpyridin-2(1H)-one Example A-30a was prepared according to the procedure used for the preparation of Example A-5b, substituting 4-trifluoromethoxy-2-iodophenol for 4-chloro-2-iodophenol, to provide the title compound.

Example A-30b

Example A-30b was prepared according to the procedure used for the preparation of Example A-15a, substituting Example A-30a for Example A-5b, to provide the title compound.

Example A-30c 5-(5-amino-2-(2-iodo-4-(trifluoromethoxy)phenoxy)phenyl)-4-(but-3-en-1-yloxy)-1-methylpyridin-2(1H)-one Example A-30c was prepared according to the procedure used for the preparation of Example A-22a, substituting Example A-30b for Example A-1b, to provide the title compound.

Example A-30d (E)-17-amino-2-methyl-11-(trifluoromethoxy)-6,7-dihydrodibenzo[4,5:7,8][1,6]dioxacyclododecino[3,2-c]pyridin-3(2H)-one Example A-30d was prepared according to the procedure used for the preparation of Example A-15d, substituting Example A-30c for Example A-15c, to provide the title compound.

Example A-30e 17-amino-2-methyl-11-(trifluoromethoxy)-6,7,8,9-tetrahydrodibenzo[4,5:7,8][1,6]dioxacyclododecino[3,2-c]pyridin-3(2H)-one Example A-30e was prepared according to the procedure used for the preparation of Example A-1i, substituting Example A-30d for Example A-1h, to provide the title compound.

Example A-30f

N-[2-methyl-3-oxo-11-(trifluoromethoxy)-2,3,6,7,8,9-hexahydrodibenzo[4,5:7,8][1,6]dioxacyclododecino[3,2-c]pyridin-17-yl]methanesulfonamide Example A-30f was prepared according to the procedure used for the preparation of Example A-5f, substituting Example A-30e for Example A-5e, and methanesulfonyl chloride for ethanesulfonyl chloride, respectively, to provide the title compound. $^1$H NMR (400 MHz, CD$_3$OD) δ 7.61 (s, 1H), 7.25 (s, 1H), 7.20-7.14 (m, 4H), 6.51 (d, J=8.7 Hz, 1H), 6.01 (s, 1H), 4.18-4.16 (m, 2H), 3.56 (s, 3H), 2.95 (s, 3H), 2.58-2.54 (m, 2H), 1.84-1.81 (m, 3H), 1.53-1.39 (m, 1H). MS (ESI+) m/z 525.2 (M+H)$^+$.

Example A-31 methyl 11-chloro-2-methyl-3-oxo-2,3,6,7,8,9-hexahydrobenzo[11,12][1,6]dioxacyclododecino[2,3-b:4,5-c']dipyridine-17-carboxylate

Example A-31a

Methyl 2-chloro-4'-(4-(5-chloro-2-methoxyphenyl)butoxy)-1'-methyl-6'-oxo-1',6'-dihydro-[3,3'-bipyridine]-5-carboxylate Example A-32a (0.88 g, 1.965 mmol), methyl 5-bromo-6-chloronicotinate (0.541 g, 2.162 mmol), tris(dibenzylideneacetone)dipalladium(0) (0.063 g, 0.069 mmol), tri-tert-butylphosphonium tetrafluoroborate (0.040 g, 0.138 mmol) and cesium fluoride (0.896 g, 5.90 mmol) were combined in anhydrous tetrahydrofuran (19.65 mL), sparged with argon for 10 minutes and stirred for 3 hours at 65° C. The mixture was cooled to ambient temperature, partitioned between ethyl acetate and water, and filtered through Celite to remove elemental palladium. The organic layer was washed with saturated aqueous sodium chloride, dried (anhydrous sodium sulfate), treated with 3-mercaptopropyl functionalized silica gel, filtered and concentrated. The residue was purified by flash chromatography (silica gel, 35-60% of 3:1 ethyl acetate/ethanol in heptanes) to afford the title compound (0.71 g, 74%).

Example A-31b

Methyl 2-chloro-4'-(4-(5-chloro-2-hydroxyphenyl)butoxy)-1'-methyl-6'-oxo-1',6'-dihydro-[3,3'-bipyridine]-5-carboxylate To a solution of Example A-31a (0.71 g, 1.445 mmol) in dichloromethane (14.5 mL) at −78° C. under nitrogen was added dropwise 1.0 M boron tribromide in dichloromethane (7.22 mL, 7.22 mmol). The mixture was slowly warm to 0° C. over 4 hours, then cooled to −78° C., and carefully treated with dropwise addition of methanol (5 mL). The mixture was warmed to 0° C. and carefully neutralized to pH 7 by the addition of saturated aqueous sodium bicarbonate. The organic layer was washed with saturated aqueous sodium chloride, dried (anhydrous sodium sulfate), filtered, and concentrated. The resulting solid was triturated in 9:1 heptanes/ethyl acetate and collected by filtration to afford the title compound (0.61 g, 88%).

Example A-31c methyl 11-chloro-2-methyl-3-oxo-2,3,6,7,8,9-hexahydrobenzo[11,12][1,6]dioxacyclododecino[2,3-b:4,5-c']dipyridine-17-carboxylate The product from Example A-31b (0.6 g, 1.257 mmol) and cesium carbonate (0.491 g, 1.508 mmol) were combined in acetonitrile (80 mL)/DMSO (5 mL) under argon and heated at 85° C. for 5 hours. The reaction mixture was cooled and concentrated to remove most of the acetonitrile. The concentrate was partitioned between ethyl acetate and water and about 10 mL of methanol was added to give complete dissolution of solids. The aqueous layer was separated and extracted three times with ethyl acetate. The organics were combined, washed with saturated aqueous sodium chloride, dried over anhydrous sodium sulfate, filtered and concentrated. Purification by flash chromatography (silica gel, 1-4% methanol in dichloromethane) afforded the title compound (0.5 g, 90%). $^1$H NMR (400 MHz, DMSO-$d_6$) δ 8.60 (d, J=2.44 Hz, 1H), 8.17 (d, J=2.14 Hz, 1H), 7.83 (s, 1H), 7.41 (d, J=2.75 Hz, 1H), 7.30 (dd, J=8.54, 2.75 Hz, 1H), 7.11 (d, J=8.85 Hz, 1H), 5.92 (s, 1H), 4.09-4.16 (m, 2H), 3.85 (s, 3H), 3.41 (s, 3H), 2.53-2.61 (m, 1H), 2.23-2.38 (m, 1H), 1.54-1.79 (m, 3H), 1.34-1.46 (m, 1H). MS (APCI+) m/z 441 (M+H)$^+$.

Example A-32

17-amino-11-chloro-2-methyl-6,7,8,9-tetrahydrobenzo[11,12][1,6]dioxacyclododecino[2,3-b:4,5-c']dipyridin-3(2H)-one Example A-32a 4-(4-(5-chloro-2-methoxyphenyl)butoxy)-1-methyl-5-(4,4,5,5-tetramethyl-1,3,2-dioxaborolan-2-yl)pyridin-2(1H)-one Dicyclohexyl(2',4',6'-triisopropyl-[1,1'-biphenyl]-2-yl)phosphine (0.297 g, 0.624 mmol), potassium acetate (1.408 g, 14.35 mmol), tris(dibenzylideneacetone)dipalladium(0) (0.143 g, 0.156 mmol), Example A-27c (2.5 g, 6.24 mmol) and 4,4,4',4',5,5,5',5'-octamethyl-2,2'-bi(1,3,2-dioxaborolane) (1.901 g, 7.49 mmol) were combined in anhydrous dioxane (31.2 mL) and sparged with argon for 20 minutes. The mixture was heated under nitrogen for 7 hours at 80° C., cooled, and partitioned between ethyl acetate and water. The organic layer was washed with saturated aqueous sodium chloride, dried (anhydrous sodium sulfate), filtered, and concentrated. Purification by flash chromatography (silica gel, 25-50% of 3:1 ethyl acetate/ethanol in heptanes) afforded the title compound (1.9 g, 61%).

Example A-32b

2'-chloro-4-(4-(5-chloro-2-methoxyphenyl)butoxy)-1-methyl-5'-nitro-[3,3'-bipyridin]-6(1H)-one 3-bromo-2-chloro-5-nitropyridine (1.108 g, 4.67 mmol), Example A-32a (1.9 g, 4.24 mmol), tris(dibenzylideneacetone)dipalladium(0) (0.117 g, 0.127 mmol), 1,3,5,7-tetramethyl-6-phenyl-2,4,8-trioxa-6-phosphaadamantane (0.124 g, 0.424 mmol) and potassium phosphate (3.15 g, 14.85 mmol) were combined and sparged with argon for 15 minutes. Meanwhile a solution of 4:1 dioxane/water (4.5 mL) was sparged with nitrogen for 15 minutes and transferred by syringe into the reaction vessel under argon. The mixture was stirred for 2 hours at 50° C., cooled, and partitioned between ethyl acetate and water. The ethyl acetate layer was washed twice with saturated aqueous sodium chloride, dried (anhydrous sodium sulfate), treated with 3-mercaptopropyl functionalized silica gel for twenty minutes, filtered, and concentrated. Purification by flash chromatography (silica gel, 0.5-2.5% methanol in dichloromethane) afforded the title compound (0.79 g, 35%).

Example A-32c

2'-chloro-4-(4-(5-chloro-2-hydroxyphenyl)butoxy)-1-methyl-5'-nitro-[3,3'-bipyridin]-6(1H)-one To a solution of Example A-32b (0.79 g, 1.652 mmol) in dichloromethane (16.52 mL) at −78° C. under nitrogen was added dropwise 1M boron tribromide in dichloromethane (8.26 mL, 8.26 mmol). The mixture was allowed to warm to 0° C., stirred for 45 minutes and carefully neutralized with saturated aqueous sodium bicarbonate to pH 10. The mixture was then diluted with dichloromethane and water. The organic layer was washed with saturated aqueous sodium chloride, dried (anhydrous sodium sulfate), filtered, and concentrated. Purification by flash chromatography (silica gel, 50-100% ethyl acetate in heptanes) afforded the title compound (0.65 g, 85%).

Example A-32d 11-chloro-2-methyl-17-nitro-6,7,8,9-tetrahydrobenzo[11,12][1,6]dioxacyclododecino[2,3-b:4,5-c']dipyridin-3(2H)-one Example A-32c (0.65 g, 1.400 mmol) and cesium carbonate (0.547 g, 1.680 mmol) were combined in acetonitrile (87 mL) under argon and heated at 75° C. for 1 hour. The reaction mixture was cooled and concentrated to remove acetonitrile. The residue was partitioned between ethyl acetate and water. The organic layer was washed with saturated aqueous sodium chloride, dried (anhydrous

Example A-32e 17-amino-11-chloro-2-methyl-6,7,8,9-tetrahydrobenzo[11,12][1,6]dioxacyclododecino[2,3-b:4,5-c']dipyridin-3(2H)-one Example A-32d (0.4 g, 0.935 mmol), iron (0.261 g, 4.67 mmol) and ammonia hydrochloride (0.100 g, 1.870 mmol) were combined in tetrahydrofuran (10.02 mL), ethanol (10.02 mL) and water (3.34 mL) and heated at 90° C. for 2 hours. The mixture was cooled, diluted with tetrahydrofuran and methanol and filtered through Celite to remove solids. The filtrate was concentrated. The residue was partitioned between ethyl acetate and saturated saturated aqueous sodium chloride. The ethyl acetate layer was washed with saturated aqueous sodium chloride, dried over anhydrous sodium sulfate, filtered, and concentrated. Purification by flash chromatography (silica gel, 1-5% methanol in dichloromethane) afforded the title compound (0.35 g, 94%). $^1$H NMR (400 MHz, DMSO-$d_6$) δ 7.68 (s, 1H), 7.31-7.33 (m, 2H), 7.23 (dd, J=8.54, 2.75 Hz, 1H), 7.02 (d, J=8.54 Hz, 1H), 6.94 (d, J=2.75 Hz, 1H), 5.87 (s, 1H), 4.94 (s, 2H), 4.01-4.15 (m, 2H), 3.39 (s, 3H), 2.43-2.52 (m, 1H), 2.26-2.36 (m, J=4.88 Hz, 1H), 1.60-1.77 (m, 3H), 1.30-1.40 (m, 1H). MS (ESI+) m/z 398 (M+H)$^-$.

Example A-33

N-(11-chloro-2-methyl-3-oxo-2,3,6,7,8,9-hexahydrobenzo[11,12][1,6]dioxacyclododecino[2,3-b:4,5-c']dipyridin-17-yl)ethanesulfonamide Example A-32e (0.3 g, 0.754 mmol), ethanesulfonyl chloride (0.291 g, 2.262 mmol) and triethylamine (0.631 mL, 4.52 mmol) were combined in dichloromethane (10.05 mL), and stirred for 1 hour. The mixture was concentrated and azeotroped with dichloromethane. The residue was dissolved in dioxane (5 mL), treated with 1M aqueous sodium hydroxide (2 mL) and heated at 80° C. for 1.5 hours. The mixture was cooled and partitioned with ethyl acetate and water adjusting the pH to 9 with 1M HCl. The ethyl acetate layer was washed with saturated aqueous sodium chloride, dried over anhydrous sodium sulfate, filtered and concentrated. Purification by flash chromatography (silica gel, 1-5% methanol in dichloromethane) afforded the title compound (0.294 g, 80%). $^1$H NMR (400 MHz, DMSO-$d_6$) δ 9.80 (s, 1H), 7.86 (d, J=2.75 Hz, 1H), 7.76 (s, 1H), 7.53 (d, J=2.75 Hz, 1H), 7.37 (d, J=2.75 Hz, 1H), 7.27 (dd, J=8.54, 2.75 Hz, 1H), 7.07 (d, J=8.54 Hz, 1H), 5.91 (s, 1H), 4.09-4.14 (m, 2H), 3.41 (s, 3H), 3.11-3.20 (m, 2H), 2.52-2.58 (m, 1H), 2.25-2.36 (m, 1H), 1.55-1.80 (m, 3H), 1.34-1.45 (m, 1H), 1.25 (t, J=7.32 Hz, 3H). MS (ESI+) m/z 490 (M+H)$^+$.

Example A-34

11-chloro-17-(ethylsulfonyl)-2-methyl-6,7,8,9-tetrahydrobenzo[11,12][1,6]dioxacyclododecino[2,3-b:4,5-c']dipyridin-3(2H)-one

Example A-34a 3-bromo-2-chloro-5-(ethylsulfonyl)pyridine

Sodium sulfite (4.94 g, 39.2 mmol) and sodium hydrogencarbonate (3.46 g, 41.2 mmol) were combined in water (100 mL), heated to 75° C., and 5-bromo-6-chloropyridine-3-sulfonyl chloride (6.0 g, 20.62 mmol) was added portionwise over 45 minutes. The resulting solution was heated at 75° C. for an additional hour, cooled, and concentrated to dryness. The residue was stirred in N,N-dimethylformamide (38 mL) treated with sodium hydrogencarbonate (3.46 g, 41.2 mmol) and iodoethane (1.666 mL, 20.62 mmol) and heated at 75° C. for 2 hours. The mixture was cooled to ambient temperature and partitioned between ethyl acetate and water. The ethyl acetate layer was washed with saturated aqueous sodium chloride, dried over anhydrous sodium sulfate, filtered, and concentrated. Purification by recrystallization from 5:1 hexane/ethyl acetate afforded the title compound (1.34 g, 23%).

Example A-34b

2'-chloro-4-(4-(5-chloro-2-methoxyphenyl)butoxy)-5'-(ethylsulfonyl)-1-methyl-[3,3'-bipyridin]-6(1H)-one Example A-32a (0.818 g, 1.827 mmol), Example A-34a (0.4 g, 1.406 mmol), tris(dibenzylideneacetone)dipalladium (0) (0.045 g, 0.049 mmol), tri-tert-butylphosphonium tetrafluoroborate (0.029 g, 0.098 mmol) and cesium fluoride (0.641 g, 4.22 mmol) were combined in anhydrous tetrahydrofuran (14.06 mL), sparged with argon for 10 minutes, and stirred for 18 hours at 50° C. The mixture was cooled to ambient temperature, partitioned into ethyl acetate and water, and filtered through Celite. The organic layer was washed with saturated aqueous sodium chloride, dried (anhydrous sodium sulfate), treated with 3-mercaptopropyl functionalized silica, filtered, and concentrated. Purification by flash chromatography (silica gel, 30-60% of 3:1 ethyl acetate/ethanol in heptanes) afforded the title compound (0.36 g, 49%).

Example A-34c

2'-chloro-4-(4-(5-chloro-2-hydroxyphenyl)butoxy)-5'-(ethylsulfonyl)-1-methyl-[3,3'-bipyridin]-6(1H)-one To a solution Example A-34b (0.36 g, 0.685 mmol) in dichloromethane (6.85 mL) at −78° C. under nitrogen was added dropwise 1M boron tribromide in dichloromethane (3.43 mL, 3.43 mmol). The mixture was allowed to warm to 0° C., stirred for 45 minutes and carefully neutralized with saturated aqueous sodium bicarbonate to pH 9. The mixture was then diluted with dichloromethane and water and filtered to collect the title compound as a white solid that was dried to constant mass (0.29 g, 83%).

Example A-34d 11-chloro-17-(ethylsulfonyl)-2-methyl-6,7,8,9-tetrahydrobenzo[11,12][1,6]dioxacyclododecino[2,3-b:4,5-c']dipyridin-3(2H)-one Example A-34c (0.29 g, 0.567 mmol) and cesium carbonate (0.24 g, 0.737 mmol) were combined in acetonitrile (50 mL)/DMSO (5 mL) and heated at 95° C. for 2 hours, cooled, and concentrated. The residue was partitioned between ethyl acetate and water. The organic layer was washed with saturated aqueous sodium chloride, dried (anhydrous sodium sulfate), filtered, and concentrated. Purification by flash chromatography (silica gel, 1-4% methanol in dichloromethane) afforded the title compound (0.237 g, 88%). $^1$H NMR (500 MHz, DMSO-d$_6$) δ 8.51 (d, J=2.44 Hz, 1H), 8.16 (d, J=2.44 Hz, 1H), 7.86 (s, 1H), 7.43 (d, J=2.75 Hz, 1H), 7.31 (dd, J=8.70, 2.59 Hz, 1H), 7.14 (d, J=8.54 Hz, 1H), 5.94 (s, 1H), 4.07-4.18 (m, 2H), 3.43 (s, 3H), 3.38-3.43 (m, 2H), 2.53-2.61 (m, 1H), 2.28-2.37 (m, 1H), 1.68-1.78 (m, 2H), 1.64 (dd, J=9.31, 4.12 Hz, 1H), 1.37-1.45 (m, 1H), 1.17 (t, J=7.48 Hz, 3H). MS (ESI+) m/z 475 (M+H)$^-$.

Example A-35

N-(11,13-difluoro-2-methyl-3-oxo-2,3,6,7,8,9-hexahydrobenzo[11,12][1,6]dioxacyclododecino[2,3-b:4,5-c']dipyridin-17-yl)ethanesulfonamide Example A-35a 4-(2-((3-bromo-5-nitropyridin-2-yl)oxy)-3,5-difluorophenyl)butan-1-ol A mixture of Example A-20b (0.40 g, 2.0 mmol), 3-bromo-2-chloro-5-nitropyridine (0.470 g, 2.0 mmol) and cesium carbonate (0.645 g, 2.0 mmol) in DMSO (5.0 mL) under nitrogen was heated at 65° C. for 1 hour. The mixture was partitioned between ethyl acetate and water and the layers separated. The water layer was extracted again with ethyl acetate. The organics were combined, washed with saturated aqueous sodium chloride, dried (anhydrous sodium sulfate), filtered, and concentrated. Purification by flash chromatography (silica gel, 20-50% ethyl acetate in heptanes) afforded the title compound (0.74 g, 93%).

Example A-35b

2'-(2,4-difluoro-6-(4-hydroxybutyl)phenoxy)-4-((2,4-dimethoxybenzyl)oxy)-1-methyl-5'-nitro-[3,3'-bipyridin]-6(1H)-one Example A-35a (0.74 g, 1.835 mmol), Example A-36h (0.810 g, 2.019 mmol), tris(dibenzylideneacetone)dipalladium(0) (0.059 g, 0.064 mmol), tri-tert-butylphosphonium tetrafluoroborate (0.037 g, 0.128 mmol) and cesium fluoride (0.836 g, 5.51 mmol) were combined in anhydrous tetrahydrofuran (9.2 mL), sparged with argon for 10 minutes, and stirred for 18 hours at 50° C. The mixture was cooled, partitioned into ethyl acetate and water and filtered through Celite. The organic layer was washed with saturated aqueous sodium chloride, dried (anhydrous sodium sulfate), treated with 3-mercaptopropyl functionalized silica gel, filtered, and concentrated. Purification by flash chromatography (silica gel, 1-4% methanol in dichloromethane) afforded the title compound (0.41 g, 37%).

Example A-35c

2'-(2,4-difluoro-6-(4-hydroxybutyl)phenoxy)-4-hydroxy-1-methyl-5'-nitro-[3,3'-bipyridin]-6(1H)-one A solution of Example A-35b (0.41 g, 0.686 mmol) in dichloromethane (20 mL) at 0° C. was treated dropwise with a solution of 2,2,2-trifluoroacetic acid (0.529 mL, 6.86 mmol) in dichloromethane (1 mL). The reaction mixture was stirred at 0° C. for 15 minutes and carefully treated with saturated aqueous sodium bicarbonate to a constant pH of 8. The mixture was filtered to remove a white solid. The filtrate layers were separated and the aqueous layer was extracted three times with 50 mL of dichloromethane. The organics were combined, dried over anhydrous sodium sulfate, filtered, and concentrated to afford the title compound (0.324 g, quantitative yield).

Example A-35d 11,13-difluoro-2-methyl-17-nitro-6,7,8,9-tetrahydrobenzo[11,12][1,6]dioxacyclododecino[2,3-b:4,5-c']dipyridin-3(2H)-one A mixture of Example A-35c (0.32 g, 0.715 mmol) in toluene (71.5 mL) under argon was treated with cyanomethylenetributylphosphorane (0.563 mL, 2.146 mmol), stirred at 80° C. for 2 hours and concentrated. Purification by flash chromatography (silica gel, 1-3% methanol in dichloromethane) afforded the title compound (0.10 g, 33%).

Example A-35e 17-amino-11,13-difluoro-2-methyl-6,7,8,9-tetrahydrobenzo[11,12][1,6]dioxacyclododecino[2,3-b:4,5-c']dipyridin-3(2H)-one Example A-35d (0.1 g, 0.233 mmol), iron powder (0.065 g, 1.164 mmol) and ammonia hydrochloride (0.025 g, 0.466 mmol) were combined in tetrahydrofuran (3 mL), ethanol (3.0 mL) and water (1.0 mL) and heated at 90° C. for 2 hours. The mixture was cooled, diluted with tetrahydrofuran and methanol and filtered through Celite to remove solids. The filtrate was concentrated. The residue was partitioned between ethyl acetate and saturated aqueous sodium chloride. The ethyl acetate layer was dried over anhydrous sodium sulfate, filtered and concentrated. Purification by flash chromatography (silica gel, 1-5% methanol in dichloromethane) afforded the title compound (0.075 mg, 81%).

Example A-35f

N-(11,13-difluoro-2-methyl-3-oxo-2,3,6,7,8,9-hexahydrobenzo[11,12][1,6]dioxacyclododecino[2,3-b:4,5-c']dipyridin-17-yl)ethanesulfonamide Example A-35e (0.075 g, 0.188 mmol), ethanesulfonyl chloride (0.072 g, 0.563 mmol) and triethylamine (0.157 mL, 1.127 mmol) were combined in dichloromethane (2.50 mL), and stirred for 1 hour. The mixture was concentrated and azeotroped with dichloromethane. The residue was dissolved in dioxane (5 mL), treated with 1M sodium hydroxide (2 mL) and heated at 80° C. for 1.5 hours, cooled, and partitioned between ethyl acetate and water, adjusting the pH to 8 with 1M HCl. The ethyl acetate layer was washed with saturated aqueous sodium chloride, dried over anhydrous sodium sulfate, filtered, and concentrated. Purification by flash chromatography (silica gel, 1-5% methanol in dichloromethane) afforded the title compound (0.062 g, 67%). $^1$H NMR (500 MHz, DMSO-d$_6$) δ 9.84 (s, 1H), 7.88 (d, J=2.75 Hz, 1H), 7.84 (s, 1H), 7.54 (d, J=2.44 Hz, 1H), 7.17-7.23 (m, 1H), 7.06 (d, J=8.85 Hz, 1H), 5.92 (s, 1H), 4.09-4.16 (m, 2H), 3.41 (s, 3H), 3.12-3.20 (m, 2H), 2.56-2.65 (m, 1H), 2.32-2.39 (m, 1H), 1.65-1.79 (m, 2H), 1.52-1.61 (m, 1H), 1.37-1.47 (m, 1H), 1.25 (t, J=7.32 Hz, 3H). MS (ESI+) m/z 492 (M+H)$^+$.

Example A-36

11-chloro-2-methyl-17-((methylsulfonyl)methyl)-6,7,8,9-tetrahydrodibenzo[4,5:7,8][1,6]dioxacyclodo-decino[3,2-c]pyridin-3(2H)-one

Example A-36a 3-bromo-4-(4-chloro-2-iodophenoxy)benzaldehyde

A mixture of 3-bromo-4-fluorobenzaldehyde (1.015 g, 5 mmol), 4-chloro-2-iodophenol (1.272 g, 5.00 mmol), and cesium carbonate (1.629 g, 5.00 mmol) in DMSO (10 mL) was heated at 90° C. overnight. After cooling to ambient temperature the reaction mixture was partitioned between water and ethyl acetate. The aqueous layer was extracted with additional ethyl acetate three times. The combined organic layers were washed with saturated aqueous sodium chloride, dried over anhydrous magnesium sulfate, filtered, and concentrated. The residue was purified by flash column chromatography on silica gel, eluting with 3:7 ethyl acetate/heptanes to give the title compound (2.05 g, 4.69 mmol, 94% yield).

Example A-36b (3-bromo-4-(4-chloro-2-iodophenoxy)phenyl)methanol

A mixture of Example A-36a (2.01 g, 4.59 mmol) and sodium tetrahydroborate (0.087 g, 2.297 mmol) in tetrahydrofuran (20 mL) was stirred at ambient temperature for three hours. The reaction mixture was quenched with methanol (2 mL). The solvent was evaporated under reduced pressure, and the residue was dissolved in ethyl acetate. The organic layer was washed with saturated aqueous sodium chloride, dried over anhydrous magnesium sulfate, filtered, and concentrated. The residue was purified by flash column chromatography on silica gel, eluting with 1:1 ethyl acetate/heptanes to give the title compound (2.0 g, 4.55 mmol, 99% yield).

Example A-36c 2-bromo-4-(bromomethyl)-1-(4-chloro-2-iodophenoxy)benzene

A mixture of Example A-36b (2.12 g, 4.82 mmol), and lithium bromide (0.461 g, 5.31 mmol) in dimethylformamide (20 mL) was cooled to 0° C. To this solution was added tribromophosphine (0.500 mL, 5.31 mmol). The reaction mixture was stirred at ambient temperature for 3 hours. The reaction mixture was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by flash column chromatography on silica gel, eluting with 1:10 ethyl acetate/heptanes to give the title compound (2.2 g, 4.38 mmol, 91% yield).

Example A-36d 2-bromo-1-(4-chloro-2-iodophenoxy)-4-((methylsulfonyl)methyl)benzene A mixture of Example A-36c (2.12 g, 4.22 mmol), and sodium methanesulfinate (0.646 g, 6.33 mmol), in dimethylformamide (20 mL) was heated at 65° C. for 3 hours. After cooling to ambient temperature the reaction mixture was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by flash column chromatography on silica gel, eluting with 1:1 ethyl acetate/heptanes to give the title compound (2.05 g, 4.09 mmol, 97% yield).

Example A-36e 4-(2-(2-bromo-4-((methylsulfonyl)methyl)phenoxy)-5-chlorophenyl)but-3-yn-1-ol Example A-36e was prepared according to the procedure used for the preparation of Example A-1h, substituting but-3-yn-1-ol for prop-2-yn-1-ol, and Example A-36d for Example A-1g, respectively, to provide the title compound.

Example A-36f 4-(2-(2-bromo-4-((methylsulfonyl)methyl)phenoxy)-5-chlorophenyl)butan-1-ol Example A-36f was prepared according to the procedure used for the preparation of Example A-1i, substituting Example A-36e for Example A-1h, to provide the title compound.

Example A-36g

Example A-36g was prepared according to the procedure used for the preparation of Example A-22a, substituting (2,4-dimethoxyphenyl)methanol for but-3-en-1-ol, to provide the title compound.

Example A-36h 4-((2,4-dimethoxybenzyl)oxy)-1-methyl-5-(4,4,5,5-tetramethyl-1,3,2-dioxaborolan-2-yl)pyridin-2(1H)-one A 250 mL flask was charged with Example A-36g (8.416 g, 23.76 mmol), 4,4,4',4',5,5,5',5'-octamethyl-2,2'-bi(1,3,2-dioxaborolane) (9.05 g, 35.6 mmol), dicyclohexyl(2',4',6'-triisopropyl-[1,1'-biphenyl]-2-yl)phosphine (1.133 g, 2.376 mmol), potassium acetate (dried in vacuo at 60° C. for 18 hours, 5.36 g, 54.6 mmol), and tris(dibenzylideneacetone)dipalladium (0.544 g, 0.594 mmol). The solids were sparged with argon for 5 minutes, and dioxane (80 mL) that was degassed by argon for 15 minutes, was added. The mixture was degassed with argon for 10 minutes and heated at 80° C. overnight under nitrogen. The reaction mixture was concentrated on to silica gel (200 g). This material was loaded on to a funnel plug of silica gel (700 mL) and eluted with a 0-10% methanol/dichloromethane gradient. The fractions containing the title compound were combined and concentrated. The resulting material was triturated in diethyl ether (300 mL) and the resulting solid was purified by flash chromatography (silica gel, 0-3% methanol in dichloromethane) to give the title compound (5.71 g, 60% yield).

Example A-36i 5-(2-(4-chloro-2-(4-hydroxybutyl)phenoxy)-5-((methylsulfonyl)methyl)phenyl)-4-((2,4-dimethoxybenzyl)oxy)-1-methylpyridin-2(1H)-one Example A-36i was prepared according to the procedure used for the preparation of Example A-1f, substituting Example A-36f for Example A-1b, and Example A-36h for Example A-1e, respectively, to provide the title compound.

Example A-36j 5-(2-(4-chloro-2-(4-hydroxybutyl)phenoxy)-5-((methylsulfonyl)methyl)phenyl)-4-hydroxy-1-methylpyridin-2(1H)-one A mixture of Example A-36i (0.37 g, 0.58 mmol), and trifluoroacetic acid (1.78 mL, 23.1 mmol) in dichloromethane (10 mL) was stirred at ambient temperature for 2 hours. The reaction mixture was partitioned between water and ethyl acetate. The aqueous layer was extracted with additional ethyl acetate twice. The combined organic layers were washed with saturated aqueous sodium chloride, dried over anhydrous magnesium sulfate, filtered, and concentrated. The residue was purified by flash column chromatography (silica gel, 15% methanol in ethyl acetate) to give the title compound (0.16 g, 56% yield).

Example A-36k 11-chloro-2-methyl-17-[(methylsulfonyl)methyl]-6,7,8,9-tetrahydrodibenzo[4,5:7,8][1,6]dioxacyclododecino[3,2-c]pyridin-3(2H)-one Example A-36j (0.16 g, 0.325 mmol) in toluene (25 mL) was treated with (cyanomethylene)trimethylphosphorane (1.626 mL, 0.5 M in tetrahydrofuran, 0.813 mmol). The reaction flask was capped and heated at 60° C. overnight. Tetrahydrofuran (5 mL) and additional cyanomethylenetrimethylphosphorane (3.25 mL, 0.5 M in tetrahydrofuran, 1.62 mmol) was added. The reaction mixture was heated at 65° C. for 6 hours. The solvent was evaporated under reduced pressure, and the residue was purified by flash column chromatography in silica gel, eluting with 10% methanol in ethyl acetate to give about 0.04 g of crude product. The crude product was further purified by Preparative HPLC (C18, 10-70% acetonitrile/water (0.1% TFA)) to give the title compound (0.030 g, 19% yield). $^1$H NMR (500 MHz, DMSO-d$_6$) δ 7.66 (s, 1H), 7.47 (d, J=2.75 Hz, 1H), 7.33 (dd, J=8.54, 2.44 Hz, 1H), 7.26-7.29 (m, 2H), 7.11 (d, J=8.54 Hz, 1H), 6.52-6.54 (m, 1H), 5.88 (s, 1H), 4.36-4.48 (m, 2H), 4.09-4.11 (m, 2H), 3.42 (s, 3H), 2.94 (s, 3H), 2.43-2.51 (m, 2H), 1.70 (m, 3H), 1.36 (m, 1H). MS (ESI+) m/z 474.1 (M+H)$^+$.

Example A-37

N-[2-methyl-3-oxo-11-(trifluoromethoxy)-2,3,6,7,8,9-hexahydrodibenzo[4,5:7,8][1,6]dioxacyclododecino[3,2-c]pyridin-17-yl]ethanesulfonamide Example A-37 was prepared according to the procedure used for the preparation of Example A-5f, substituting Example A-30e for Example A-5e, to provide the title compound. $^1$H NMR (400 MHz, CD$_3$OD) δ 7.60 (s, 1H), 7.25 (d, J=2.4 Hz, 1H), 7.21-7.08 (m, 4H), 6.50 (d, J=8.8 Hz, 1H), 6.01 (s, 1H), 4.19-4.17 (m, 2H), 3.56 (s, 3H), 3.08 (q, J=7.4 Hz, 2H), 2.58-2.54 (m, 2H), 1.85-1.81 (m, 3H), 1.51-1.38 (m, 1H), 1.32 (t, J=8.0 Hz, 3H). MS (ESI+) m/z 539.2 (M+H)$^+$.

Example A-38

11-chloro-2-methyl-3-oxo-2,3,6,7,8,9-hexahydrobenzo[11,12][1,6]dioxacyclododecino[2,3-b:4,5-c']dipyridine-17-carboxylic acid The product from Example A-31c (0.6 g, 1.361 mmol) and lithium hydroxide (0.326 g, 13.61 mmol) were combined in a solvent mixture of dioxane (15 mL) and water (15 mL) and heated at 50° C. for 2 hours. The mixture was cooled, diluted into ethyl acetate and the pH was carefully adjusted to pH 3 by addition of 2.5 M aqueous HCl. The aqueous layer was extracted three times with ethyl acetate. The organics were combined, washed with a minimal volume of saturated aqueous sodium chloride, dried over anhydrous sodium sulfate, filtered and concentrated to afford the title compound (0.55 g, 95%). $^1$H NMR (400 MHz, DMSO-d$_6$) δ 13.21 (s, 1H), 8.57 (d, J=2.44 Hz, 1H), 8.14 (d, J=2.14 Hz, 1H), 7.83 (s, 1H), 7.41 (d, J=2.44 Hz, 1H), 7.30 (dd, J=8.70, 2.59 Hz, 1H), 7.11 (d, J=8.54 Hz, 1H), 5.92 (s, 1H), 4.11 (d, J=5.19 Hz, 2H), 3.41 (s, 3H), 2.54-2.61 (m, 1H), 2.25-2.38 (m, 1H), 1.57-1.78 (m, 3H), 1.35-1.45 (m, 1H). MS (ESI+) m/z 427 (M+H)$^+$.

Example A-39

11-chloro-17-(hydroxymethyl)-2-methyl-6,7,8,9-tetrahydrobenzo[11,12][1,6]dioxacyclododecino[2,3-b:4,5-c']dipyridin-3(2H)-one To a solution of Example A-38 (0.3 g, 0.703 mmol) in tetrahydrofuran (14.1 mL) under nitrogen was added dropwise borane-tetrahydrofuran complex (1.0 M, 2.81 mL, 2.81 mmol). The reaction mixture was stirred at 50° C. for 24 hours, cooled, carefully quenched with methanol until bubbling subsided, heated at 50° C. for 1 hour, cooled, and concentrated. Purification by flash chromatography (silica gel, 1-5% methanol in dichloromethane) afforded the title compound (0.12 g, 41%). $^1$H NMR (500 MHz, DMSO-d$_6$) δ 7.94 (d, J=2.14 Hz, 1H), 7.73 (s, 1H), 7.64 (d, J=2.44 Hz, 1H), 7.37 (d, J=2.75 Hz, 1H), 7.27 (dd, J=8.54, 2.75 Hz, 1H), 7.06 (d, J=8.55 Hz, 1H), 5.90 (s, 1H), 5.25 (t, J=5.34 Hz, 1H), 4.47 (d, J=5.19 Hz, 2H), 4.10 (d, J=6.41 Hz, 2H), 3.41 (s, 3H), 2.53-2.57 (m, 1H), 2.29-2.37 (m, 1H), 1.57-1.76 (m, 3H), 1.36-1.42 (m, 1H). MS (ESI+) m/z 413 (M+H)$^+$.

Example A-40

11-chloro-2-methyl-17-((methylsulfonyl)methyl)-6,7,8,9-tetrahydrobenzo[11,12][1,6]dioxacyclododecino[2,3-b:4,5-c']dipyridin-3(2H)-one

Example A-40a 17-(bromomethyl)-11-chloro-2-methyl-6,7,8,9-tetrahydrobenzo[11,12][1,6]dioxacyclododecino[2,3-b:4,5-c']dipyridin-3(2H)-one To a solution of Example A-39 (0.100 g, 0.242 mmol) in dichloromethane (4.84 mL) was added dropwise phosphorous tribromide (0.023 mL, 0.242 mmol). The reaction mixture was stirred for 2 hours at ambient temperature, and diluted with ice water. The pH of the reaction mixture was adjusted to 9 with saturated aqueous sodium bicarbonate. The aqueous layer was extracted 3 times with ethyl acetate. The organics were combined, washed with saturated aqueous sodium chloride, dried over anhydrous sodium sulfate, filtered, and concentrated to afford the title compound (0.077 g, 67%).

Example A-40b 11-chloro-2-methyl-17-((methylsulfonyl)methyl)-6,7,8,9-tetrahydrobenzo[11,12][1,6]dioxacyclododecino[2,3-b:4,5-c']dipyridin-3(2H)-one To a solution of Example A-40a (0.077 g, 0.162 mmol) in dimethylformamide (0.809 mL) was added sodium methanesulfinate (0.025 g, 0.243 mmol). The mixture was heated at 60° C. for 1 hour and then stirred at ambient temperature for 18 hours. The mixture was diluted with 20 mL of water and the resulting white solid was collected by filtration and dried to afford the title compound (0.081 g, 100%). $^1$H NMR (400 MHz, DMSO-$d_6$) δ 8.02 (d, J=2.14 Hz, 1H), 7.72-7.75 (m, 2H), 7.39 (d, J=2.75 Hz, 1H), 7.28 (dd, J=8.54, 2.75 Hz, 1H), 7.07-7.11 (d, J=8.54 Hz, 1H), 5.92 (s, 1H), 4.40-4.58 (m, 2H), 4.09-4.15 (m, 2H,) 3.42 (s, 3H), 3.00 (s, 3H), 2.53-2.59 (m, 1H), 2.29-2.37 (m, 1H), 1.55-1.82 (m, 3H), 1.34-1.44 (m, 1H). MS (ESI+) m/z 475 (M+H)$^+$.

Example A-41

N-(3-chloro-12-methyl-11-oxo-5,6,7,8,11,12-hexahydrobenzo[4,5][1,6]dioxacyclododecino[7,8-b:3,2-c']dipyridin-15-yl)ethanesulfonamide

Example A-41a 4-(but-3-en-1-yloxy)-5-(2-fluoro-5-nitrophenyl)-1-methylpyridin-2(1H)-one In an oven dried flask, a mixture of Example A-22a (500 mg, 1.94 mmol), (2-fluoro-5-nitrophenyl)boronic acid (716 mg, 3.87 mmol), and cesium fluoride (880 mg, 5.79 mmol) was stirred under of flow of nitrogen for 12 minutes. Tetrahydrofuran (10 mL) was added and nitrogen was bubbled through the solution for 10 minutes. Tri-tert-butylphosphonium tetrafluoroborate (40 mg, 0.138 mmol) and tris(dibenzylideneacetone)dipalladium(0) (62 mg, 0.068 mmol) were added and nitrogen was bubbled through the solution for another 6 minutes. The reaction mixture was stirred at 45° C. for 16 hours. Water and ethyl acetate were added and the layers were separated. The aqueous layer was extracted three more times with ethyl acetate. The combined ethyl acetate extracts were washed with water, saturated aqueous sodium chloride, dried (anhydrous magnesium sulfate), filtered, and concentrated. The residue was absorbed onto silica gel and was purified by flash chromatography (silica gel, eluting with heptanes containing a gradient with ethyl acetate, 20% to 100%) to provide the title compound.

Example A-41b 4-(but-3-en-1-yloxy)-5-(2-hydroxy-5-nitrophenyl)-1-methylpyridin-2(1H)-one Sodium hydroxide (1.2 mL, 2M, 2.400 mmol) was added to a solution of Example A-41a (370 mg, 1.16 mmol) and DMSO (6.0 mL). The reaction mixture was stirred at 90° C. for 2 hours. The reaction mixture was cooled to room temperature and HCl (25 mL, 0.5 N) was added slowly with rapid stirring. The mixture was stirred for 2 hours. The resulting solid was filtered, rinsed with water and was dried (in-vacuo). The crude product was triturated with 25 mL of a solution of 1:1 diethyl ether/heptane, filtered, and dried to provide the title compound.

Example A-41c 5-(2-((3-bromo-5-chloropyridin-2-yl)oxy)-5-nitrophenyl)-4-(but-3-en-1-yloxy)-1-methylpyridin-2(1H)-one In a sealed tube, a solution of Example A-41b (121 mg, 0.383 mmol), 3-bromo-5-chloro-2-fluoropyridine (162 mg, 0.770 mmol), cesium carbonate (125 mg, 0.383 mmol) and DMSO (2.5 mL) was stirred at 85° C. for 18 hours, and then at 95° C. for 6 hours. The reaction mixture was cooled to room temperature and HCl (15 mL 0.5 N) was added. The mixture was extracted with ethyl acetate. The ethyl acetate layer was washed with water, saturated aqueous sodium chloride, dried (anhydrous magnesium sulfate), filtered, and concentrated. The crude product was absorbed onto silica gel and was purified by flash chromatography (silica gel, eluting with heptane containing a gradient with ethyl acetate, 20% to 100%) to provide the title compound.

Example A-41d 5-(5-amino-2-((3-bromo-5-chloropyridin-2-yl)oxy)phenyl)-4-(but-3-en-1-yloxy)-1-methylpyridin-2(1H)-one A suspension of Example A-41c (210 mg, 0.414 mmol), iron powder (112 mg, 2.01 mmol), ammonia hydrochloride (22 mg, 0.411 mmol), ethanol (11 mL), tetrahydrofuran (4.5 mL) and water (2.7 mL) was stirred at 85° C. for 2 hours. Another 60 mg of iron powder (1.07 mmol) was added, and the reaction mixture was stirred at 85° C. for 1 hour. The warm reaction mixture was filtered through Celite. The filter pad was washed well with ethanol followed by tetrahydrofuran. The filtrate was concentrated and the residue was partitioned between ethyl acetate and water. The layers were separated and the organic layer was washed with saturated aqueous sodium chloride, dried (anhydrous magnesium sulfate), filtered, and evaporated to provide the title compound.

Example A-41e 15-amino-3-chloro-12-methyl-7,8-dihydrobenzo[4,5][1,6]dioxacyclododecino[7,8-b:3,2-c']dipyridin-11(12H)-one A solution of Example A-41d (200 mg, 0.420 mmol), tri-o-tolylphosphine (18.4 mg, 0.060 mmol), diacetoxypalladium (7.6 mg, 0.034 mmol), triethylamine (0.37 mL, 2.65 mmol) and acetonitrile (12.4 mL) was degassed by bubbling nitrogen through the solution. The solution was then heated in a microwave reactor at 150° C. for 15 minutes. The solvent was evaporated and water/ethyl acetate was added to the residue. The aqueous layer was extracted three times with ethyl acetate. The combined extracts were washed with water, saturated aqueous sodium chloride, dried (anhydrous magnesium sulfate), filtered, and evaporated. The crude product was absorbed on silica gel and purified by flash chromatography (silica gel, eluting with dichloromethane containing a gradient with methanol, 0% to 9%) to provide the title compound as a mixture of E and Z isomers.

Example A-41f 15-amino-3-chloro-12-methyl-5,6,7,8-tetrahydrobenzo[4,5][1,6]dioxacyclododecino[7,8-b:3,2-c']dipyridin-11(12H)-one A solution of Example A-41e (35 mg, 0.088 mmol) and tetrahydrofuran (10 mL) was added to 5% Pt/C wet (42.0 mg, 0.088 mmol) in a 50 mL pressure bottle and was stirred for 45 minutes at 30 psi hydrogen at room temperature. The mixture was filtered through a nylon membrane and was concentrated to dryness. The crude product was purified by flash chromatography (silica gel, eluting with heptane containing a gradient with a solution of 3:1 ethyl acetate:ethanol, 20% to 90%) to provide the title compound.

Example A-41g

N-(3-chloro-12-methyl-11-oxo-5,6,7,8,11,12-hexahydrobenzo[4,5][1,6]dioxacyclododecino[7,8-b:3,2-c']dipyridin-15-yl)ethanesulfonamide Using the procedure described for Example A-5f and substituting Example A-41f for Example A-5e provided the title compound. $^1$H NMR (400 MHz, DMSO-$d_6$) δ 9.61 (s, 1H), 8.19 (d, J=2.6 Hz, 1H), 7.97 (d, J=2.7 Hz, 1H), 7.67 (s, 1H), 7.09 (dt, J=7.2, 2.7 Hz, 2H), 6.82 (d, J=8.8 Hz, 1H), 5.87 (s, 1H), 4.14 (s, 2H), 3.40 (s, 3H), 3.18-2.99 (m, 2H), 2.48-2.40 (m, 1H), 1.78 (s, 1H), 1.70 (s, 2H), 1.55 (s, 1H), 1.23 (t, J=7.3 Hz, 3H). MS (ESI+) m/z 490.1 (M+H)$^+$.

Example A-42

17-(ethylsulfonyl)-2-methyl-6,7,8,9-tetrahydrobenzo[4,5][1,6]dioxacyclododecino[3,2-c:7,8-c']dipyridin-3(2H)-one Example A-42a 5-(5-(ethylsulfonyl)-2-fluorophenyl)-4-(4-(3-methoxypyridin-4-yl)butoxy)-1-methylpyridin-2(1H)-one Example A-42a was prepared according to the procedure used for the preparation of Example A-1f, substituting Example A-26b for Example A-1b, to provide the title compound.

Example A-42b 5-(5-(ethylsulfonyl)-2-fluorophenyl)-4-(4-(3-hydroxypyridin-4-yl)butoxy)-1-methylpyridin-2(1H)-one Example A-42b was prepared according to the procedure used for the preparation of Example A-26e, substituting Example A-42a for Example A-26d, to provide the title compound.

Example A-42c 17-(ethylsulfonyl)-2-methyl-6,7,8,9-tetrahydrobenzo[4,5][1,6]dioxacyclododecino[3,2-c:7,8-c']dipyridin-3(2H)-one Example A-42c was prepared according to the procedure used for the preparation of Example A-26f, substituting Example A-42b for Example A-26e, to provide the title compound. The crude product was further purified by reverse phase Preparative HPLC (C18, 10-70% acetonitrile/water (0.1% TFA)) to provide the title compound as TFA salt. $^1$H NMR (500 MHz, DMSO-$d_6$) δ 8.52-8.53 (m, 2H), 7.78-7.81 (m, 3H), 7.63 (d, J=4.88 Hz, 1H), 6.80-6.82 (m, 1H), 5.92 (s, 1H), 4.10-4.18 (m, 2H), 3.44 (s, 3H), 3.31 (q, J=7.32 Hz, 2H), 2.48-2.62 (m, 2H), 1.70-1.80 (m, 3H), 1.37-1.43 (m, 1H), 1.15 (t, J=7.32 Hz, 3H). MS (ESI+) m/z 441.2 (M+H)$^+$.

Example A-43

11,13-difluoro-2-methyl-17-((methylsulfonyl)methyl)-6,7,8,9-tetrahydrobenzo[11,12][1,6]dioxacyclododecino[2,3-b:4,5-c']dipyridin-3(2H)-one Example A-43a methyl 5-bromo-6-(2,4-difluoro-6-(4-hydroxybutyl)phenoxy)nicotinate Example A-20b (3.40 g, 16.8 mmol), methyl 5-bromo-6-chloronicotinate (4.21 g, 16.8 mmol) and cesium carbonate (5.48 g, 16.8 mmol) were combined in dimethyl sulfoxide (42 mL). The reaction mixture was heated at 90° C. for 1 hour, cooled to ambient temperature, and partitioned with ethyl acetate and water. The organic layer was washed with saturated aqueous sodium chloride, dried with anhydrous sodium sulfate, filtered, and concentrated. The residue was purified by flash chromatography (silica gel, 2-4% methanol in dichloromethane) to provide the title compound (5.08 g, 73%).

Example A-43b methyl 5-bromo-6-(2-(4-((tert-butyldimethylsilyl)oxy)butyl)-4,6-difluorophenoxy)nicotinate Example A-43a (4.80 g, 11.5 mmol), tert-butylchlorodimethylsilane (2.08 g, 13.8 mmol) and imidazole (1.57 g, 23.1 mmol) were combined in dimethylformamide (30 mL). The reaction mixture was stirred at room temperature for 16 hours and then partitioned with ethyl acetate and water. The organic layer was washed with saturated aqueous sodium chloride twice, dried with anhydrous sodium sulfate, filtered and concentrated. The residue was purified by flash chromatography (silica gel, 10-20% ethyl acetate in heptanes) to provide the title compound (5.43 g, 89%).

Example A-43c (5-bromo-6-(2-(4-((tert-butyldimethylsilyl)oxy)butyl)-4,6-difluorophenoxy)pyridin-3-yl)methanol A solution of Example A-43b (5.30 g, 10.0 mmol) in tetrahydrofuran (40 mL) at 0° C. was treated with 1.0 M diisobutylaluminum hydride in tetrahydrofuran (30.0 mL, 30.0 mmol). The reaction mixture was stirred at room temperature for 2 hours, cooled to 0° C. and additional 1.0 M diisobutylaluminum hydride in tetrahydrofuran (30.0 mL, 30.0 mmol) was added. The reaction mixture was stirred at room temperature for 2 hours, cooled to 0° C. and additional 1.0 M diisobutylaluminum hydride in tetrahydrofuran (30.0 mL, 30.0 mmol) was added again. The resulting reaction mixture was stirred at room temperature for another 2 hours. The volume of solvent was reduced to half by evaporation. The resulting reaction mixture was cooled to 0° C., quenched with saturated aqueous sodium potassium tartrate, stirred vigorously for 1 hour, and extracted with ethyl acetate twice. The combined organic layers were washed with saturated aqueous sodium chloride, dried with anhydrous sodium sulfate, filtered and concentrated. The residue was purified by flash chromatography (silica gel, 10-40% ethyl acetate in heptanes) to provide the title compound (4.41 g, 88%).

Example A-43d 3-bromo-2-(2-(4-((tert-butyldimethylsilyl)oxy)butyl)-4,6-difluorophenoxy)-5-((methylsulfonyl)methyl)pyridine Example A-43c (3.70 g, 7.36 mmol), triethylamine (2.05 mL, 14.7 mmol) and methanesulfonyl chloride (0.631 mL, 8.10 mmol) were combined in dimethylformamide (30 mL). The reaction mixture was stirred at room temperature for 2 hours. To this reaction mixture was added triethylamine (1.03 mL, 7.36 mmol) and methanesulfonyl chloride (0.287 mL, 3.68 mmol) again. The resulting reaction mixture was stirred at room temperature for an additional 1 hour. To this reaction mixture was added sodium methanesulfinate (1.50 g, 14.7 mmol), and the reaction mixture was heated at 60° C. for 2 hours. The mixture was then cooled to ambient temperature and partitioned with ethyl acetate and water. The organic layer was washed with saturated aqueous sodium chloride, dried with anhydrous sodium sulfate, filtered and concentrated. The residue was purified by flash chromatography (silica gel, 10-40% ethyl acetate in heptanes) to provide the title compound (2.31 g, 56%).

Example A-43e

2'-(2-(4-(((tert-butyldimethylsilyl)oxy)butyl)-4,6-difluorophenoxy)-4-((2,4-dimethoxybenzyl)oxy)-1-methyl-5'-((methylsulfonyl)methyl)-[3,3'-bipyridin]-6(1H)-one Example A-43d (2.20 g, 3.90 mmol), Example A-36h (2.81 g, 7.01 mmol), potassium phosphate (2.90 g, 13.6 mmol), tris(dibenzylideneacetone)dipalladium(0) (0.107 g, 0.117 mmol) and 1,3,5,7-tetramethyl-6-phenyl-2,4,8-trioxa-6-phosphaadamantane (0.103 g, 0.351 mmol) were combined and purged with nitrogen for 15 minutes. A mixture of dioxane (16 mL) and water (4 mL) was purged with nitrogen for 15 minutes and transferred to the reaction vessel. The reaction mixture was heated at 60° C. for 8 hours, cooled to ambient temperature, and partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 60-100% ethyl acetate in heptanes) to provide the title compound (2.21 g, 75%).

Example A-43f

2'-(2,4-difluoro-6-(4-hydroxybutyl)phenoxy)-4-hydroxy-1-methyl-5'-((methylsulfonyl)methyl)-[3,3'-bipyridin]-6(1H)-one To a solution of Example A-43e (2.16 g, 2.85 mmol) in dichloromethane (80 mL) at 0° C. was added 2,2,2-trifluoroacetic acid (1.10 mL, 14.3 mmol) dropwise. The reaction mixture was stirred at 0° C. for 3 hours, and the pH was carefully adjusted to 7 by the addition of saturated aqueous sodium bicarbonate. The mixture was filtered and the aqueous layer was extracted with dichloromethane five times. The combined organic layers were dried with anhydrous sodium sulfate, filtered, and concentrated. The residue was purified by flash chromatography (silica gel, 2-6% methanol in dichloromethane) to provide the title compound (0.929 g, 66%).

Example A-43g 11,13-difluoro-2-methyl-17-((methylsulfonyl)methyl)-6,7,8,9-tetrahydrobenzo[11,12][1,6]dioxacyclododecino[2,3-b:4,5-c']dipyridin-3(2H)-one Example A-43f (861 mg, 1.74 mmol) and cyanomethylenetributylphosphorane (1.37 mL, 5.22 mmol) were combined in dioxane (170 mL). The reaction mixture was heated at 80° C. for 1 hour. To this reaction mixture was added cyanomethylenetributylphosphorane (0.457 mL, 1.74 mmol) again, and the mixture was heated at 80° C. for another 2 hours, cooled to ambient temperature, and then concentrated. The residue was purified by flash chromatography (silica gel, 2-6% methanol in dichloromethane) and the resulting product was further purified by trituration with dichloromethane to provide the title compound (0.436 g, 53%). $^1$H NMR (400 MHz, DMSO-$d_6$) δ ppm 8.04 (d, J=2.2 Hz, 1H), 7.83 (s, 1H), 7.75 (d, J=2.2 Hz, 1H), 7.27-7.17 (m, 1H), 7.11-7.04 (m, 1H), 5.93 (s, 1H), 4.62-4.44 (m, 2H), 4.18-4.10 (m, 2H), 3.42 (s, 3H), 3.01 (s, 3H), 2.69-2.56 (m, 1H), 2.42-2.32 (m, 1H), 1.83-1.66 (m, 2H), 1.65-1.51 (m, 1H), 1.50-1.37 (m, 1H). (ESI+) m/z 477 (M+H)$^+$.

Example A-44

N-(12-chloro-2-methyl-3-oxo-2,3,6,7,8,9-hexahydrodibenzo[4,5:7,8][1,6]dioxacyclododecino[3,2-c]pyridin-17-yl)methanesulfonamide Example A-44a 4-chloro-5-(2-(5-chloro-2-iodophenoxy)-5-nitrophenyl)-1-methylpyridin-2(1H)-one Example A-44a was prepared according to the procedure used for the preparation of Example A-5b, substituting 5-chloro-2-iodophenol for 4-chloro-2-iodophenol, to provide the title compound.

Example A-44b 5-(5-amino-2-(5-chloro-2-iodophenoxy)phenyl)-4-chloro-1-methylpyridin-2(1H)-one Example A-44b was prepared according to the procedure used for the preparation of Example A-15a, substituting Example A-44a for Example A-5b, to provide the title compound.

Example A-44c 5-(5-amino-2-(5-chloro-2-iodophenoxy)phenyl)-4-(but-3-en-1-yloxy)-1-methylpyridin-2(1H)-one Example A-44c was prepared according to the procedure used for the preparation of Example A-22a, substituting Example A-44b for Example A-1b, to provide the title compound.

Example A-44d (E)-17-amino-12-chloro-2-methyl-6,7-dihydrodibenzo[4,5:7,8][1,6]dioxacyclododecino[3,2-c]pyridin-3(2H)-one Example A-44d was prepared according to the procedure used for the preparation of Example A-15d, substituting Example A-44c for Example A-15c, to provide the title compound.

Example A-44e 17-amino-12-chloro-2-methyl-6,7,8,9-tetrahydrodibenzo[4,5:7,8][1,6]dioxacyclododecino[3,2-c]pyridin-3(2H)-one Example A-44e was prepared according to the procedure used for the preparation of Example A-1i, substituting Example A-44d for Example A-1h, to provide the title compound.

Example A-44f

N-(12-chloro-2-methyl-3-oxo-2,3,6,7,8,9-hexahydrodibenzo[4,5:7,8][1,6]dioxacyclododecino[3,2-c]pyridin-17-yl)methanesulfonamide Example A-44f was prepared according to the procedure used for the preparation of Example A-5f, substituting Example A-44e for Example A-5e, and methanesulfonyl chloride for ethanesulfonyl chloride, respectively, to provide the title compound. $^1$H NMR (400 MHz, CD$_3$OD) δ 7.62 (s, 1H), 7.31 (d, J=8.2 Hz, 1H), 7.23-7.11 (m, 3H), 7.07-7.05 (m, 1H), 6.53 (d, J=8.4 Hz, 1H), 6.01 (s, 1H), 4.20-4.16 (m, 2H), 3.57 (s, 3H), 2.96 (s, 3H), 2.56-2.52 (m, 2H), 1.87-1.81 (m, 3H), 1.47-1.42 (m, 1H). MS (ESI+) m/z 475.1 (M+H)$^-$.

Example A-45

N-(11-cyano-2-methyl-3-oxo-2,3,6,7,8,9-hexahydrodibenzo[4,5:7,8][1,6]dioxacyclododecino[3,2-c]pyridin-17-yl)ethanesulfonamide A mixture of Example A-9 (180 mg, 0.368 mmol), potassium hexacyanoferrate(II) trihydrate (39 mg, 0.092 mmol), tris(dibenzylideneacetone)dipalladium(0) (16.85 mg, 0.018 mmol), dicyclohexyl(2',4',6'-triisopropyl-[1,1'-biphenyl]-2-yl)phosphine (8.77 mg, 0.018 mmol), palladium(II) acetate (4.13 mg, 0.018 mmol) and cesium carbonate (180 mg, 0.552 mmol) in dioxane (8 mL) and water (2.000 mL) was sealed and heated at 130° C. in a microwave reactor for 3 hours. The reaction mixture was cooled and filtered through Celite. The filtrate was washed with ethyl acetate and then concentrated. The residue was purified by reverse phase Prep HPLC (C18, 25-55% acetonitrile/0.1N NH$_4$CO$_3$ water) to give the title compound (89 mg, 0.186 mmol, 50.4% yield). $^1$H NMR (400 MHz, DMSO-d$_6$) δ 9.67 (s, 1H), 7.89 (d, J=2.1 Hz, 1H), 7.76 (dd, J=8.4, 2.1 Hz, 1H), 7.69 (s, 1H), 7.27 (d, J=8.4 Hz, 1H), 7.13-7.04 (m, 2H), 6.57-6.49 (m, 1H), 5.88 (s, 1H), 4.15-4.07 (m, 2H), 3.41 (s, 3H), 3.15-3.04 (m, 2H), 2.54-2.51 (m, 2H), 1.76-1.64 (m, 3H), 1.44-1.35 (m, 1H), 1.22 (t, J=7.3 Hz, 3H). MS (ESI+) m/z 480.1 (M+H)$^+$.

Example A-46

N-(12-methyl-11-oxo-5,6,7,8,11,12-hexahydrobenzo[4,5][1,6]dioxacyclododecino[7,8-b:3,2-c']dipyridin-15-yl)ethanesulfonamide

Example A-46a 15-amino-12-methyl-5,6,7,8-tetrahydrobenzo[4,5][1,6]dioxacyclododecino[7,8-b:3,2-c']dipyridin-11(12H)-one A solution of Example A-41f (30 mg, 0.076 mmol) in tetrahydrofuran (10 mL) was added to a suspension of 5% Pd/C (wet, 6 mg, 0.025 mmol) and triethylamine (0.021 mL, 0.152 mmol) in a 50 mL pressure bottle. The reaction mixture was stirred at room temperature for 48 hours at 30 psi of hydrogen gas. The reaction mixture was filtered and the filtrate was concentrated to dryness to provide the title compound.

Example A-46b

N-(12-methyl-11-oxo-5,6,7,8,11,12-hexahydrobenzo[4,5][1,6]dioxacyclododecino[7,8-b:3,2-c']dipyridin-15-yl)ethanesulfonamide Using the procedure described for Example A-5f and substituting Example A-46a for Example A-5e provided the title compound as TFA salt. $^1$H NMR (500 MHz, DMSO-d$_6$) δ 9.63 (s, 1H), 8.16 (dd, J=4.8, 1.9 Hz, 1H), 7.80 (dd, J=7.4, 1.8 Hz, 1H), 7.68 (s, 1H), 7.20 (dd, J=7.3, 4.9 Hz, 1H), 7.14 7.00 (m, 2H), 6.78 (d, J=8.8 Hz, 1H), 5.88 (s, 1H), 4.14 (s, 2H), 3.40 (s, 3H), 3.14 3.06 (m, 2H), 2.62 2.52 (m, 1H), 2.40 (d, J=33.7 Hz, 1H), 1.79 (s, 1H), 1.69 (d, J=8.9 Hz, 2H), 1.53 (s, 1H), 1.27 1.20 (m, 3H). MS (ESI+) m/z 456.2 (M+H)$^+$.

Example A-47

N-(11-cyano-2-methyl-3-oxo-2,3,6,7,8,9-hexahydrodibenzo[4,5:7,8][1,6]dioxacyclododecino[3,2-c]pyridin-17-yl)methanesulfonamide

Example A-47a

N-(11-chloro-2-methyl-3-oxo-2,3,6,7,8,9-hexahydrodibenzo[4,5:7,8][1,6]dioxacyclododecino[3,2-c]pyridin-17-yl)methanesulfonamide Example A-47a was prepared according to the procedure used for the preparation of Example A-5f, substituting Example A-8c for Example A-5e, and methanesulfonyl chloride for ethanesulfonyl chloride, respectively, to provide the title compound.

Example A-47b

N-(11-cyano-2-methyl-3-oxo-2,3,6,7,8,9-hexahydrodibenzo[4,5:7,8][1,6]dioxacyclododecino[3,2-c]pyridin-17-yl)methanesulfonamide Example A-47b was prepared according to the procedure used for the preparation of Example A-45, substituting Example A-47a for Example A-9, to provide the title compound. $^1$H NMR (400 MHz, DMSO-$d_6$) δ 9.61 (s, 1H), 7.90 (d, J=2.0 Hz, 1H), 7.76 (dd, J=8.4, 2.1 Hz, 1H), 7.70 (s, 1H), 7.27 (d, J=8.4 Hz, 1H), 7.13-7.06 (m, 2H), 6.54 (d, J=9.4 Hz, 1H), 5.88 (s, 1H), 4.15-4.08 (m, 2H), 3.41 (s, 3H), 2.99 (s, 3H), 2.56-2.52 (m, 2H), 1.77-1.63 (m, 3H), 1.46-1.33 (m, 1H). MS (ESI+) m/z 466.1 (M+H)$^+$.

Example A-48

N-(11,12-difluoro-2-methyl-3-oxo-2,3,6,7,8,9-hexahydrodibenzo[4,5:7,8][1,6]dioxacyclododecino[3,2-c]pyridin-17-yl)ethanesulfonamide

Example A-48a 4-chloro-5-(2-(4,5-difluoro-2-iodophenoxy)-5-nitrophenyl)-1-methylpyridin-2(1H)-one Example A-48a was prepared according to the procedure used for the preparation of Example A-5b, substituting 4,5-difluoro-2-iodophenol for 4-chloro-2-iodophenol, to provide the title compound.

Example A-48b 5-(5-amino-2-(4,5-difluoro-2-iodophenoxy)phenyl)-4-chloro-1-methylpyridin-2(1H)-one Example A-48b was prepared according to the procedure used for the preparation of Example A-15a, substituting Example A-48a for Example A-5b, to provide the title compound.

Example A-48c 5-(5-amino-2-(4,5-difluoro-2-iodophenoxy)phenyl)-4-(but-3-en-1-yloxy)-1-methylpyridin-2(1H)-one Example A-48c was prepared according to the procedure used for the preparation of Example A-22a, substituting Example A-48b for Example A-1b, to provide the title compound.

Example A-48d (E)-17-amino-11,12-difluoro-2-methyl-6,7-dihydrodibenzo[4,5:7,8][1,6]dioxacyclododecino[3,2-c]pyridin-3(2H)-one Example A-48d was prepared according to the procedure used for the preparation of Example A-15d, substituting Example A-48c for Example A-15c, to provide the title compound.

Example A-48e 17-amino-11,12-difluoro-2-methyl-6,7,8,9-tetrahydrodibenzo[4,5:7,8][1,6]dioxacyclododecino[3,2-c]pyridin-3(2H)-one Example A-48e was prepared according to the procedure used for the preparation of Example A-1i, substituting Example A-48d for Example A-1h, to provide the title compound.

Example A-48f

N-(11,12-difluoro-2-methyl-3-oxo-2,3,6,7,8,9-hexahydrodibenzo[4,5:7,8][1,6]dioxacyclododecino[3,2-c]pyridin-17-yl)ethanesulfonamide Example A-48f was prepared according to the procedure used for the preparation of Example A-5f, substituting Example A-48e for Example A-5e, to provide the title compound. $^1$H NMR (400 MHz, CD$_3$OD) δ 7.59 (s, 1H), 7.27-7.23 (m, 1H), 7.15-7.12 (m, 2H), 7.00 (dd, J=11.0, 7.2 Hz, 1H), 6.52 (d, J=9.1 Hz, 1H), 6.00 (s, 1H), 4.18-4.14 (m, 2H), 3.56 (s, 3H), 3.08 (q, J=7.4 Hz, 2H), 2.53-2.48 (m, 2H), 1.85-1.76 (m, 3H), 1.43-1.38 (m, 1H), 1.32 (t, J=7.4 Hz, 3H). MS (ESI+) m/z 491.1 (M+H)$^+$.

Example A-49

N-(11-fluoro-2-methyl-3-oxo-2,3,6,7,8,9-hexahydrodibenzo[4,5:7,8][1,6]dioxacyclododecino[3,2-c]pyridin-17-yl)ethanesulfonamide

Example A-49a 4-chloro-5-(2-(4-fluoro-2-iodophenoxy)-5-nitrophenyl)-1-methylpyridin-2(1H)-one Example A-49a was prepared according to the procedure used for the preparation of Example A-5b, substituting 4-fluoro-2-iodophenol for 4-chloro-2-iodophenol, to provide the title compound.

Example A-49b 5-(5-amino-2-(4-fluoro-2-iodophenoxy)phenyl)-4-chloro-1-methylpyridin-2(1H)-one Example A-49b was prepared according to the procedure used for the preparation of Example A-15a, substituting Example A-49a for Example A-5b, to provide the title compound.

Example A-49c 5-(5-amino-2-(4-fluoro-2-iodophenoxy)phenyl)-4-(but-3-en-1-yloxy)-1-methylpyridin-2(1H)-one Example A-49c was prepared according to the procedure used for the preparation of Example A-22a, substituting Example A-49b for Example A-1b, to provide the title compound.

Example A-49d (E)-17-amino-11-fluoro-2-methyl-6,7-dihydrodibenzo[4,5:7,8][1,6]dioxacyclododecino[3,2-c]pyridin-3(2H)-one Example A-49d was prepared according to the procedure used for the preparation of Example A-15d, substituting Example A-49c for Example A-15c, to provide the title compound.

Example A-49e 17-amino-11-fluoro-2-methyl-6,7,8,9-tetrahydrodibenzo[4,5:7,8][1,6]dioxacyclododecino[3,2-c]pyridin-3(2H)-one Example A-49e was prepared according to the procedure used for the preparation of Example A-1i, substituting Example A-49d for Example A-1h, to provide the title compound.

Example A-49f

N-(11-fluoro-2-methyl-3-oxo-2,3,6,7,8,9-hexahydrodibenzo[4,5:7,8][1,6]dioxacyclododecino[3,2-c]pyridin-17-yl)ethanesulfonamide Example A-49f was prepared according to the procedure used for the preparation of Example A-5f, substituting Example A-49e for Example A-5e, to provide the title compound. $^1$H NMR (400 MHz, CD$_3$OD) δ 7.59 (s, 1H), 7.14 (d, J=2.6 Hz, 1H), 7.12-7.06 (m, 2H), 7.03-6.94 (m, 2H), 6.48 (d, J=8.8 Hz, 1H), 6.01 (s, 1H), 4.19-4.16 (m, 2H), 3.56 (s, 3H), 3.07 (q, J=7.4 Hz, 2H), 2.56-2.48 (m, 2H), 1.87-1.79 (m, 3H), 1.49-1.42 (m, 1H), 1.32 (t, J=7.4 Hz, 3H). MS (ESI+) m/z 473.0 (M+H)$^+$.

Example A-50

N-(11-fluoro-2-methyl-3-oxo-2,3,6,7,8,9-hexahydrodibenzo[4,5:7,8][1,6]dioxacyclododecino[3,2-c]pyridin-17-yl)methanesulfonamide Example A-50 was prepared according to the procedure used for the preparation of Example A-5f, substituting Example A-49e for Example A-5e, and methanesulfonyl chloride for ethanesulfonyl chloride, respectively, to provide the title compound. $^1$H NMR (400 MHz, CD$_3$OD) δ 7.61 (s, 1H), 7.15-7.06 (m, 3H), 7.02-6.97 (m, 2H), 6.50 (d, J=8.8 Hz, 1H), 6.02 (s, 1H), 4.19-4.16 (m, 2H), 3.57 (s, 3H), 2.95 (s, 3H), 2.55-2.51 (m, 2H), 1.85-1.80 (m, 3H), 1.47-1.41 (m, 1H). MS (ESI+) m/z 459.1 (M+H)$^+$.

Example A-51

N-(2-methyl-3-oxo-11-(trifluoromethyl)-2,3,6,7,8,9-hexahydrodibenzo[4,5:7,8][1,6]dioxacyclododecino[3,2-c]pyridin-17-yl)methanesulfonamide Example A-51 was prepared according to the procedure used for the preparation of Example A-5f, substituting Example A-29e for Example A-5e, and methanesulfonyl chloride for ethanesulfonyl chloride, respectively, to provide the title compound. $^1$H NMR (400 MHz, CD$_3$OD) δ 7.65-7.63 (m, 1H), 7.62 (s, 1H), 7.58-7.56 (m, 1H), 7.21 (d, J=8.4 Hz, 1H), 7.17-7.12 (m, 2H), 6.54 (d, J=8.8 Hz, 1H), 6.01 (s, 1H), 4.22-4.14 (m, 2H), 3.55 (s, 3H), 2.95 (s, 3H), 2.66-2.55 (m, 2H), 1.87-1.80 (m, 3H), 1.51-1.45 (m, 1H). MS (ESI+) m/z 509.2 (M+H)$^+$.

Example A-52

N-(12-chloro-2-methyl-3-oxo-2,3,6,7,8,9-hexahydrodibenzo[4,5:7,8][1,6]dioxacyclododecino[3,2-c]pyridin-17-yl)ethanesulfonamide Example A-52 was prepared according to the procedure used for the preparation of Example A-5f, substituting Example A-44e for Example A-5e, to provide the title compound. $^1$H NMR (400 MHz, CD$_3$OD) δ 7.61 (s, 1H), 7.31 (d, J=8.4 Hz, 1H), 7.20-7.12 (m, 3H), 7.05 (d, J=1 Hz, 1H), 6.52 (d, J=8.4 Hz, 1H), 6.01 (s, 1H), 4.19-4.16 (m, 2H), 3.57 (s, 3H), 3.09 (q, J=7.6 Hz, 2H), 2.55-2.51 (m, 2H), 1.85-1.77 (m, 3H), 1.46-1.41 (m, 1H), 1.33 (q, J=7.2 Hz, 3H). MS (ESI+) m/z 489.1 (M+H)$^+$.

Example A-53

11-chloro-17-(ethylsulfonyl)-2-methyl-6,7,8,9-tetrahydrodibenzo[4,5:7,8][1,6]dioxacyclododecino[3,2-c]pyridazin-3(2H)-one

Example A-53a 5,6-dichloropyridazin-3(2H)-one 3,4,6-Trichloropyridazine (12 g, 65.4 mmol) in acetic acid (45 mL) was heated at 130° C. for two hours. After cooling to ambient temperature, the reaction mixture was poured into ice water (200 mL). The solid was collected by filtration to give 3.7 g of the title compound.

Example A-53b 5,6-dichloro-2-methylpyridazin-3(2H)-one

Example A-53b was prepared according to the procedure used for the preparation of Example A-1b, substituting Example A-53a for Example A-1a, to provide the title compound.

Example A-53c 6-chloro-5-(4-(5-chloro-2-methoxyphenyl)butoxy)-2-methylpyridazin-3(2H)-one Example A-53c was prepared according to the procedure used for the preparation of Example A-27c, substituting Example A-53b for Example A-1b, to provide the title compound.

Example A-53d 5-(4-(5-chloro-2-methoxyphenyl)butoxy)-6-(5-(ethylsulfonyl)-2-fluorophenyl)-2-methylpyridazin-3(2H)-one Example A-53d was prepared according to the procedure used for the preparation of Example A-1f, substituting Example A-53c for Example A-1b, to provide the title compound.

Example A-53e 5-(4-(5-chloro-2-hydroxyphenyl)butoxy)-6-(5-(ethylsulfonyl)-2-fluorophenyl)-2-methylpyridazin-3(2H)-one Example A-53e was prepared according to the procedure used for the preparation of Example A-26e, substituting Example A-53d for Example A-26d, to provide the title compound.

Example A-53f 11-chloro-17-(ethylsulfonyl)-2-methyl-6,7,8,9-tetrahydrodibenzo[4,5:7,8][1,6]dioxacyclododecino[3,2-c]pyridazin-3(2H)-one Example A-53f was prepared according to the procedure used for the preparation of Example A-26f, substituting Example A-53e for Example A-26e, to provide the title compound. $^1$H NMR (400 MHz, CDCl$_3$) δ 7.90 (d, J=2.3 Hz, 1H), 7.78 (dd, J=8.8, 2.4 Hz, 1H), 7.28-7.26 (m, 1H), 7.22 (dd, J=8.5, 2.6 Hz, 1H), 6.97 (d, J=8.5 Hz, 1H), 6.70 (d, J=8.8 Hz, 1H), 6.22 (s, 1H), 4.15-4.05 (m, 2H), 3.78 (s, 3H), 3.13 (q, J=7.4 Hz, 2H), 2.51-2.40 (m, 2H), 1.84-1.74 (m, 2H), 1.31 (t, J=7.4 Hz, 3H). MS (ESI+) m/z 475.1 (M+H)$^+$

Example A-54

17-(ethylsulfonyl)-2-methyl-3-oxo-2,3,6,7,8,9-hexahydrodibenzo[4,5:7,8][1,6]dioxacyclododecino[3,2-c]pyridazine-11-carbonitrile Example A-54 was prepared according to the procedure used for the preparation of Example A-45, substituting Example A-53f for Example A-9, to provide the title compound. $^1$H NMR (400 MHz, CDCl$_3$) δ 7.98 (d, J=2.3 Hz, 1H), 7.84 (dd, J=8.8, 2.4 Hz, 1H), 7.68-7.59 (m, 2H), 7.20 (d, J=8.2 Hz, 1H), 6.72 (d, J=8.8 Hz, 1H), 6.26 (s, 1H), 4.16 (t, J=5.4 Hz, 2H), 3.83 (s, 3H), 3.18 (q, J=7.4 Hz, 2H), 2.58 (t, J=7.8 Hz, 2H), 1.87-1.66 (m, 4H), 1.35 (t, J=7.4 Hz, 3H). MS (ESI+) m/z 466.1 (M+H)$^+$.

Example A-55

N-(11-chloro-2-methyl-3-oxo-2,3,6,7,8,9-hexahydrodibenzo[4,5:7,8][1,6]dioxacyclododecino[3,2-c]pyridazin-17-yl)ethanesulfonamide

Example A-55a 5-(4-(5-chloro-2-methoxyphenyl)butoxy)-6-(2-fluoro-5-nitrophenyl)-2-methylpyridazin-3(2H)-one Example A-55a was prepared according to the procedure used for the preparation of Example A-1f, substituting Example A-53c for Example A-1b, and substituting 2-(2-fluoro-5-nitrophenyl)-4,4,5,5-tetramethyl-1,3,2-dioxaborolane for Example A-1e, respectively, to provide the title compound.

Example A-55b 5-(4-(5-chloro-2-hydroxyphenyl)butoxy)-6-(2-fluoro-5-nitrophenyl)-2-methylpyridazin-3(2H)-one Example A-55b was prepared according to the procedure used for the preparation of Example A-26e, substituting Example A-55a for Example A-26d, to provide the title compound.

Example A-55c 11-chloro-2-methyl-17-nitro-6,7,8,9-tetrahydrodibenzo[4,5:7,8][1,6]dioxacyclododecino[3,2-c]pyridazin-3(2H)-one Example A-55c was prepared according to the procedure used for the preparation of Example A-26f, substituting Example A-55b for Example A-26e, to provide the title compound.

Example A-55d 17-amino-11-chloro-2-methyl-6,7,8,9-tetrahydrodibenzo[4,5:7,8][1,6]dioxacyclododecino[3,2-c]pyridazin-3(2H)-one Example A-55d was prepared according to the procedure used for the preparation of Example A-32e, substituting Example A-55c for Example A-32d, to provide the title compound.

Example A-55e

N-(11-chloro-2-methyl-3-oxo-2,3,6,7,8,9-hexahydrodibenzo[4,5:7,8][1,6]dioxacyclododecino[3,2-c]pyridazin-17-yl)ethanesulfonamide Example A-55e was prepared according to the procedure used for the preparation of Example A-33, substituting Example A-55d for Example A-32e, to provide the title compound. $^1$H NMR (400 MHz, CDCl$_3$) δ 7.79 (s, 1H), 7.31 (d, J=2.7 Hz, 1H), 7.27-7.17 (m, 3H), 6.97 (d, J=8.5 Hz, 1H), 6.55 (d, J=8.9 Hz, 1H), 6.33 (s, 1H), 4.14 (s, 2H), 3.81 (s, 3H), 3.14 (q, J=7.4 Hz, 2H), 2.50 (t, J=7.8 Hz, 2H), 2.08-1.91 (m, 1H), 1.89-1.65 (m, 3H), 1.40 (t, J=7.4 Hz, 3H). MS (ESI+) m/z 490.2 (M+H)$^+$.

Example A-56

N-(11-cyano-2-methyl-3-oxo-2,3,6,7,8,9-hexahydrodibenzo[4,5:7,8][1,6]dioxacyclododecino[3,2-c]pyridazin-17-yl)ethanesulfonamide Example A-56 was prepared according to the procedure used for the preparation of Example A-45, substituting Example A-55e for Example A-9, to provide the title compound. $^1$H NMR (400 MHz, CDCl$_3$) δ 7.91 (s, 1H), 7.62-7.54 (m, 2H), 7.36 (d, J=2.7 Hz, 1H), 7.28 (dd, J=8.8, 2.8 Hz, 1H), 7.16 (d, J=8.3 Hz, 1H), 6.57 (d, J=8.9 Hz, 1H), 6.35 (s, 1H), 4.17 (t, J=5.3 Hz, 2H), 3.81 (s, 3H), 3.16 (q, J=7.4

Hz, 2H), 2.58 (t, J=7.9 Hz, 2H), 1.91-1.80 (m, 2H), 1.76-1.56 (m, 2H), 1.41 (t, J=7.4 Hz, 3H). MS (ESI+) m/z 481.2 (M+H)+.

Example A-57

17-(ethylsulfonyl)-11,13-difluoro-2-methyl-6,7,8,9-tetrahydrodibenzo[4,5:7,8][1,6]dioxacyclododecino[3,2-c]pyridazin-3(2H)-one

Example A-57a 4-(3,5-difluoro-2-methoxyphenyl)but-3-yn-1-ol

Example A-57a was prepared according to the procedure used for the preparation of Example A-27a, substituting 1-bromo-3,5-difluoro-2-methoxybenzene for 2-bromo-4-chloro-1-methoxybenzene, to provide the title compound.

Example A-57b 4-(3,5-difluoro-2-methoxyphenyl)butan-1-ol

Example A-57b was prepared according to the procedure used for the preparation of Example A-27b, substituting Example A-57a for Example A-27a, to provide the title compound.

Example A-57c 6-chloro-5-(4-(3,5-difluoro-2-methoxyphenyl)butoxy)-2-methylpyridazin-3(2H)-one Example A-57c was prepared according to the procedure used for the preparation of Example A-27c, substituting Example A-53b for Example A-1b, and Example A-57b for Example A-27b, respectively, to provide the title compound.

Example A-57d 5-(4-(3,5-difluoro-2-methoxyphenyl)butoxy)-6-(5-(ethylsulfonyl)-2-fluorophenyl)-2-methylpyridazin-3(2H)-one Example A-57d was prepared according to the procedure used for the preparation of Example A-1f, substituting Example A-57c for Example A-1b, to provide the title compound.

Example A-57e 5-(4-(3,5-difluoro-2-hydroxyphenyl)butoxy)-6-(5-(ethylsulfonyl)-2-fluorophenyl)-2-methylpyridazin-3(2H)-one Example A-57e was prepared according to the procedure used for the preparation of Example A-26e, substituting Example A-57d for Example A-26d, to provide the title compound.

Example A-57f 17-(ethylsulfonyl)-11,13-difluoro-2-methyl-6,7,8,9-tetrahydrodibenzo[4,5:7,8][1,6]dioxacyclododecino[3,2-c]pyridazin-3(2H)-one Example A-57f was prepared according to the procedure used for the preparation of Example A-26f, substituting Example A-57e for Example A-26e, to provide the title compound. $^1$H NMR (400 MHz, CDCl$_3$) δ 7.94 (d, J=2.3 Hz, 1H), 7.85 (dd, J=8.7, 2.3 Hz, 1H), 6.90-6.80 (m, 2H), 6.69 (dd, J=8.7, 2.6 Hz, 1H), 6.24 (s, 1H), 4.22-4.05 (m, 2H), 3.82 (s, 3H), 3.17 (q, J=7.4 Hz, 2H), 2.64-2.43 (m, 2H), 1.92-1.69 (m, 3H), 1.54 (s, 1H), 1.36 (t, J=7.4 Hz, 3H). MS (ESI+) m/z 477.0 (M+H)+.

Example A-58

N-(11,13-difluoro-2-methyl-3-oxo-2,3,6,7,8,9-hexahydrodibenzo[4,5:7,8][1,6]dioxacyclododecino[3,2-c]pyridazin-17-yl)ethanesulfonamide

Example A-58a 5-(4-(3,5-difluoro-2-methoxyphenyl)butoxy)-6-(2-fluoro-5-nitrophenyl)-2-methylpyridazin-3(2H)-one Example A-58a was prepared according to the procedure used for the preparation of Example A-1f, substituting Example A-57c for Example A-1b, and substituting 2-(2-fluoro-5-nitrophenyl)-4,4,5,5-tetramethyl-1,3,2-dioxaborolane for Example A-1e, respectively, to provide the title compound.

Example A-58b 5-(4-(3,5-difluoro-2-hydroxyphenyl)butoxy)-6-(2-fluoro-5-nitrophenyl)-2-methylpyridazin-3(2H)-one Example A-58b was prepared according to the procedure used for the preparation of Example A-26e, substituting Example A-58a for Example A-26d, to provide the title compound.

Example A-58c 11,13-difluoro-2-methyl-17-nitro-6,7,8,9-tetrahydrodibenzo[4,5:7,8][1,6]dioxacyclododecino[3,2-c]pyridazin-3(2H)-one Example A-58c was prepared according to the procedure used for the preparation of Example A-26f, substituting Example A-58b for Example A-26e, to provide the title compound.

Example A-58d 17-amino-11,13-difluoro-2-methyl-6,7,8,9-tetrahydrodibenzo[4,5:7,8][1,6]dioxacyclododecino[3,2-c]pyridazin-3(2H)-one Example A-58d was prepared according to the procedure used for the preparation of Example A-32e, substituting Example A-58c for Example A-32d, to provide the title compound.

Example A-58e

N-(11,13-difluoro-2-methyl-3-oxo-2,3,6,7,8,9-hexahydrodibenzo[4,5:7,8][1,6]dioxacyclododecino[3,2-c]pyridazin-17-yl)ethanesulfonamide Example A-58e was prepared according to the procedure used for the preparation of Example A-33, substituting Example A-58d for Example A-32e, to provide the title compound. ¹H NMR (400 MHz, CDCl₃) δ 7.26-7.18 (m, 2H), 6.85-6.76 (m, 2H), 6.55 (s, 1H), 6.49 (dd, J=8.8, 2.5 Hz, 1H), 6.25 (s, 1H), 4.19-4.04 (m, 2H), 3.81 (s, 3H), 3.15 (q, J=7.4 Hz, 2H), 2.59-2.49 (m, 2H), 1.91-1.73 (m, 3H), 1.56-1.47 (m, 1H), 1.42 (t, J=7.4 Hz, 3H). MS (ESI+) m/z 492.1 (M+H)⁺.

Example A-59

17-(ethylsulfonyl)-2-methyl-6,7,8,9-tetrahydrobenzo[4,5]pyrido[3',4':7,8][1,6]dioxacyclododecino[3,2-c]pyridazin-3(2H)-one Example A-59a 6-chloro-5-(4-(3-methoxypyridin-4-yl)butoxy)-2-methylpyridazin-3(2H)-one Example A-59a was prepared according to the procedure used for the preparation of Example A-27c, substituting Example A-53b for Example A-1b, and substituting Example A-26b for Example A-27b, respectively, to provide the title compound.

Example A-59b 6-(5-(ethylsulfonyl)-2-fluorophenyl)-5-(4-(3-methoxypyridin-4-yl)butoxy)-2-methylpyridazin-3(2H)-one Example A-59b was prepared according to the procedure used for the preparation of Example A-1f, substituting Example A-59a for Example A-1b, to provide the title compound.

Example A-59c 6-(5-(ethylsulfonyl)-2-fluorophenyl)-5-(4-(3-hydroxypyridin-4-yl)butoxy)-2-methylpyridazin-3(2H)-one Example A-59c was prepared according to the procedure used for the preparation of Example A-26e, substituting Example A-59b for Example A-26d, to provide the title compound.

Example A-59d 17-(ethylsulfonyl)-2-methyl-6,7,8,9-tetrahydrobenzo[4,5]pyrido[3',4':7,8][1,6]dioxacyclododecino[3,2-c]pyridazin-3(2H)-one Example A-59d was prepared according to the procedure used for the preparation of Example A-26f, substituting Example A-59c for Example A-26e, to provide the crude compound. This material was purified by reverse phase preparative HPLC (C18, 10-70% acetonitrile/water (0.1% trifluoroacetic acid)) to provide the title compound as a trifluoroacetic acid salt. ¹H NMR (400 MHz, CDCl₃) δ 8.39 (d, J=4.8 Hz, 1H), 8.31 (s, 1H), 7.89 (d, J=2.2 Hz, 1H), 7.76 (dd, J=8.7, 2.2 Hz, 1H), 7.20 (s, 1H), 6.65 (d, J=8.8 Hz, 1H), 6.18 (s, 1H), 4.07 (d, 2H), 3.76 (s, 3H), 3.10 (q, J=7.4 Hz, 2H), 2.49 (t, J=7.6 Hz, 2H), 1.77 (s, 3H), 1.67-1.48 (m, 1H), 1.28 (t, J=7.4 Hz, 3H). MS (ESI+) m/z 442.0 (M+H)⁺.

Example A-60

17-(ethylsulfonyl)-2,13-dimethyl-6,7,8,9-tetrahydrodibenzo[4,5:7,8][1,6]dioxacyclododecino[3,2-c]pyridin-3(2H)-one Example A-60a 4-(2-methoxy-3-methylphenyl)but-3-yn-1-ol A mixture of 1-bromo-2-methoxy-3-methylbenzene (1.0 g, 4.97 mmol), but-3-yn-1-ol (0.697 g, 9.95 mmol), copper (I) iodide (0.095 g, 0.497 mmol), and tetrakis(triphenylphosphine)palladium(0) (0.287 g, 0.249 mmol) in pyrrololidine (10 mL) was heated at 80° C. overnight. The reaction mixture was diluted with ethyl acetate, filtered, and concentrated. The residue was purified by flash column chromatography (silica gel, eluting with 4:1 haptanes/ethyl acetate) to give the title compound (0.49 g, 2.58 mmol, 51.8% yield).

Example A-60b 4-(2-methoxy-3-methylphenyl)butan-1-ol

Example A-60b was prepared according to the procedure used for the preparation of Example A-27b, substituting Example A-60a for Example A-27a, to provide the title compound.

Example A-60c 5-bromo-4-(4-(2-methoxy-3-methylphenyl)butoxy)-1-methylpyridin-2(1H)-one Example A-60c was prepared according to the procedure used for the preparation of Example A-22a, substituting Example A-60b for but-3-en-1-ol, to provide the title compound.

Example A-60d 5-(5-(ethylsulfonyl)-2-fluorophenyl)-4-(4-(2-methoxy-3-methylphenyl)butoxy)-1-methylpyridin-2(1H)-one Example A-60d was prepared according to the procedure used for the preparation of Example A-1f, substituting Example A-60c for Example A-1b, to provide the title compound.

Example A-60e 5-(5-(ethylsulfonyl)-2-fluorophenyl)-4-(4-(2-hydroxy-3-methylphenyl)butoxy)-1-methylpyridin-2(1H)-one Example A-60e was prepared according to the procedure used for the preparation of Example A-26e, substituting Example A-60d for Example A-26d, to provide the title compound.

Example A-60f 17-(ethylsulfonyl)-2,13-dimethyl-6,7,8,9-tetrahydrodibenzo[4,5:7,8][1,6]dioxacyclododecino[3,2-c]pyridin-3(2H)-one Example A-60f was prepared according to the procedure used for the preparation of Example A-26f, substituting Example A-60e for Example A-26e, to provide the crude compound. This material was purified by reverse phase preparative HPLC (C18, 10-70% acetonitrile/water (0.1% TFA)) to provide the title compound. $^1$H NMR (400 MHz, DMSO-$d_6$) δ 7.81 (s, 1H), 7.80-7.73 (m, 2H), 7.27-7.09 (m, 3H), 6.44 (d, J=9.1 Hz, 1H), 5.90 (s, 1H), 4.11 (dd, J=6.8, 2.8 Hz, 2H), 3.44 (s, 3H), 3.29 (q, J=7.4 Hz, 2H), 2.50-2.37 (m, 2H), 1.86-1.55 (m, 3H), 1.29 (dd, J=13.4, 6.5 Hz, 1H), 1.14 (t, J=7.4 Hz, 3H). MS (ESI+) m/z 454.0 (M+H)$^+$.

Example B-1

N-(11-chloro-8-ethyl-2-methyl-3-oxo-2,3,6,7,8,9-hexahydrodibenzo[f,i]pyrido[3,4-k][1,8,4]dioxazacyclododecin-17-yl)ethanesulfonamide

Example B-1a tert-butyl (2-((5-bromo-1-methyl-2-oxo-1,2-dihydropyridin-4-yl)oxy)ethyl)carbamate To the mixture of tert-butyl (2-hydroxyethyl)carbamate (4.84 g, 30.0 mmol) in tetrahydrofuran (50 mL) was added 1.0 M potassium tert-butoxide in 2-methyl-2-propanol (30.0 mL, 30.0 mmol) dropwise at 0° C. under nitrogen. The reaction mixture was stirred at 0° C. for 5 minutes. To this reaction mixture was added a mixture of Example A-1b (1.11 g, 5.00 mmol) in tetrahydrofuran (5 mL) and the reaction mixture was stirred at room temperature for 16 hours. The reaction mixture was partitioned with ethyl acetate and water. The organic layer was washed with saturated aqueous sodium chloride, dried with anhydrous sodium sulfate, filtered, and concentrated. The residue was purified by flash chromatography (silica gel, 60-100% ethyl acetate in heptanes) to provide the title compound (915 mg, 53%).

Example B-1b tert-butyl (2-((5-(2-fluoro-5-nitrophenyl)-1-methyl-2-oxo-1,2-dihydropyridin-4-yl)oxy)ethyl)carbamate Example B-1a (590 mg, 1.70 mmol), (2-fluoro-5-nitrophenyl)boronic acid (377 mg, 2.04 mmol), tris(dibenzylideneacetone)dipalladium(0) (46.7 mg, 0.051 mmol), tri-tert-butylphosphonium tetrafluoroborate (29.6 mg, 0.102 mmol) and cesium fluoride (775 mg, 5.10 mmol) were combined in tetrahydrofuran (8.5 mL). The reaction mixture was purged with nitrogen for 15 minutes and heated at 50° C. for 16 hours. The reaction mixture was partitioned with ethyl acetate and water. The organic layer was washed with saturated aqueous sodium chloride, dried with anhydrous sodium sulfate, treated with 3-mercaptopropyl functionalized silica gel, filtered, and concentrated. The residue was purified by flash chromatography (silica gel, 2-4% methanol in dichloromethane) to provide the title compound (598 mg, 86%).

Example B-1c 4-(2-aminoethoxy)-5-(2-fluoro-5-nitrophenyl)-1-methylpyridin-2(1H)-one Example B-1b (680 mg, 1.67 mmol) was added to 4M HCl in dioxane (20 mL, 80 mmol). The reaction mixture was stirred at room temperature for 1 hour. The reaction mixture was concentrated to provide the title compound as a hydrochloric acid salt in quantitative yield.

Example B-1d 4-(2-((5-chloro-2-hydroxybenzyl)amino)ethoxy)-5-(2-fluoro-5-nitrophenyl)-1-methylpyridin-2(1H)-one Example B-1c (500 mg, 1.46 mmol), 5-chloro-2-hydroxybenzaldehyde (273 mg, 1.75 mmol) and acetic acid (0.416 mL, 7.27 mmol) were combined in tetrahydrofuran (50 mL). The reaction mixture was stirred at room temperature for 1 hour. To this reaction mixture was added sodium triacetoxyborohydride (617 mg, 2.91 mmol) and the mixture was stirred at room temperature for 16 hours. To this reaction mixture was added additional 5-chloro-2-hydroxybenzaldehyde (273 mg, 1.75 mmol), and the mixture was stirred at room temperature for 1 hour, followed by addition of sodium triacetoxyborohydride (617 mg, 2.91 mmol). The reaction mixture was stirred at room temperature for another 2 hours. The reaction mixture was concentrated, diluted with water, the pH adjusted to 7 by addition of saturated sodium carbonate, and extracted with ethyl acetate. The organic layer was washed with saturated aqueous sodium chloride, dried with anhydrous sodium sulfate, filtered, and concentrated. The residue was purified by flash chromatography (silica gel, 2-5% methanol in dichloromethane) to provide the title compound (515 mg, 79%).

Example B-1e 11-chloro-2-methyl-17-nitro-6,7,8,9-tetrahydrodibenzo[f,i]pyrido[3,4-k][1,8,4]dioxaazacyclododecin-3(2H)-one Example B-1d (493 mg, 1.10 mmol) and cesium carbonate (430 mg, 1.32 mmol) were combined in acetonitrile (55 mL). The reaction mixture was refluxed for 1 hour, cooled and concentrated. The residue was partitioned between ethyl acetate and water. The organic layer was washed with saturated aqueous sodium chloride, dried with anhydrous sodium sulfate, filtered, and concentrated. The residue was purified by flash chromatography (silica gel, 2-6% methanol in dichloromethane) to provide the title compound (402 mg, 85%).

Example B-1f 11-chloro-8-ethyl-2-methyl-17-nitro-6,7,8,9-tetrahydrodibenzo[f,i]pyrido[3,4-k][1,8,4]dioxaazacyclododecin-3(2H)-one Example B-1e (47.1 mg, 0.110 mmol), iodoethane (0.0130 mL, 0.165 mmol) and potassium carbonate (30.4 mg, 0.220 mmol) were combined in acetonitrile (2 mL). The reaction mixture was heated under reflux for 4 hours. To this reaction mixture was added iodoethane (0.0130 mL, 0.165 mmol) and potassium carbonate (30.4 mg, 0.220 mmol) again and the reaction mixture heated under reflux for another 20 hours. The reaction mixture was cooled to ambient temperature and concentrated. To this resulting residue was added water, and the mixture was stirred for 5 minutes. The resulting solid was collected by filtration, washed with water, and dried to give the title compound (47 mg, 94%).

Example B-1g 17-amino-11-chloro-8-ethyl-2-methyl-6,7,8,9-tetrahydrodibenzo[f,i]pyrido[3,4-k][1,8,4]dioxaazacyclododecin-3(2H)-one Example B-1f (46.0 mg, 0.101 mmol), iron powder (56.3 mg, 1.01 mmol) and ammonium chloride (27.0 mg, 0.505 mmol) were combined in the mixture of tetrahydrofuran (3 mL)/methanol (3 mL)/water (1 mL). The reaction mixture was heated at 90° C. for 4 hours, cooled, filtered, and washed with ethyl acetate. The filtrate was partitioned between ethyl acetate and water. The aqueous layer was extracted with ethyl acetate twice. The combined organic layers were washed with saturated aqueous sodium chloride, dried with anhydrous sodium sulfate, filtered, and concentrated to provide the title compound (43 mg, 100%).

Example B-1h

N-(11-chloro-8-ethyl-2-methyl-3-oxo-2,3,6,7,8,9-hexahydrodibenzo[f,i]pyrido[3,4-k][1,8,4]dioxazacyclododecin-17-yl)ethanesulfonamide Example B-1g (41 mg, 0.096 mmol), ethanesulfonyl chloride (0.027 mL, 0.29 mmol) and triethylamine (0.081 mL, 0.58 mmol) were combined in dichloromethane (2 mL). The reaction mixture was stirred at room temperature for 2 hours and then concentrated. To this resulting residue was added dioxane (3 mL) and 1M sodium hydroxide (1 mL). The reaction mixture was heated at 60° C. for 2 hours, cooled, and followed by addition of water. The pH of the reaction mixture was adjusted to 7 by the addition of 1M HCl, followed by extraction by ethyl acetate. The organic layer was washed with saturated aqueous sodium chloride, dried with anhydrous sodium sulfate, filtered, and concentrated. The residue was purified by flash chromatography (silica gel, 2-4% methanol in dichloromethane) to provide the title compound (27 mg, 54%). $^1$H NMR (400 MHz, DMSO-$d_6$) δ ppm 9.56 (s, 1H), 7.66 (s, 1H), 7.46-7.37 (m, 2H), 7.12-6.98 (m, 3H), 6.19 (d, J=8.8 Hz, 1H), 5.82 (s, 1H), 4.08-3.90 (m, 2H), 3.53-3.35 (m, 5H), 3.13-3.01 (m, 2H), 2.82-2.62 (m, 2H), 2.60-2.51 (m, 1H), 2.46-2.37 (m, 1H), 1.22 (t, J=7.3 Hz, 3H), 0.89 (t, J=7.0 Hz, 3H). (ESI+) m/z 518 (M+H)$^+$.

Example B-2

N-(8-acetyl-11-chloro-2-methyl-3-oxo-2,3,6,7,8,9-hexahydrodibenzo[f,i]pyrido[3,4-k][1,8,4]dioxazacyclododecin-17-yl)acetamide Example B-2a 4-chloro-2-(((2-hydroxyethyl)amino)methyl)phenol A mixture of 2-aminoethanol (1.23 g, 20.16 mmol) and 5-chloro-2-hydroxybenzaldehyde (3.13 g, 20 mmol) in ethanol (40.0 mL) was heated at 50° C. for 1 hour, cooled to 5-10° C., treated portion-wise with sodium tetrahydroborate (1.135 g, 30.0 mmol) and stirred at ambient temperature for 2 hours. The reaction mixture was cooled in an ice bath and carefully quenched with 6M HCl bringing the pH to 3 to give a heavy precipitate. The thick mixture was stirred for two hours, treated carefully with 50% NaOH bringing the pH to 11. The suspension was concentrated and the residue was triturated in 40 mL of ethyl acetate and filtered to remove solids. The ethyl acetate filtrate was dried (anhydrous sodium sulfate), filtered and concentrated to give an off-white solid. Purification by flash chromatography (silica gel, 2-10% methanol in dichloromethane, 0.1% ammonia) afforded the title compound as a white solid (1.94 g, 48%).

Example B-2b tert-butyl 5-chloro-2-hydroxybenzyl(2-hydroxyethyl)carbamate

Di-tert-butyl dicarbonate (1.295 mL, 5.58 mmol) and Example B-2a (0.9 g, 4.46 mmol) were combined in tetrahydrofuran (35.7 mL) and treated with a solution of sodium bicarbonate (1.875 g, 22.32 mmol) in water (8.93 mL). The mixture was stirred at ambient temperature for 24 hours and then filtered, and the collected solid was rinsed with ethyl acetate. The filtrate layers were separated. The aqueous layer was extracted again with ethyl acetate. The organics were combined, dried (anhydrous sodium sulfate), filtered and concentrated. Purification by trituration in 50 mL of 2:1 heptanes/dichloromethane afforded the title compound (1.19 g, 88%).

Example B-2c tert-butyl 5-chloro-2-(2-(4-chloro-1-methyl-6-oxo-1,6-dihydropyridin-3-yl)-4-nitrophenoxy)benzyl(2-hydroxyethyl)carbamate Example A-5a (0.3 g, 1.06 mmol), Example B-2b (0.34 g, 1.14 mmol) and cesium carbonate (0.37 g, 1.14 mmol) were combined in DMSO (5.3 mL) and stirred at 50° C. for 2 hours. The mixture was cooled and partitioned between ethyl acetate and water. The organic layer was washed with saturated aqueous sodium chloride, dried (anhydrous sodium sulfate), filtered, and concentrated. Purification by flash chromatography (silica gel, 0-10% methanol in dichloromethane) afforded the title compound (0.514 g, 86%).

Example B-2d tert-butyl 2-(4-amino-2-(4-chloro-1-methyl-6-oxo-1,6-dihydropyridin-3-yl)phenoxy)-5-chlorobenzyl(2-hydroxyethyl)carbamate Example B-2c (0.3 g, 0.532 mmol), iron powder (0.148 g, 2.66 mmol) and ammonia hydrochloride (0.057 g, 1.063 mmol) were combined in tetrahydrofuran (4.5 mL), ethanol (4.5 mL) and water (1.5 mL) and heated at 90° C. for 2 hours. The mixture was cooled, diluted with tetrahydrofuran and methanol and filtered through Celite to remove solids. The filtrate was concentrated. The residue was triturated in ethyl acetate and filtered to remove inorganic solids. The ethyl acetate filtrate was dried over anhydrous sodium sulfate, filtered, and concentrated to afford the title compound (0.288 g, 100%).

Example B-2e 5-(5-amino-2-(4-chloro-2-(((2-hydroxyethyl)amino)methyl)phenoxy)phenyl)-4-chloro-1-methylpyridin-2(1H)-one (TFA salt)

Example B-2d (0.25 g, 0.468 mmol) in dichloromethane (2.4 mL) was treated with trifluoroacetic acid (2.4 mL), stirred at ambient temperature for 2 hours, concentrated and azeotroped with toluene (3×20 mL) to afford the title compound as the TFA salt (0.32 g, 100%).

Example B-2f 5-(5-amino-2-(4-chloro-2-(((2-hydroxyethyl)amino)methyl)phenoxy)phenyl)-4-chloro-1-methylpyridin-2(1H)-one Example B-2e (0.33 g, 0.498 mmol) and triethylamine (0.486 mL, 3.49 mmol) in dichloromethane (5 mL) was treated with acetyl chloride (0.124 mL, 1.744 mmol), stirred at ambient temperature for 18 hours, and partitioned between ethyl acetate and water. The organic layer was washed with saturated aqueous sodium chloride, dried (anhydrous sodium sulfate), filtered and concentrated. Purification by flash chromatography (silica gel, 0-10% methanol in dichloromethane) afforded the title compound (0.038 g, 15%).

Example B-2g

N-(8-acetyl-11-chloro-2-methyl-3-oxo-2,3,6,7,8,9-hexahydrodibenzo[f,i]pyrido[3,4-k][1,8,4]dioxazacyclododecin-17-yl)acetamide A solution of Example B-2f (0.1 g, 0.193 mmol) in tetrahydrofuran (1.0 mL) and N,N-dimethylacetamide (1.0 mL) at 5° C. under nitrogen was treated with 1M potassium tert-butoxide (0.386 mL, 0.386 mmol), heated at 50° C. for 16 hours, cooled, and partitioned between ethyl acetate and water. The aqueous layer was back extracted again with ethyl acetate. The organic extracts were combined, washed repeatedly with saturated aqueous sodium chloride, dried (anhydrous sodium sulfate), filtered, and concentrated. Purification by flash chromatography (silica gel, 0.5-10% methanol in dichloromethane) afforded the title compound (0.0035 g, 3.8%). %). $^1$H NMR (400 MHz, DMSO-$d_6$) δ 9.60 (s, 1H), 7.47-7.51 (m, 3H), 7.40 (d, J=8.54 Hz, 1H), 7.26 (dd, J=8.54, 2.75 Hz, 1H), 6.88 (d, J=8.85 Hz, 1H), 6.47 (s, 1H), 5.80 (s, 1H), 4.46 (s, 2H), 4.29 (s, 2H), 3.44-3.50 (m, 2H), 3.39 (s, 3H), 2.04 (s, 3H), 2.01 (s, 3H). MS (ESI+) m/z 482 (M+H)$^+$.

Example B-3

17-amino-11-chloro-2-methyl-7,8-dihydrodibenzo[f,i]pyrido[3,4-k][1,8,4]dioxazacyclododecine-3,9(2H,6H)-dione

Example B-3a methyl 2-(2-(4-(2-((tert-butoxycarbonyl)amino)ethoxy)-1-methyl-6-oxo-1,6-dihydropyridin-3-yl)-4-nitrophenoxy)-5-chlorobenzoate Example B-1b (550 mg, 1.35 mmol), methyl 5-chloro-2-hydroxybenzoate (277 mg, 1.49 mmol) and cesium carbonate (484 mg, 1.49 mmol) were combined in dimethyl sulfoxide (5 mL). The reaction mixture was heated at 60° C. for 24 hours, cooled to ambient temperature, and partitioned between ethyl acetate and water. The organic layer was washed with saturated aqueous sodium chloride, dried with anhydrous sodium sulfate, filtered, and concentrated. The residue was purified by flash chromatography (silica gel, 2-4% methanol in dichloromethane) to provide the title compound (680 mg, 88%).

Example B-3b 2-(2-(4-(2-((tert-butoxycarbonyl)amino)ethoxy)-1-methyl-6-oxo-1,6-dihydropyridin-3-yl)-4-nitrophenoxy)-5-chlorobenzoic acid Example B-3a (689 mg, 1.20 mmol) and lithium hydroxide (144 mg, 6.00 mmol) were combined in the mixture of dioxane (8 mL)/water (2 mL). The reaction mixture was stirred at room temperature for 2 hours, diluted with water, adjusted the pH to 4 by addition of 1M HCl. The resulting solid was collected by filtration, washed with water, and dried to provide the title compound (640 mg, 95%).

Example B-3c 2-(2-(4-(2-aminoethoxy)-1-methyl-6-oxo-1,6-dihydropyridin-3-yl)-4-nitrophenoxy)-5-chlorobenzoic acid Example B-3b (616 mg, 1.10 mmol) was added to 4M HCl in dioxane (20 mL, 80 mmol). The reaction mixture was stirred at room temperature for 1 hour. The reaction mixture was concentrated to provide the title compound as a hydrochloric acid salt in quantitative yield.

Example B-3d 11-chloro-2-methyl-17-nitro-7,8-dihydrodibenzo[f,i]pyrido[3,4-k][1,8,4]dioxaazacyclododecine-3,9(2H,6H)-dione Example B-3c (546 mg, 1.10 mmol) and triethylamine (0.767 mL, 5.50 mmol) were combined in tetrahydrofuran (220 mL). To this slurry mixture was added 2-(3H-[1,2,3]triazolo[4,5-b]pyridin-3-yl)-1,1,3,3-tetramethylisouronium hexafluorophosphate(V) (418 mg, 1.10 mmol) and the reaction mixture was stirred at room temperature for 20 hours. The reaction mixture was concentrated. The residue was partitioned between ethyl acetate and water. The organic layer was washed with saturated aqueous sodium chloride, dried with anhydrous sodium sulfate, filtered, and concentrated. The residue was purified by flash chromatography (silica gel, 2-4% methanol in dichloromethane) to provide the title compound (190 mg, 39%).

Example B-3e 17-amino-11-chloro-2-methyl-7,8-dihydrodibenzo[f,i]pyrido[3,4-k][1,8,4]dioxazacyclododecine-3,9(2H,6H)-dione Example B-3e was prepared according to the procedure used for the preparation of Example B-1g, substituting Example B-3d for Example B-1f. Purification by trituration (30% ethyl acetate in heptanes) provided the title compound (37 mg, 75%). $^1$H NMR (400 MHz, DMSO-$d_6$) δ ppm 7.92

(dd, J=7.6, 2.7 Hz, 1H), 7.58 (s, 1H), 7.54-7.48 (m, 2H), 7.14 (d, J=8.5 Hz, 1H), 6.45-6.37 (m, 2H), 6.10 (d, J=9.0 Hz, 1H), 5.84 (s, 1H), 4.76 (s, 2H), 4.18-4.04 (m, 2H), 3.82-3.70 (m, 1H), 3.38 (s, 3H), 3.29-3.20 (m, 1H). MS (ESI+) m/z 412 (M+H)$^+$.

Example B-4

N-(11-chloro-2-methyl-3,9-dioxo-2,3,6,7,8,9-hexa-hydrodibenzo[f,i]pyrido[3,4-k][1,8,4]dioxazacy-clododecin-17-yl)ethanesulfonamide Example B-3e (28.8 mg, 0.070 mmol), ethanesulfonyl chloride (0.020 mL, 0.21 mmol) and triethylamine (0.059 mL, 0.42 mmol) were combined in dichloromethane (2 mL). The reaction mixture was stirred at room temperature for 2 hours and concentrated. To this resulting residue was added dioxane (3 mL) and 1M sodium hydroxide (1 mL). The reaction mixture was heated at 50° C. for 1 hour, cooled to ambient temperature, and water was added. The pH was adjusted to 7 by addition of 1M HCl and the mixture was extracted with ethyl acetate. The organic layer was washed with saturated aqueous sodium chloride, dried with anhydrous sodium sulfate, filtered, and concentrated. The residue was triturated with 30% ethyl acetate in heptanes to provide the title compound (29 mg, 82%). $^1$H NMR (500 MHz, DMSO-d$_6$) δ ppm 9.58 (s, 1H), 8.08 (d, J=7.2 Hz, 1H), 7.63 (s, 1H), 7.59-7.51 (m, 2H), 7.20 (d, J=8.4 Hz, 1H), 7.04 (dd, J=8.9, 2.5 Hz, 1H), 7.00 (d, J=2.4 Hz, 1H), 6.32 (d, J=8.9 Hz, 1H), 5.86 (s, 1H), 4.17-4.02 (m, 2H), 3.91-3.75 (m, 1H), 3.40 (s, 3H), 3.23-3.14 (m, 1H), 3.11-2.99 (m, 2H), 1.22 (t, J=7.3 Hz, 3H). MS (ESI+) m/z 504 (M+H)$^+$.

Example B-5

N-(11-chloro-2-methyl-3-oxo-2,3,6,7-tetrahydro-9H-dibenzo[6,7:9,10][1,4,8]trioxacyclododecino[11,12-c]pyridin-17-yl)ethanesulfonamide Example B-5a 4-chloro-2-((2-hydroxyethoxy)methyl)phenol A solution of 4-chloro-2-(hydroxymethyl)phenol (CAS 5330-38-1, 2.0 g, 12.61 mmol), ethane-1,2-diol (10 mL, 179 mmol), and 4-methylbenzenesulfonic acid hydrate (240 mg, 1.262 mmol) was stirred at 80° C. for 3 hours and then for 18 hours at room temperature. The reaction mixture was diluted with ethyl acetate, and was washed with water, saturated aqueous sodium chloride, dried (anhydrous magnesium sulfate), filtered, and concentrated to provide the title compound.

Example B-5b 4-chloro-5-(2-(4-chloro-2-((2-hydroxyethoxy) methyl)phenoxy)-5-nitrophenyl)-1-methylpyridin-2 (1H)-one A solution of Example A-5a (1.69 g, 5.98 mmol), Example B-5a (1.21 g, 5.98 mmol), cesium carbonate (2.9 g, 8.90 mmol) and DMSO (36 mL) was stirred at 70° C. for 2 hours. After cooling to room temperature, the reaction mixture was added to 300 mL 0.5 N HCl at 0° C. with stirring. After stirring for 30 minutes at 0° C., the resulting solid was filtered, rinsed with water and was dried (in-vacuo) to afford 2.39 g white solid. The crude product was purified by flash chromatography (silica gel, eluting with dichloromethane containing a gradient with methanol, 1% to 8%) to provide the title compound.

Example B-5c 5-(5-amino-2-(4-chloro-2-((2-hydroxyethoxy) methyl)phenoxy)phenyl)-4-chloro-1-methylpyridin-2 (1H)-one Using the procedure described for Example A-41d and substituting Example B-5b for Example A-41c provided the title compound.

Example B-5d 17-amino-11-chloro-2-methyl-6,7-dihydro-2H-dibenzo[6,7:9,10][1,4,8]trioxacyclododecino[11,12-c]pyridin-3(9H)-one A solution of Example B-5c (544 mg, 1.25 mmol) in dimethylformamide (32 mL) was degassed with nitrogen and was cooled to 0° C. After adding sodium hydride (60% dispersion in oil, 308 mg, 7.70 mmol), the solution was degassed again, then was heated slowly to 85° C. The reaction mixture was stirred at 85° C. for 4 hours. The reaction mixture was cooled to room temperature, diluted with 250 mL ethyl acetate and was washed with water, saturated aqueous sodium chloride, dried (anhydrous magnesium sulfate), filtered, and concentrated. The crude product was purified by flash chromatography (silica gel, eluting with dichloromethane containing a gradient with methanol, 1% to 8%) to provide the title compound.

Example B-5e

N-(11-chloro-2-methyl-3-oxo-2,3,6,7-tetrahydro-9H-dibenzo[6,7:9,10][1,4,8]trioxacyclododecino[11,12-c]pyridin-17-yl)ethanesulfonamide Using the procedure described for Example A-5f and substituting Example B-5d for Example A-5e provided the title compound. $^1$H NMR (400 MHz, DMSO-d$_6$) δ 9.61 (s, 1H), 7.67 (s, 1H), 7.57 (d, J=2.7 Hz, 1H), 7.48 (dd, J=8.6, 2.7 Hz, 1H), 7.11 (d, J=2.7 Hz, 1H), 7.09-7.03 (m, 2H), 6.26 (d, J=8.8 Hz, 1H), 5.85 (s, 1H), 4.43-4.28 (m, 2H), 4.05 (d, J=16.5 Hz, 2H), 3.80 (d, J=13.2 Hz, 1H), 3.75-3.62 (m, 1H), 3.42 (s, 3H), 3.14-3.00 (m, 2H), 1.22 (t, J=7.3 Hz, 3H). MS (ESI+) m/z 491.1 (M+H)$^-$.

Example B-6

N-[11-chloro-2-methyl-8-(methylsulfonyl)-3-oxo-2, 3,6,7,8,9-hexahydrodibenzo[f,i]pyrido[3,4-k][1,8,4] dioxazacyclododecin-17-yl]ethanesulfonamide Example B-6a 11-chloro-2-methyl-8-(methylsulfonyl)-17-nitro-6,7, 8,9-tetrahydrodibenzo[f,i]pyrido[3,4-k][1,8,4]diox-aazacyclododecin-3(2H)-one Example B-1e (47.1 mg, 0.110 mmol), methanesulfonyl chloride (0.017 mL, 0.22 mmol) and triethylamine (0.046 mL, 0.33 mmol) were combined in tetrahydrofuran (1 mL). The reaction mixture was stirred at room temperature for 4 hours and concentrated. To this resulting residue was added water. The mixture was stirred for 5 minutes. The solid was collected by filtration and purified by flash chromatography (silica gel, 2-4% methanol in dichloromethane) to provide the title compound (38 mg, 68%).

Example B-6b 17-amino-11-chloro-2-methyl-8-(methylsulfonyl)-6,7,8,9-tetrahydrodibenzo[f,i]pyrido[3,4-k][1,8,4]dioxaazacyclododecin-3(2H)-one Example B-6b was prepared according to the procedure used for the preparation of Example B-1g, substituting Example B-6a for Example B-1f, to provide the title compound (33 mg, 97%).

Example B-6c

N-[11-chloro-2-methyl-8-(methylsulfonyl)-3-oxo-2,3,6,7,8,9-hexahydrodibenzo[f,i]pyrido[3,4-k][1,8,4]dioxazacyclododecin-17-yl]ethanesulfonamide Example B-6b (32 mg, 0.067 mmol), ethanesulfonyl chloride (0.019 mL, 0.20 mmol) and triethylamine (0.056 mL, 0.40 mmol) were combined in dichloromethane (2 mL). The reaction mixture was stirred at room temperature for 2 hours and concentrated. To this resulting residue was added dioxane (3 mL) and 1M sodium hydroxide (1 mL). The reaction mixture was heated at 60° C. for 8 hours and cooled to ambient temperature. Water was added, and the pH was adjusted to 7 by the addition of 1M HCl followed by extraction with ethyl acetate. The organic layer was washed with saturated aqueous sodium chloride, dried with anhydrous sodium sulfate, filtered, and concentrated. The residue was purified by flash chromatography (silica gel, 2-4% methanol in dichloromethane) to provide the title compound (21 mg, 55%). $^1$H NMR (400 MHz, DMSO-$d_6$) δ ppm 9.65 (s, 1H), 7.67 (s, 1H), 7.58 (d, J=2.7 Hz, 1H), 7.37 (dd, J=8.6, 2.7 Hz, 1H), 7.16-7.05 (m, 2H), 6.92 (d, J=8.7 Hz, 1H), 6.41 (d, J=8.6 Hz, 1H), 5.88 (s, 1H), 4.48-4.29 (m, 2H), 4.25-4.08 (m, 2H), 3.63-3.46 (m, 1H), 3.41 (s, 3H), 3.39-3.30 (m, 1H), 3.14-3.05 (m, 2H), 3.00 (s, 3H), 1.23 (t, J=7.3 Hz, 3H). (ESI+) m/z 568 (M+H)$^+$.

Example B-7

N-(8-acetyl-11-chloro-2-methyl-3-oxo-2,3,6,7,8,9-hexahydrodibenzo[f,i]pyrido[3,4-k][1,8,4]dioxazacyclododecin-17-yl)ethanesulfonamide

Example B-7a 8-acetyl-11-chloro-2-methyl-17-nitro-6,7,8,9-tetrahydrodibenzo[f,i]pyrido[3,4-k][1,8,4]dioxaazacyclododecin-3(2H)-one Example B-1e (47.1 mg, 0.110 mmol), acetyl chloride (0.016 mL, 0.22 mmol) and triethylamine (0.046 mL, 0.33 mmol) were combined in tetrahydrofuran (1 mL). The reaction mixture was stirred at room temperature for 2 hours and concentrated. To this resulting residue was added water, and the mixture was stirred for 5 minutes, filtered, and the resulting solid dried to provide the title compound (49 mg, 95%).

Example B-7b 8-acetyl-17-amino-11-chloro-2-methyl-6,7,8,9-tetrahydrodibenzo[f,i]pyrido[3,4-k][1,8,4]dioxaazacyclododecin-3(2H)-one Example B-7b was prepared according to the procedure used for the preparation of Example B-1g, substituting Example B-7a for Example B-1f, to provide the title compound (44 mg, 98%).

Example B-7c

N-(8-acetyl-11-chloro-2-methyl-3-oxo-2,3,6,7,8,9-hexahydrodibenzo[f,i]pyrido[3,4-k][1,8,4]dioxazacyclododecin-17-yl)ethanesulfonamide Example B-7b (42 mg, 0.095 mmol), ethanesulfonyl chloride (0.027 mL, 0.29 mmol) and triethylamine (0.080 mL, 0.57 mmol) were combined in dichloromethane (2 mL). The reaction mixture was stirred at room temperature for 2 hours and concentrated. To this resulting residue was added dioxane (3 mL) and 1M sodium hydroxide (1 mL). The reaction mixture was heated at 60° C. for 2 hours and then cooled to ambient temperature. Water was added, and the pH was adjusted to 7 by the addition of 1M HCl. The mixture was extracted with ethyl acetate. The organic layer was washed with saturated aqueous sodium chloride, dried with anhydrous sodium sulfate, filtered, and concentrated. The residue was purified by flash chromatography (silica gel, 2-6% methanol in dichloromethane) to provide the title compound (33 mg, 65%). $^1$H NMR (400 MHz, DMSO-$d_6$, 90° C.) δ ppm 9.31 (s, br, 1H), 7.56-7.45 (m, 2H), 7.27 (dd, J=8.7, 2.7 Hz, 1H), 7.18-7.06 (m, 2H), 6.88 (d, J=8.6 Hz, 1H), 6.50 (s, br, 1H), 5.81 (s, br, 1H), 4.46 (s, br, 2H), 4.29 (s, br, 2H), 3.48 (s, br, 2H), 3.40 (s, 3H), 3.08 (q, J=7.3 Hz, 2H), 2.03 (s, br, 3H), 1.24 (t, J=7.3 Hz, 3H). (ESI+) m/z 532 (M+H)$^+$.

Example B-8 ethyl 11-chloro-17-[(ethylsulfonyl)amino]-2-methyl-3-oxo-2,3,6,7-tetrahydrodibenzo[f,i]pyrido[3,4-k][1,8,4]dioxazacyclododecine-8(9H)-carboxylate

Example B-8a ethyl 11-chloro-2-methyl-17-nitro-3-oxo-2,3,6,7-tetrahydrodibenzo[f,i]pyrido[3,4-k][1,8,4]dioxaazacyclododecine-8(9H)-carboxylate Example B-1e (47.1 mg, 0.110 mmol), ethyl chloroformate (0.021 mL, 0.22 mmol) and triethylamine (0.046 mL, 0.33 mmol) were combined in tetrahydrofuran (1 mL). The reaction mixture was stirred at room temperature for 2 hours and concentrated. To the resulting residue was added water, and the mixture was stirred for 5 minutes, filtered, and the resulting solid dried to provide the title compound (52 mg, 95%).

Example B-8b ethyl 17-amino-11-chloro-2-methyl-3-oxo-2,3,6,7-tetrahydrodibenzo[f,i]pyrido[3,4-k][1,8,4]dioxaazacyclododecine-8(9H)-carboxylate Example B-8b was prepared according to the procedure used for the preparation of Example B-1g, substituting Example B-8a for Example B-1f, to provide the title compound (47 mg, 98%).

Example B-8c ethyl 11-chloro-17-[(ethylsulfonyl)amino]-2-methyl-3-oxo-2,3,6,7-tetrahydrodibenzo[f,i]pyrido[3,4-k][1,8,4]dioxazacyclododecine-8(9H)-carboxylate Example B-8b (45 mg, 0.096 mmol), ethanesulfonyl chloride (0.027 mL, 0.29 mmol) and triethylamine (0.080 mL, 0.57 mmol) were combined in dichloromethane (2 mL). The reaction mixture was stirred at room temperature for 2 hours and concentrated. To this resulting residue was added dioxane (3 mL) and 1M sodium hydroxide (1 mL). The reaction mixture was stirred at room temperature for 2 hours, and then cooled to ambient temperature. Water was added, and the pH was adjusted to 7 by the addition of 1M HCl. The mixture was extracted with ethyl acetate. The organic layer was washed with saturated aqueous sodium chloride, dried with anhydrous sodium sulfate, filtered, and concentrated. The residue was purified by flash chromatography (silica gel, 2-4% methanol in dichloromethane) to provide the title compound (35 mg, 65%). $^1$H NMR (400 MHz, DMSO-$d_6$) δ ppm 9.69 (s, br, 1H), 7.63 (s, 1H), 7.52 (s, br, 1H), 7.30 (dd, J=8.7, 2.7 Hz, 1H), 7.17-7.06 (m, 2H), 6.78 (d, J=7.5 Hz, 1H), 6.58-6.46 (m, 1H), 5.85 (s, 1H), 4.49 (s, br, 2H), 4.17-3.96 (m, 4H), 3.60 (s, br, 1H), 3.37 (s, 3H), 3.29 (s, br, 1H), 3.15-3.03 (m, 2H), 1.23 (t, J=7.3 Hz, 3H), 1.17 (t, J=7.1 Hz, 3H). (ESI+) m/z 562 (M+H)$^+$.

Example B-9

11-chloro-N-ethyl-17-[(ethylsulfonyl)amino]-2-methyl-3-oxo-2,3,6,7-tetrahydrodibenzo[f,i]pyrido[3,4-k][1,8,4]dioxazacyclododecine-8(9H)-carboxamide

Example B-9a 11-chloro-N-ethyl-2-methyl-17-nitro-3-oxo-2,3,6,7-tetrahydrodibenzo[f,i]pyrido[3,4-k][1,8,4]dioxaazacyclododecine-8(9H)-carboxamide Example B-1e (47.1 mg, 0.110 mmol), ethyl isocyanate (0.017 mL, 0.22 mmol) and triethylamine (0.046 mL, 0.33 mmol) were combined in tetrahydrofuran (1 mL). The reaction mixture was stirred at room temperature for 2 hours and concentrated. To the resulting residue was added water, and the mixture was stirred for 5 minutes, filtered and the resulting solid dried to provide the title compound (51 mg, 93%).

Example B-9b 17-amino-11-chloro-N-ethyl-2-methyl-3-oxo-2,3,6,7-tetrahydrodibenzo[f,i]pyrido[3,4-k][1,8,4]dioxaazacyclododecine-8(9H)-carboxamide Example B-9b was prepared according to the procedure used for the preparation of Example B-1g, substituting Example B-9a for Example B-1f, to provide the title compound (46 mg, 98%).

Example B-9c 11-chloro-N-ethyl-17-[(ethylsulfonyl)amino]-2-methyl-3-oxo-2,3,6,7-tetrahydrodibenzo[f,i]pyrido[3,4-k][1,8,4]dioxazacyclododecine-8(9H)-carboxamide Example B-9b (44 mg, 0.094 mmol), ethanesulfonyl chloride (0.027 mL, 0.29 mmol) and triethylamine (0.078 mL, 0.56 mmol) were combined in dichloromethane (2 mL). The reaction mixture was stirred at room temperature for 2 hours and concentrated. To this resulting residue was added dioxane (3 mL) and 1M sodium hydroxide (1 mL). The reaction mixture was heated at 60° C. for 2 hours and cooled to ambient temperature. Water was added and the pH was adjusted to 7 by the addition of 1M HCl. The mixture was extracted with ethyl acetate. The organic layer was washed with saturated aqueous sodium chloride, dried with anhydrous sodium sulfate, filtered, and concentrated. The residue was purified by flash chromatography (silica gel, 2-6% methanol in dichloromethane) to provide the title compound (17 mg, 32%). $^1$H NMR (400 MHz, DMSO-$d_6$) δ ppm 9.65 (s, br, 1H), 7.65 (s, 1H), 7.62 (d, J=2.7 Hz, 1H), 7.33 (dd, J=8.6, 2.7 Hz, 1H), 7.16-7.07 (m, 2H), 6.93 (d, J=8.6 Hz, 1H), 6.48 (t, J=5.3 Hz, 1H), 6.42 (d, J=8.9 Hz, 1H), 5.81 (s, 1H), 4.66-4.50 (m, 1H), 4.46-4.30 (m, 1H), 4.11-3.89 (m, 2H), 3.67-3.51 (m, 1H), 3.40 (s, 3H), 3.14-2.96 (m, 5H), 1.22 (t, J=7.3 Hz, 3H), 1.01 (t, J=7.1 Hz, 3H). (ESI+) m/z 561 (M+H)$^-$.

Example B-10 tert-butyl 11-chloro-17-[(ethylsulfonyl)amino]-2-methyl-3-oxo-2,3,6,7-tetrahydrodibenzo[f,i]pyrido[3,4-k][1,8,4]dioxazacyclododecine-8(9H)-carboxylate

Example B-10a tert-butyl 11-chloro-2-methyl-17-nitro-3-oxo-2,3,6,7-tetrahydrodibenzo[f,i]pyrido[3,4-k][1,8,4]dioxaazacyclododecine-8(9H)-carboxylate Example B-1e (180 mg, 0.420 mmol), di-tert-butyl dicarbonate (137 mg, 0.630 mmol) and triethylamine (0.176 mL, 1.26 mmol) were combined in tetrahydrofuran (5 mL). The reaction mixture was stirred at room temperature for 2 hours and concentrated. To this resulting residue was added water. The mixture was stirred for 5 minutes. The solid was collected by filtration and then purified by flash chromatography (silica gel, 2-4% methanol in dichloromethane) to provide the title compound (211 mg, 95%).

Example B-10b tert-butyl 17-amino-11-chloro-2-methyl-3-oxo-2,3,6,7-tetrahydrodibenzo[f,i]pyrido[3,4-k][1,8,4]dioxaazacyclododecine-8(9H)-carboxylate Example B-10b was prepared according to the procedure used for the preparation of Example B-1g, substituting Example B-10a for Example B-1f, to provide the title compound (182 mg, 93%).

Example B-10c tert-butyl 11-chloro-17-[(ethylsulfonyl)amino]-2-methyl-3-oxo-2,3,6,7-tetrahydrodibenzo[f,i]pyrido[3,4-k][1,8,4]dioxazacyclododecine-8(9H)-carboxylate Example B-10b (180 mg, 0.361 mmol), ethanesulfonyl chloride (0.103 mL, 1.08 mmol) and triethylamine (0.302 mL, 2.17 mmol) were combined in dichloromethane (4 mL). The reaction mixture was stirred at room temperature for 2 hours and concentrated. To this resulting residue was added dioxane (6 mL) and 1M sodium hydroxide (2 mL). The reaction mixture was stirred at room temperature for 24 hours, added water, adjusted the pH to 7 by addition of 1M HCl and extracted with ethyl acetate. The organic layer was washed with saturated aqueous sodium chloride, dried with anhydrous sodium sulfate, filtered, and concentrated. The residue was purified by flash chromatography (silica gel, 2-4% methanol in dichloromethane) to provide the title compound (194 mg, 91%). $^1$H NMR (400 MHz, DMSO-$d_6$) δ ppm 9.71 (s, 1H), 7.61 (s, 1H), 7.49 (s, 1H), 7.27 (dd, J=8.7, 2.7 Hz, 1H), 7.21-7.09 (m, 2H), 6.72 (d, J=8.1 Hz, 1H), 6.58 (d, J=9.1 Hz, 1H), 5.83 (s, 1H), 4.64-4.34 (m, 2H), 4.15-3.92 (m, 2H), 3.61-3.45 (m, 1H), 3.44-3.32 (m, 4H), 3.16-3.05 (m, 2H), 1.40 (s, 9H), 1.23 (t, J=7.3 Hz, 3H). (ESI+) m/z 590 (M+H)$^+$.

Example B-11

N-(11-chloro-2-methyl-3-oxo-2,3,6,7,8,9-hexahydrodibenzo[f,i]pyrido[3,4-k][1,8,4]dioxazacyclododecin-17-yl)ethanesulfonamide Example B-10c (165 mg, 0.280 mmol) was added 4M HCl in dioxane (2 mL, 8.0 mmol). The reaction mixture was stirred at room temperature for 1 hour and concentrated. To this resulting residue was added water, adjusted the pH to 7 by addition of saturated sodium bicarbonate. The solid was collected by filtration, washed with water, and dried to provide the title compound (108 mg, 79%). $^1$H NMR (500 MHz, DMSO-$d_6$) δ ppm 9.61 (s, 1H), 7.66 (s, 1H), 7.48 (d, J=2.5 Hz, 1H), 7.38 (dd, J=8.5, 2.5 Hz, 1H), 7.14-6.98 (m, 3H), 6.31 (d, J=8.7 Hz, 1H), 5.84 (s, 1H), 4.12-3.94 (m, 2H), 3.58-3.48 (m, 2H), 3.41 (s, 3H), 3.13-3.04 (m, 2H), 2.86-2.72 (m, 2H), 1.22 (t, J=7.3 Hz, 3H). (ESI+) m/z 490 (M+H)$^+$.

Example B-12

N-[11-chloro-8-(cyclopropylmethyl)-2-methyl-3-oxo-2,3,6,7,8,9-hexahydrodibenzo[f,i]pyrido[3,4-k][1,8,4]dioxazacyclododecin-17-yl]ethanesulfonamide Example B-11 (39 mg, 0.080 mmol), cyclopropanecarbaldehyde (0.012 mL, 0.16 mmol), and acetic acid (0.023 mL, 0.400 mmol) were combined in tetrahydrofuran (1 mL). The reaction mixture was stirred at 50° C. for 1 hour, cooled to room temperature, and sodium triacetoxyborohydride (51 mg, 0.24 mmol) was added. The reaction mixture was stirred at room temperature for 3 hours and concentrated. To this resulting residue was added water, and the pH was adjusted to 7 by the addition of saturated sodium bicarbonate. The resulting solid was isolated by filtration and purified by flash chromatography (silica gel, 2% to 4% methanol in dichloromethane) to provide the title compound (26 mg, 60%). $^1$H NMR (400 MHz, DMSO-$d_6$) δ ppm 9.65 (s, 1H), 7.75 (s, 1H), 7.57-7.45 (m, 2H), 7.21-7.03 (m, 3H), 6.33 (d, J=8.8 Hz, 1H), 5.91 (s, 1H), 4.20-4.11 (m, 2H), 3.61-3.52 (m, 2H), 3.50 (s, 3H), 3.23-3.09 (m, 2H), 3.04-2.87 (m, 2H), 2.50-2.29 (m, 2H), 1.30 (t, J=7.3 Hz, 3H), 0.87-0.75 (m, 1H), 0.57-0.39 (m, 2H), 0.18-0.08 (m, 1H), 0.07-0 (m, 1H). (ESI+) m/z 544 (M+H)$^+$.

Example B-13

N-[11-chloro-2-methyl-3-oxo-8-(3,3,3-trifluoropropyl)-2,3,6,7,8,9-hexahydrodibenzo[f,i]pyrido[3,4-k][1,8,4]dioxazacyclododecin-17-yl]ethanesulfonamide Example B-11 (39 mg, 0.080 mmol), 3,3,3-trifluoropropanal (0.014 mL, 0.16 mmol) and acetic acid (0.023 mL, 0.40 mmol) were combined in tetrahydrofuran (1 mL). The reaction mixture was stirred at 50° C. for 1 hour, cooled to room temperature and sodium triacetoxyborohydride (51 mg, 0.24 mmol) was added. The reaction mixture was stirred at room temperature for 22 hours. To this reaction mixture was added 3,3,3-trifluoropropanal (0.014 mL, 0.16 mmol), acetic acid (0.023 mL, 0.40 mmol) and sodium triacetoxyborohydride (51 mg, 0.24 mmol) again, and the mixture was stirred at room temperature for another 6 hours and then concentrated. To this resulting residue was added water, and the pH was adjusted to 7 by the addition of saturated sodium bicarbonate. The resulting solid was isolated by filtration and was purified by flash chromatography (silica gel, 2% to 4% methanol in dichloromethane) to provide the title compound (37 mg, 79%). $^1$H NMR (500 MHz, DMSO-$d_6$) δ ppm 9.59 (s, 1H), 7.67 (s, 1H), 7.53 (d, J=2.6 Hz, 1H), 7.43 (dd, J=8.6, 2.6 Hz, 1H), 7.12-6.99 (m, 3H), 6.19 (d, J=8.8 Hz, 1H), 5.81 (s, 1H), 4.07-3.95 (m, 2H), 3.48 (dd, J=27.7, 12.5 Hz, 2H), 3.42 (s, 3H), 3.13-2.99 (m, 2H), 2.90-2.78 (m, 1H), 2.77-2.70 (m, 2H), 2.67-2.57 (m, 1H), 2.50-2.41 (m, 1H), 2.40-2.24 (m, 1H), 1.21 (t, J=7.3 Hz, 3H). (ESI+) m/z 586 (M+H)$^+$.

Example B-14

N-(11-chloro-8-cyclobutyl-2-methyl-3-oxo-2,3,6,7,8,9-hexahydrodibenzo[f,i]pyrido[3,4-k][1,8,4]dioxazacyclododecin-17-yl)ethanesulfonamide Example B-14 was prepared according to the procedure used for the preparation of Example B-12, substituting cyclobutanone for cyclopropanecarbaldehyde, to provide the title compound (31 mg, 71%). $^1$H NMR (500 MHz, DMSO-$d_6$) δ ppm 9.58 (s, 1H), 7.66 (s, 1H), 7.46-7.33 (m, 2H), 7.10-6.98 (m, 3H), 6.22 (d, J=8.8 Hz, 1H), 5.83 (s, 1H), 4.10-3.97 (m, 2H), 3.54-3.46 (m, 1H), 3.41 (s, 3H), 3.32-3.27 (m, 1H), 3.26-3.19 (m, 1H), 3.13-3.02 (m, 2H), 2.80-2.70 (m, 1H), 2.66-2.56 (m, 1H), 2.05-1.94 (m, 1H), 1.91-

1.81 (m, 1H), 1.80-1.72 (m, 1H), 1.71-1.61 (m, 1H), 1.60-1.44 (m, 2H), 1.21 (t, J=7.3 Hz, 3H). (ESI+) m/z 544 (M+H)⁻.

Example B-15 ethyl ({11-chloro-17-[(ethylsulfonyl)amino]-2-methyl-3-oxo-2,3,6,7-tetrahydrodibenzo[f,i]pyrido[3,4-k][1,8,4]dioxazacyclododecin-8(9H)-yl}sulfonyl)carbamate Example B-15a tert-butyl 11-chloro-17-(N-(ethylsulfonyl)ethylsulfonamido)-2-methyl-3-oxo-2,3,6,7-tetrahydrodibenzo[f,i]pyrido[3,4-k][1,8,4]dioxaazacyclododecine-8(9H)-carboxylate Example B-10b (462 mg, 0.928 mmol), ethanesulfonyl chloride (0.353 mL, 3.71 mmol) and triethylamine (0.776 mL, 5.57 mmol) were combined in dichloromethane (8 mL). The reaction mixture was stirred at room temperature for 4 hours and then concentrated. The residue was partitioned between ethyl acetate and water. The organic layer was washed with saturated aqueous sodium chloride, dried with anhydrous sodium sulfate, filtered, and concentrated. The residue was purified by flash chromatography (silica gel, 2-4% methanol in dichloromethane) to provide the title compound (584 mg, 92%).

Example B-15b

N-(11-chloro-2-methyl-3-oxo-2,3,6,7,8,9-hexahydrodibenzo[f,i]pyrido[3,4-k][1,8,4]dioxaazacyclododecin-17-yl)-N-(ethylsulfonyl)ethanesulfonamide Example B-15a (150 mg, 0.22 mmol) was added to 4M HCl in dioxane (2 mL, 8.0 mmol). The reaction mixture was stirred at room temperature for 1 hour and concentrated. To this resulting residue was added water, the pH was adjusted to 7 by addition of saturated sodium bicarbonate, and the resulting solid was filtered, washed with water, and dried to provide the title compound (86 mg, 72%).

Example B-15c ((4-(dimethylamino)pyridin-1-ium-1-yl)sulfonyl)(ethoxycarbonyl)amide To a solution of ethanol (1.61 mL, 27.6 mmol) in anhydrous dichloromethane (100 mL) was added chlorosulfonyl isocyanate (2.40 mL, 27.6 mmol) dropwise at 0° C. over 15 minutes. The reaction mixture was stirred at this temperature for 15 minutes, followed by addition of N,N-dimethylpyridin-4-amine (6.90 g, 56.5 mmol). The reaction mixture was stirred at room temperature for 1 hour, washed with water (three times) and saturated aqueous sodium chloride sequentially, dried with anhydrous sodium sulfate, filtered, and concentrated to provide the title compound (5.50 g, 73%).

Example B-15d ethyl ({11-chloro-17-[(ethylsulfonyl)amino]-2-methyl-3-oxo-2,3,6,7-tetrahydrodibenzo[f,i]pyrido[3,4-k][1,8,4]dioxazacyclododecin-8(9H)-yl}sulfonyl)carbamate Example B-15b (40.7 mg, 0.070 mmol), Example B-15c (23 mg, 0.084 mmol) and triethylamine (0.059 mL, 0.42 mmol) were combined in dichloromethane (2 mL). The reaction mixture was stirred at room temperature for 2 hours and concentrated. To this resulting residue was added dioxane (3 mL) and 1M sodium hydroxide (1 mL). The reaction mixture was stirred at room temperature for 2 hours, water was added, and the pH was adjusted to 7 by the addition of 1M HCl. The mixture was extracted with ethyl acetate twice. The combined organic layers were washed with saturated aqueous sodium chloride, dried with anhydrous sodium sulfate, filtered, and concentrated. The residue was purified by flash chromatography (silica gel, 2-6% methanol in dichloromethane) to provide the title compound (33 mg, 74%). ¹H NMR (400 MHz, DMSO-d₆) δ ppm 11.59 (s, 1H), 9.65 (s, 1H), 7.67 (s, 1H), 7.52 (d, J=2.7 Hz, 1H), 7.40 (dd, J=8.6, 2.7 Hz, 1H), 7.15-7.05 (m, 2H), 6.97 (d, J=8.7 Hz, 1H), 6.37 (d, J=8.7 Hz, 1H), 5.92 (s, 1H), 4.50-4.35 (m, 2H), 4.27-4.01 (m, 4H), 3.68-3.51 (m, 1H), 3.47-3.35 (m, 4H), 3.12-3.01 (m, 2H), 1.22 (t, J=7.3 Hz, 3H), 1.17 (t, J=7.1 Hz, 3H). (ESI+) m/z 641 (M+H)⁺.

Example B-16

N-({11-chloro-17-[(ethylsulfonyl)amino]-2-methyl-3-oxo-2,3,6,7-tetrahydrodibenzo[f,i]pyrido[3,4-k][1,8,4]dioxazacyclododecin-8(9H)-yl}sulfonyl)acetamide Example B-16 was prepared according to the procedure used for the preparation of Example B-15d, substituting acetylsulfamoyl chloride for Example B-15c, to provide the title compound (22 mg, 51%). ¹H NMR (400 MHz, DMSO-d₆) δ ppm 11.71 (s, 1H), 9.65 (s, 1H), 7.67 (s, 1H), 7.54 (d, J=2.6 Hz, 1H), 7.40 (dd, J=8.7, 2.7 Hz, 1H), 7.15-7.05 (m, 2H), 6.95 (d, J=8.7 Hz, 1H), 6.37 (d, J=8.7 Hz, 1H), 5.91 (s, 1H), 4.51-4.34 (m, 2H), 4.22-4.03 (m, 2H), 3.67-3.44 (m, 2H), 3.41 (s, 3H), 3.14-3.04 (m, 2H), 1.98 (s, 3H), 1.22 (t, J=7.3 Hz, 3H). (ESI+) m/z 611 (M+H)⁺.

Example B-17

11-chloro-2-methyl-17-((methylsulfonyl)methyl)-6,7-dihydro-2H-dibenzo[6,7:9,10][1,4,8]trioxacyclododecino[11,12-c]pyridin-3(9H)-one Example B-17a 5-bromo-4-(2-((5-chloro-2-hydroxybenzyl)oxy)ethoxy)-1-methylpyridin-2(1H)-one Using the procedure described for Example A-22a and substituting Example B-5a for but-3-en-1-ol provided the title compound.

Example B-17b ethyl 3-(4-(2-((5-chloro-2-hydroxybenzyl)oxy)ethoxy)-1-methyl-6-oxo-1,6-dihydropyridin-3-yl)-4-fluorobenzoate Using the procedure described for Example A-41a, substituting Example B-17a for Example A-22a, and substituting (5-(ethoxycarbonyl)-2-fluorophenyl)boronic acid (CAS 874219-60-0) for (2-fluoro-5-nitrophenyl)boronic acid provided the title compound.

Example B-17c ethyl 11-chloro-2-methyl-3-oxo-3,6,7,9-tetrahydro-2H-dibenzo[6,7:9,10][1,4,8]trioxacyclododecino[11,12-c]pyridine-17-carboxylate A solution of Example B-17b (250 mg, 0.525 mmol), cesium carbonate (205 mg, 0.629 mmol) and acetonitrile (12.5 mL) was heated in a microwave reactor at 130° C. for 90 minutes. The reaction mixture was diluted with ethyl acetate and washed with water and then brine, dried (anhydrous magnesium sulfate), filtered, and concentrated. The crude product was absorbed onto silica gel and was purified by flash chromatography (silica gel, eluting with heptanes, containing a gradient with a solution of 3:1 ethyl acetate: ethanol, 15% to 60%) to provide the title compound. $^1$H NMR (400 MHz, DMSO-$d_6$) δ 7.88 (d, J=2.2 Hz, 1H), 7.84 (dd, J=8.6, 2.3 Hz, 1H), 7.78 (s, 1H), 7.64 (d, J=2.7 Hz, 1H), 7.56-7.51 (m, 1H), 7.18 (d, J=8.6 Hz, 1H), 6.41 (d, J=8.5 Hz, 1H), 5.86 (s, 1H), 4.42-4.22 (m, 6H), 4.06 (dt, J=5.1, 2.3 Hz, 2H), 3.68 (d, J=4.8 Hz, 1H), 3.43 (s, 3H), 1.29 (td, J=7.0, 2.0 Hz, 4H). (ESI+) m/z 456.1 (M+H)$^+$.

Example B-17d 11-chloro-17-(hydroxymethyl)-2-methyl-6,7-dihydro-2H-dibenzo[6,7:9,10][1,4,8]trioxacyclododecino[11,12-c]pyridin-3(9H)-one Aluminum (III) lithium hydride (17.48 mg, 0.461 mmol) was added to a solution of Example B-17c (210 mg, 0.461 mmol) in tetrahydrofuran (5 mL). The reaction mixture was stirred at ambient temperature for 3 hours, and then under reflux for 3 hours. Another portion of aluminum (III) lithium hydride (36 mg, 0.949 mmol) was added and the reaction mixture was stirred at ambient temperature overnight. The reaction mixture was cooled to 0° C. and the following was added successively: 54 µL water, 54 µL 15% aqueous sodium hydroxide, and 160 µL water. The resultant slurry was stirred at ambient temperature for 1 hour. The slurry was filtered through Celite. The solids were washed well with ethyl acetate. The combined filtrate was washed with saturated aqueous sodium chloride, dried (anhydrous magnesium sulfate), filtered, and concentrated. The crude product was absorbed onto silica gel and was purified by flash chromatography (silica gel, eluting with dichloromethane containing a gradient with methanol, 2% to 10%) to provide the title compound.

Example B-17e 17-(bromomethyl)-11-chloro-2-methyl-6,7-dihydro-2H-dibenzo[6,7:9,10][1,4,8]trioxacyclododecino[11,12-c]pyridin-3(9H)-one Using the procedure described for Example A-36c and substituting Example B-17d for Example A-36b provided the title compound.

Example B-17f 11-chloro-2-methyl-17-((methylsulfonyl)methyl)-6,7-dihydro-2H-dibenzo[6,7:9,10][1,4,8]trioxacyclododecino[11,12-c]pyridin-3(9H)-one Using the procedure described for Example A-36d and substituting Example B-17e for Example A-36c provided the title compound. $^1$H NMR (400 MHz, DMSO-$d_6$) δ 7.66 (s, 1H), 7.60 (d, J=2.7 Hz, 1H), 7.51 (dd, J=8.6, 2.7 Hz, 1H), 7.33 (d, J=2.2 Hz, 1H), 7.25 (dd, J=8.5, 2.2 Hz, 1H), 7.12 (d, J=8.6 Hz, 1H), 6.31 (d, J=8.5 Hz, 1H), 5.86 (s, 1H), 4.47 (d, J=13.7 Hz, 1H), 4.41-4.27 (m, 3H), 4.04 (d, J=19.6 Hz, 2H), 3.81 (d, J=13.1 Hz, 1H), 3.75-3.64 (m, 1H), 3.43 (s, 3H), 2.94 (s, 3H). MS (ESI+) m/z 476.1 (M+H)$^+$.

BIOLOGICAL EXAMPLES

Bromodomain Domain Binding Assay

A time-resolved fluorescence resonance energy transfer (TR-FRET) assay was used to determine the affinities of compounds of the Examples listed in Table 1 for the tandem domain of bromodomain BRD4. His-tagged (BDI-BDII: amino acids K57-K550) bromodomain of BRD4 was expressed and purified. An Alexa647-labeled BET-inhibitor was used as the fluorescent probe in the assay.

Synthesis of Alexa647-Labeled Bromodomain Inhibitor Compound 2-((6S,Z)-4-(4-chlorophenyl)-2,3,9-trimethyl-6H-thieno[3,2-f][1,2,4]triazolo[4,3-a][1,4]diazepin-6-yl) acetic acid Methyl 2-((6S,Z)-4-(4-chlorophenyl)-2,3,9-trimethyl-6H-thieno[3,2-f][1,2,4]triazolo[4,3-a][1,4]diazepin-6-yl)acetate (WO 2006129623) (100.95 mg, 0.243 mmol was suspended in 1 mL methanol to which was added a freshly prepared solution of lithium hydroxide monohydrate (0.973 mL, 0.5 M, 0.487 mmol) and shaken at ambient temperature for 3 hours. The methanol was evaporated and the pH adjusted with aqueous hydrochloric acid (1 M, 0.5 mL, 0.5 mmol) and extracted four times with ethyl acetate. The combined ethyl acetate layers were dried over magnesium sulfate and evaporated to afford 2-((6S,Z)-4-(4-chlorophenyl)-2,3,9-trimethyl-6H-thieno[3,2-f][1,2,4]triazolo[4,3-a][1,4]diazepin-6-yl)acetic acid (85.3 mg, 87.0%); ESI-MS m/z=401.1 [(M+H)$^+$] which was used directly in the next reaction.

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate)

2-((6S,Z)-4-(4-chlorophenyl)-2,3,9-trimethyl-6H-thieno[3,2-f][1,2,4]triazolo[4,3-a][1,4]diazepin-6-yl)acetic acid (85.3 mg, 0.213 mmol) and 2,2'-(ethane-1,2-diylbis(oxy)) diethanamine (Sigma-Aldrich, 0.315 mg, 2.13 mmol) were combined in 5 mL anhydrous dimethylformamide. (1H-benzo[d][1,2,3]triazol-1-yloxy)tripyrrolidin-1-ylphosphonium hexafluorophosphate(V) (PyBOB, CSBio, Menlo Park Calif.; 332 mg, 0.638 mmol) was added and the reaction shaken at ambient temperature for 16 hours. The reaction mixture was diluted to 6 mL with dimethylsulfoxide:water (9:1, v:v) and purified in two injections with time collection Waters Deltapak C18 200×25 mm column eluted with a gradient of 0.1% trifluoroacetic acid (v/v) in water and acetonitrile. The fractions containing the two purified products were lyophilized to afford N-(2-(2-(2-aminoethoxy) ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (134.4 mg, 82.3%); ESI-MS m/z=531.1 [(M+H)$^+$]; 529.1 [(M−H)$^-$] and (S,Z)—N,N'-(2,2'-(ethane-1,2-diylbis(oxy))bis(ethane-2,1-diyl))bis(2-((6S,Z)-4-(4-chlorophenyl)-2,3,9-trimethyl-6H-thieno[3, 2-f][1,2,4]triazolo[4,3-a][1,4]diazepin-6-yl)acetamide) bis (2,2,2-trifluoroacetate) (3.0 mg, 1.5%); ESI-MS m/z=913.2 [(M+H)+]; 911.0 [(M−H)−].

N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate)

N-(2-(2-(2-aminoethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide bis(2,2,2-trifluoroacetate) (5.4 mg, 0.0071 mmol) and Alexa Fluor® 647 carboxylic Acid, succinimidyl ester (Life Technologies, Grand Island, N.Y.; 3 mg, 0.0024 mmol) were combined in 1 mL anhydrous dimethylsulfoxide containing diisopropylethylamine (1% v/v) and shaken at ambient temperature for 16 hours. The reaction mixture was diluted to 3 mL with dimethylsulfoxide:water (9:1, v:v) and purified in one injection with time collection Waters Deltapak C18 200×25 mm column eluted with a gradient of 0.1% trifluoroacetic acid (v/v) in water and acetonitrile. The fractions containing the purified product were lyophilized to afford N-(2-(2-(2-amido-(Alexa647)-ethoxy)ethoxy)ethyl)-2-((6S,Z)-4-(4-chlorophenyl)-2,3,9-trimethyl-6H-thieno[3,2-f][1,2,4]triazolo[4,3-a][1,4]diazepin-6-yl)acetamide(2,2,2-trifluoroacetate) (1.8 mg); MALDI-MS m/z=1371.1, 1373.1 [(M+H)−] as a dark blue powder.

Assay

Compound dilution series were prepared in DMSO via an approximately 3-fold serial dilution of 0.047 mM to 0.78 nM directly into white, low-volume assay plates (Perkin Elmer Proxiplate 384 Plus #6008280) using a Labcyte Echo in conjunction with Labcyte Access and Thermo Multidrop CombinL robotics. Compounds were then suspended in eight microliters (μL) of assay buffer (20 mM Sodium Phosphate, pH 6.0, 50 mM NaCl, 1 mM Ethylenediaminetetraacetic acid disodium salt dihydrate, 0.01% Triton X-100, 1 mM DL-Dithiothreitol) containing His-tagged bromodomain, Europium-conjugated anti-His antibody (Invitrogen PV5596) and Alexa-647-conjugated probe. The final concentration of 1× assay contains 2% DMSO, 3 nM His-tagged bromodomain, 1 nM Europium-conjugated anti-His-tag antibody and 30 nM probe and compound concentration in the range of: 0.92 μM-15 pM After an one-hour incubation at room temperature, TR-FRET ratios were determined using an Envision multilabel plate reader (Ex 340, Em 495/520).

TR-FRET data were normalized to the means of 24 no-compound controls ("high") and 8 controls containing 1 μM un-labeled probe ("low"). Percent inhibition was plotted as a function of compound concentration and the data were fit with the 4 parameter logistic equation to obtain $IC_{50}$s. Inhibition constants ($K_i$) were calculated from the $IC_{50}$s, probe $K_d$ and probe concentration. Typical Z' values were between 0.65 and 0.75. The minimum significant ratio was determined to evaluate assay reproducibility (Eastwood et al., (2006) J Biomol Screen, 11: 253-261). The MSR was determined to be 2.46, and a moving MSR (last six run MSR overtime) was typically <3. The $K_i$ values are reported in Table 1.

MX-1 Cell Line Proliferation Assay

The impact of compounds of the Examples on cancer cell proliferation was determined using the breast cancer cell line MX-1 (ATCC) in a 3-day proliferation assay and the data are reported in Table 1. MX-1 cells were maintained in RPMI 1640 medium (Sigma) supplemented with 10% FBS at 37 C.° and an atmosphere of 5% $CO_2$. For compound testing, MX-1 cells were plated in 96-well black bottom plates at a density of 5000 cells/well in 90 μL of culture media and incubated at 37° overnight to allow cell adhesion and spreading. Compound dilution series were prepared in DMSO via a 3-fold serial dilution from 3 mM to 0.1 μM. The DMSO dilution series were then diluted 1:100 in phosphate buffered saline, and 10 μL of the resulted solution were added to the appropriate wells of the MX-1 cell plate. The final compound concentrations in the wells were 3, 1, 0.3, 0.1, 0.03, 0.01, 0.003, 0.001, 0.0003, and 0.0001 μM, or 1, 0.3, 0.1, 0.03, 0.01, 0.003, 0.001, 0.0003, 0.0001, and 0.00003 μM. After the addition of compounds, the cells were incubated for 72 more hours and the amounts of viable cells were determined using the Cell Titer Glo assay kit (Promega) according to manufacturer suggested protocol.

Luminescence readings from the Cell Titer Glo assay were normalized to the DMSO treated cells and analyzed using the GraphPad Prism software with sigmoidal curve fitting to obtain $EC_{50}$s. The minimum significant ratio (MSR) was determined to evaluate assay reproducibility (Eastwood et al., (2006) J Biomol Screen, 11: 253-261). The overall MSR was determined to be 2.1 and a moving MSR (last six run MSR overtime) has been <2.

TABLE 1

| Example # | TR-FRET Binding $K_i$: BRD4 (BDI-BDII_K57-K550) (μM) | Cellular proliferation: $EC_{50}$ (μM) |
|---|---|---|
| A-1 | 0.00458 | 0.00689 |
| A-2 | 0.234 | 0.709 |
| A-3 | 0.00754 | 0.0311 |
| A-4 | 0.00307 | 0.0104 |
| A-5 | 0.0013 | 0.0128 |
| A-6 | 0.00151 | 0.0096 |
| A-7 | 0.0257 | 0.109 |
| A-8 | 0.0252 | ND |
| A-9 | 0.00093 | 0.00569 |
| A-10 | 0.0352 | 0.347 |
| A-11 | 0.00537 | 0.0306 |
| A-12 | 0.00216 | 0.0191 |
| A-13 | 0.00099 | 0.0136 |
| A-14 | 0.00147 | 0.00557 |
| A-15 | 0.00306 | 0.0424 |
| A-16 | 0.00166 | 0.0152 |
| A-17 | 0.00225 | 0.00782 |
| A-18 | 0.00406 | 0.00887 |
| A-19 | 0.00245 | 0.0162 |
| A-20 | 0.00125 | 0.00869 |
| A-21 | 0.00088 | 0.00571 |
| A-22 | 0.00151 | 0.0090 |
| A-23 | 0.00127 | 0.00786 |
| A-24 | 0.00334 | 0.0164 |
| A-25 | 0.00129 | 0.0108 |
| A-26 | 0.00201 | 0.0149 |
| A-27 | 0.0122 | 0.0628 |
| A-28 | 0.0859 | >1.0 |
| A-29 | 0.00074 | 0.00397 |
| A-30 | 0.00115 | 0.00877 |
| A-31 | 0.0243 | 0.302 |
| A-32 | 0.0887 | ND |
| A-33 | 0.00145 | 0.00568 |
| A-34 | 0.00692 | 0.0333 |
| A-35 | 0.00068 | 0.00418 |
| A-36 | 0.00285 | 0.0192 |
| A-37 | 0.00087 | 0.00612 |
| A-38 | 0.0147 | >1.0 |
| A-39 | 0.0157 | 0.173 |
| A-40 | 0.00609 | 0.0237 |
| A-41 | 0.00805 | 0.0268 |
| A-42 | 0.00086 | 0.0102 |
| A-43 | 0.00382 | 0.0107 |
| A-44 | 0.00122 | 0.00405 |

TABLE 1-continued

| Example # | TR-FRET Binding K$_i$: BRD4 (BDI-BDII_K57-K550) (μM) | Cellular proliferation: EC$_{50}$ (μM) |
| --- | --- | --- |
| A-45 | 0.00184 | 0.00382 |
| A-46 | 0.0321 | 0.0507 |
| A-47 | 0.00368 | 0.0244 |
| A-48 | 0.00132 | 0.00431 |
| A-49 | 0.00157 | 0.00364 |
| A-50 | 0.00224 | 0.00372 |
| A-51 | 0.00172 | 0.014 |
| A-52 | 0.00075 | 0.00576 |
| A-53 | 0.00632 | 0.0475 |
| A-54 | 0.0197 | 0.162 |
| A-55 | 0.00291 | 0.0142 |
| A-56 | 0.00399 | 0.0169 |
| A-57 | 0.00844 | 0.0531 |
| A-58 | 0.00201 | 0.0184 |
| A-59 | 0.0242 | 0.111 |
| A-60 | 0.00580 | 0.00116 |
| B-1 | 0.0151 | 0.00877 |
| B-2 | 0.0156 | 0.142 |
| B-3 | 0.172 | >1.0 |
| B-4 | 0.0105 | 0.257 |
| B-5 | 0.00119 | 0.00279 |
| B-6 | 0.00157 | 0.0171 |
| B-7 | 0.00161 | 0.0454 |
| B-8 | 0.00097 | 0.017 |
| B-9 | 0.00064 | 0.0473 |
| B-10 | 0.00124 | 0.0297 |
| B-11 | 0.00945 | 0.0251 |
| B-12 | 0.0051 | 0.00801 |
| B-13 | 0.00222 | 0.0168 |
| B-14 | 0.00214 | 0.00595 |
| B-15 | 0.00100 | 0.153 |
| B-16 | 0.00128 | >1.0 |
| B-17c | 0.0107 | 0.0067 |
| B-17 | 0.0077 | 0.0309 |

ND = Not Determined

LPS (Lipopolysaccharide) Induced IL-6 Production Mouse Assay

Compounds of the Examples listed in Table 2 were assayed for their ability to inhibit LPS (lipopolysaccharide) induced IL-6 (Interleukin-6) production in mice. Fox Chase SCID® female mice (Charles Rivers Labs, 8 per group) or CD1 female mice received an intraperitoneal challenge of lipopolysaccharide (2.5 mg/kg, L2630 E. coli 0111:B4) one hour after oral administration of compounds. Mice were euthanized 2 hours after lipopolysaccharide injection, blood was removed by cardiac puncture, and then the serum harvested from the blood samples was frozen at −80° C. On the day of the assay the serum samples were brought to room temperature and then diluted 1:20 in phosphate-buffered saline containing 2% bovine serum albumin. Interleukin-6 measurements were performed using a cytokine assay from Meso Scale Discovery (Gaithersburg, Md.) for mouse serum analysis according to the manufacturer's protocol and read on a SECTOR Imager 6000 (Meso Scale Discovery, Gaithersburg, Md.) instrument. Statistical analysis was performed using Prism software (version 5.0) incorporating Dunnett's one way ANOVA. The IL-6 mean and standard deviation of the group of vehicle treated animals were compared with the IL-6 mean and standard deviation of the group treated with drug. A p value <0.05 means that there is less than a 5% probability that the mean values in the two groups are equal. The % inhibition values in Table 2 all exhibited a p value less than 0.05.

TABLE 2

Inhibition of LPS induced IL-6 production

| Compound of Example # | % inhibition | Mouse strain |
| --- | --- | --- |
| A-3 | 78 | SCID |
| A-5 | 73 | SCID |
| A-6 | 86 | CD1 |
| A-9 | 83 | CD1 |
| A-12 | 47 | CD1 |
| A-13 | 82 | CD1 |
| A-14 | 77 | CD1 |
| A-20 | 81 | CD1 |
| A-22 | 83 | CD1 |
| A-33 | 74 | CD1 |
| A-36 | 68 | CD1 |
| B-1 | 43 | CD1 |
| B-5 | 61 | CD1 |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All publications, patents, and patent applications cited herein are hereby incorporated by reference in their entirety for all purposes.

The invention claimed is:

1. A compound of formula (I) or a pharmaceutically acceptable salt thereof

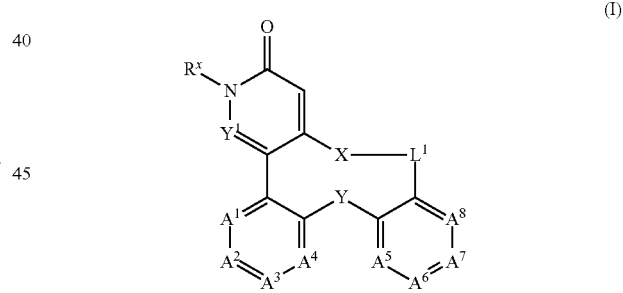

wherein
R$^x$ is C$_1$-C$_3$ alkyl;
Y$^1$ is CR$^y$, wherein R is H, halogen, C$_1$-C$_3$ alkyl, or C$_1$-C$_3$ haloalkyl;
A$^1$ is CR$^1$, A$^2$ is CR$^2$, A$^3$ is CR$^3$; and A$^4$ is N;
A$^5$ is CR$^5$, A$^6$ is CR$^6$, A$^7$ is CR$^7$; and A$^8$ is CR$^8$;
R$^1$, R$^2$, R$^3$, R$^5$, R$^6$, R$^7$, and R$^8$, are each independently hydrogen, halogen, NO$_2$, G$^a$, C$_1$-C$_6$ haloalkyl, —CN, —OR$^a$, —S(O)$_2$R$^c$, —C(O)R$^a$, —C(O)OR$^a$, —S(O)$_2$NR$^a$R$^b$, —C(O)NR$^a$R$^b$, NR$^a$R$^b$, —N(R$^b$)S(O)$_2$R$^c$, —N(R$^b$)C(O)OR$^c$, —N(R$^b$)C(O)NR$^a$R$^b$, —N(R$^b$)C(O)R$^c$, C$_2$-C$_6$ alkenyl, C$_2$-C$_6$ alkynyl, or C$_1$-C$_6$ alkyl; wherein the C$_2$-C$_6$ alkenyl, C$_2$-C$_6$ alkynyl, and C$_1$-C$_6$ alkyl are optionally substituted with one substituent selected from the group consisting of—

CN, —OR$^a$, —S(O)$_2$R$^c$, —S(O)$_2$NR$^a$R$^b$, —C(O)R$^a$, —C(O)OR$^a$, —C(O)NR$^a$R$^b$, NR$^a$R$^b$, —N(R$^b$)S(O)$_2$R$^c$, —N(R$^b$)C(O)OR$^c$, —N(R$^b$)C(O)NR$^a$R$^b$, —N(R$^b$)C(O)R, and G$^a$;

X is O;

Y is O;

R$^9$ and R$^{10}$ are each independently hydrogen, halogen, —CN, C$_1$-C$_6$ haloalkyl, G$^b$, C$_1$-C$_6$ alkyl, —OR$^d$, —NR$^d$R$^e$, or —C(O)NR$^d$R$^e$;

R$^{11}$ and R$^{12}$ are each independently hydrogen or C$_1$-C$_3$ alkyl;

L$^1$ is —(CR$^{13}$R$^{14}$)$_m$—W—(CR$^{15}$R$^{16}$)$_n$—; wherein —(CR$^{15}$R$^{16}$)$_n$— is attached to the ring containing A$^5$, A$^6$, A$^7$, and A$^8$; wherein m is 1, 2, or 3;

n is 0, 1, 2, or 3;

W is a bond, O, N(R$^{17}$), —CH=CH—, —C(O)—N(R$^{18}$)—, —S(O)$_2$—N(R$^{18}$)—, —N(R$^{18}$)—C(O)—, or —N(R$^{18}$)—S(O)$_2$—; wherein R$^{17}$ is hydrogen, C$_1$-C$_6$ haloalkyl, G$^c$, —S(O)$_2$R$^f$, —S(O)$_2$N(R$^g$)$_2$, —S(O)$_2$N(R$^g$)C(O)R$^f$, —S(O)$_2$N(R$^g$)C(O) OR$^f$, —C(O)R$^f$, —C(O)OR$^f$, —C(O)N(R$^g$)$_2$, C$_2$-C$_6$ alkenyl, C$_2$-C$_6$ alkynyl, or C$_1$-C$_6$ alkyl; wherein the C$_2$-C$_6$ alkenyl, C$_2$-C$_6$ alkynyl, and C$_1$-C$_6$ alkyl are optionally substituted with one substituent selected from the group consisting of—CN, —OR$^a$, —S(O)$_2$R$^a$, —S(O)$_2$NR$^a$R$^b$, —C(O)R$^a$, —C(O)OR$^a$, —C(O)NR$^a$R$^b$, NR$^a$R$^b$, —N(R$^b$)S(O)$_2$R$^c$, —N(R$^b$)C(O)OR$^c$, —N(R$^b$)C(O)NR$^a$R$^b$, —N(R$^b$)C(O)R$^c$, and G$^c$; and R$^{18}$, at each occurrence, is independently hydrogen, C$_1$-C$_6$ haloalkyl, G$^c$, C$_2$-C$_6$ alkenyl, C$_2$-C$_6$ alkynyl, or C$_1$-C$_6$ alkyl; wherein the C$_2$-C$_6$ alkenyl, C$_2$-C$_6$ alkynyl, and C$_1$-C$_6$ alkyl are optionally substituted with one substituent selected from the group consisting of —CN, —OR$^a$, —S(O)$_2$R$^a$, —S(O)$_2$NR$^a$R$^b$, —C(O)R$^a$, —C(O)OR$^a$, —C(O)NR$^a$R$^b$, NR$^a$R$^b$, —N(R$^b$)S(O)$_2$R$^c$, —N(R$^b$)C(O)OR$^c$, —N(R$^b$)C(O)NR$^a$R$^b$, —N(R$^b$)C(O)R$^c$, and G$^c$;

R$^{13}$ and R$^{14}$, at each occurrence, are each independently hydrogen, halogen, —CN, C$_1$-C$_6$ haloalkyl, G$^b$, C$_1$-C$_6$ alkyl, —OR$^d$, —NR$^d$R$^e$, or —C(O)NR$^d$R$^e$; R$^{13}$ and R$^{14}$ together may be an oxo group;

R$^{15}$ and R$^{16}$, at each occurrence, are each independently hydrogen, halogen, —CN, C$_1$-C$_6$ haloalkyl, G$^b$, C$_1$-C$_6$ alkyl, —OR$^d$, —NR$^d$R$^e$, or —C(O)NR$^d$R$^e$; R$^{15}$ and R$^{16}$ together may be an oxo group;

R$^a$ and R$^b$, at each occurrence, are each independently hydrogen, C$_1$-C$_6$ alkyl, C$_1$-C$_6$ haloalkyl, G$^a$, or —(C$_1$-C$_6$ alkylenyl)-G$^a$;

R$^c$, at each occurrence, is independently C$_1$-C$_6$ alkyl, C$_1$-C$_6$ haloalkyl, G$^a$, or —(C$_1$-C$_6$ alkylenyl)-G$^a$;

R$^d$, at each occurrence, is independently hydrogen, C$_1$-C$_6$ haloalkyl, G$^b$, or C$_1$-C$_6$ alkyl; wherein the C$_1$-C$_6$ alkyl is optionally substituted with one substituent selected from the group consisting of—CN, —OR$^a$, —S(O)$_2$R$^a$, —S(O)$_2$NR$^a$R$^b$, —C(O)R$^a$, —C(O)OR$^a$, —C(O)NR$^a$R$^b$, NR$^a$R$^b$, —N(R$^b$)S(O)$_2$R$^c$, —N(R$^b$)C(O)OR$^c$, —N(R$^b$)C(O)NR$^a$R$^b$, —N(R$^b$)C(O)R, and G$^b$;

R$^e$, at each occurrence, is independently hydrogen, C$_1$-C$_6$ alkyl, C$_1$-C$_6$ haloalkyl, G$^b$, or —(C$_1$-C$_6$ alkylenyl)-G$^b$;

R$^f$, at each occurrence, is independently C$_1$-C$_6$ alkyl, C$_1$-C$_6$ haloalkyl, G$^c$, or —(C$_1$-C$_6$ alkylenyl)-G;

R$^g$, at each occurrence, is independently hydrogen, C$_1$-C$_6$ alkyl, C$_1$-C$_6$ haloalkyl, G$^c$, or —(C$_1$-C$_6$ alkylenyl)-G$^c$;

G$^a$, G$^b$, and G$^c$, at each occurrence, are each independently phenyl, C$_3$-C$_6$ cycloalkyl, C$_4$-C$_6$ heterocycle, or C$_5$-C$_6$ heteroaryl, each of which is optionally substituted with 1, 2, 3, 4, or 5 R$^u$ groups;

R$^u$, at each occurrence, is independently C$_1$-C$_6$ alkyl, C$_2$-C$_6$ alkenyl, C$_2$-C$_6$ alkynyl, halogen, C$_1$-C$_6$ haloalkyl, —CN, oxo, NO$_2$, —OR$^h$, —OC(O)R$^i$, —OC(O)NR$^j$R$^k$, —SR$^h$, —S(O)$_2$R$^h$, —S(O)$_2$NR$^j$R$^k$, —C(O)R$^h$, —C(O)OR$^h$, —C(O)NR$^j$R$^k$, —NR$^j$R$^k$, —N(R$^h$)C(O)R$^i$, —N(R$^h$)S(O)$_2$R$^i$, —N(R$^h$)C(O)O(R$^i$), —N(R$^h$)C(O)NR$^j$R$^k$, —(C$_1$-C$_6$ alkylenyl)-OR$^h$, —(C$_1$-C$_6$ alkylenyl)-OC(O)R$^i$, —(C$_1$-C$_6$ alkylenyl)-OC(O)NR$^j$R$^k$, —(C$_1$-C$_6$ alkylenyl)-SR$^h$, —(C$_1$-C$_6$ alkylenyl)-S(O)$_2$R$^h$, —(C$_1$-C$_6$ alkylenyl)-S(O)$_2$NR$^j$R$^k$, —(C$_1$-C$_6$ alkylenyl)-C(O)R$^h$, —(C$_1$-C$_6$ alkylenyl)-C(O)OR$^h$, —(C$_1$-C$_6$ alkylenyl)-C(O)NR$^j$R$^k$, —(C$_1$-C$_6$ alkylenyl)-NR$^j$R$^k$, —(C$_1$-C$_6$ alkylenyl)-N(R$^h$)C(O)R$^i$, —(C$_1$-C$_6$ alkylenyl)-N(R$^h$)S(O)$_2$R$^i$, —(C$_1$-C$_6$ alkylenyl)-N(R$^h$)C(O)O(R$^i$), —(C$_1$-C$_6$ alkylenyl)-N(R$^h$)C(O)NR$^j$R$^k$, or —(C$_1$-C$_6$ alkylenyl)-CN;

R$^h$, R$^j$, R$^k$, at each occurrence, are each independently hydrogen, C$_1$-C$_6$ alkyl, or C$_1$-C$_6$ haloalkyl; and R$^i$, at each occurrence, is independently C$_1$-C$_6$ alkyl or C$_1$-C$_6$ haloalkyl.

2. The compound of claim 1 or a pharmaceutically acceptable salt thereof, wherein R$^x$ is methyl; and R$^y$ is H.

3. The compound of claim 1 or a pharmaceutically acceptable salt thereof, wherein R$^x$ is methyl;

R$^y$ is H;

R$^1$, R$^3$, R$^5$, R$^6$, and R$^8$ are each independently hydrogen or halogen;

R$^7$ is hydrogen, halogen, C$_1$-C$_6$ haloalkyl, —OR$^a$, —CN, or unsubstituted C$_1$-C$_6$ alkyl; and R$^2$ is hydrogen, —S(O)$_2$R$^c$, —C(O)OR$^a$, —S(O)$_2$NR$^a$R$^b$, NR$^a$R$^b$, —N(R$^b$)S(O)$_2$R$^c$, —N(R$^b$)C(O)NR$^a$R$^b$, —N(R$^b$)C(O)R$^c$, or C$_1$-C$_6$ alkyl wherein the C$_1$-C$_6$ alkyl is substituted with one substituent selected from the group consisting of —OR$^a$ and —S(O)$_2$R$^c$.

4. The compound of claim 1 or a pharmaceutically acceptable salt thereof, wherein R$^x$ is methyl;

R$^y$ is H; and

L$^1$ is —(CR$^{13}$R$^{14}$)$_m$—W—(CR$^{15}$R$^{16}$)$_n$—; wherein W is a bond, O, N(R$^{17}$), —CH=CH—, or —N(R$^{18}$)—C(O)—.

5. The compound of claim 1 or a pharmaceutically acceptable salt thereof, wherein R$^x$ is methyl;

R$^y$ is H; and

L$^1$ is —(CR$^{13}$R$^{14}$)$_m$—W—(CR$^{15}$R$^{16}$)$_n$—; wherein m is 1, 2, or 3, n is 1 or 2, and W is a bond.

6. The compound of claim 1 or a pharmaceutically acceptable salt thereof, wherein
$R^x$ is methyl;
$R^y$ is H; and
$L^1$ is —$(CR^{13}R^{14})_m$—W—$(CR^{15}R^{16})_n$—; wherein m is 2, n is 1, and W is O, $N(R^{17})$, or —CH=CH—.

7. The compound of claim 1 or a pharmaceutically acceptable salt thereof, wherein
$R^x$ is methyl;
$R^y$ is H; and
$L^1$ is —$(CR^{13}R^{14})_m$—W—$(CR^{15}R^{16})_n$—; wherein m is 2 or 3, n is 0, and W is —CH=CH— or —$N(R^{18})$—C(O)—.

8. A compound of formula (I-a) or a pharmaceutically acceptable salt thereof,

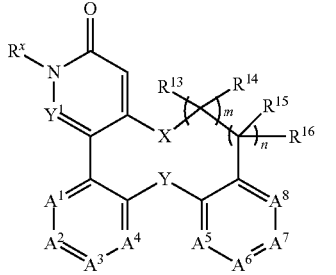

(I-a)

wherein
n is 1 or 2;
m is 1, 2, or 3;
$R^x$ is $C_1$-$C_3$ alkyl;
$Y^1$ is $CR^y$, wherein $R^y$ is H, halogen, $C_1$-$C_3$ alkyl, or $C_1$-$C_3$ haloalkyl;
$A^1$ is $CR^1$, $A^2$ is $CR^2$, $A^3$ is $CR^3$; and $A^4$ is N;
$A^5$ is $CR^5$, $A^6$ is $CR^6$, $A^7$ is $CR^7$; and $A^8$ is $CR^8$;
$R^1$, $R^2$, $R^3$, $R^5$, $R^6$, $R^7$, and $R^8$, are each independently hydrogen, halogen, $NO_2$, $G^a$, $C_1$-$C_6$ haloalkyl, —CN, —$OR^a$, —$S(O)_2R^c$, —$C(O)R^a$, —$C(O)OR^a$, —$S(O)_2NR^aR^b$, —$C(O)NR^aR^b$, $NR^aR^b$, —$N(R^b)S(O)_2R^c$, —$N(R^b)C(O)OR^c$, —$N(R^b)C(O)NR^aR^b$, —$N(R^b)C(O)R^c$, $C_2$-$C_6$ alkenyl, $C_2$-$C_6$ alkynyl, or $C_1$-$C_6$ alkyl; wherein the $C_2$-$C_6$ alkenyl, $C_2$-$C_6$ alkynyl, and $C_1$-$C_6$ alkyl are optionally substituted with one substituent selected from the group consisting of—
CN, —$OR^a$, —$S(O)_2R^c$, —$S(O)_2NR^aR^b$, —$C(O)R^a$, —$C(O)OR^a$, —$C(O)NR^aR^b$, $NR^aR^b$, —$N(R^b)S(O)_2R^c$, —$N(R^b)C(O)OR^c$, —$N(R^b)C(O)NR^aR^b$, —$N(R^b)C(O)R$, and $G^a$;
X is O;
Y is O;
$R^{13}$ and $R^{14}$, at each occurrence, are each independently hydrogen, halogen, —CN, $C_1$-$C_6$ haloalkyl, $G^b$, $C_1$-$C_6$ alkyl, —$OR^d$, —$NR^dR^e$, or —$C(O)NR^dR^e$; $R^{13}$ and $R^{14}$ together may be an oxo group;
$R^{15}$ and $R^{16}$, at each occurrence, are each independently hydrogen, halogen, —CN, $C_1$-$C_6$ haloalkyl, $G^b$, $C_1$-$C_6$ alkyl, —$OR^d$, —$NR^dR^e$, or —$C(O)NR^dR^e$; $R^{15}$ and $R^{16}$ together may be an oxo group;
$R^a$ and $R^b$, at each occurrence, are each independently hydrogen, $C_1$-$C_6$ alkyl, $C_1$-$C_6$ haloalkyl, $G^a$, or —($C_1$-$C_6$ alkylenyl)-$G^a$;

$R^c$, at each occurrence, is independently $C_1$-$C_6$ alkyl, $C_1$-$C_6$ haloalkyl, $G^a$, or —($C_1$-$C_6$ alkylenyl)-$G^a$;
$R^d$, at each occurrence, is independently hydrogen, $C_1$-$C_6$ haloalkyl, $G^b$, or $C_1$-$C_6$ alkyl; wherein the $C_1$-$C_6$ alkyl is optionally substituted with one substituent selected from the group consisting of—
CN, —$OR^a$, —$S(O)_2R^a$, —$S(O)_2NR^aR^b$, —$C(O)R^a$, —$C(O)OR^a$, —$C(O)NR^aR^b$, $NR^aR^b$, —$N(R^b)S(O)_2R^c$, —$N(R^b)C(O)OR^c$, —$N(R^b)C(O)NR^aR^b$, —$N(R^b)C(O)R$, and $G^b$;
$R^e$, at each occurrence, is independently hydrogen, $C_1$-$C_6$ alkyl, $C_1$-$C_6$ haloalkyl, $G^b$, or —($C_1$-$C_6$ alkylenyl)-$G^b$;
$G^a$ and $G^b$, at each occurrence, are each independently phenyl, $C_3$-$C_6$ cycloalkyl, $C_4$-$C_6$ heterocycle, or $C_5$-$C_6$ heteroaryl, each of which is optionally substituted with 1, 2, 3, 4, or 5 $R^u$ groups;
$R^u$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, $NO_2$, —$OR^h$, —$OC(O)R^i$, —$OC(O)NR^jR^k$, —$SR^h$, —$S(O)_2R^h$, —$S(O)_2NR^jR^k$, —$C(O)R^h$, —$C(O)OR^h$, —$C(O)NR^jR^k$, —$NR^jR^k$, —$N(R^h)C(O)R^i$, —$N(R^h)S(O)_2R^i$, —$N(R^h)C(\,)O(R^i)$, —$N(R^h)C(O)NR^jR^k$, —($C_1$-$C_6$ alkylenyl)-$OR^h$, —($C_1$-$C_6$ alkylenyl)-$OC(O)R^i$, —($C_1$-$C_6$ alkylenyl)-$OC(O)NR^jR^k$, —($C_1$-$C_6$ alkylenyl)-$SR^h$, —($C_1$-$C_6$ alkylenyl)-$S(O)_2R^h$, —($C_1$-$C_6$ alkylenyl)-$S(O)_2NR^jR^k$, —($C_1$-$C_6$ alkylenyl)-$C(O)R^h$, —($C_1$-$C_6$ alkylenyl)-$C(O)OR^h$, —($C_1$-$C_6$ alkylenyl)-$C(O)NR^jR^k$, —($C_1$-$C_6$ alkylenyl)-$NR^jR^k$, —($C_1$-$C_6$ alkylenyl)-$N(R^h)C(O)R^i$, —($C_1$-$C_6$ alkylenyl)-$N(R^h)S(O)_2R^i$, —($C_1$-$C_6$ alkylenyl)-$N(R^h)C(O)O(R^i)$, —($C_1$-$C_6$ alkylenyl)-$N(R^h)C(O)NR^jR^k$, or —($C_1$-$C_6$ alkylenyl)-CN;
$R^h$, $R^j$, $R^k$, at each occurrence, are each independently hydrogen, $C_1$-$C_6$ alkyl, or $C_1$-$C_6$ haloalkyl; and
$R^i$, at each occurrence, is independently $C_1$-$C_6$ alkyl or $C_1$-$C_6$ haloalkyl.

9. The compound of claim 8 or a pharmaceutically acceptable salt thereof, wherein
$R^x$ is methyl;
$R^y$ is H; and
$R^2$ is hydrogen, —$S(O)_2R^c$, —$C(O)OR^a$, —$S(O)_2NR^aR^b$, $NR^aR^b$, —$N(R^b)S(O)_2R^c$, —$N(R^b)C(O)NR^aR^b$, —$N(R^b)C(O)R^c$, —$CH_2$—$OR^a$ or —$CH_2$—$S(O)_2R$.

10. The compound of claim 9 or a pharmaceutically acceptable salt thereof, wherein
$R^{13}$, $R^{14}$, $R^{15}$, and $R^{16}$, at each occurrence, are each independently hydrogen or $C_1$-$C_6$ alkyl.

11. The compound of claim 9 or a pharmaceutically acceptable salt thereof, wherein
$R^2$ is —$S(O)_2R^c$, —$N(R^b)S(O)_2R^c$, or —$CH_2$—$S(O)_2R^c$; and
$R^7$ is hydrogen, halogen, $C_1$-$C_6$ haloalkyl, —CN, or —$OR^a$.

12. The compound of claim 11 or a pharmaceutically acceptable salt thereof, wherein
m is 3;
n is 2;
$R^1$, $R^3$, $R^5$, $R^6$, and $R^8$, are each independently hydrogen or halogen; and
$R^{13}$, $R^{14}$, $R^{15}$, and $R^{16}$, at each occurrence, are each independently hydrogen or $C_1$-$C_6$ alkyl.

13. The compound of claim 11 or a pharmaceutically acceptable salt thereof, wherein
m is 2;
n is 1;
$R^1$, $R^3$, $R^5$, $R^6$, and $R^8$, are each independently hydrogen or halogen; and
$R^{13}$, $R^{14}$, $R^{15}$, and $R^{16}$, at each occurrence, are each independently hydrogen or $C_1$-$C_6$ alkyl.

14. The compound of claim 11 or a pharmaceutically acceptable salt thereof, wherein
m is 1;
n is 1;
$R^1$, $R^3$, $R^5$, $R^6$, and $R^8$, are each independently hydrogen or halogen; and
$R^{13}$, $R^{14}$, $R^{15}$, and $R^{16}$, at each occurrence, are each independently hydrogen or $C_1$-$C_6$ alkyl.

15. The compound of claim 11 or a pharmaceutically acceptable salt thereof, wherein
m is 3;
n is 1;
$R^1$, $R^3$, $R^5$, $R^6$, and $R^8$, are each independently hydrogen or halogen; and
$R^{13}$, $R^{14}$, $R^{15}$, and $R^{16}$, at each occurrence, are each independently hydrogen or $C_1$-$C_6$ alkyl.

16. The compound of claim 12, or a pharmaceutically acceptable salt thereof, wherein
$R^y$ is H;
$R^1$, $R^3$, $R^5$, $R^6$, and $R^8$ are hydrogen;
$R^7$ is halogen;
$R^{13}$, $R^{14}$, $R^{15}$, and $R^{16}$ are hydrogen;
$R^b$ is hydrogen; and
$R^c$ is $C_1$-$C_3$ alkyl.

17. The compound of claim 8 or a pharmaceutically acceptable salt thereof, wherein the compound is selected from the group consisting of
methyl 11-chloro-2-methyl-3-oxo-2,3,6,7, 8,9-hexahydrobenzo[11,12][1,6]dioxacyclododecino[2,3-b:4,5-c']dipyridine-17-carboxylate;
17-amino-11-chloro-2-methyl-6,7,8,9-tetrahydrobenzo[11,12][1,6]dioxacyclododecino[2,3-b:4, 5-c']dipyridin-3 (2H)-one;
N-(11-chloro-2-methyl-3-oxo-2,3,6,7,8,9-hexahydrobenzo[11,12][1,6]dioxacyclododecino[2,3-b:4,5-c']dipyridin-17-yl)ethanesulfonamide;
11-chloro-17-(ethyl sulfonyl)-2-methyl-6,7, 8,9-tetrahydrobenzo[11,12][1,6]dioxacyclododecino[2,3-b:4,5-c']dipyridin-3 (2H)-one;
N-(11,13-difluoro-2-methyl-3-oxo-2,3,6,7,8,9-hexahydrobenzo[11,12][1,6]dioxacyclododecino[2,3-b:4,5-c']dipyridin-17-yl)ethanesulfonamide;
11-chloro-2-methyl-3-oxo-2,3,6,7,8,9-hexahydrobenzo[11,12][1,6]dioxacyclododecino[2,3-b:4,5-c']dipyridine-17-carboxylic acid;
11-chloro-17-(hydroxymethyl)-2-methyl-6,7,8,9-tetrahydrobenzo[11,12][1,6]dioxacyclododecino[2,3-b:4,5-c']dipyridin-3 (2H)-one;
11-chloro-2-methyl-17-((methylsulfonyl)methyl)-6,7, 8,9-tetrahydrobenzo[11,12][1,6]dioxacyclododecino[2,3-b:4,5-c']dipyridin-3(2H)-one; and
11,13-difluoro-2-methyl-17-((methylsulfonyl)methyl)-6, 7, 8,9-tetrahydrobenzo[11,12][1,6]dioxacyclododecino[2,3-b:4,5-c']dipyridin-3 (2H)-one.

18. A compound of formula (I-b), or a pharmaceutically acceptable salt thereof (I-b)

wherein W is O, $N(R^{17})$, —CH=CH—, —C(O)—N($R^{18}$)—, —S(O)$_2$—N($R^{18}$)—, —N($R^{18}$)—C(O)—, or —N($R^{18}$)—S(O)$_2$—;
m is 1, 2, or 3;
$R^x$ is $C_1$-$C_3$ alkyl;
$Y^1$ is $CR^y$, wherein $R^y$ is H, halogen, $C_1$-$C_3$ alkyl, or $C_1$-$C_3$ haloalkyl;
$A^1$ is $CR^1$, $A^2$ is $CR^2$, $A^3$ is $CR^3$; and $A^4$ is N;
$A^5$ is $CR^5$, $A^6$ is $CR^6$, $A^7$ is $CR^7$ and $A^8$ is $CR^8$;
$R^1$, $R^2$, $R^3$, $R^5$, $R^6$, $R^7$, and $R^8$, are each independently hydrogen, halogen, $NO_2$, $G^a$, $C_1$-$C_6$ haloalkyl, —CN, —$OR^a$, —$S(O)_2R^c$, —$C(O)R^a$, —$C(O)OR^a$, —$S(O)_2NR^aR^b$, —$C(O)NR^aR^b$, $NR^aR^b$, —$N(R^b)S(O)_2R^c$, —$N(R^b)C(O)OR^c$, —$N(R^b)C(O)NR^aR^b$, —$N(R^b)C(O)R^c$, $C_2$-$C_6$ alkenyl, $C_2$-$C_6$ alkynyl, or $C_1$-$C_6$ alkyl wherein the $C_2$-$C_6$ alkenyl, $C_2$-$C_6$ alkynyl, and $C_1$-$C_6$ alkyl are optionally substituted with one substituent selected from the group consisting of—
CN, —$OR^a$, —$S(O)_2R$, —$S(O)_2NR^aR^b$, —$C(O)R^a$, —$C(O)OR^a$, —$C(O)NR^aR^b$, $NR^aR^b$, —$N(R^b)S(O)_2R^c$, —$N(R^b)C(O)OR^c$, —$N(R^b)C(O)NR^aR^b$, —$N(R^b)C(O)R$, and $G^a$;
X is O
Y is O
$R^{13}$ and $R^{14}$, at each occurrence, are each independently hydrogen, halogen, —CN, $C_1$-$C_6$ haloalkyl, $G^b$, $C_1$-$C_6$ alkyl, —$OR^d$, —$NR^dR^e$, or —$C(O)NR^dR^e$: $R^{13}$ and $R^{14}$ together may be an oxo group;
$R^a$ and $R^b$, at each occurrence, are each independently hydrogen, $C_1$-$C_6$ alkyl, $C_1$-$C_6$ haloalkyl, $G^a$, or —($C_1$-$C_6$ alkylenyl)-$G^a$;
$R^c$, at each occurrence, is independently $C_1$-$C_6$ alkyl, $C_1$-$C_6$ haloalkyl, $G^a$, or —($C_1$-$C_6$ alkylenyl)-$G^a$;
$R^d$, at each occurrence, is independently hydrogen, $C_1$-$C_6$ haloalkyl, $G^b$, or $C_1$-$C_6$ alkyl; wherein the $C_1$-$C_6$ alkyl is optionally substituted with one substituent selected from the group consisting of—
CN, —$OR^a$, —$S(O)_2R^a$, —$S(O)_2NR^aR^b$, —$C(O)R^a$, —$C(O)OR^a$, —$C(O)NR^aR^b$, $NR^aR^b$, —$N(R^b)S(O)_2R$, —$N(R^b)C(O)OR$, —$N(R^b)C(O)NR^aR^b$, —$N(R^b)C(O)R$, and $G^b$;
$R^e$, at each occurrence, is independently hydrogen, $C_1$-$C_6$ alkyl, $C_1$-$C_6$ haloalkyl, $G^b$, or —($C_1$-$C_6$ alkylenyl)-$G^b$;
$G^a$ and $G^b$ at each occurrence, are each independently phenyl, $C_3$-$C_6$ cycloalkyl, $C_4$-$C_6$ heterocycle, or $C_5$-$C_6$ heteroaryl, each of which is optionally substituted with 1, 2, 3, 4, or 5 $R^u$ groups;
$R^u$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo,
$NO_2$, —$OR^h$, —$OC(O)R^i$, —$OC(O)NR^jR^k$, —$SR^h$, —$S(O)_2R^h$, —$S(O)_2NR^jR^k$, —$C(O)R^h$, —$C(O)OR^h$, —$C(O)NR^jR^k$, —$NR^jR^k$, —$N(R^h)C(O)R^i$, —$N(R^h)$ $S(O)_2R^i$, —$N(R^h)C(O)O(R^i)$, —$N(R^h)C(O)NR^jR^k$, —$(C_1-C_6$ alkylenyl$)$-$OR^h$, —$(C_1-C_6$ alkylenyl$)$-$OC(O)R^i$, —$(C_1-C_6$ alkylenyl$)$-$OC(O)NR^jR^k$, —$(C_1-C_6$ alkylenyl$)$-$SR^h$, —$(C_1-C_6$ alkylenyl$)$-$S(O)_2R^h$, —$(C_1-C_6$ alkylenyl$)$-$S(O)_2NR^jR^k$, —$(C_1-C_6$ alkylenyl$)$-$C(O)R^h$, —$(C_1-C_6$ alkylenyl$)$-$C(O)OR^h$, —$(C_1-C_6$ alkylenyl$)$-$C(O)NR^jR^k$, —$(C_1-C_6$ alkylenyl$)$-$NR^jR^k$, —$(C_1-C_6$ alkylenyl$)$-$N(R^h)C(O)R^i$, —$(C_1-C_6$ alkylenyl$)$-$N(R^h)S(O)_2R^i$, —$(C_1-C_6$ alkylenyl$)$-$N(R^h)C(O)O(R^i)$, —$(C_1-C_6$ alkylenyl$)$-$N(R^h)C(O)NR^jR^k$, or —$(C_1-C_6$ alkylenyl$)$-$CN$;

$R^h$, $R^j$, $R^k$, at each occurrence, are each independently hydrogen, $C_1-C_6$ alkyl, or $C_1-C_6$ haloalkyl; and $R^i$, at each occurrence, is independently $C_1-C_6$ alkyl or $C_1-C_6$ haloalkyl.

19. The compound of claim 18 or a pharmaceutically acceptable salt thereof, wherein
$R^x$ is methyl;
$R^y$ is H;
m is 2 or 3; and
W is —CH=CH— or —$N(R^{18})$—C(O)—.

20. The compound of claim 18 or a pharmaceutically acceptable salt thereof, wherein
$R^x$ is methyl.

21. The compound of claim 18 or a pharmaceutically acceptable salt thereof, wherein
$R^x$ is methyl;
$R^y$ is H;
m is 2 or 3;
W is —CH=CH— or —$N(R^{18})$—C(O)—; and
$R^2$ is hydrogen, —$S(O)_2R^c$, —$C(O)OR^a$, —$S(O)_2NR^aR^b$, $NR^aR^b$, —$N(R^b)S(O)_2R^c$, —$N(R^b)C(O)NR^aR^b$, —$N(R^b)C(O)R^c$, —$CH_2$—$OR^a$ or —$CH_2$—$S(O)_2R$.

22. A pharmaceutical composition comprising a therapeutically effective amount of a compound of formula (I) according to claim 1, or a pharmaceutically acceptable salt thereof, in combination with a pharmaceutically acceptable carrier.

\* \* \* \* \*